(12) United States Patent
Kajino et al.

(10) Patent No.: US 7,592,453 B2
(45) Date of Patent: Sep. 22, 2009

(54) FUSED QUINOLINE DERIVATIVE AND USE THEREOF

(75) Inventors: Masahiro Kajino, Osaka (JP); Yasuhiko Kawano, Osaka (JP)

(73) Assignee: Takeda Pharmaceutical Company Limited, Osaka-Shi (JP)

( * ) Notice: Subject to any disclaimer, the term of this patent is extended or adjusted under 35 U.S.C. 154(b) by 523 days.

(21) Appl. No.: 11/587,788

(22) PCT Filed: Apr. 28, 2005

(86) PCT No.: PCT/JP2005/008558

§ 371 (c)(1),
(2), (4) Date: Oct. 25, 2006

(87) PCT Pub. No.: WO2005/105802

PCT Pub. Date: Nov. 10, 2005

(65) Prior Publication Data

US 2008/0039452 A1 Feb. 14, 2008

(30) Foreign Application Priority Data

Apr. 28, 2004 (JP) .............................. 2004-134705

(51) Int. Cl.
C07D 221/06 (2006.01)
A61K 31/4375 (2006.01)
(52) U.S. Cl. .............................. 546/80; 546/79; 514/290
(58) Field of Classification Search .................... 546/79, 546/80; 514/290
See application file for complete search history.

(56) References Cited

U.S. PATENT DOCUMENTS 5,288,725 A 2/1994 Witherup et al.

FOREIGN PATENT DOCUMENTS

| WO | WO-94/09001 | 4/1994 |
|---|---|---|
| WO | WO-02/38547 | 5/2002 |
| WO | WO-02/38548 | 5/2002 |
| WO | WO-02/083663 | 10/2002 |
| WO | WO-02/083664 | 10/2002 |

OTHER PUBLICATIONS

K. Frank et al., "Cyclizations of Substituted Benzylidene-3-alkenylamines: Synthesis of the Tricyclic Core of the Martinellines," *J. Org. Chem.*, vol. 65, pp. 655-666 (2000).
C. Leach et al., "Reversible Inhibitors of the Gastric (H+/K+)-ATPase. 2: 1-Arylpyrrolo[3,2-c]quinolines: Effect of the 4-Substituent," *J. Med. Chem.*, vol. 35, pp. 1845-1852 (1992).
D. Ma et al., "Aromatic Nucleophilic Substitution or CuI-Catalyzed Coupling Route to Martinellic Acid," *J. Org. Chem.*, vol. 68, pp. 442-451 (2003).
D. Ma et al., "First Total Synthesis of Martinellic Acid, a Naturally Occurring Bradykinin Receptor Antagonist," *Organic Letters*, vol. 3, pp. 2189-2191 (2001).
M. Hadden et al., "Synthesis and reactivity of hexahydropyrroloquinolines," *Tetrahedron*, vol. 57, pp. 5615-5624 (2001).
M. Hadden et al, "Regioselective Synthesis of Pyrroloquinolines—Approaches to Martinelline," *Tetrahedron Letters*, vol. 40, pp. 1215-1218 (1999).
B. Snider et al., Synthesis of the Tricyclic Triamine Core of Martinelline and Martinellic Acid, *Tetrahedron Letters*, vol. 40, pp. 3339-3342 (1999).
M. Nyerges, "Construction of Pyrrolo[3,2-c]quinolines—Recent Advances in the Synthesis of the Martinelline Alkaloids," *Heterocycles*, vol. 63 pp. 1685-1712 (2004).
B. Snider et al., "Total Synthesis (±)-Martinellic Acid," Organic Letters, vol. 3, pp. 4217-4220 (2001).
K. Frank, et al., "Cyclizations of Substituted Benzylidene-3-alkenylamines: Synthesis of the Tricyclic Core of the Martinellines," *Journal of Organic Chemistry*, vol. 65, pp. 655-666 (2000).
C. Leach, et al., "Reversible Inhibitors of the Gastric (H+/K+)-ATPase. 2. 1-Arylpyrrolo[3,2-c]quinolines: Effect of the 4-Substituent," *Journal of Medicinal Chemistry*, vol. 35, pp. 1845-1852 (1992).

*Primary Examiner*—Rita J Desai
(74) *Attorney, Agent, or Firm*—Edwards Angell Palmer & Dodge LLP; David G. Conlin; Lisa Swiszcz Hazzard

(57) ABSTRACT

The present invention aims at provision of a quinoline derivative having a neurokinin 2 (NK2) receptor antagonistic action and relates to a compound represented by the formula (I)

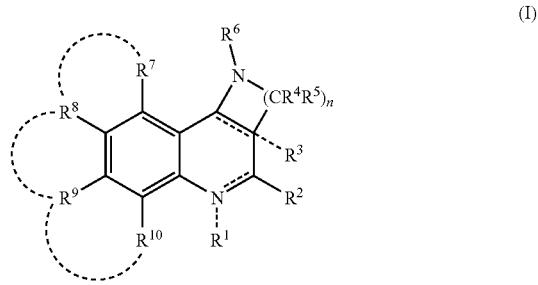

(I)

wherein $R^1$ is a hydrogen atom and the like; $R^2$ is a hydrogen atom, a hydrocarbon group optionally having substituent(s) and the like; $R^3$ is unsubstituted (i.e., absence), a hydrogen atom and the like; $R^4$ and $R^5$ are the same or different and each is a hydrogen atom, a hydrocarbon group optionally having substituent(s), and the like; $R^6$ is (cyclic group optionally having substituent(s))-carbonyl, and the like; $R^7$, $R^8$, $R^9$ and $R^{10}$ are the same or different and each is a hydrogen atom, halogen and the like; or $R^7$ and $R^8$, $R^8$ and $R^9$, and $R^9$ and $R^{10}$ may form a ring together with the adjacent carbon atoms; n is an integer of 1 to 5;

--- represents unsubstituted (i.e., absence) or a single bond; and

=== represents a single bond or a double bond, or a salt thereof, and the like.

1 Claim, No Drawings

FUSED QUINOLINE DERIVATIVE AND USE THEREOF

CROSS-REFERENCE TO RELATED APPLICATION(S)

This application is a §371 application of copending international patent application PCT/JP2005/008558 which was filed on Apr. 28, 2005, and which claims priority to Japanese Patent Application Serial No. 2004-134705 which was filed on Apr. 28, 2004, both of which are incorporated by reference.

TECHNICAL FIELD

The present invention relates to a novel fused quinoline compound having a superior tachykinin receptor antagonistic action, a production method thereof, a pharmaceutical composition comprising the compound, the use of the compound for a pharmaceutical agent and the like.

BACKGROUND ART

Tachykinin is a generic term of a group of neuropeptides, and substance P (hereinafter SP), neurokinin A (hereinafter abbreviated as NKA) and neurokinin B (hereinafter abbreviated as NKB) in mammals are known. These peptides are known to be bound with receptors (neurokinin 1, neurokinin 2, neurokinin 3, hereinafter abbreviated as NK1, NK2, NK3, respectively) thereof present in vivo to exert various biological activities.

Particularly, the NK2 receptor antagonist is considered to be useful for the prophylaxis or treatment of neurokinin A dependent pathology, and they are considered to be useful for the prophylaxis or treatment of diseases such as pulmonary diseases (particularly, bronchospasm due to asthma, cough, chronic obstructive pulmonary diseases and pulmonary anaphylaxis), gastrointestinal tract diseases (particularly, enterospasm, irritable bowel syndrome, inflammatory bowel diseases, non-ulcer dyspepsia, esophageal reflux and GI tract disorders), central nervous diseases (e.g., melancholia, anxiety), urinary diseases (e.g., dysuria), pain (e.g., neurotic pain, pain associated with inflammatory diseases such as rheumatism and the like) (Expert Opin. Ther. Targets, (2003) vol. 7(3), p. 343).

Heretofore, selective peptidic antagonists for NK2 receptor have been known (Br. J. Pharmacol., 1990, 100, 588-592 and WO 97/31941). However, these known peptidic NK2 antagonists show weak activity and metabolically unstable, and therefore, it is difficult to put to use for practical prophylactic or therapeutic agent.

As the selective non-peptidic NK2 receptor antagonist, SR 48968 (Brit. J. Pharmacol. (1992), vol. 105, p. 77), GR-159897 (Bioorg. Med. Chem. Lett. (1994), vol. 4, p. 1951), CP 96345 (Science, 1991, vol. 251, p. 435), RP 67580 (Proc. Nat. Acad. Sci. 1991, vol. 88, p. 10208), ZD 7944 (Abstracts of Papers, Part 1, 214th National Meeting of the American Chemical Society, Las Vegas, Nev., Sep. 7-11, 1997, MEDI 264), WO 02/38547, WO 02/38548, WO 02/083663, WO 02/083664 and the like are known.

In addition, as a quinoline derivative fused with nitrogen-containing heterocycle, the compounds described in J. Org. Chem., 2000, 65, 655-666; J. Org. Chem., 2003, 68, 442-451; Org. Lett., 2001, 3, 2189-2191; Org. Lett., 2001, 3, 4217-4220; Tetrahedron 57, 2001, 5615-5624; Tetrahedron Letters 40, 1999, 1215-1218; Tetrahedron Letters 40, 1999, 3339-3342; Heterocycles, 2004, 63, 1685-1712; U.S. Pat. No. 5,288,725, and the like are known.

DISCLOSURE OF INVENTION

At present, a compound having a potent NK2 receptor antagonistic action, which is safe and superior in duration (e.g., absorbability, metabolism, in vivo kinetics), as a therapeutic agent for the above-mentioned various diseases considered to be caused by hyperstimulation to NK2 receptor, has not been found. Thus, the development of a compound having a novel chemical structure different from that of known NK2 receptor antagonists and fully satisfiable as a drug for the prophylaxis or treatment of such pathology, as well as a pharmaceutical composition containing the compound as an active ingredient has been desired.

The present invention provides a compound having a novel chemical structure different from that of known NK2 receptor antagonists, which shows a superior NK2 receptor antagonistic action and is clinically fully satisfiable from the aspects of safety and duration (e.g., absorbability, metabolism, in vivo kinetics) and the like, and a pharmaceutical composition containing the compound as an active ingredient.

Accordingly, the present invention relates to the following [1]-[24] and the like.

[1] A compound represented by the formula (I) (hereinafter sometimes to be abbreviated as compound (I))

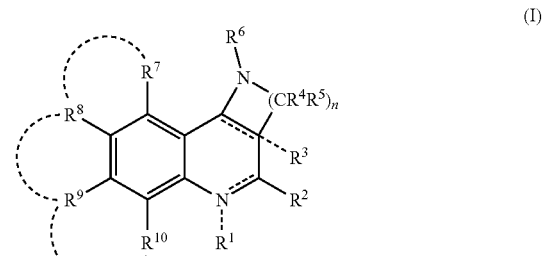

wherein $R^1$ is (1) unsubstituted (i.e., absence), (2) a hydrogen atom, (3) a hydrocarbon group optionally having substituent(s) or (4) acyl;

$R^2$ is (1) a hydrogen atom, (2) a hydrocarbon group optionally having substituent(s), (3) hydroxy optionally having a substituent, (4) amino optionally having substituent(s), (5) thiol optionally having a substituent, (6) a heterocyclic group optionally having substituent(s) or (7) acyl;

$R^3$ is (1) unsubstituted (i.e., absence), (2) a hydrogen atom, (3) a hydrocarbon group optionally having substituent(s), (4) hydroxy optionally having a substituent, (5) amino optionally having substituent(s), (6) thiol optionally having a substituent or (7) acyl;

$R^4$ and $R^5$ are the same or different and each is (1) a hydrogen atom, (2) a hydrocarbon group optionally having substituent(s), (3) hydroxy optionally having a substituent, (4) amino optionally having substituent(s), (5) thiol optionally having a substituent or (6) acyl;

$R^6$ is (1) (cyclic group optionally having substituent(s))-carbonyl, (2) alkenylcarbonyl optionally having substituent(s), (3) alkylcarbonyl having substituent(s) selected from (i) cycloalkyl optionally having substituent(s), (ii) amino optionally having substituent(s) and (iii) a heterocyclic group optionally having substituent(s) or (4) a heterocyclic group optionally having substituent(s);

R⁷, R⁸, R⁹, and R¹⁰ are the same or different and each is (1) a hydrogen atom, (2) halogen, (3) cyano, (4) nitro, (5) a hydrocarbon group optionally having substituent(s) (6) hydroxy optionally having a substituent, (7) amino optionally having substituent(s), (8) thiol optionally having a substituent, (9) a heterocyclic group optionally having substituent(s) or (10) acyl; or R⁷ and R⁸, R⁸ and R⁹, and R⁹ and R¹⁰ may form a ring together with the adjacent carbon atoms;

n is an integer of 1 to 5;

--- represents unsubstituted (i.e., absence) or a single bond; and;

=== represents a single bond or a double bond, or a salt thereof.

[2] The compound of the above-mentioned [1], wherein R⁶ is (1) (cyclic group optionally having substituent(s))-carbonyl, (2) alkenylcarbonyl optionally having substituent(s), (3) alkylcarbonyl having substituent(s) selected from (i) cycloalkyl optionally having substituent(s) and (ii) amino optionally having substituent(s) or (4) a heterocyclic group optionally having substituent(s).

[3] The compound of the above-mentioned [1], wherein $R^1$ is (1) unsubstituted, (2) a hydrogen atom, (3) $C_{1-6}$ alkyl, (4) $C_{7-12}$ aralkyl or (5) $C_{1-6}$ alkyl-carbonyl;

$R^2$ is (1) a hydrogen atom, (2) $C_{1-6}$ alkyl optionally having 1 to 3 substituents selected from (1') hydroxy, (2') $C_{1-6}$ alkoxy, (3') $C_{7-12}$ aralkyloxy, (4') mono- or di-$C_{1-6}$ alkylamino, (5') N—$C_{1-6}$ alkoxy-carbonyl-N—$C_{1-6}$ alkylamino, (6') amino, (7') $C_{1-6}$ alkyl-carbonylamino optionally having 1 to 3 halogens, (8') $C_{7-12}$ aralkyloxy-carbonylamino and (9') $C_{1-6}$ alkoxy-carbonylamino optionally having 1 to 3 halogens, (3) $C_{3-8}$ cycloalkyl, (4) $C_{6-10}$ aryl optionally having 1 to 3 substituents selected from (1') halogen, (2') $C_{1-6}$ alkyl optionally having 1 to 3 halogens, (3') cyano, (4') $C_{1-6}$ alkoxy-carbonyl and (5') $C_{1-6}$ alkyl-thio, (5) $C_{1-6}$ alkoxy-carbonyl, or (6) a 5- or 6-membered heterocyclic group optionally having substituent(s) selected from (1') hydroxy, (2') $C_{1-6}$ alkyl optionally having $C_{1-6}$ alkyl-carbonyloxy, (3') $C_{7-19}$ aralkyl optionally having $C_{1-6}$ alkoxy, (4') $C_{7-12}$ aralkyloxy, (5') $C_{7-12}$ aralkyloxy-carbonyl, (6') mono-$C_{1-6}$ alkyl-carbamoyl and (7') $C_{1-6}$ alkoxy-carbonyl;

$R^3$ is (1) unsubstituted, (2) a hydrogen atom or (3) $C_{1-6}$ alkyl;

$R^4$ is a hydrogen atom;

$R^5$ is a hydrogen atom;

$R^6$ is (1) a group represented by the formula

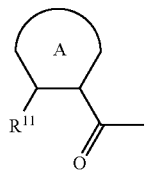

wherein ring A is cyclopentane, cyclohexane or bicyclo [2.2.2]octane;

$R^{11}$ is (1') amino, (2') $C_{7-12}$ aralkylamino, (3') $C_{1-6}$ alkyl-carbonylamino optionally having substituent(s) selected from (1") halogen, (2") hydroxy, (3") $C_{1-6}$ alkoxy-carbonyl, (4") mono- or di-$C_{1-6}$ alkylamino optionally substituted by hydroxy, (5") morpholino, (6") $C_{1-6}$ alkyl-carbonylamino, (7") carbamoylamino, (8") a 5- or 6-membered aromatic heterocyclic group, (9") $C_{6-10}$ arylamino, (10") (5- or 6-membered aromatic heterocyclic group)-carbonylamino and (11") $C_{1-6}$ alkoxy, (4') $C_{2-6}$ alkenyl-carbonylamino optionally having substituent(s) selected from (1") $C_{6-10}$ aryl optionally having substituent(s) selected from halogen, $C_{1-6}$ alkyl, $C_{1-6}$ alkoxy and halogeno-$C_{1-6}$ alkyl and (2") a 5- or 6-membered aromatic heterocyclic group optionally having $C_{1-6}$ alkyl, (5') $C_{3-8}$ cycloalkyl-carbonylamino, (6') $C_{6-10}$ aryl-carbonylamino optionally having substituent(s) selected from (1") halogen, (2") cyano, (3") $C_{1-6}$ alkyl optionally having amino or $C_{1-6}$ alkyl-carbonylamino, (4") halogeno-$C_{1-6}$ alkyl, (5") hydroxy-$C_{1-6}$ alkyl, (6") $C_{1-6}$ alkoxy, (7") carboxy, (8") $C_{1-6}$ alkoxy-carbonyl, (9") mono- or di-$C_{1-6}$ alkylamino optionally having hydroxy or $C_{1-6}$ alkoxy, (10") carbamoyl, (11") halogeno-$C_{1-6}$ alkoxy, (12") $C_{1-6}$ alkyl-carbonylamino, (13") aminosulfonyl, (14") $C_{1-6}$ alkyl-sulfonyl and (15") a 5- or 6-membered heterocyclic group, or a fused ring group of benzene ring and 5- or 6-membered heterocycle, which may have substituent(s) selected from $C_{1-6}$ alkyl and oxo, (7') $C_{7-12}$ aralkyl-carbonylamino, (8') $C_{1-6}$ alkoxy-carbonylamino, (9') (5- or 6-membered heterocyclic group, or fused ring group of benzene ring and 5- or 6-membered heterocycle)-carbonylamino, which may have substituent(s) selected from (1") amino, (2") $C_{1-6}$ alkyl, (3") halogeno-$C_{1-6}$ alkyl, (4") $C_{6-10}$ aryl, (5") oxo and (6") a 5- or 6-membered heterocyclic group optionally having $C_{1-6}$ alkyl, (10') $C_{6-10}$ aryl-sulfonylamino, (11') carbamoylcarbonylamino, (12') 3-$C_{1-6}$ alkyl-ureido optionally having substituent(s) selected from (1") hydroxy, (2") carboxy, (3") $C_{1-6}$ alkoxy, (4") $C_{1-6}$ alkoxy-carbonyl, (5") $C_{1-6}$ alkoxy-carbonylamino, (6") amino, (7") halogen, (8") carbamoyl, (9") $C_{1-6}$ alkylsulfonyl, (10") a heterocyclic group optionally substituted by oxo and (11") $C_{1-6}$ alkyl-carbonylamino, (13') 3-$C_{3-8}$ cycloalkyl-ureido, (14') 3-$C_{6-10}$ aryl-ureido optionally having substituent(s) selected from (1") halogen, (2") cyano, (3") halogeno-$C_{1-16}$ alkyl, (4") $C_{1-6}$ alkyl, (5") $C_{1-6}$ alkoxy, (6") methylenedioxy, (7") $C_{1-6}$ alkoxy-carbonyl, (8") carbamoyl and (9") a 5- or 6-membered aromatic heterocyclic group, (15') 3-$C_{1-6}$ alkyl-3-$C_{6-10}$ aryl-ureido, (16') 3-$C_{7-12}$ aralkyl-ureido optionally having substituent(s) selected from (1") halogen and (2") $C_{1-6}$ alkoxy, (17') 3-$C_{1-6}$ alkoxy-ureido, (18') 3-$C_{6-10}$ arylsulfonyl-ureido, (19') 3-(5- or 6-membered heterocyclic group, or fused ring group of benzene ring and 5- or 6-membered heterocycle)-ureido, which may have 5- or 6-membered heterocyclic group, (20') piperidylureido optionally having $C_{1-6}$ alkyl-carbonyl, or (21') phthalimide, (2) a group represented by the formula

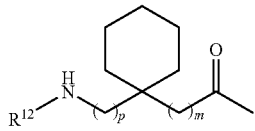

wherein $R^{12}$ is (1') a hydrogen atom, (2') $C_{6-10}$ aryl-carbonyl optionally having halogeno-$C_{1-6}$ alkyl, (3') $C_{7-12}$ aralkyl-oxycarbonyl or (4') $C_{6-10}$ aryl-aminocarbonyl; m is 0 or 1; and p is 0 or 1, (3) a group represented by the formula

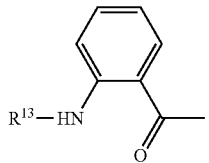

wherein $R^{13}$ is $C_{6-10}$ aryl-carbonyl, (4) a group represented by the formula

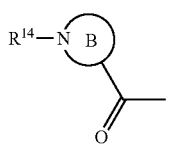

wherein ring B is a pyrrolidine ring or a piperidine ring, each optionally substituted by amino; $R^{14}$ is (1') a hydrogen atom, (2') $C_{7-12}$ aralkyl, (3') $C_{1-6}$ alkyl-carbonyl, (4') $C_{6-10}$ aryl-carbonyl, (5') $C_{7-12}$ aralkyl-carbonyl, (6') $C_{1-6}$ alkoxy-carbonyl or (7') $C_{7-12}$ aralkyl-carbamoyl, (5) $C_{2-6}$ alkenyl-carbonyl optionally having substituent(s) selected from (1') carboxy, (2') $C_{1-6}$ alkoxy-carbonyl and (3') $C_{6-10}$ aryl-aminocarbonyl, (6) $C_{1-6}$ alkyl-carbonyl having substituent(s) selected from (1') amino, (2') $C_{6-10}$ aryl-carbonylamino, (3') $C_{1-6}$ alkoxy-carbonylamino and (4') a 5- or 6-membered heterocyclic group, or a fused ring group of benzene ring and 5- or 6-membered heterocycle, each optionally substituted by oxo, (7) 1,2,3,4-tetrahydronaphthylcarbonyl, (8) pyrrolidinyl having $C_{7-12}$ aralkyl, or (9) a group represented by the formula

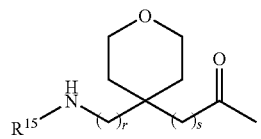

wherein $R^{15}$ is $C_{6-10}$ aryl-carbonyl; r is 0 or 1; and s is 0 or 1;

$R^7$ is a hydrogen atom;

$R^8$ is (1) a hydrogen atom, (2) halogen, (3) cyano, (4) $C_{1-6}$ alkyl optionally having 1 to 3 halogens, (5) $C_{6-10}$ aryl-carbonyl, (6) $C_{1-6}$ alkoxy, (7) $C_{6-10}$ aryloxy or (8) sulfamoyl;

$R^9$ is (1) a hydrogen atom, (2) halogen, (3) cyano, (4) $C_{1-6}$ alkyl or (5) $C_{1-6}$ alkoxy;

$R^{10}$ is (1) a hydrogen atom, (2) halogen, (3) $C_{1-6}$ alkyl or (4) $C_{1-6}$ alkoxy; and n is 2 or 3.

[4] The compound of the above-mentioned [1] or [2], wherein $R^1$ is (1) unsubstituted, (2) a hydrogen atom, (3) $C_{1-6}$ alkyl or (4) $C_{1-6}$ alkyl-carbonyl;

$R^2$ is (1) a hydrogen atom, (2) $C_{1-6}$ alkyl optionally having 1 to 3 substituents selected from (1') hydroxy, (2') $C_{1-6}$ alkoxy, (3') $C_{7-12}$ aralkyloxy, (4') mono-$C_{1-6}$ alkylamino and (5') N—$C_{1-6}$ alkoxy-carbonyl-N—$C_{1-6}$ alkylamino, (3) $C_{3-8}$ cycloalkyl, (4) $C_{6-10}$ aryl optionally having 1 to 3 substituents selected from (1') halogen, (2') $C_{1-6}$ alkyl optionally having 1 to 3 halogens, (3") cyano and (4') $C_{1-6}$ alkoxy-carbonyl, or (5) a 5- or 6-membered aromatic heterocyclic group optionally having substituent(s) selected from (1') hydroxy, (2') $C_{1-6}$ alkyl optionally having $C_{1-6}$ alkyl-carbonyloxy, (3') $C_{7-12}$ aralkyl optionally having $C_{1-6}$ alkoxy and (4') $C_{7-12}$ aralkyloxy;

$R^3$ is (1) unsubstituted, (2) a hydrogen atom or (3) $C_{1-6}$ alkyl;

$R^4$ is a hydrogen atom;

$R^5$ is a hydrogen atom;

$R^6$ is (1) a group represented by the formula

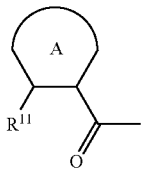

wherein ring A is cyclopentane, cyclohexane or bicyclo[2.2.2]octane; $R^{11}$ is (1') amino, (2') $C_{7-12}$ aralkylamino, (3') $C_{1-6}$ alkyl-carbonylamino optionally having substituent(s) selected from (1") halogen, (2") hydroxy, (3") $C_{1-6}$ alkoxy-carbonyl, (4") di-$C_{1-6}$ alkylamino and (5") morpholino, (4') $C_{3-6}$ cycloalkyl-carbonylamino, (5') $C_{6-10}$ aryl-carbonylamino optionally having substituent(s) selected from (1") halogen, (2") cyano, (3") $C_{1-6}$ alkyl, (4") halogeno-$C_{1-6}$ alkyl, (5") hydroxy-$C_{1-6}$ alkyl, (6") $C_{1-6}$ alkoxy, (7") carboxy and (8") $C_{1-6}$ alkoxy-carbonyl, (6') $C_{7-12}$ aralkyl-carbonylamino, (7') $C_{1-6}$ alkoxy-carbonylamino, (8') (5- or 6-membered aromatic heterocyclic group)-carbonylamino, (9') piperidinocarbonylamino, (10') $C_{6-10}$ aryl-sulfonylamino, (11') 3-$C_{1-6}$ alkyl-ureido optionally having substituent(s) selected from (1") hydroxy, (2") carboxy, (3") $C_{1-6}$ alkoxy and (4") $C_{1-6}$ alkoxy-carbonyl, (12') 3-$C_{3-8}$ cycloalkyl-ureido, (13') 3-$C_{6-10}$ aryl-ureido optionally having substituent(s) selected from (1") halogen, (2") cyano, (3") halogeno-$C_{1-6}$ alkyl, (4") $C_{1-6}$ alkyl, (5") $C_{1-6}$ alkoxy and (6") methylenedioxy, (14') 3-$C_{7-12}$ aralkyl-ureido optionally having substituent(s) selected from (1") halogen and (2") $C_{1-6}$ alkoxy, (15') 3-(5- or 6-membered aromatic heterocyclic group)-ureido, (16') piperidylureido, preferably piperidinoureido, optionally having $C_{1-6}$ alkyl-carbonyl or (17') phthalimide, (2) a group represented by the formula

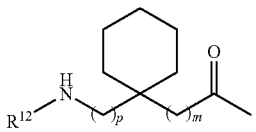

wherein $R^{12}$ is (1') a hydrogen atom, (2') $C_{6-10}$ aryl-carbonyl optionally having halogeno-$C_{1-6}$ alkyl or (3') $C_{7-12}$ aralkyl-oxycarbonyl; m is 0 or 1; and p is 0 or 1, (3) a group represented by the formula

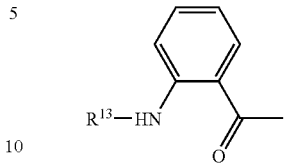

wherein $R^{13}$ is $C_{6-10}$ aryl-carbonyl, (4) a group represented by the formula

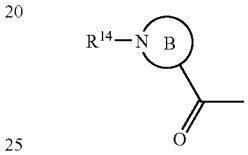

wherein ring B is a pyrrolidine ring or a piperidine ring; $R^{14}$ is (1') a hydrogen atom, (2') $C_{7-12}$ aralkyl, (3') $C_{1-6}$ alkyl-carbonyl, (4') $C_{6-10}$ aryl-carbonyl, (5') $C_{7-12}$ aralkyl-carbonyl or (6') $C_{1-6}$ alkoxy-carbonyl, (5) $C_{2-6}$ alkenyl-carbonyl optionally having substituent(s) selected from (1') carboxy, (2') $C_{1-6}$ alkoxy-carbonyl and (3') $C_{6-10}$ aryl-aminocarbonyl, (6) $C_{1-6}$ alkyl-carbonyl having substituent(s) selected from (1') amino, (2') $C_{6-10}$ aryl-carbonylamino and (3') $C_{1-6}$ alkoxy-carbonylamino, (7) 1,2,3,4-tetrahydronaphthylcarbonyl or (8) pyrrolidinyl having $C_{7-12}$ aralkyl;

$R^7$ is a hydrogen atom;

$R^8$ is (1) a hydrogen atom, (2) halogen, (3) cyano, (4) $C_{1-6}$ alkyl optionally having 1 to 3 halogens, (5) $C_{6-10}$-aryl-carbonyl, (6) $C_{1-6}$ alkoxy or (7) $C_{6-10}$ aryloxy;

$R^9$ is (1) a hydrogen atom, (2) halogen, (3) cyano, (4) $C_{1-6}$ alkyl or (5) $C_{1-6}$ alkoxy;

$R^{10}$ is (1) a hydrogen atom, (2) halogen, (3) $C_{1-6}$ alkyl or (4) $C_{1-6}$ alkoxy; and n is 2 or 3.

[5] The compound of the above-mentioned [1] or [2], wherein $R^1$ is a hydrogen atom.

[6] The compound of the above-mentioned [1] or [2], wherein $R^2$ is (1) $C_{1-6}$ alkyl optionally having substituent(s) selected from (1') $C_{1-6}$ alkoxy and (2') mono-$C_{1-6}$ alkylamino, (2) $C_{3-8}$ cycloalkyl, (3) $C_{6-10}$ aryl optionally having halogen or (4) a 5- or 6-membered aromatic heterocyclic group optionally having $C_{1-6}$ alkyl.

[7] The compound of the above-mentioned [1] or [2], wherein $R^3$ is (1) a hydrogen atom or (2) $C_{1-6}$ alkyl.

[8] The compound of the above-mentioned [1] or [2], wherein $R^6$ is (1) a group represented by the formula

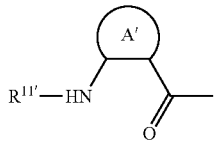

wherein ring A' is cyclohexane or bicyclo[2.2.2]octane, $R^{11'}$ is (1') $C_{1-6}$ alkyl-carbonyl optionally having substituent(s) selected from (1") halogen, (2") hydroxy, (3") $C_{1-6}$ alkoxy-carbonyl and (4") morpholino, (2') $C_{6-10}$ aryl-carbonyl optionally having substituent(s) selected from (1") halogen, (2") cyano, (3") $C_{1-6}$ alkyl, (4") halogeno-$C_{1-6}$ alkyl, (5") hydroxy-$C_{1-6}$ alkyl, (6") $C_{1-6}$ alkoxy and (7") $C_{1-6}$ alkoxy-carbonyl, (3') $C_{7-12}$ aralkyl-carbonyl, (4') (5- or 6-membered aromatic heterocyclic group)-carbonyl, (5') $C_{1-6}$ alkyl-aminocarbonyl optionally having substituent(s) selected from (1") hydroxy, (2") $C_{1-6}$ alkoxy and (3") $C_{1-6}$ alkoxy-carbonyl, (6') $C_{3-8}$ cycloalkyl-aminocarbonyl, (7') $C_{6-10}$ aryl-aminocarbonyl optionally having substituent(s) selected from (1") halogen, (2") cyano, (3") halogeno-$C_{1-6}$ alkyl, (4") $C_{1-6}$ alkyl, (5") $C_{1-6}$ alkoxy and (6") methylenedioxy, (8') $C_{7-12}$ aralkyl-aminocarbonyl optionally having substituent(s) selected from (1") halogen and (2") $C_{1-6}$ alkoxy, (9') (5- or 6-membered aromatic heterocyclic group)-aminocarbonyl or (10') piperidylaminocarbonyl, preferably piperidinoaminocarbonyl optionally having $C_{1-6}$ alkyl-carbonyl, or (2) a group represented by the formula

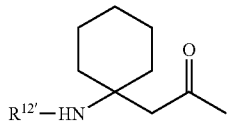

wherein $R^{12'}$ is $C_{6-10}$ aryl-carbonyl.

[9] The compound of the above-mentioned [1] or [2], wherein $R^8$ is a hydrogen atom or halogen.

[10] The compound of the above-mentioned [1] or [2], wherein $R^9$ is a hydrogen atom or halogen.

[11] The compound of the above-mentioned [1] or [2], wherein $R^{10}$ is a hydrogen atom or halogen.

[12] The compound of the above-mentioned [1] or [2], wherein n is 2.

[13] N-((1R,2S)-2-{[(3aR,4R,9bR)-4-(1H-imidazol-2-yl)-2,3,3a,4,5,9b-hexahydro-1H-pyrrolo[3,2-c]quinolin-1-yl]carbonyl}cyclohexyl)benzamide, N-phenyl-N'-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)urea, 2-methyl-N-((1R,2S)-2-{[(3aR,4S,9bR)-4-propyl-2,3,3a,4,5,9b-hexahydro-1H-pyrrolo[3,2-c]quinolin-1-yl]carbonyl}cyclohexyl)-1H-benzimidazole-5-carboxamide, N-((1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexyl)-1H-1,2,3-benzotriazole-5-carboxamide, 4-(1H-imidazol-2-yl)-N-((1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexyl)benzamide, N-((1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexyl)-N'-[4-(1H-pyrazol-1-yl)phenyl]urea or 4-cyano-N-((1R,2S)-2-{[(3aR,4R,9bR)-4-(1H-imidazol-2-yl)-2,3,3a,4,5,9b-hexahydro-1H-pyrrolo[3,2-c]quinolin-1-yl]carbonyl}cyclohexyl)benzamide.

[14] A production method of a compound represented by the formula (Ic)

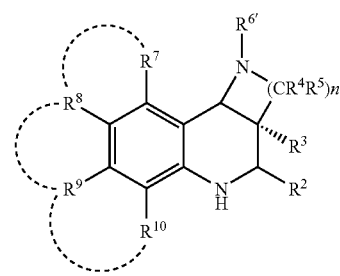

(Ic)

wherein $R^{6'}$ is (1) (cyclic group optionally having substituent(s))-carbonyl, (2) alkenylcarbonyl optionally having substituent(s) or (3) alkylcarbonyl having substituent(s) selected from (i) cycloalkyl optionally having substituent(s) and (ii) amino optionally having substituent(s), and other symbols are as defined in the above-mentioned [1], or a salt thereof, which comprises (1) subjecting a compound represented by the formula (II)

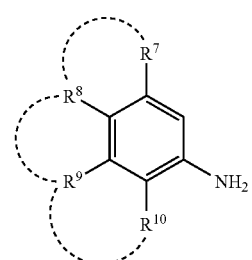

(II)

wherein each symbol is as defined in the above-mentioned [1], or a salt thereof, a compound represented by the formula (III)

$$R^2\text{—CHO} \qquad (III)$$

wherein $R^2$ is as defined in the above-mentioned [1], or a salt thereof, and a compound represented by the formula (IV)

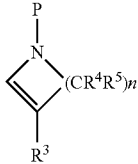
(IV)

wherein P is a protecting group, and other symbols are as defined in the above-mentioned [1], or a salt thereof to a condensation reaction to give a compound represented by the formula (Ia)

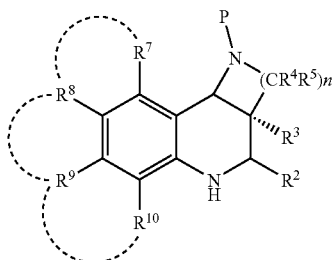
(Ia)

wherein each symbol is as defined above, or a salt thereof, and then eliminating the protecting group P, or (2) subjecting a compound represented by the formula (II)

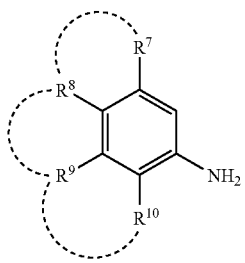
(II)

wherein each symbol is as defined above, or a salt thereof, a compound represented by the formula (III)

 R²—CHO (III)

wherein R² is as defined above, or a salt thereof, and a compound represented by the formula (V)

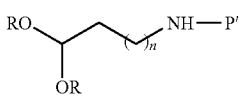
(V)

wherein Rs are the same or different and each is $C_{1-6}$ alkyl, P' is a protecting group, and n is as defined in the above-mentioned [1], or a salt thereof to a condensation reaction to give a compound represented by the formula (Ib)

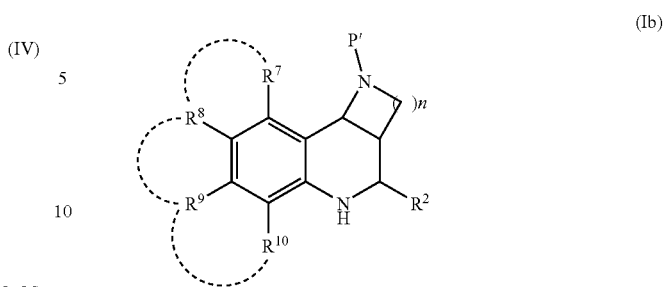
(Ib)

wherein each symbol is as defined above, or a salt thereof, and then eliminating the protecting group P', and reacting a compound represented by the formula (VI)

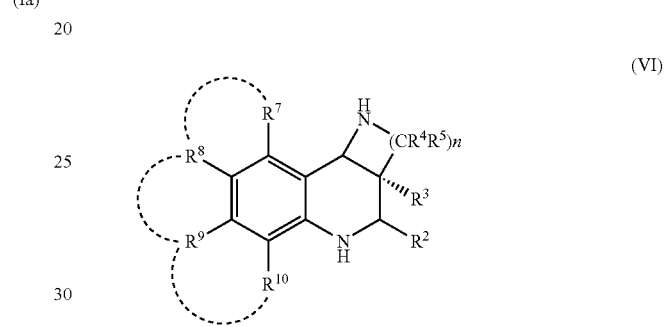
(VI)

wherein each symbol is as defined above, or a salt thereof, which is obtained in the above (1) or (2), with a compound represented by the formula (VII)

 $R^{6'}$—OH (VII)

wherein $R^{6'}$ is as defined above, or a salt thereof.

[15] A NK2 receptor antagonist comprising a compound having a partial structure represented by the formula

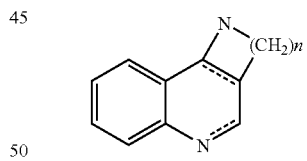

wherein n is an integer of 1 to 5; and

--- represents a single bond or a double bond, or a salt thereof.

[16] A prodrug of the compound of the above-mentioned [1] or [2].

[17] A pharmaceutical agent comprising the compound of the above-mentioned [1] or [2] or a prodrug thereof.

[18] The pharmaceutical agent of the above-mentioned [17], which is a NK2 receptor antagonist.

[19] The pharmaceutical agent of the above-mentioned [17], which is an agent for the prophylaxis or treatment of functional gastrointestinal diseases.

[20] The pharmaceutical agent of the above-mentioned [17], which is an agent for the prophylaxis or treatment of irritable bowel syndrome or nonulcer dyspepsia.

[21] A method of antagonizing a NK2 receptor, which comprises administering an effective amount of the compound of the above-mentioned [1] or [2] or a prodrug thereof to a mammal.

[22] A method of preventing or treating functional gastrointestinal diseases, which comprises administering an effective amount of the compound of the above-mentioned [1] or [2] or a prodrug thereof to a mammal.

[23] Use of the compound of the above-mentioned [1] or [2] or a prodrug thereof for the production of a NK2 receptor antagonist.

[24] Use of the compound of the above-mentioned [1] or [2] or a prodrug thereof for the production of an agent for the prophylaxis or treatment of functional gastrointestinal diseases.

DETAILED DESCRIPTION OF THE INVENTION

Since the compound (I), a salt thereof and a prodrug thereof according to the present invention have a NK2 receptorantagonistic action and show less toxicity, they are particularly useful as agents for the prophylaxis or treatment of functional gastrointestinal diseases (e.g., irritable bowel syndrome, nonulcer dyspepsia and the like.

BEST MODE FOR CARRYING OUT THE INVENTION

The present invention is explained in detail in the following.

As the "halogen", for example, fluorine, chlorine, bromine, iodine atom and the like can be mentioned.

As the "hydrocarbon group optionally having substituent(s)" for $R^1$, $R^2$, $R^3$, $R^4$, $R^5$, $R^7$, $R^8$, $R^9$ or $R^{10}$, for example, (1) $C_{1-6}$ alkyl (e.g., methyl, ethyl, propyl, isopropyl, butyl, isobutyl, sec-butyl, tert-butyl, pentyl, hexyl etc.) optionally having 1 to 5 substituents selected from the substituent group A to be mentioned later, (2) $C_{2-6}$ alkenyl (e.g., ethenyl, 1-propenyl, 2-propenyl etc.) optionally having 1 to 5 substituents selected from the substituent group A to be mentioned later, (3) $C_{2-6}$ alkynyl (e.g., ethynyl, 1-propynyl, 2-propynyl etc.) optionally having 1 to 5 substituents selected from the substituent group A to be mentioned later, (4) $C_{3-8}$ cycloalkyl (e.g., cyclopropyl, cyclobutyl, cyclopentyl, cyclohexyl (i.e., $C_{3-6}$ cycloalkyl), cycloheptyl, cyclooctyl, bicyclo[2.2.2]octyl etc.) optionally having 1 to 5 substituents selected from the substituent group A to be mentioned later, (5) $C_{6-10}$ aryl (e.g., phenyl, 1-naphthyl, 2-naphthyl etc.) optionally having 1 to 5 substituents selected from the substituent group A to be mentioned later, (6) $C_{7-12}$ aralkyl (e.g., benzyl, phenethyl, 1-naphthylmethyl, 2-naphthylmethyl etc.) optionally having 1 to 5 substituents selected from the substituent group A to be mentioned later, and the like can be mentioned.

As the "acyl" for by $R^1$, $R^2$, $R^3$, $R^4$, $R^5$, $R^7$, $R^8$, $R^9$ or $R^{10}$, for example, (1) $C_{1-6}$ alkyl-carbonyl (e.g., acetyl, ethylcarbonyl, propylcarbonyl, isopropylcarbonyl, butylcarbonyl, isobutylcarbonyl, sec-butylcarbonyl, tert-butylcarbonyl, pentylcarbonyl, hexylcarbonyl etc.) optionally having 1 to 5 substituents selected from the substituent group A to be mentioned later, (2) $C_{2-6}$ alkenyl-carbonyl (e.g., ethenylcarbonyl, 1-propenylcarbonyl, 2-propenylcarbonyl etc.) optionally having 1 to 5 substituents selected from the substituent group A to be mentioned later, (3) $C_{2-6}$ alkynyl-carbonyl (e.g., ethynylcarbonyl, 1-propynylcarbonyl, 2-propynylcarbonyl etc.) optionally having 1 to 5 substituents selected from the substituent group A to be mentioned later, (4) $C_{3-6}$ cycloalkyl-carbonyl (e.g., cyclopropylcarbonyl, cyclobutylcarbonyl, cyclopentylcarbonyl, cyclohexylcarbonyl etc.) optionally having 1 to 5 substituents selected from the substituent group A to be mentioned later, (5) $C_{6-10}$ aryl-carbonyl (e.g., benzoyl, 1-naphthoyl, 2-naphthoyl etc.) optionally having 1 to 5 substituents selected from the substituent group A to be mentioned later, (6) $C_{7-12}$ aralkyl-carbonyl (e.g., benzylcarbonyl, phenethylcarbonyl, 1-naphthylmethylcarbonyl, 2-naphthylmethylcarbonyl etc.) optionally having 1 to 5 substituents selected from the substituent group A to be mentioned later, (7) $C_{1-6}$ alkoxy-carbonyl (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentoxycarbonyl, hexyloxycarbonyl etc.) optionally having 1 to 5 substituents selected from the substituent group A to be mentioned later, (8) $C_{2-6}$ alkenyloxy-carbonyl (e.g., ethenyloxycarbonyl, 1-propenyloxycarbonyl, 2-propenyloxycarbonyl etc.) optionally having 1 to 5 substituents selected from the substituent group A to be mentioned later, (9) $C_{2-6}$ alkynyloxy-carbonyl (e.g., ethynyloxycarbonyl, 1-propynyloxycarbonyl, 2-propynyloxycarbonyl etc.) optionally having 1 to 5 substituents selected from the substituent group A to be mentioned later,

(10) $C_{3-6}$ cycloalkyloxy-carbonyl (e.g., cyclopropyloxycarbonyl, cyclobutyloxycarbonyl, cyclopentyloxycarbonyl, cyclohexyloxycarbonyl etc.) optionally having 1 to 5 substituents selected from the substituent group A to be mentioned later,

(11) $C_{6-10}$ aryloxy-carbonyl (e.g., phenoxycarbonyl, 1-naphthyloxycarbonyl, 2-naphthyloxycarbonyl etc.) optionally having 1 to 5 substituents selected from the substituent group A to be mentioned later,

(12) $C_{7-12}$ aralkyloxy-carbonyl (e.g., benzyloxycarbonyl, phenethyloxycarbonyl, 1-naphthylmethoxycarbonyl, 2-naphthylmethoxycarbonyl etc.) optionally having 1 to 5 substituents selected from the substituent group A to be mentioned later,

(13) carbamoyl optionally mono- or di-substituted by (1') $C_{1-6}$ alkyl (e.g., methyl, ethyl, propyl, isopropyl, butyl, isobutyl, sec-butyl, tert-butyl, pentyl, hexyl etc.) optionally having 1 to 5 substituents selected from the substituent group A to be mentioned later, (2') $C_{2-6}$ alkenyl (e.g., ethenyl, 1-propenyl, 2-propenyl etc.) optionally having 1 to 5 substituents selected from the substituent group A to be mentioned later, (3') $C_{2-6}$ alkynyl (e.g., ethynyl, 1-propynyl, 2-propynyl etc.) optionally having 1 to 5 substituents selected from the substituent group A to be mentioned later, (4') $C_{3-6}$ cycloalkyl (e.g., cyclopropyl, cyclobutyl, cyclopentyl, cyclohexyl etc.) optionally having 1 to 5 substituents selected from the substituent group A to be mentioned later, (5') $C_{6-10}$ aryl (e.g., phenyl, 1-naphthyl, 2-naphthyl etc.) optionally having 1 to 5 substituents selected from the substituent group A to be mentioned later, (6') $C_{7-12}$ aralkyl (e.g., benzyl, phenethyl, 1-naphthylmethyl, 2-naphthylmethyl etc.) optionally having 1 to 5 substituents selected from the substituent group A to be mentioned later, (7') $C_{1-6}$ alkyl-carbonyl (e.g., acetyl, ethylcarbonyl, propylcarbonyl, isopropylcarbonyl, butylcarbonyl, isobutylcarbonyl, sec-butylcarbonyl, tert-butylcarbonyl, pentylcarbonyl, hexylcarbonyl etc.) optionally having 1 to 5 substituents selected from the substituent group A to be mentioned later, (8') $C_{2-6}$ alkenyl-carbonyl (e.g., ethenylcarbonyl, 1-propenylcarbonyl, 2-propenylcarbonyl etc.) optionally having 1 to 5 substituents selected from the substituent group A to be mentioned later, (9') $C_{2-6}$ alkynyl-carbonyl (e.g., ethynylcarbonyl, 1-propynylcarbonyl, 2-propynylcarbonyl etc.) optionally having 1 to 5 substituents selected from the substituent group A to be mentioned later, (10') $C_{3-6}$ cycloalkyl-carbonyl (e.g., cyclopropylcarbonyl, cyclobutylcarbonyl, cyclopentylcarbonyl, cyclohexylcarbonyl etc.) optionally having 1 to 5 substituents selected from the substituent group A to be mentioned later, (11') $C_{6-10}$ aryl-carbonyl (e.g., benzoyl, 1-naphthoyl, 2-naphthoyl etc.) optionally having 1 to 5 substituents selected from the substituent group A to be mentioned later, (12') $C_{7-12}$ aralkyl-carbonyl (e.g., benzylcarbonyl, phenethylcarbonyl, 1-naphthylmethylcarbonyl, 2-naphthylmethylcarbonyl etc.) optionally having 1 to 5 substituents selected from the substituent group A to be mentioned later, (13') $C_{1-6}$ alkoxy-carbonyl (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentoxycarbonyl, hexyloxycarbonyl etc.) optionally having 1 to 5 substituents selected from the substituent group A to be mentioned later, (14') $C_{2-6}$ alkenyloxy-carbonyl (e.g., ethenyloxycarbonyl, 1-propenyloxycarbonyl, 2-propenyloxycarbonyl etc.) optionally having 1 to 5 substituents selected from the substituent group A to be mentioned later, (15') $C_{2-6}$ alkynyloxy-carbonyl (e.g., ethynyloxycarbonyl, 1-propynyloxycarbonyl, 2-propynyloxycarbonyl etc.) optionally having 1 to 5 substituents selected from the substituent group A to be mentioned later, (16') $C_{3-6}$ cycloalkyloxy-carbonyl (e.g., cyclopropyloxycarbonyl, cyclobutyloxycarbonyl, cyclopentyloxycarbonyl, cyclohexyloxycarbonyl etc.) optionally having 1 to 5 substituents selected from the substituent group A to be mentioned later, (17') $C_{6-10}$ aryloxy-carbonyl (e.g., phenoxycarbonyl, 1-naphthyloxycarbonyl, 2-naphthyloxycarbonyl etc.) optionally having 1 to 5 substituents selected from the substituent group A to be mentioned later, and (18') $C_{7-12}$ aralkyloxy-carbonyl (e.g., benzyloxycarbonyl, phenethyloxycarbonyl, 1-naphthylmethoxycarbonyl, 2-naphthylmethoxycarbonyl etc.) optionally having 1 to 5 substituents selected from the substituent group A to be mentioned later,

(14) sulfamoyl, and the like can be mentioned.

Substituent group A:

(1) $C_{1-6}$ alkyl (e.g., methyl, ethyl, propyl, isopropyl, butyl, isobutyl, sec-butyl, tert-butyl, pentyl, hexyl etc.) optionally having 1 to 3 substituents selected from (1') halogen (e.g., fluorine, chlorine, bromine, iodine), (2') hydroxy, (3') amino, (4') $C_{6-10}$ aryl-carbonylamino (e.g., phenylcarbonylamino, naphthylcarbonylamino etc.). stylylcarbonylamino, optionally having halogeno-$C_{1-6}$ alkyl (e.g., trifluoromethyl etc.), (5') $C_{7-12}$ aralkyl-oxycarbonylamino (e.g., benzyloxycarbonylamino etc.), (6') $C_{1-6}$ alkyl-carbonyloxy (e.g., acetoxy, ethylcarbonyloxy, propylcarbonyloxy, isopropylcarbonyloxy, butylcarbonyloxy, isobutylcarbonyloxy, sec-butylcarbonyloxy, tert-butylcarbonyloxy, pentylcarbonyloxy, hexylcarbonyloxy etc.), (2) $C_{2-6}$ alkenyl (e.g., ethenyl, 1-propenyl, 2-propenyl etc.), (3) $C_{2-6}$ alkynyl (e.g., ethynyl, 1-propynyl, 2-propynyl etc.), (4) $C_{6-10}$ aryl (e.g., phenyl, 1-naphthyl, 2-naphthyl etc.), (5) $C_{7-19}$ aralkyl (e.g., benzyl, phenethyl, 1-naphthylmethyl, 2-naphthylmethyl, trityl etc.) optionally having 1 to 3 $C_{1-6}$ alkoxy (e.g., methoxy, ethoxy, propoxy, isopropoxy, butoxy, isobutoxy, sec-butoxy, tert-butoxy, pentoxy, hexyloxy etc.), (6) hydroxy, (7) $C_{1-6}$ alkoxy (e.g., methoxy, ethoxy, propoxy, isopropoxy, butoxy, isobutoxy, sec-butoxy, tert-butoxy, pentoxy, hexyloxy etc.), (8) $C_{6-10}$ aryloxy (e.g., phenoxy, 1-naphthyloxy, 2-naphthyloxy etc.), (9) $C_{7-12}$ aralkyloxy (e.g., benzyloxy, phenethyloxy, 1-naphthylmethoxy, 2-naphthylmethoxy etc.),

(10) $C_{1-6}$ alkyl-carbonyloxy (e.g., acetoxy, ethylcarbonyloxy, propylcarbonyloxy, isopropylcarbonyloxy, butylcarbonyloxy, isobutylcarbonyloxy, sec-butylcarbonyloxy, tert-butylcarbonyloxy, pentylcarbonyloxy, hexylcarbonyloxy etc.),

(11) $C_{2-6}$ alkenyl-carbonyloxy (e.g., ethenylcarbonyloxy, 1-propenylcarbonyloxy, 2-propenylcarbonyloxy etc.),

(12) $C_{2-6}$ alkynyl-carbonyloxy (e.g., ethynylcarbonyloxy, 1-propynylcarbonyloxy, 2-propynylcarbonyloxy etc.),

(13) $C_{1-6}$ alkylthio (e.g., methylthio, ethylthio, propylthio, isopropylthio, butylthio, isobutylthio, sec-butylthio, tert-butylthio, pentylthio, hexylthio etc.),

(14) $C_{6-10}$ arylthio (e.g., phenylthio, 1-naphthylthio, 2-naphthylthio etc.),

(15) $C_{7-12}$ aralkylthio (e.g., benzylthio, phenethylthio, 1-naphthylmethylthio, 2-naphthylmethylthio etc.),

(16) carboxy,

(17) $C_{1-6}$ alkyl-carbonyl (e.g., acetyl, ethylcarbonyl, propylcarbonyl, isopropylcarbonyl, butylcarbonyl, isobutylcarbonyl, sec-butylcarbonyl, tert-butylcarbonyl, pentylcarbonyl, hexylcarbonyl etc.),

(18) $C_{2-6}$ alkenyl-carbonyl (e.g., ethenylcarbonyl, 1-propenylcarbonyl, 2-propenylcarbonyl etc.),

(19) $C_{2-6}$ alkynyl-carbonyl (e.g., ethynylcarbonyl, 1-propynylcarbonyl, 2-propynylcarbonyl etc.),

(20) $C_{6-10}$ aryl-carbonyl (e.g., benzoyl, 1-naphthoyl, 2-naphthoyl etc.),

(21) $C_{7-12}$ aralkyl-carbonyl (e.g., benzylcarbonyl, phenethylcarbonyl, 1-naphthylmethylcarbonyl, 2-naphthylmethylcarbonyl etc.),

(22) $C_{1-6}$ alkoxy-carbonyl (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentoxycarbonyl, hexyloxycarbonyl etc.),

(23) $C_{2-6}$ alkenyloxy-carbonyl (e.g., ethenyloxycarbonyl, 1-propenyloxycarbonyl, 2-propenyloxycarbonyl etc.),

(24) $C_{2-6}$ alkynyloxy-carbonyl (e.g., ethynyloxycarbonyl, 1-propynyloxycarbonyl, 2-propynyloxycarbonyl etc.),

(25) $C_{6-10}$ aryloxy-carbonyl (e.g., phenoxycarbonyl, 1-naphthyloxycarbonyl, 2-naphthyloxycarbonyl etc.),

(26) $C_{7-12}$ aralkyloxy-carbonyl (e.g., benzyloxycarbonyl, phenethyloxycarbonyl, 1-naphthylmethoxycarbonyl, 2-naphthylmethoxycarbonyl etc.),

(27) carbamoyl,

(28) mono-$C_{1-6}$ alkyl-carbamoyl (e.g., methylcarbamoyl, ethylcarbamoyl, propylcarbamoyl, isopropylcarbamoyl, butylcarbamoyl, isobutylcarbamoyl, sec-butylcarbamoyl, tert-butylcarbamoyl, pentylcarbamoyl, hexylcarbamoyl etc.),

(29) di-$C_{1-6}$ alkyl-carbamoyl (e.g., dimethylcarbamoyl, diethylcarbamoyl, dipropylcarbamoyl, N-ethyl-N-methyl-carbamoyl etc.),

(30) $C_{6-10}$ aryl-carbamoyl (herein sometimes to be abbreviated as $C_{6-10}$ aryl-aminocarbonyl) (e.g., phenylcarbamoyl, naphthylcarbamoyl etc.),

(31) $C_{7-12}$ aralkyl-carbamoyl (e.g., benzylcarbamoyl, phenethylcarbamoyl, naphthylmethylcarbamoyl etc.),

(32) $C_{1-6}$ alkylsulfonyl (e.g., methylsulfonyl, ethylsulfonyl, propylsulfonyl, isopropylsulfonyl, butylsulfonyl, isobutylsulfonyl, sec-butylsulfonyl, tert-butylsulfonyl etc.),

(33) $C_{2-6}$ alkenylsulfonyl (e.g., ethenylsulfonyl, 1-propenylsulfonyl, 2-propenylsulfonyl etc.),

(34) $C_{2-6}$ alkynylsulfonyl (e.g., ethynylsulfonyl, 1-propynylsulfonyl, 2-propynylsulfonyl etc.),

(35) amino,

(36) mono-$C_{1-6}$ alkylamino (e.g., methylamino, ethylamino, propylamino, isopropylamino, butylamino, isobutylamino, sec-butylamino, tert-butylamino, pentylamino, hexylamino etc.),

(37) di-$C_{1-6}$ alkylamino (e.g., dimethylamino, diethylamino, dipropylamino, diisopropylamino, N-ethyl-N-methylamino etc.),

(38) mono-$C_{2-6}$ alkenylamino (e.g., ethenylamino, 1-propenylamino, 2-propenylamino etc.),

(39) di-$C_{2-6}$ alkenylamino (e.g., diethenylamino, di(1-propenyl)amino, di(2-propenyl)amino etc.),

(40) mono-$C_{2-6}$ alkynylamino (e.g., ethynylamino, 1-propynylamino, 2-propynylamino etc.),

(41) di-$C_{2-6}$ alkynylamino (e.g., diethynylamino, di(1-propynyl)amino, di(2-propynyl)amino etc.),

(42) $C_{6-10}$ arylamino (e.g., phenylamino etc.),

(43) $C_{7-12}$ aralkylamino (e.g., benzylamino etc.),

(44) $C_{1-6}$ alkyl-carbonylamino (e.g., acetylamino, ethylcarbonylamino, propylcarbonylamino, isopropylcarbonylamino, butylcarbonylamino, isobutylcarbonylamino, sec-butylcarbonylamino, tert-butylcarbonylamino, pentylcarbonylamino, hexylcarbonylamino etc.) optionally having 1 to 3 substituents selected from (1') halogen (e.g., fluorine, chlorine, bromine, iodine), (2') $C_{1-6}$ alkoxy-carbonyl (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentoxycarbonyl, hexyloxycarbonyl etc.), (3') mono- or di-$C_{1-6}$ alkylamino (e.g., methylamino, ethylamino, propylamino, isopropylamino, butylamino, isobutylamino, sec-butylamino, tert-butylamino, pentylamino, hexylamino, dimethylamino, diethylamino, dipropylamino, diisopropylamino, N-ethyl-N-methylamino) optionally substituted by hydroxy, (4') hydroxy, (5') $C_{1-6}$ alkyl-carbonylamino (e.g., acetylamino, ethylcarbonylamino, propylcarbonylamino, isopropylcarbonylamino, butylcarbonylamino, isobutylcarbonylamino, sec-butylcarbonylamino, tert-butylcarbonylamino, pentylcarbonylamino, hexylcarbonylamino etc.), (6') carbamoylamino, (7') a heterocyclic group (wherein the heterocyclic group is the same as the "heterocyclic group" of the "heterocyclic group optionally having substituent(s)" defined below), (8') $C_{6-10}$ arylamino (e.g., phenylamino etc.), (9') (heterocyclic group)-carbonylamino (wherein the heterocyclic group is the same as the "heterocyclic group" of the "heterocyclic group optionally having substituent(s)" defined below), and (10') $C_{1-6}$ alkoxy (e.g., methoxy, ethoxy, propoxy, isopropoxy, butoxy, isobutoxy, sec-butoxy, tert-butoxy, pentoxy, hexyloxy etc.),

(45) $C_{3-8}$ cycloalkyl-carbonylamino (e.g., cyclopropylcarbonylamino, cyclobutylcarbonylamino, cyclopentylcarbonylamino, cyclohexylcarbonylamino etc.),

(46) $C_{2-6}$ alkenyl-carbonylamino (e.g., ethenylcarbonylamino, 1-propenylcarbonylamino, 2-propenylcarbonylamino etc.) optionally having 1 to 3 substituents selected from (1') $C_{6-10}$ aryl (e.g., phenyl, 1-naphthyl, 2-naphthyl) optionally having 1 to 3 substituents selected from halogen (e.g., fluorine, chlorine, bromine, iodine), $C_{1-6}$ alkyl (e.g., methyl, ethyl, propyl, isopropyl, butyl, isobutyl, sec-butyl, tert-butyl, pentyl, hexyl etc.), $C_{1-6}$ alkoxy (e.g., methoxy, ethoxy, propoxy, isopropoxy, butoxy, isobutoxy, sec-butoxy, tert-butoxy, pentoxy, hexyloxy etc.) and halogeno-$C_{1-6}$ alkyl (e.g., trifluoromethyl, 2,2,2-trifluoroethyl), and (2') a heterocyclic group (wherein the heterocyclic group is the same as the "heterocyclic group" of the "heterocyclic group optionally having substituent(s)" defined below) optionally having $C_{1-6}$ alkyl (e.g., methyl, ethyl, propyl, isopropyl, butyl, isobutyl, sec-butyl, tert-butyl, pentyl, hexyl),

(47) $C_{2-6}$ alkynyl-carbonylamino (e.g., ethynylcarbonylamino, 1-propynylcarbonylamino, 2-propynylcarbonylamino etc.),

(48) $C_{6-10}$ aryl-carbonylamino (e.g., phenylcarbonylamino, stylylcarbonylamino, naphthylcarbonylamino etc.) optionally having 1 to 3 substituents selected from (1') halogen (e.g., fluorine, chlorine, bromine, iodine), (2') $C_{1-6}$ alkyl (e.g., methyl, ethyl, propyl, isopropyl, butyl, isobutyl, sec-butyl, tert-butyl, pentyl, hexyl etc.) optionally having 1 to 3 substituents selected from halogen (e.g., fluorine, chlorine, bromine, iodine) hydroxy, amino and $C_{1-6}$ alkyl-carbonylamino (e.g., acetylamino, ethylcarbonylamino, propylcarbonylamino, isopropylcarbonylamino, butylcarbonylamino, isobutylcarbonylamino, sec-butylcarbonylamino, tert-butylcarbonylamino, pentylcarbonylamino, hexylcarbonylamino), (3') $C_{1-6}$ alkoxy (e.g., methoxy, ethoxy, propoxy, isopropoxy, butoxy, isobutoxy, sec-butoxy, tert-butoxy, pentoxy, hexyloxy etc.) optionally having 1 to 3 halogens (e.g., fluorine, chlorine, bromine, iodine), (4') $C_{1-6}$ alkoxy-carbonyl (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentoxycarbonyl, hexyloxycarbonyl etc.), (5') cyano, (6') carboxy, (7') mono- or di-$C_{1-6}$ alkylamino (e.g., methylamino, ethylamino, propylamino, isopropylamino, butylamino, isobutylamino, sec-butylamino, tert-butylamino, pentylamino, hexylamino, dimethylamino, diethylamino, dipropylamino, diisopropylamino, N-ethyl-N-methylamino) optionally having 1 to 3 substituents selected from hydroxy and $C_{1-6}$ alkoxy (e.g., methoxy, ethoxy, propoxy, isopropoxy, butoxy, isobutoxy, sec-butoxy, tert-butoxy, pentoxy, hexyloxy), (8') carbamoyl, (9') $C_{1-6}$ alkyl-carbonylamino (e.g., acetylamino, ethylcarbonylamino, propylcarbonylamino, isopropylcarbonylamino, butylcarbonylamino, isobutylcarbonylamino, sec-butylcarbonylamino, tert-butylcarbonylamino, pentylcarbonylamino, hexylcarbonylamino), (10') aminosulfonyl, (11') $C_{1-6}$ alkyl-sulfonyl (e.g., methylsulfonyl, ethylsulfonyl, propylsulfonyl, isopropylsulfonyl, butylsulfonyl, isobutylsulfonyl, sec-butylsulfonyl, tert-butylsulfonyl, pentylsulfonyl, hexylsulfonyl) and (12') a heterocyclic group (wherein the heterocyclic group is the same as the "heterocyclic group" of the "heterocyclic group optionally having substituent(s)" defined below) optionally having 1 to 3 substituents selected from $C_{1-6}$ alkyl (e.g., methyl, ethyl, propyl, isopropyl, butyl, isobutyl, sec-butyl, tert-butyl, pentyl, hexyl) and oxo (=O),

(49) $C_{7-12}$ aralkyl-carbonylamino (e.g., benzylcarbonylamino, phenethylcarbonylamino etc.),

(50) (heterocyclic group (wherein the heterocyclic group is the same as the "heterocyclic group" of the "heterocyclic group optionally having substituent(s)" defined below))—carbonylamino (e.g., thienylcarbonylamino, pyridylcarbonylamino, piperidylcarbonylamino (e.g., piperidinocarbonylamino etc.), pyrazinylcarbonylamino, imidazolylcarbonylamino, benzimidazolylcarbonylamino, 1H-benzotriazolylcarbonylamino, indolylcarbonylamino, pyranylcarbonylamino, furanylcarbonylamino, 1,2,3,6-tetrahydropyrimidinylcarbonylamino, tetrazolylcarbonylamino, pyrazolylcarbonylamino, quinoxalinylcarbonylamino, quinolylcarbonylamino, imidazo[1,2-a]pyridylcarbonylamino, benzothiazolylcarbonylamino, 3,4-dihydro-2H-1,4-benzoxazinylcarbonylamino, pyrimidinylcarbonylamino, 1,2,4-triazolylcarbonylamino, 2,3-dihydro-1-benzofuranylcarbonylamino, 2,1-benzoisoxazolylcarbonylamino etc.), which may have 1 to 3 substituents selected from (1') amino, (2') $C_{1-6}$ alkyl (e.g., methyl, ethyl, propyl, isopropyl, butyl, isobutyl, sec-butyl, tert-butyl, pentyl, hexyl), (3') halogeno-$C_{1-6}$ alkyl (e.g., trifluoromethyl, 2,2,2-trifluoroethyl), (4') $C_{6-10}$ aryl (e.g., phenyl, 1-naphthyl, 2-naphthyl), (5') oxo (=O) and (6') a heterocyclic group (wherein the heterocyclic group is the same as the "heterocyclic group" of the "heterocyclic group optionally having substituent(s)" defined below) optionally having $C_{1-6}$ alkyl (e.g., methyl, ethyl, propyl, isopropyl, butyl, isobutyl, sec-butyl, tert-butyl, pentyl, hexyl),

(51) $C_{1-6}$ alkyl-sulfonylamino (e.g., methylsulfonylamino, ethylsulfonylamino, propylsulfonylamino, isopropylsulfonylamino, butylsulfonylamino, isobutylsulfonylamino, sec-butylsulfonylamino, tert-butylsulfonylamino, pentylsulfonylamino, hexylsulfonylamino etc.),

(52) $C_{2-6}$ alkenyl-sulfonylamino (e.g., ethenylsulfonylamino, 1-propenylsulfonylamino, 2-propenylsulfonylamino etc.),

(53) $C_{2-6}$ alkynyl-sulfonylamino (e.g., ethynylsulfonylamino, 1-propynylsulfonylamino, 2-propynylsulfonylamino etc.),

(54) $C_{6-10}$ aryl-sulfonylamino (e.g., phenylsulfonylamino, naphthylsulfonylamino etc.),

(55) $C_{7-12}$ aralkyl-sulfonylamino (e.g., benzylsulfonylamino etc.),

(56) $C_{1-6}$ alkoxy-carbonylamino (e.g., methoxycarbonylamino, ethoxycarbonylamino, propoxycarbonylamino, isopropoxycarbonylamino, butoxycarbonylamino, isobutoxycarbonylamino, sec-butoxycarbonylamino, tert-butoxycarbonylamino, pentoxycarbonylamino, hexyloxycarbonylamino etc.) optionally having 1 to 3 halogens (e.g., fluorine, chlorine, bromine, iodine),

(57) N—$C_{1-6}$ alkoxy-carbonyl-N—$C_{1-6}$ alkylamino (e.g., N-tert-butoxycarbonyl-N-methylamino, N-methoxycarbonyl-N-methylamino etc.),

(58) $C_{6-10}$ aryloxy-carbonylamino (e.g., phenoxycarbonylamino etc.),

(59) $C_{7-12}$ aralkyloxy-carbonylamino (e.g., benzyloxycarbonylamino etc.),

(60) carbamoylcarbonylamino,

(61) 3-$C_{1-6}$ alkyl-ureido (e.g., 3-methylureido, 3-ethylureido, 3-propylureido, 3-isopropylureido, 3-butylureido, 3-pentylureido, 3-isopentylureido, 3-hexylureido etc.) optionally having 1 to 3 substituents selected from (1') $C_{1-6}$ alkoxy (e.g., methoxy, ethoxy, propoxy, isopropoxy, butoxy, isobutoxy, sec-butoxy, tert-butoxy, pentoxy, hexyloxy etc.), (2') $C_{1-6}$ alkoxy-carbonyl (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentoxycarbonyl, hexyloxycarbonyl etc.), (3') carboxy, (4') hydroxy, (5') $C_{1-6}$ alkoxy-carbonylamino (e.g., methoxycarbonylamino, ethoxycarbonylamino, propoxycarbonylamino, isopropoxycarbonylamino, butoxycarbonylamino, isobutoxycarbonylamino, sec-butoxycarbonylamino, tert-butoxycarbonylamino, pentoxycarbonylamino, hexyloxycarbonylamino), (6') amino, (7') halogen (e.g., fluorine, chlorine, bromine, iodine), (8') carbamoyl, (9') $C_{1-6}$ alkylsulfonyl (e.g., methylsulfonyl, ethylsulfonyl, propylsulfonyl, isopropylsulfonyl, butylsulfonyl, isobutylsulfonyl, sec-butylsulfonyl, tert-butylsulfonyl etc.), (10') a heterocyclic group (wherein the heterocyclic group is the same as the "heterocyclic group" of the "heterocyclic group optionally having substituent(s)" defined below) optionally substituted by oxo, and (11') $C_{1-6}$ alkyl-carbonylamino (e.g., acetylamino, ethylcarbonylamino, propylcarbonylamino, isopropylcarbonylamino, butylcarbonylamino, isobutylcarbonylamino, sec-butylcarbonylamino, tert-butylcarbonylamino, pentylcarbonylamino, hexylcarbonylamino etc.),

(62) 3-$C_{3-8}$ cycloalkyl-ureido (e.g., 3-cyclopentylureido, 3-cyclobutylureido, 3-cyclopentylureido, 3-cyclohexylureido, 3-cycloheptylureido, 3-cyclooctylureido etc.),

(63) 3-$C_{6-10}$ aryl-ureido (e.g., 3-phenylureido, 3-naphthylureido etc.) optionally having 1 to 3 substituents selected from (1') halogen (e.g., fluorine, chlorine, bromine, iodine), (2') cyano, (3') $C_{1-6}$ alkyl (e.g., methyl, ethyl, propyl, isopropyl, butyl, isobutyl, sec-butyl, tert-butyl, pentyl, hexyl etc.) optionally having 1 to 3 halogens (e.g., fluorine, chlorine, bromine, iodine), (4') $C_{1-6}$ alkoxy (e.g., methoxy, ethoxy, propoxy, isopropoxy, butoxy, isobutoxy, sec-butoxy, tert-butoxy, pentoxy, hexyloxy etc.), (5') $C_{1-4}$ alkylenedioxy (e.g., —OCH$_2$O—, —OCH$_2$CH$_2$O—, —OCH$_2$CH$_2$CH$_2$O—, —OCH$_2$CH$_2$CH$_2$CH$_2$O— etc.), (6') $C_{1-6}$ alkoxy-carbonyl (e.g. methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentoxycarbonyl, hexyloxycarbonyl), (7') carbamoyl and (8') a heterocyclic group (wherein the heterocyclic group is the same as the "heterocyclic group" of the "heterocyclic group optionally having substituent(s)" defined below),

(64) 3-$C_{1-6}$ alkyl-3-$C_{6-10}$ aryl-ureido (wherein, as the $C_{1-6}$ alkyl moiety, for example, methyl, ethyl, propyl, isopropyl, butyl, isobutyl, sec-butyl, tert-butyl, pentyl, hexyl and the like can be mentioned, and as the $C_{6-10}$ aryl moiety, for example, phenyl, 1-naphthyl, 2-naphthyl and the like can be mentioned, specifically, 3-methyl-3-phenylureido and the like can be mentioned),

(65) 3-$C_{7-12}$ aralkyl-ureido (e.g., 3-benzylureido, 3-phenethylureido etc.) optionally having 1 to 3 substituents selected from (1') halogen (e.g., fluorine, chlorine, bromine, iodine), (2') cyano, (3') $C_{1-6}$ alkyl (e.g., methyl, ethyl, propyl, isopropyl, butyl, isobutyl, sec-butyl, tert-butyl, pentyl, hexyl etc.) optionally having 1 to 3 halogens (e.g., fluorine, chlorine, bromine, iodine), (4') $C_{1-6}$ alkoxy (e.g., methoxy, ethoxy, propoxy, isopropoxy, butoxy, isobutoxy, sec-butoxy, tert-butoxy, pentoxy, hexyloxy etc.), and (5') $C_{1-4}$ alkylenedioxy (e.g., —OCH$_2$O—, —OCH$_2$CH$_2$O—, —OCH$_2$CH$_2$CH$_2$O—, —OCH$_2$CH$_2$CH$_2$CH$_2$O— etc.),

(66) 3-$C_{1-6}$ alkoxy-ureido (e.g., 3-methoxyureido, 3-ethoxyureido, 3-propoxyureido, 3-isopropoxyureido, 3-butoxyureido, 3-isobutoxyureido, 3-(sec-butoxy)ureido, 3-(tert-butoxy)ureido, 3-pentoxyureido, 3-hexyloxyureido),

(67) 3-$C_{6-10}$ arylsulfonyl-ureido (e.g., 3-(phenylsulfonyl)ureido, 3-(1-naphthylsulfonyl)ureido, 3-(2-naphthylsulfonyl)ureido),

(68) 3-(heterocyclic group (wherein the heterocyclic group is the same as the "heterocyclic group" of the "heterocyclic group optionally having substituent(s)" defined below))-ureido (e.g., 2-pyridylureido, 3-pyridylureido, 4-pyridylureido, 3-(1H-benzotriazolyl)-ureido) optionally having 1 to 3 substituents selected from $C_{1-6}$ alkyl (e.g., methyl, ethyl, propyl, isopropyl, butyl, isobutyl, sec-butyl, tert-butyl, pentyl, hexyl etc.) and a heterocyclic group (wherein the heterocyclic group is the same as the "heterocyclic group" of the "heterocyclic group optionally having substituent(s)" defined below),

(69) piperidylureido optionally having 1 to 3 $C_{1-6}$ alkyl-carbonyl (e.g., acetyl, ethylcarbonyl, propylcarbonyl, isopropylcarbonyl, butylcarbonyl, isobutylcarbonyl, sec-butylcarbonyl, tert-butylcarbonyl, pentylcarbonyl, hexylcarbonyl),

(70) phthalimide:

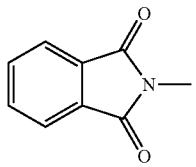

(71) a heterocyclic group (wherein the heterocyclic group is the same as the "heterocyclic group" of the "heterocyclic group optionally having substituent(s)" defined below, and for example, a 5- or 6-membered aromatic monocyclic heterocyclic group such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl and the like, and a 8-to 12-membered aromatic fused heterocyclic group such as benzofuranyl, isobenzofuranyl, benzo[b]thienyl, indolyl, 3H-indolyl, indolinyl, isoindolyl, isoindolinyl, 1H-indazolyl, benzimidazolyl, benzoxazolyl, 1,2-benzisoxazolyl, 2,1-benzisoxazolyl, benzothiazolyl, benzopyranyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, phenoxazinyl, phenothiazinyl, phenazinyl, acridinyl, phenoxathiinyl, thianthrenyl, phenanthridinyl, phenanthrol inyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl, benzoxazinyl and the like, and a 3- to 8-membered saturated or unsaturated non-aromatic heterocyclic group such as oxiranyl, azetidinyl, oxetanyl, thietanyl, pyranyl, pyrrolidinyl, tetrahydrofuryl, thiolanyl, piperidyl, tetrahydropyranyl, morpholinyl, thiomorpholinyl, piperazinyl, 3-hexahydrocyclopenta[c]pyrrolyl, homopiperidyl, homopiperazinyl, 1,2,3,6-tetrahydropyrimidinyl and the like, and the like, or a non-aromatic heterocyclic group wherein the double bonds of the aforementioned aromatic monocyclic heterocyclic group or aromatic fused heterocyclic group are partly or entirely saturated, such as dihydropyridyl, dihydropyrimidyl, 1,2,3,4-tetrahydroquinolyl, 1,2,3,4-tetrahydroisoquinolyl, 3,4-dihydro-2H-1,4-benzoxazinyl, 2,3-dihydro-1-benzofuranyl, 1,3-benzodioxaindanyl, chromenyl and the like, and the like can be mentioned)

(72) halogen (e.g., fluorine, chlorine, bromine, iodine),

(73) azido,

(74) nitro,

(75) cyano,

(76) oxo (═O),

(77) $C_{1-6}$ alkylene (e.g., $C_{1-4}$ alkylene such as —CH$_2$—, —CH$_2$CH$_2$—, —CH$_2$CH$_2$CH$_2$—, —CH$_2$CH$_2$CH$_2$CH$_2$—, and the like),

(78) $C_{1-4}$ alkylenedioxy (e.g., —OCH$_2$O—, —OCH$_2$CH$_2$O—, —OCH$_2$CH$_2$CH$_2$O—, —OCH$_2$CH$_2$CH$_2$CH$_2$O— and the like)

(79) a group represented by the formula: $R^{12}$—NH—(CH$_2$)p- wherein $R^{12}$ is (1') a hydrogen atom, (2') $C_{6-10}$ aryl-carbonyl (e.g., benzoyl, 1-naphthoyl, 2-naphthoyl) optionally having 1 to 3 halogeno-$C_{1-6}$ alkyl (e.g., trifluoromethyl, 2,2,2-trifluoroethyl), (3') $C_{7-12}$ aralkyl-oxycarbonyl (e.g., benzyloxycarbonyl, phenethyloxycarbonyl, 1-naphthylmethoxycarbonyl, 2-naphthylmethoxycarbonyl) or (4') $C_{6-10}$ aryl-aminocarbonyl (e.g., phenylaminocarbonyl, 1-naphthylaminocarbonyl, 2-naphthylaminocarbonyl), and p is 0 or 1,

(80) a group represented by the formula: $R^{15}$—NH—(CH$_2$)r- wherein $R^{15}$ is $C_{6-10}$ aryl-carbonyl (e.g., benzoyl, 1-naphthoyl, 2-naphthoyl), and r is 0 or 1.

The above-mentioned substituent group A further optionally has 1 to 3 substituents selected from the substituent group A as defined above at substitutable position.

As the substituent of the "hydroxy optionally having a substituent" for $R^2$, $R^3$, $R^4$, $R^5$, $R^7$, $R^8$, $R^9$ or $R^{10}$, for example, the aforementioned "hydrocarbon group optionally having substituent(s)" for $R^1$, $R^2$, $R^3$, $R^4$, $R^5$, $R^7$, $R^8$, $R^9$ or $R^{10}$ can be mentioned.

As the substituent of the "amino optionally having substituent(s)" for $R^2$, $R^3$, $R^4$, $R^5$, $R^7$, $R^8$, $R^9$ or $R^{10}$, for example, the aforementioned "hydrocarbon group optionally having substituent(s)" for $R^1$, $R^2$, $R^3$, $R^4$, $R^5$, $R^7$, $R^8$, $R^9$ or $R^{10}$ can be mentioned, and the number of substituents is 1 or 2.

As the "thiol optionally having a substituent" for $R^2$, $R^3$, $R^4$, $R^5$, $R^7$, $R^8$, $R^9$ or $R^{10}$, for example, a group represented by the formula —$SR^{20}$ (wherein $R^{20}$ is a hydrocarbon group optionally having substituent(s)), a group represented by the formula —$S(O)R^{21}$ (wherein $R^{21}$ is a hydrocarbon group optionally having substituent(s)) and a group represented by the formula —$S(O)_2R^{22}$ (wherein $R^{22}$ is a hydrocarbon group optionally having substituent(s)) can be mentioned. As the "hydrocarbon group optionally having substituent(s)" for $R^{20}$, $R^{21}$ or $R^{22}$, those similar to the aforementioned "hydrocarbon group optionally having substituent(s)" for $R^1$, $R^2$, $R^3$, $R^4$, $R^5$, $R^7$, $R^8$, $R^9$ or $R^{10}$ can be mentioned.

As the "heterocyclic group" of the "heterocyclic group optionally having substituent(s)" for $R^2$, $R^6$, $R^7$, $R^8$, $R^9$ or $R^{10}$, in the present specification, unless otherwise specified, for example, 5- to 14-membered (monocyclic, bicyclic or tricyclic) aromatic heterocyclic group or non-aromatic heterocyclic group containing, besides carbon atoms, 1 to 5 (preferably 1 to 3) of 1 to 3 kinds of hetero atoms selected from nitrogen atom, sulfur atom and oxygen atom as a ring-constituting atom can be mentioned.

As the "aromatic heterocyclic group", for example, 5- or 6-membered aromatic monocyclic heterocyclic group such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl and the like, and, 8- to 12-membered aromatic fused heterocyclic group such as benzofuranyl, isobenzofuranyl, benzo[b]thienyl, indolyl, 3H-indolyl, indolinyl, isoindolyl, isoindolinyl, 1H-indazolyl, benzimidazolyl, benzoxazolyl, 1,2-benzisoxazolyl, 2,1-benzisoxazolyl, benzothiazolyl, benzopyranyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl, 1,4-benzoxazinyl and the like (preferably, a heterocycle wherein the aforementioned 5- or 6-membered aromatic monocyclic heterocyclic group is fused with a benzene ring, or a heterocycle wherein the same or different two heterocycles of the aforementioned 5- or 6-membered aromatic monocyclic heterocyclic group are fused, more preferably a heterocycle wherein the aforementioned 5- or 6-membered aromatic monocyclic heterocyclic group is fused with a benzene ring, particularly preferably benzofuranyl, benzopyranyl, benzo[b]thienyl etc.) and the like can be mentioned.

As the "non-aromatic heterocyclic group", for example, a 3- to 8-membered saturated or unsaturated non-aromatic heterocyclic group such as oxiranyl, azetidinyl, oxetanyl, thietanyl, pyranyl, pyrrolidinyl, tetrahydrofuryl, thiolanyl, piperidyl (containing piperidino), tetrahydropyranyl, morpholinyl, thiomorpholinyl, piperazinyl, 3-hexahydrocyclopenta[c]pyrrolyl, homopiperidyl, homopiperazinyl, 1,2,3,6-tetrahydropyrimidinyl and the like, and the like, or a non-aromatic heterocyclic group wherein the double bonds of the aforementioned aromatic monocyclic heterocyclic group or aromatic fused heterocyclic group are partly or entirely saturated, such as dihydropyridyl, dihydropyrimidyl, 1,2,3,4-tetrahydroquinolyl, 1,2,3,4-tetrahydroisoquinolyl, 3,4-dihydro-2H-1,4-benzoxazinyl, 2,3-dihydro-1-benzofuranyl, 1,3-benzodioxaindanyl, chromenyl and the like, and the like can be mentioned.

Of the above-mentioned "heterocyclic groups", as the "5- or 6-membered heterocyclic group", for example, furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, pyranyl, pyrrolidinyl, tetrahydrofuryl, thiolanyl, piperidyl, tetrahydropyranyl, morpholinyl, thiomorpholinyl, piperazinyl and the like can be mentioned, and as the "5- or 6-membered aromatic heterocyclic group", for example, furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl and the like can be mentioned.

Of the above-mentioned "heterocyclic groups", as the "fused ring group of benzene ring and 5- or 6-membered heterocycle", for example, isoindolyl, benzimidazolyl, 1,3-benzodioxaindanyl, 1H-benzotriazolyl, indolyl, quinoxalinyl, 2,3-dihydro-1-benzofuranyl, 1,2-benzoisoxazolyl, benzothiazolyl, 1,4-benzoxazinyl, isobenzofuranyl, chromenyl, 3H-indolyl, 1H-indazolyl, isoquinolyl, quinolyl, phthalazinyl, quinazolinyl, cinnolinyl, indolinyl, isoindolinyl, benzofuranyl and the like can be mentioned.

As the "substituent(s)" of the "heterocyclic group optionally having substituent(s)" for $R^2$, $R^6$, $R^7$, $R^8$, $R^9$ or $R^{10}$, the substituents selected from the aforementioned substituent group A, and the like can be mentioned. The number of substituents is 1 to 5.

As the "cyclic group optionally having substituent(s)" of the "(cyclic group optionally having substituent(s))—carbonyl" for $R^6$, (1) a homocyclic ring group optionally having substituent(s) and (2) a heterocyclic group optionally having substituent(s) can be mentioned.

As the "homocyclic ring group" of the "homocyclic ring group optionally having substituent(s)", (1) $C_{3-8}$ cycloalkyl (e.g., cyclopropyl, cyclobutyl, cyclopentyl, cyclohexyl, cycloheptyl, cyclooctyl, bicyclo[2.2.2]octyl etc.), (2) $C_{6-10}$ aryl (e.g., phenyl, 1-naphthyl, 2-naphthyl etc.) and (3) a group wherein $C_{3-8}$ cycloalkyl of (1) and $C_{6-10}$ aryl of (2) are fused (e.g., 1,2,3,4-tetrahydronaphthyl) can be mentioned.

As the "substituent" of the "homocyclic ring group optionally having substituent(s)", those similar to the aforementioned substituent group A can be mentioned. The number of the substituents is 1 to 5.

As the "heterocyclic group optionally having substituent(s)", those similar to the aforementioned "heterocyclic group optionally having substituent(s)" for $R^2$, $R^6$, $R^7$, $R^8$, $R^9$ or $R^{10}$ can be mentioned.

As the "alkenylcarbonyl optionally having substituent(s)" for $R^6$, $C_{2-6}$ alkenyl-carbonyl (e.g., ethenylcarbonyl, 1-propenylcarbonyl, 2-propenylcarbonyl etc.) optionally having 1 to 5 substituents selected from the aforementioned substituent group A, and the like can be mentioned.

As the "alkylcarbonyl" of the "alkylcarbonyl having substituent(s) selected from (i) cycloalkyl optionally having substituent(s), (ii) amino optionally having substituent(s) and (iii) a heterocyclic group optionally having substituent(s)" for $R^6$, for example, $C_{1-6}$ alkyl-carbonyl (e.g., acetyl, ethylcarbonyl, propylcarbonyl, isopropylcarbonyl, butylcarbonyl, isobutylcarbonyl, sec-butylcarbonyl, tert-butylcarbonyl, pentylcarbonyl, hexylcarbonyl etc.) and the like can be mentioned.

As the "cycloalkyl optionally having substituent(s)" of the "alkylcarbonyl having substituent(s) selected from (i) cycloalkyl optionally having substituent(s), (ii) amino optionally having substituent(s) and (iii) a heterocyclic group optionally having substituent(s)" for $R^6$, for example, $C_{3-6}$ cycloalkyl (e.g., cyclopropyl, cyclobutyl, cyclopentyl, cyclohexyl etc.) optionally having 1 to 5 substituents selected from the aforementioned substituent group A, and the like can be mentioned.

As the "amino optionally having substituent(s)" of the "alkylcarbonyl having substituent(s) selected from (i) cycloalkyl optionally having substituent(s), (ii) amino optionally having substituent(s) and (iii) a heterocyclic group optionally having substituent(s)" for $R^6$, those similar to the aforementioned "amino optionally having substituent(s)" for $R^2$, $R^3$, $R^4$, $R^5$, $R^7$, $R^8$, $R^9$ or $R^{10}$ can be mentioned.

As the "heterocyclic group optionally having substituent(s)" of the "alkylcarbonyl having substituent(s) selected from (i) cycloalkyl optionally having substituent(s), (ii) amino optionally having substituent(s) and (iii) a heterocyclic group optionally having substituent(s)" for $R^6$, those similar to the aforementioned "heterocyclic group optionally having substituent(s)" for $R^2$, $R^6$, $R^7 R^8$, $R^9$ or $R^{10}$ can be mentioned, and the "substituent" is selected from the substituent group A.

The number of the substituents, which the above-mentioned alkylcarbonyl has, is 1 to 3.

As the ring which $R^7$ and $R^8$, $R^8$ and $R^9$ or $R^9$ and $R^{10}$ form together with the adjacent carbon atoms, (1) homocyclic ring optionally having 1 to 5 substituents selected from the aforementioned substituent group A, or (2) heterocycle optionally having 1 to 5 substituents selected from the aforementioned substituent group A, can be mentioned.

As the "homocyclic ring" of the "homocyclic ring optionally having 1 to 5 substituents selected from the aforementioned substituent group A", for example, $C_{3-6}$ cycloalkyl ring (e.g., cyclopropane ring, cyclobutane ring, cyclopentane ring, cyclohexane ring etc.), $C_{6-10}$ aryl ring (e.g., benzene ring, naphthalene ring etc.) and the like can be mentioned.

As the "heterocycle" of the "heterocycle optionally having 1 to 5 substituents selected from the aforementioned substituent group A", unless otherwise specified, for example, a 5- to 14-membered (monocyclic, bicyclic or tricyclic) aromatic heterocyclic group or non-aromatic heterocyclic group containing, besides carbon atoms, 1 to 5 (preferably 1 to 3) of 1 to 3 kinds of hetero atoms selected from nitrogen atom, sulfur atom and oxygen atom as a ring-constituting atom, can be mentioned.

As the "aromatic heterocycle", for example, 5- or 6-membered aromatic monocyclic heterocycle such as furan ring, thiophene ring, pyrrole ring, oxazole ring, isoxazole ring, thiazole ring, isothiazole ring, imidazole ring, pyrazole ring, 1,2,3-oxadiazole ring, 1,2,4-oxadiazole ring, 1,3,4-oxadiazole ring, furazan ring, 1,2,3-thiadiazole ring, 1,2,4-thiadiazole ring, 1,3,4-thiadiazole ring, 1,2,3-triazole ring, 1,2,4-triazole ring, tetrazole ring, pyridine ring, pyridazine ring, pyrimidine ring, pyrazine ring, triazine ring and the like, and 8- to 12-membered aromatic fused heterocycle such as benzofuran ring, isobenzofuran ring, benzo[b]thiophene ring, indole ring, isoindole ring, 1H-indazole ring, benzimidazole ring, benzoxazole ring, 1,2-benzisoxazole ring, 2,1-benzisoxazole ring, benzothiazole ring, benzopyran ring, 1,2-benzisothiazole ring, 1H-benzotriazole ring, quinoline ring, isoquinoline ring, cinnoline ring, quinazoline ring, quinoxaline ring, phthalazine ring, naphthyridine ring, purine ring, pteridine ring, carbazole ring, α-carboline ring, β-carboline ring, γ-carboline ring, acridine ring, phenoxazine ring, phenothiazine ring, phenazine ring, phenoxathiin ring, thianthrene ring, phenanthridine ring, phenanthroline ring, indolizine ring, pyrrolo[1,2-b]pyridazine ring, pyrazolo[1,5-a]pyridine ring, imidazo[1,2-a]pyridine ring, imidazo[1,5-a]pyridine ring, imidazo[1,2-b]pyridazine ring, imidazo[1,2-a]pyrimidine ring, 1,2,4-triazolo[4,3-a]pyrid me ring, 1,2,4-triazolo[4,3-b]pyridazine ring, 1,4-benzoxazine ring and the like (preferably, a heterocycle wherein the aforementioned 5- or 6-membered aromatic monocyclic heterocycle is fused with a benzene ring, or a heterocycle wherein the same or different two heterocycles of the aforementioned 5- or 6-membered aromatic monocyclic heterocycle are fused, more preferably a heterocycle wherein the aforementioned 5- or 6-membered aromatic monocyclic heterocycle fused with a benzene ring, particularly preferably benzofuran ring, benzopyran ring, benzo[b]thiophene ring etc.) and the like can be mentioned.

As the "non-aromatic heterocycle", for example, a 3- to 8-membered saturated or unsaturated non-aromatic heterocycle such as oxirane ring, azetidine ring, oxetane ring, thietane ring, pyran ring, pyrrolidine ring, tetrahydrofuran ring, thioran ring, piperidine ring, tetrahydropyran ring, morpholine ring, thiomorpholine ring, piperazine ring, 3-hexahydrocyclopenta[c]pyrrole ring, homopiperidine ring, homopiperazine ring, 1,2,3,6-tetrahydropyrimidine ring and the like, and the like, or a non-aromatic heterocycle wherein the double bonds of the aforementioned aromatic monocyclic heterocycle or aromatic fused heterocycle are partly or entirely saturated, such as dihydropyridine ring, dihydropyrimidine ring, 1,2,3,4-tetrahydroquinoline ring, 1,2,3,4-tetrahydroisoquinoline ring, 3,4-dihydro-2H-1,4-benzoxazine ring, 2,3-dihydro-1-benzofuran ring, 1,3-benzodioxaindan ring, chromene ring and the like, and the like can be mentioned.

When n is an integer of 2 to 5, $R^4$ and $R^5$ may be different, respectively, due to redundancy of n.

$R^1$ is preferably (1) unsubstituted, (2) a hydrogen atom, (3) $C_{1-6}$ alkyl optionally having 1 to 5 substituents selected from the aforementioned substituent group A, (4) $C_{7-12}$ aralkyl optionally having 1 to 5 substituents selected from the aforementioned substituent group A, or (5) $C_{1-6}$ alkyl-carbonyl optionally having 1 to 5 substituents selected from the aforementioned substituent group A, and more preferably (1) unsubstituted, (2) a hydrogen atom, (3) $C_{1-6}$ alkyl optionally having 1 to 5 substituents selected from the aforementioned substituent group A, or (4) $C_{1-6}$ alkyl-carbonyl optionally having 1 to 5 substituents selected from the aforementioned substituent group A.

Of these, $R^1$ is preferably (1) unsubstituted, (2) a hydrogen atom, (3) $C_{1-6}$ alkyl, (4) $C_{7-12}$ aralkyl or (5) $C_{1-6}$ alkyl-carbonyl, and particularly preferably (1) unsubstituted, (2) a hydrogen atom, (3) $C_{1-6}$ alkyl or (4) $C_{1-6}$ alkyl-carbonyl.

Particularly, a hydrogen atom is preferable.

As $R^2$, (1) a hydrogen atom, (2) $C_{1-6}$ alkyl optionally having 1 to 5 substituents selected from the aforementioned substituent group A, (3) $C_{3-8}$ cycloalkyl optionally having 1 to 5 substituents selected from the aforementioned substituent group A, (4) $C_{6-10}$ aryl optionally having 1 to 5 substituents selected from the aforementioned substituent group A, (5) $C_{1-6}$ alkoxy-carbonyl optionally having 1 to 5 substituents selected from the aforementioned substituent group A and (6) a 5- or 6-membered heterocyclic group optionally having 1 to 5 substituents selected from the aforementioned substituent group A are preferable, and (1) a hydrogen atom, (2) $C_{1-6}$ alkyl optionally having 1 to 5 substituents selected from the aforementioned substituent group A, (3) $C_{3-8}$ cycloalkyl optionally having 1 to 5 substituents selected from the aforementioned substituent group A, (4) $C_{6-10}$ aryl optionally having 1 to 5 substituents selected from the aforementioned substituent group A and (5) a 5- or 6-membered aromatic heterocyclic group optionally having 1 to 5 substituents selected from the aforementioned substituent group A are more preferable.

Of these, (1) a hydrogen atom, (2) $C_{1-6}$ alkyl optionally having 1 to 3 substituents selected from (1') hydroxy, (2') $C_{1-6}$ alkoxy, (3') $C_{7-12}$ aralkyloxy, (4') mono- or di-$C_{1-6}$ alkylamino, (5') N—$C_{1-6}$ alkoxy-carbonyl-N—$C_{1-6}$ alkylamino, (6') amino, (7') $C_{1-6}$ alkyl-carbonylamino optionally having 1 to 3 halogens, (8') $C_{7-12}$ aralkyloxy-carbonylamino and (9') $C_{1-6}$ alkoxy-carbonylamino optionally having 1 to 3 halogens, (3) $C_{3-8}$ cycloalkyl, (4) $C_{6-10}$ aryl optionally having 1 to 3 substituents selected from (1') halogen, (2') $C_{1-6}$ alkyl optionally having 1 to 3 halogens, (3') cyano, (4') $C_{1-6}$ alkoxy-carbonyl and (5') $C_{1-6}$ alkyl-thio, (5) $C_{1-6}$ alkoxy-carbonyl and (6) a 5- or 6-membered heterocyclic group optionally having substituent(s) selected from (1') hydroxy, (2') $C_{1-6}$ alkyl optionally having $C_{1-6}$ alkyl-carbonyloxy, (3') $C_{7-19}$ aralkyl optionally having $C_{1-6}$ alkoxy, (4') $C_{7-12}$ aralkyloxy, (5') $C_{7-12}$ aralkyloxy-carbonyl, (6') mono-$C_{1-6}$ alkyl-carbamoyl and (7') $C_{1-6}$ alkoxy-carbonyl are preferable, and (1) a hydrogen atom, (2) $C_{1-6}$ alkyl optionally having 1 to 3 substituents selected from (i) hydroxy, (ii) $C_{1-6}$ alkoxy, (iii) $C_{7-12}$ aralkyloxy, (iv) mono-$C_{1-6}$ alkylamino and (v) N—$C_{1-6}$ alkoxy-carbonyl-N—$C_{1-6}$ alkylamino, (3) $C_{3-8}$ cycloalkyl, (4) $C_{6-10}$ aryl optionally having 1 to 3 substituents selected from (i) halogen, (ii) $C_{1-6}$ alkyl optionally having 1 to 3 halogens, (iii) cyano and (iv) $C_{1-6}$ alkoxy-carbonyl, and (5) a 5- or 6-membered aromatic heterocyclic group optionally having substituent(s) selected from (i) hydroxy, (ii) $C_{1-6}$ alkyl optionally having $C_{1-6}$ alkyl-carbonyloxy, (iii) $C_{7-12}$ aralkyl optionally having $C_{1-6}$ alkoxy and (iv) $C_{7-12}$ aralkyloxy are more preferable.

Particularly, (1) $C_{1-6}$ alkyl optionally having substituent(s) selected from (i) $C_{1-6}$ alkoxy and (ii) mono-$C_{1-6}$ alkylamino, (2) $C_{3-8}$ cycloalkyl, (3) $C_{6-10}$ aryl optionally having halogen, and (4) a 5- or 6-membered aromatic heterocyclic group optionally having $C_{1-6}$ alkyl are preferable.

$R^3$ is preferably (1) unsubstituted, (2) a hydrogen atom or (3) $C_{1-6}$ alkyl optionally having 1 to 5 substituents selected from the aforementioned substituent group A.

Of these, $R^3$ is preferably (1) unsubstituted, (2) a hydrogen atom or (3) $C_{1-6}$ alkyl.

Particularly, (1) a hydrogen atom or (2) $C_{1-6}$ alkyl is preferable.

As $R^4$ and $R^5$, hydrogen atoms are preferable.

As $R^6$, (1) a group represented by the formula

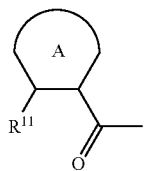

wherein ring A is cyclopentane, cyclohexane or bicyclo[2.2.2]octane;

$R^{11}$ is (1') amino, (2') $C_{7-12}$ aralkylamino, (3') $C_{1-6}$ alkyl-carbonylamino optionally having substituent(s) selected from (1") halogen, (2") hydroxy, (3") $C_{1-6}$ alkoxy-carbonyl, (4") mono- or di-$C_{1-6}$ alkylamino optionally substituted by hydroxy, (5") morpholino, (6") $C_{1-6}$ alkyl-carbonylamino, (7") carbamoylamino, (8") a 5- or 6-membered aromatic heterocyclic group, (9") $C_{6-10}$ arylamino, (10") (5- or 6-membered aromatic heterocyclic group)-carbonylamino and (11") $C_{1-6}$ alkoxy, (4') $C_{2-6}$ alkenyl-carbonylamino optionally having substituent(s) selected from (1") $C_{6-10}$ aryl optionally having substituent(s) selected from halogen, $C_{1-6}$ alkyl, $C_{1-6}$ alkoxy and halogeno-$C_{1-6}$ alkyl and (2") a 5- or 6-membered aromatic heterocyclic group optionally having $C_{1-6}$ alkyl, (5') $C_{3-8}$ cycloalkyl-carbonylamino, (6') $C_{6-10}$ aryl-carbonylamino optionally having substituent(s) selected from (1") halogen, (2") cyano, (3") $C_{1-6}$ alkyl optionally having amino or $C_{1-6}$ alkyl-carbonylamino, (4") halogeno-$C_{1-6}$ alkyl, (5") hydroxy-$C_{1-6}$ alkyl, (6") $C_{1-6}$ alkoxy, (7") carboxy, (8") $C_{1-6}$ alkoxy-carbonyl, (9") mono- or di-$C_{1-6}$ alkylamino optionally having hydroxy or $C_{1-6}$ alkoxy, (10") carbamoyl, (11") halogeno-$C_{1-6}$ alkoxy, (12") $C_{1-6}$ alkyl-carbonylamino, (13") aminosulfonyl, (14") $C_{1-6}$ alkyl-sulfonyl and (15") a 5- or 6-membered heterocyclic group, or a fused ring group of benzene ring and 5- or 6-membered heterocycle, which may have substituent(s) selected from $C_{1-6}$ alkyl and oxo, (7') $C_{7-12}$ aralkyl-carbonylamino, (8') $C_{1-6}$ alkoxy-carbonylamino, (9') (5- or 6-membered heterocyclic group, or fused ring group of benzene ring and 5- or 6-membered heterocycle)-carbonylamino, which may have substituent(s) selected from (1") amino, (2") $C_{1-6}$ alkyl, (3") halogeno-$C_{1-6}$ alkyl, (4") $C_{6-10}$ aryl, (5") oxo and (6") a 5- or 6-membered heterocyclic group optionally having $C_{1-6}$ alkyl, (10') $C_{6-10}$ aryl-sulfonylamino, (11') carbamoylcarbonylamino, (12') 3-$C_{1-6}$ alkyl-ureido optionally having substituent(s) selected from (1") hydroxy, (2") carboxy, (3") $C_{1-6}$ alkoxy, (4") $C_{1-6}$ alkoxy-carbonyl, (5") $C_{1-6}$ alkoxy-carbonylamino, (6") amino, (7") halogen, (8") carbamoyl, (9") $C_{1-6}$ alkylsulfonyl, (10") a heterocyclic group optionally substituted by oxo and (11") $C_{1-6}$ alkyl-carbonylamino, (13') 3-$C_{3-8}$ cycloalkyl-ureido, (14') 3-$C_{6-10}$ aryl-ureido optionally having substituent(s) selected from (1") halogen, (2") cyano, (3") halogeno-$C_{1-6}$ alkyl, (4") $C_{1-6}$ alkyl, (5") $C_{1-6}$ alkoxy, (6") methylenedioxy, (7") $C_{1-6}$ alkoxy-carbonyl, (8") carbamoyl and (9") a 5- or 6-membered aromatic heterocyclic group, (15') 3-$C_{1-6}$ alkyl-3-$C_{6-10}$ aryl-ureido, (16') 3-$C_{7-12}$ aralkyl-ureido optionally having substituent(s) selected from (1") halogen and (2") $C_{1-6}$ alkoxy, (17') 3-$C_{1-6}$ alkoxy-ureido, (18') 3-$C_{6-10}$ arylsulfonyl-ureido, (19') 3-(5- or 6-membered heterocyclic group, or fused ring group of benzene ring and 5- or 6-membered heterocycle)-ureido, which may have 5- or 6-membered heterocyclic group, (20') piperidylureido optionally having $C_{1-6}$ alkyl-carbonyl, or (21') phthalimide, (2) a group represented by the formula

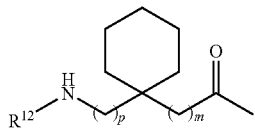

wherein $R^{12}$ is (1') a hydrogen atom, (2') $C_{6-10}$ aryl-carbonyl optionally having halogeno-$C_{1-6}$ alkyl, (3') $C_{7-12}$ aralkyl-oxycarbonyl or (4') $C_{6-10}$ aryl-aminocarbonyl; m is 0 or 1; and p is 0 or 1, (3) a group represented by the formula

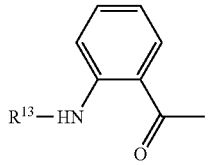

wherein $R^{13}$ is $C_{6-10}$ aryl-carbonyl, (4) a group represented by the formula

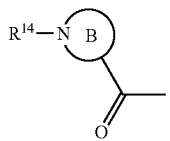

wherein ring B is a pyrrolidine ring or a piperidine ring, each optionally substituted by amino; $R^{14}$ is (1') a hydrogen atom, (2') $C_{7-12}$ aralkyl, (3') $C_{1-6}$ alkyl-carbonyl, (4') $C_{6-10}$ arylcarbonyl, (5') $C_{7-12}$ aralkyl-carbonyl, (6') $C_{1-6}$ alkoxy-carbonyl or (7') $C_{7-12}$ aralkyl-carbamoyl, (5) $C_{2-6}$ alkenyl-carbonyl optionally having substituent(s) selected from (1') carboxy, (2') $C_{1-6}$-alkoxy-carbonyl and (3') $C_{6-10}$ aryl-aminocarbonyl, (6) $C_{1-6}$ alkyl-carbonyl having substituent(s) selected from (1') amino, (2') $C_{6-10}$ aryl-carbonylamino, (3') $C_{1-6}$ alkoxycarbonylamino and (4') a 5- or 6-membered heterocyclic group, or a fused ring group of benzene ring and 5- or 6-membered heterocycle, each optionally substituted by oxo, (7) 1,2,3,4-tetrahydronaphthylcarbonyl, (8) pyrrolidinyl having $C_{7-12}$ aralkyl, or (9) a group represented by the formula

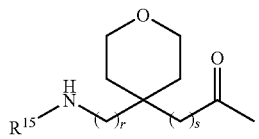

wherein $R^{15}$ is $C_{6-10}$ aryl-carbonyl; r is 0 or 1; and s is 0 or 1, is preferable, and (1) a group represented by the formula

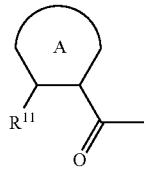

wherein ring A is cyclopentane, cyclohexane or bicyclo[2.2.2]octane; $R^{11}$ is (1') amino, (2') $C_{7-12}$ aralkylamino, (3') $C_{1-6}$ alkyl-carbonylamino optionally having substituent(s) selected from (1") halogen, (2") hydroxy, (3") $C_{1-6}$ alkoxycarbonyl, (4") di-$C_{1-6}$ alkylamino and (5") morpholino, (4') $C_{3-8}$ cycloalkyl-carbonylamino, (5') $C_{6-10}$ aryl-carbonylamino optionally having substituent(s) selected from (1") halogen, (2") cyano, (3") $C_{1-6}$ alkyl, (4") halogeno-$C_{1-6}$ alkyl, (5") hydroxy-$C_{1-6}$ alkyl, (6") $C_{1-6}$ alkoxy, (7") carboxy and (8") $C_{1-6}$ alkoxy-carbonyl, (6') $C_{7-12}$ aralkyl-carbonylamino, (7') $C_{1-6}$ alkoxy-carbonylamino, (8') (5- or 6-membered aromatic heterocyclic group)-carbonylamino, (9') piperidinocarbonylamino, (10') $C_{6-10}$ aryl-sulfonylamino, (11') 3-$C_{1-6}$ alkyl-ureido optionally having substituent(s) selected from (1") hydroxy, (2") carboxy, (3") $C_{1-6}$ alkoxy and (4") $C_{1-6}$ alkoxy-carbonyl, (12') 3-$C_{3-8}$ cycloalkyl-ureido, (13') 3-$C_{6-10}$ aryl-ureido optionally having substituent(s) selected from (1") halogen, (2") cyano, (3") halogeno-$C_{1-6}$ alkyl, (4") $C_{1-6}$ alkyl, (5") $C_{1-6}$ alkoxy and (6") methylenedioxy, (14') 3-$C_{7-12}$ aralkyl-ureido optionally having substituent(s) selected from (1") halogen and (2") $C_{1-6}$ alkoxy, (15') 3-(5- or 6-membered aromatic heterocyclic group)-ureido, (16') piperidylureido, preferably piperidinoureido, optionally having $C_{1-6}$ alkyl-carbonyl or (17') phthalimide, (2) a group represented by the formula

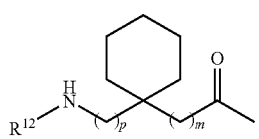

wherein $R^{12}$ is (1') a hydrogen atom, (2') $C_{6-10}$ aryl-carbonyl optionally having halogeno-$C_{1-6}$ alkyl or (3') $C_{7-12}$ aralkyl-oxycarbonyl; m is 0 or 1; and p is 0 or 1, (3) a group represented by the formula $$R^{13}-HN-\underset{O}{\text{C}_6H_4-C(=O)-}$$

wherein $R^{13}$ is $C_{6-10}$ aryl-carbonyl, (4) a group represented by the formula $$R^{14}-N\underset{B}{\diagup}-C(=O)-$$

wherein ring B is a pyrrolidine ring or a piperidine ring; $R^{14}$ is (1') a hydrogen atom, (2') $C_{7-12}$ aralkyl, (3') $C_{1-6}$ alkyl-carbonyl, (4') $C_{6-10}$ aryl-carbonyl, (5') $C_{7-12}$ aralkyl-carbonyl or (6') $C_{1-6}$ alkoxy-carbonyl, (5) $C_{2-6}$ alkenyl-carbonyl optionally having substituent(s) selected from (1') carboxy, (2') $C_{1-6}$ alkoxy-carbonyl and (3') $C_{6-10}$ aryl-aminocarbonyl, (6) $C_{1-6}$ alkyl-carbonyl having substituent(s) selected from (1') amino, (2') $C_{6-10}$ aryl-carbonylamino and (3') $C_{1-6}$ alkoxy-carbonylamino, (7) 1,2,3,4-tetrahydronaphthylcarbonyl, and (8) pyrrolidinyl having $C_{7-12}$ aralkyl are more preferable.

Of these, (1) a group represented by the formula $$R^{11'}-HN-\underset{A'}{\bigcirc}-C(=O)-$$

wherein ring A' is cyclohexane or bicyclo[2.2.2]octane, $R^{11'}$ is (1') $C_{1-6}$ alkyl-carbonyl optionally having substituent(s) selected from (1") halogen, (2") hydroxy, (3") $C_{1-6}$ alkoxy-carbonyl and (4") morpholino, (2') $C_{6-10}$ aryl-carbonyl optionally having substituent(s) selected from (1") halogen, (2") cyano, (3") $C_{1-6}$ alkyl, (4") halogeno-$C_{1-6}$ alkyl, (5") hydroxy-$C_{1-6}$ alkyl, (6") $C_{1-6}$ alkoxy and (7") $C_{1-6}$ alkoxy-carbonyl, (3') $C_{7-12}$ aralkyl-carbonyl, (4') (5- or 6-membered aromatic heterocyclic group)-carbonyl, (5') $C_{1-6}$ alkyl-aminocarbonyl optionally having substituent(s) selected from (1") hydroxy, (2") $C_{1-6}$ alkoxy and (3") $C_{1-6}$ alkoxy-carbonyl, (6') $C_{3-8}$ cycloalkyl-aminocarbonyl, (7') $C_{6-10}$ aryl-aminocarbonyl optionally having substituent(s) selected from (1") halogen, (2") cyano, (3") halogeno-$C_{1-6}$ alkyl, (4") $C_{1-6}$ alkyl, (5") $C_{1-6}$ alkoxy and (6") methylenedioxy, (8') $C_{7-12}$ aralkyl-aminocarbonyl optionally having substituent(s) selected from (1") halogen and (2") $C_{1-6}$ alkoxy, (9') (5- or 6-membered aromatic heterocyclic group)-aminocarbonyl or (10')

piperidylaminocarbonyl, preferably piperidinoaminocarbonyl, optionally having $C_{1-6}$ alkyl-carbonyl, and (2) a group represented by the formula $$R^{12'}-HN-\underset{}{\bigcirc}-CH_2-C(=O)-$$

wherein $R^{12'}$ is $C_{6-10}$ aryl-carbonyl, are particularly preferable.

As $R^7$, hydrogen atom is preferable.

As $R^8$, (1) a hydrogen atom, (2) halogen, (3) cyano, (4) $C_{1-6}$ alkyl optionally having 1 to 3 halogens, (5) $C_{6-10}$ aryl-carbonyl, (6) $C_{1-6}$ alkoxy, (7) $C_{6-10}$ aryloxy and (8) sulfamoyl are preferable, and (1) a hydrogen atom, (2) halogen, (3) cyano, (4) $C_{1-6}$ alkyl optionally having 1 to 3 halogens, (5) $C_{6-10}$ aryl-carbonyl, (6) $C_{1-6}$ alkoxy and (7) $C_{6-10}$ aryloxy are more preferable. Particularly, hydrogen atom, halogen, $C_{1-6}$ alkyl and $C_{1-6}$ alkoxy are preferable, and hydrogen atom and halogen are particularly preferable.

As $R^9$, (1) a hydrogen atom, (2) halogen, (3) cyano, (4) $C_{1-6}$ alkyl and (5) $C_{1-6}$ alkoxy are preferable. Particularly, hydrogen atom, halogen, cyano and $C_{1-6}$ alkyl are preferable, and hydrogen atom and halogen are particularly preferable.

As $R^{10}$, (1) a hydrogen atom, (2) halogen, (3) $C_{1-6}$ alkyl and (4) $C_{1-6}$ alkoxy are preferable. Particularly, hydrogen atom and halogen are preferable.

As n, 2 and 3 are preferable. Particularly, n=2 is preferable.

Of the compound represented by the formula (I), a compound represented by the formula wherein each symbol is as defined above, is particularly preferable.

Specifically, as preferable examples of compound (I),

N-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)benzamide, N-((1R,2S)-2-{[(3aR,4R,9bR)-4-(3-thienyl)-2,3,3a,4,5,9b-hexahydro-1H-pyrrolo[3,2-c]quinolin-1-yl]carbonyl}cyclohexyl)benzamide, N-((1R,2S)-2-{[(3aR,4R,9bR)-4-(1H-pyrrol-2-yl)-2,3,3a,4,5,9b-hexahydro-1H-pyrrolo[3,2-c]quinolin-1-yl]carbonyl}cyclohexyl)benzamide, N-((1R,2S)-2-{[(3aR,4R,9bR)-4-cyclopropyl-2,3,3a,4,5,9b-hexahydro-1H-pyrrolo[3,2-c]quinolin-1-yl]carbonyl}cyclohexyl)benzamide, N-((1R,2S)-2-{[(3aR,4R,9bR)-4-(1H-imidazol-2-yl)-2,3,3a,4,5,9b-hexahydro-1H-pyrrolo[3,2-c]quinolin-1-yl]carbonyl}cyclohexyl)benzamide (Example 81), N-phenyl-N'-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)urea (Example 135), 2-methyl-N-((1R,2S)-2-{[(3aR,4S,9bR)-4-propyl-2,3,3a,4,5,9b-hexahydro-1H-pyrrolo[3,2-c]quinolin-1-yl]carbonyl}cyclohexyl)-1H-benzimidazole-5-carboxamide (Example 201), N-((1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexyl)-1H-1,2,3-benzotriazole-5-carboxamide (Example 219), 4-(1H-imidazol-2-yl)-N-((1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexyl)benzamide (Example 281), N-((1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexyl)-N'-[4-(1H-pyrazol-1-yl)phenyl]urea (Example 284), 4-cyano-N-((1R,2S)-2-{[(3aR,4R,9bR)-4-(1H-imidazol-2-yl)-2,3,3a,4,5,9b-hexahydro-1H-pyrrolo[3,2-c]quinolin-1-yl]carbonyl}cyclohexyl)benzamide (Example 304)

and the like can be mentioned.

Of these, N-((1R,2S)-2-{[(3aR,4R,9bR)-4-(1H-imidazol-2-yl)-2,3,3a,4,5,9b-hexahydro-1H-pyrrolo[3,2-c]quinolin-1-yl]carbonyl}cyclohexyl)benzamide (Example 81), N-phenyl-N'-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)urea (Example 135), 2-methyl-N-((1R,2S)-2-{[(3aR,4S,9bR)-4-propyl-2,3,3a,4,5,9b-hexahydro-1H-pyrrolo[3,2-c]quinolin-1-yl]carbonyl}cyclohexyl)-1H-benzimidazole-5-carboxamide (Example 201), N-((1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexyl)-1H-1,2,3-benzotriazole-5-carboxamide (Example 219), 4-(1H-imidazol-2-yl)-N-((1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexyl)benzamide (Example 281), N-((1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexyl)-N'-[4-(1H-pyrazol-1-yl)phenyl]urea (Example 284) and 4-cyano-N-((1R,2S)-2-{[(3aR,4R,9bR)-4-(1H-imidazol-2-yl)-2,3,3a,4,5,9b-hexahydro-1H-pyrrolo[3,2-c]quinolin-1-yl]carbonyl}cyclohexyl)benzamide (Example 304) are particularly preferable.

As the salts of compound (I), for example, metal salts, ammonium salts, salts with organic bases, salts with inorganic acids, salts with organic acids, salts with basic or acidic amino acids, and the like can be mentioned. As preferable examples of the metal salt, for example, alkali metal salts such as sodium salt, potassium salt and the like; alkaline earth metal salts such as calcium salt, magnesium salt, barium salt and the like; aluminum salt, and the like can be mentioned. As preferable examples of the salt with the organic base, for example, salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine, tromethamine [i.e., tris(hydroxymethyl)methylamine], tert-butylamine and the like can be mentioned. As preferable examples of the salt with the inorganic acid, for example, salts with hydrochloric acid, hydrobromic acid, nitric acid, sulfuric acid, phosphoric acid and the like can be mentioned. As preferable examples of the salt with the organic acid, for example, salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like can be mentioned. As preferable examples of the salt with the basic amino acid, for example, salts with arginine, lysin, ornithine and the like can be mentioned, and as preferable examples of the salt with the acidic amino acid, for example, salts with aspartic acid, glutamic acid and the like can be mentioned.

Of these, pharmaceutically acceptable salts are preferable. For example, when a compound has an acidic functional group therein, for example, inorganic salts such as alkali metal salts (e.g., sodium salt, potassium salt etc.), alkaline earth metal salts (e.g., calcium salt, magnesium salt, barium salt etc.) and the like, ammonium salts and the like can be mentioned, and when a compound has an basic functional group therein, for example, salts with inorganic acid such as hydrochloric acid, hydrobromic acid, nitric acid, sulfuric acid, phosphoric acid and the like, and salts with organic acid such as acetic acid, phthalic acid, fumaric acid, oxalic acid, tartaric acid, maleic acid, citric acid, succinic acid, methanesulfonic acid, p-toluenesulfonic acid and the like can be mentioned.

The compound (I) may be a hydrate or non-hydrate. As the hydrate, for example, 0.5 hydrate, 1 hydrate, 1.5 hydrate, 2 hydrate and the like can be mentioned.

When compound (I) can contain optical isomers, respective optical isomers and mixture thereof are substantially encompassed in the present invention. When desired, these isomers can be optical resolved by a method known per se, or can be produced individually.

When compound (I) is present as a configurational isomer, diastereomer, conformer or the like, they can be isolated as desired by known separation and purification means, respectively.

When compound (I) has a stereoisomer, such isomer alone and a mixture thereof are also encompassed in the present invention.

When compound (I) is obtained as a mixture of optically active compounds (e.g., racemate), it can be separated into the object (R) form and (S) form by optical resolution means known per se.

The compound (I) may be labeled with isotope (e.g., $^3$H, $^{14}$C, $^{35}$S) and the like.

The prodrug of compound (I) means a compound which is converted to compound (I), under physiological conditions in vivo, as a result of a reaction with an enzyme, gastric acid etc. Thus, the compound is converted into compound (I) by enzymatical oxidation, reduction, hydrolysis or the like, or by hydrolysis due to gastric acid or the like, etc.

As a prodrug of compound (I), a compound obtained by subjecting an amino of compound (I) to an acylation, alkylation or phosphorylation (e.g., a compound obtained by subjecting an amino of compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation, tert-butylation, etc.); a compound obtained by subjecting hydroxy in compound (I) to an acylation, alkylation, phosphorylation and boration (e.g., a compound obtained by subjecting hydroxy of compound (I) to an acetylation, palmitoylation, propanoylation, pivaloylation, succinylation, fumarylation, alanylation, dimethylaminomethylcarbonylation, etc.); a compound obtained by subjecting carboxy of compound (I) to an esterification or amidation (e.g., a compound obtained by subjecting carboxy of compound (I) to an ethyl-esterification, phenyl-esterification, carboxymethyl-esterification, dimethylaminomethyl-esterification, pivaloyloxymethyl-esterification, ethoxycarbonyloxyethyl-esterification, phthalidyl-esterification, (5-methyl-2-oxo-1,3-dioxolen-4-yl)methyl-esterification, cyclohexyloxycarbonylethyl-esterification, methylamidation, etc.) and the like can be mentioned. These compounds can be produced from compound (I) by a method known per se.

In addition, the prodrug of compound (I) may be a compound, which is converted to compound (I) under the physiological conditions, as described in *Pharmaceutical Research and Development*, Vol. 7 (Drug Design), pp. 163-198 (1990), published by Hirokawa Publishing Co.

The production methods of compound (I) are described in the following. The compounds in the schemes include salts, and as such salt, for example, those similar to the salts of compound (I) and the like can be mentioned.

As the aromatic amine solvents, halogenated hydrocarbon solvents, aliphatic hydrocarbon solvents, aromatic hydrocarbon solvents, ether solvents, amide solvents and nitrile solvents to be used in the present production methods, for example, the following solvents can be used.

aromatic amine solvents:

halogenated hydrocarbon solvents: methylene chloride, dichloroethane and the like aliphatic hydrocarbon solvents: pentane, hexane, heptane and the like aromatic hydrocarbon solvents: toluene, xylene and the like ether solvents: diethyl ether, tetrahydrofuran and the like amide solvents: N,N-dimethylformamide, N,N-dimethylacetamide and the like nitrile solvents: acetonitrile, propionitrile and the like The room temperature generally means about 10° C. to about 35° C.

Scheme 1

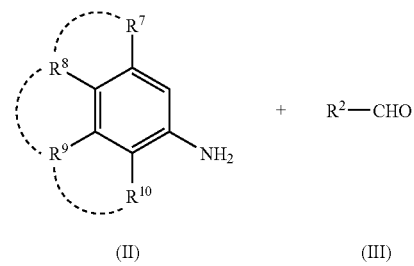

(II)                    (III)

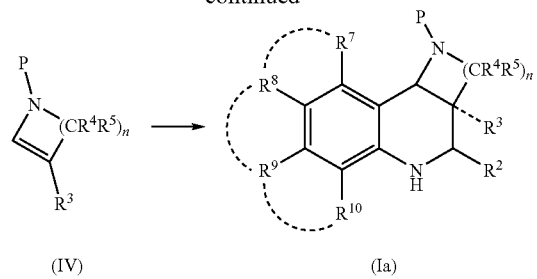

(IV)                    (Ia)

wherein P is a protecting group, and other symbols are as defined above.

Scheme 1 relates to a synthetic method of compound (Ia), wherein, in compound (I), $R^1$=H, $R^6$=P (wherein P is a protecting group) and n=2 or 3, which can be synthesized according to the method by R. A. Batey et al. (*Chem. Commun.*, 1999, 651). Three components of compound (II), compound (III) and compound (IV) are condensed in the presence of a catalyst to give a mixture of stereoisomers: an endo-form and an exo-form. Advantageously, this reaction is carried out without solvent or in the presence of a solvent inert to the reaction. While the solvent is not particularly limited as long as the reaction proceeds, for example, aromatic amine solvents, halogenated hydrocarbon solvents, aliphatic hydrocarbon solvents, aromatic hydrocarbon solvents, ether solvents, amide solvents, nitrile solvents, a mixture of two or more kinds thereof, and the like are used. Of these, acetonitrile, toluene and the like are preferable. The reaction temperature is generally −30° C. to 100° C., preferably room temperature. The reaction time is generally 1 hr to 24 hr, preferably 1 hr to 2 hr. As the catalyst, protonic acid (e.g., sulfuric acid, trifluoroacetic acid etc.) and Lewis acids (e.g., $BF_3.Et_2O$, $TiCl_4$, $AlCl_3$, $InCl_3$, $Dy(OTf)_3$, $Yb(OTf)_3$, $Sc(OTf)_3$, $La(OTf)_3$, $Eu(OTf)_3$, $Cu(OTf)_2$, $Zn(OTf)_2$, etc.) and the like can be used.

As the protecting group represented by P, groups generally used in peptide chemistry and the like can be mentioned. For example, the groups described in *Protective Grours in Organic Synthesis*, 3$^{rd}$ Ed. (1999), authored by Theodora W. Greene, Peter G. M. Wuts, published by Wiley-Interscience, and the like can be mentioned. Specifically, tert-butoxycarbonyl group (BOC group), benzyloxycarbonyl group (Cbz group) and the like can be mentioned.

Scheme 2

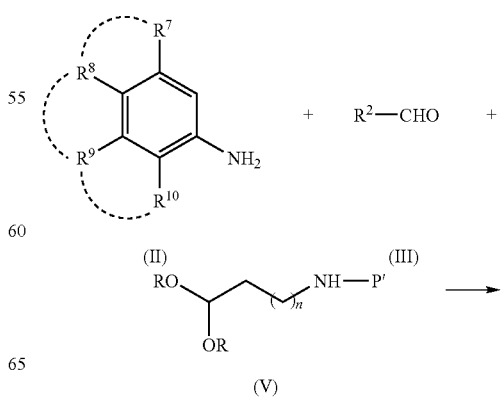

(V)

-continued

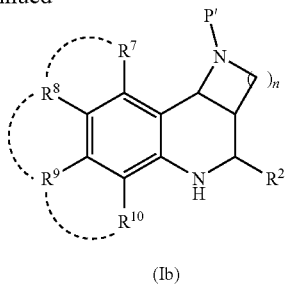

(Ib)

wherein Rs are the same or different and each is $C_{1-6}$ alkyl (e.g., methyl, ethyl etc.), P' is a protecting group, and other symbols are as defined above.

Scheme 2 relates to a synthetic method of compound (Ib), wherein, in compound (I), $R^1=R^3=R^4=R^5=H$, $R^6=P'$ (wherein P' is a protecting group), and compound (V) instead of compound (IV) in Scheme 1 is condensed with compound (II) and compound (III) in the presence of a catalyst to synthesize compound (Ib). While the solvent for this reaction is not particularly limited as long as the reaction proceeds, for example, aromatic amine solvents, halogenated hydrocarbon solvents, aliphatic hydrocarbon solvents, aromatic hydrocarbon solvents, ether solvents, amide solvents, nitrile solvents, a mixture of two or more kinds thereof, and the like are used. Of these, acetonitrile, toluene and the like are preferable. The reaction temperature is generally 0° C. to 100° C., preferably 50° C. to 60° C. The reaction time is generally 1 hr to 24 hr, preferably 2 hr to 3 hr.

In the aforementioned reaction, as the protecting group represented by P', those similar to the aforementioned protecting group represented by P can be mentioned.

The stereoisomer mixture of endo-form and exo-form compounds obtained in Scheme 1 or Scheme 2 (Ia or Ib) can be isolated and purified by known means, such as fractionation, crystallization, chromatography and the like.

Scheme 3

(Ia) or (Ib) →

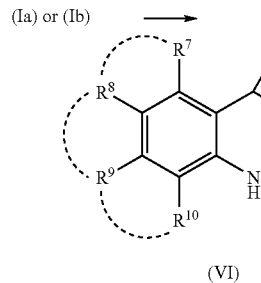

(VI)

$R^{6'}$—OH
(VII)

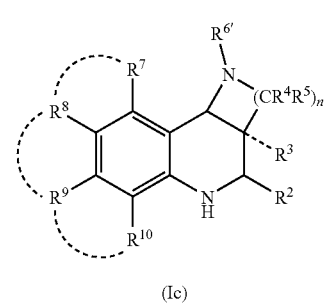

(Ic)

wherein $R^{6'}$ is (1) (cyclic group optionally having substituent(s))-carbonyl, (2) alkenylcarbonyl optionally having substituent(s) or (3) alkylcarbonyl having substituent(s) selected from (i) cycloalkyl optionally having substituent(s) and (ii) amino optionally having substituent(s), and other symbols are as defined above.

Scheme 3 relates to removal of the protecting group in a stereoisomer mixture of endo-form and exo-form compounds ((Ia) or (Ib)), or in isolated stereoisomers thereof. The protecting group can be removed according to the methods known per se, such as the method described in *Protective Groups in Organic Synthesis*, 3$^{rd}$ Ed. (1999), authored by Theodora W. Greene, Peter G. M. Wuts, published by Wiley-Interscience, and the like.

The compound (Ic) can be obtained by a method comprising reacting compound (VI) with compound (VII) in the presence of a suitable condensing agent and, where necessary, a base. The amount of compound (VII) to be used is about 1.0 mol to 1.5 mol, preferably about 1.1 mol to 1.2 mol, per 1.0 mol of compound (VI). The amount of the condensing agent to be used is about 1.0 to 1.5 mol, preferably about 1.1 mol to 1.3 mol, per 1.0 mol of compound (VI). As the condensing agent, for example, carbodiimides (DCC (i.e., 1,3-dicyclohexylcarbodiimide), WSC (i.e., 1-ethyl-3-(3-dimethylaminopropyl)carbodiimide hydrochloride), DIC (i.e., 2-dimethylaminoisopropylchloride hydrochloride) etc.), phosphotic acid derivatives (e.g., diethyl cyanophosphate, diphenylphosphoryl azide, BOP-CL (i.e., bis(2-oxo-3-oxazolidinyl)phosphoryl chloride) etc.) and the like can be mentioned. The amount of the base to be used is about 2.0 mol to 5.0 mol, preferably about 3.0 mol to 4.0 mol, per 1.0 mol of compound (VI). As the base, for example, inorganic bases such as sodium hydride, sodium hydroxide, potassium hydroxide and the like, aromatic amines such as pyridine, lutidine and the like, tertiary amines such as triethylamine, tripropylamine, tributylamine cyclohexyldimethylamine, 4-dimethylaminopyridine, N,N-dimethylaniline, N-methylpiperidine, N-methylpyrrolidine, N-methylmorpholine and the like, ammonia or a mixture of two or more kinds thereof, and the like are used. In addition, compound (Ic) can be also obtained by a method comprising reacting compound (VI) with a reactive derivative of compound (VII) (e.g., acid halides, acid anhydrides, active esters, esters, acid imidazolides, acidazides etc.), and the like.

Advantageously, this reaction is carried out without solvent or in the presence of a solvent inert to the reaction. While the solvent is not particularly limited as long as the reaction proceeds, for example, aromatic amine solvents, halogenated hydrocarbon solvents, aliphatic hydrocarbon solvents, aromatic hydrocarbon solvents, ether solvents, amide solvents, nitrile solvents, a mixture of two or more kinds thereof, and the like are used. Of these, acetonitrile, N,N-dimethylformamide and the like are preferable. The reaction temperature is generally 0° C. to 40° C., preferably room temperature (ca. 10° C. to ca. 35° C., more preferably ca. 15° C. to ca. 25° C.). The reaction time is generally 0.5 hr to 24 hr, preferably 1 hr to 2 hr.

The compound (Ic) can be converted to the corresponding oxidized form by treating with an oxidizing agent, such as manganese dioxide, DDQ (i.e., 2,3-dichloro-5,6-dicyano-1,4-benzoquinone) and the like.

In any case, when further desired, compound (I) can be synthesized by known deprotection, acylation, alkylation, hydrogenation, oxidation, reduction, carbon chain extension or substituent exchange reaction alone, or in a combination of two or more of them. As these reactions, for example, the method described in Shinjikkenkagakukoza 14, vol. 15, 1977 (Maruzen Press) and the like are employed.

The compound (I) thus obtained can be isolated and purified from the reaction mixture by the means known per se, such as extraction, concentration, neutralization, filtration, distillation, recrystallization, column chromatography, thin layer chromatography, preparative high performance liquid chromatography (HPLC), moderate-pressure preparative liquid chromatography (moderate-pressure preparative LC) and the like.

When a desired product is obtained in a free form by the above-mentioned reaction, it may be converted into a salt according to conventional methods or, when a desired product is obtained as a salt, it can be converted into a free form or another salt according to conventional methods. The compound (I) thus obtained can be isolated and purified from the reaction mixture by known means, such as phase transfer, concentration, solvent extraction, fractionation, crystallization, recrystallization, chromatography and the like.

The compound (I), a salt thereof and a prodrug thereof according to the present invention (hereinafter sometimes to be abbreviated as the compound of the present invention) have a superior NK2 receptor antagonistic action. The compound of the present invention shows low toxicity (e.g., acute toxicity, chronic toxicity, genetic toxicity, reproductive toxicity, cardiotoxicity, drug interaction, carcinogenicity) and is safe.

The present inventors have found that a tricyclic compound having a partial structure represented by the formula

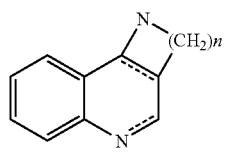

wherein n is an integer of 1 to 5; and

--- represents a single bond or a double bond, and a salt thereof have a potent NK2 receptor antagonistic action, and are safe and superior in duration (e.g., absorbability, metabolism, in vivo kinetics).

The compounds of the present invention having a superior NK2 receptor antagonistic action are useful as agents for the prophylaxis and/or treatment of diseases such as inflammation or allergic diseases (e.g., atopy, dermatitis, herpes, psoriasis, asthma, bronchitis, chronic obstructive pulmonary disease, sputum, rhinitis, rheumatism arthritis, osteoarthritis, osteoporosis, multiple sclerosis, conjunctivitis, cystitis and the like), pain, migraine, neuralgic pain, pruritus, cough, and further the diseases in the central nervous system [e.g., schizophrenia, Parkinsonism, melancholia, anxiety neurosis, compulsive neurosis, panic disorder, dementia (e.g., Alzheimer's disease and the like) and the like], gastrointestinal diseases [for example, functional gastrointestinal diseases (e.g., irritable bowel syndrome, nonulcer dyspepsia and the like), ulcerative colitis, Crohn's disease, abnormalities caused by urease positive herical gram negative bacteria (e.g., *Helicobacter pylori* and the like) (e.g., gastritis, gastric ulcer and the like) and the like], vomiting, abnormal urination (e.g., pollakiuria, incontinence of urine, and the like), circulatory diseases (e.g., angina pectoris, hypertension, cardiac failure, thrombosis and the like), immune abnormality, cancer, HIV infection, cardiovascular diseases, solar dermatitis, sexual inadequacy, ataxia, dysgnosia or circadian rhythm disorder and the like in mammals (e.g., mice, rats, hamsters, rabbits, cats, dogs, bovines, sheep, monkeys, humans and the like).

Of these, they are useful as agents for the prophylaxis and/or treatment of functional gastrointestinal diseases (e.g., irritable bowel syndrome, nonulcer dyspepsia and the like.

When the compound of the present invention is administered as a pharmaceutical agent to mammals such as human and the like, the administration generally includes, for example, oral administration as tablet, capsule (including soft capsule, microcapsule), powder, granule and the like, and parenteral administration as injection, suppository, pellet and the like. The "parenteral" includes intravenous, intramuscular, subcutaneous, intraorgan, intranasal, intradermal, instillation, intracerebral, rectal, vaginal, intraperitoneal, intratumor, tumor proximal administration and the like and direct administration into a lesion.

While the dose of the compound of the present invention varies depending on the administration route, symptoms and the like, it is, for example, 0.01-1000 mg/kg body weight/day, preferably 0.01-100 mg/kg body weight/day, more preferably 0.5-100 mg/kg body weight/day, particularly preferably 0.1-10 mg/kg body weight/day, further preferably 1-50 mg/kg body weight/day, particularly preferably 1-25 mg/kg body weight/day, for, for example, oral administration to patients with irritable bowel syndrome (adult, body weight 40 to 80 kg: e.g., 60 kg). This amount can be administered once a day or in 2, or 3 portions a day.

The compound of the present invention can be admixed with phamacologically acceptable carriers and administered orally or parenterally as solid preparations such as tablet, capsule, granule, powder and the like; or liquid preparations such as syrup, injection and the like.

As phamacologically acceptable carrier, various organic or inorganic carriers conventionally used as starting materials of preparations are used, which are added as excipient, lubricant, binder and disintegrant for solid preparations; solvent, dissolution aid, suspending agent, isotonicity agent, buffer and soothing agent for liquid preparations; and the like. Where necessary, additives for preparations such as preservative, antioxidant, coloring agent, sweetener and the like can be also used.

While the pharmaceutical composition varies depending on the dosage form, the administration method, carrier and the like, the composition can be produced by adding the compound of the present invention in a proportion of generally 0.01-100% (w/w), preferably 0.1-95% (w/w), of the total amount of the preparation according to a conventional method.

For example, the compound of the present invention can be used in combination with other active ingredients (hereinafter to be abbreviated as concomitant drug).

While the compound of the present invention shows a superior NK2 receptor antagonistic action when used as a single agent, its effect can be still more enhanced by the use together with one or more of the concomitant drugs (combined use of multi-agents).

As the concomitant drug, for example, the following can be mentioned.

(1) Therapeutic Agents for Diabetes

Insulin preparations [e.g., animal insulin preparations extracted from the bovine or swine pancreas; human insulin preparations synthesized by a genetic engineering technique using *Escherichia coli* or a yeast; insulin zinc; protamine zinc insulin; fragment or derivative of insulin (e.g., INS-1 etc.) and the like], insulin resistance improving agents (e.g., pioglitazone hydrochloride, troglitazone, rosiglitazone or its maleate, JTT-501, MCC-555, YM-440, GI-262570, KRP-297, FK-614, CS-011 etc.), α-glucosidase inhibitors (e.g., voglibose, acarbose, miglitol, emiglitate etc.), biguanides (e.g., phenformin, metformin, buformin etc.), sulfonylureas (e.g., tolbutamide, glibenclamide, gliclazide, chlorpropamide, tolazamide, acetohexamide, glyclopyramide, glimepiride etc.), and other insulin secretagogues (e.g., repaglinide, senaglinide, mitiglinide or its calcium salt hydrate, GLP-1, nateglinide etc.), dipeptidylpeptidase IV inhibitors (e.g., NVP-DPP-278, PT-100, P32/98 etc.), β3 agonists (e.g., CL-316243, SR-58611-A, UL-TG-307, AJ-9677, AZ40140 etc.), amyrin agonists (e.g., pramlintide etc.), phosphotyrosine phosphatase inhibitors (e.g., vanadic acid etc.), gluconeogenesis inhibitors (e.g., glycogen phosphorylase inhibitors, glucose-6-phosphatase inhibitors, glucagon antagonists etc.), SGLT (i.e., sodium-glucose cotransporter) inhibitors (e.g., T-1095 etc.) and the like.

(2) Therapeutic Agents for Diabetic Complications

Aldose reductase inhibitors (e.g., tolrestat, epalrestat, zenarestat, zopolrestat, fidarestat (SNK-860), minalrestat (ARI-509), CT-112 etc.), neurotrophic factors (e.g., NGF, NT-3 etc.), AGE inhibitors (e.g., ALT-945, pimagedine, pyratoxathine, N-phenacylthiazolium bromide (ALT-766), EXO-226 etc.), active oxygen scavengers (e.g., thioctic acid etc.), cerebral vasodilators (e.g., tiapuride etc.) and the like.

(3) Antihyperlipidemic Agents

Statin compounds which are cholesterol synthesis inhibitors (e.g., pravastatin, simvastatin, lovastatin, atorvastatin, fluvastatin, cerivastatin or their salts (e.g., sodium salt etc.) etc.), squalene synthase inhibitors or fibrate compounds having triglyceride lowering action (e.g., bezafibrate, clofibrate, simfibrate, clinofibrate etc.) and the like.

(4) hypotensive agents

Angiotensin converting enzyme inhibitors (e.g., captopril, enalapril, delapril etc.), angiotensin II antagonists (e.g., losartan, candesartan cilexetil etc.), calcium antagonists (e.g., manidipine, nifedipine, amlodipine, efonidipine, nicardipine etc.), clonidine and the like.

(5) Antiobesity agents

Antiobesity drugs acting on the central nervous system (e.g. dexfenfluramine, fenfluramine, phentermine, sibutramine, anfepramon, dexamphetamine, mazindol, phenylpropanolamine, clobenzorex etc.), pancreatic lipase inhibitors (e.g. orlistat etc.), ρ3 agonists (e.g. CL-316243, SR-58611-A, UL-TG-307, AJ-9677, AZ40140 etc.), anorectic peptides (e.g. leptin, CNTF (Ciliary Neurotrophic Factor) etc.), cholecystokinin agonists (e.g. lintitript, FPL-15849 etc.) and the like.

(6) Diuretic Agents

Xanthine derivatives (e.g., theobromine and sodium salicylate, theobromine and calcium salicylate etc.), thiazide preparations (e.g., ethiazide, cyclopenthiazide, trichlormethiazide, hydrochlorothiazide, hydroflumethiazide, benzylhydrochlorothiazide, penflutizide, polythiazide, methyclothiazide etc.), antialdosterone preparations (e.g., spironolactone, triamterene etc.), carbonate dehydratase inhibitors (e.g., acetazolamide etc.), chlorobenzenesulfonamide preparations (e.g., chlorthalidone, mefruside, indapamide etc.), azosemide, isosorbide, ethacrynic acid, piretanide, bumetanide, furosemide and the like.

(7) Chemotherapeutic Agents

Alkylating agents (e.g., cyclophosphamide, ifosfamide etc.), metabolic antagonists (e.g., methotrexate, 5-fluorouracil etc.), carcinostatic antibiotics (e.g., mitomycin, adriamycin etc.), plant-derived carcinostatics (e.g., vincristine, vindesine, Taxol etc.), cisplatin, carboplatin, etoposide and the like. Particularly, 5-fluorouracil derivatives such as Furtulon, Neo-Furtulon and the like.

(8) Immunotherapeutic Agents

Microorganism- or bacterium-derived components (e.g., muramyl dipeptide derivatives, Picibanil etc.), immunopotentiator polysaccharides (e.g., lentinan, schizophyllan, krestin etc.), genetically engineered cytokines (e.g., interferons, interleukins (IL) etc.), colony stimulating agents (e.g., granulocyte colony stimulating factor, erythropoietin etc.) and the like. Particularly, IL-1, IL-2, IL-12 and the like.

(9) Pharmaceutical Agents Confirmed to Show Cachexia Improving Effect in Animal Model or Clinical Use Progesterone derivatives (e.g., megestrol acetate) [*Journal of Clinical Oncology*, vol. 12, p. 213-225, (1994)], metoclopramide pharmaceutical agent, tetrahydrocannabinol pharmaceutical agents (literatures are as mentioned above), fat metabolism improvers (e.g., eicosapentaenoic acid etc.) *British Journal of Cancer*, vol. 68, p. 314-318 (1993)], growth hormone, IGF-1, antibodies against TNF-α, LIF, IL-6 and oncostatin M, which are the factors introducing cachexia, and the like.

(10) Antiphlogistics

Steroidal agents (e.g., dexamethasone etc.), sodium hyaluronate, cyclooxygenase inhibitors (e.g., indomethacin, ketoprofen, loxoprofen, meloxicam, ampiroxicam, celecoxib, rofecoxib etc.) and the like.

(11) Others

Glycation inhibitors (e.g., ALT-711 etc.), nerve regeneration stimulators (e.g., Y-128, VX853, prosaptide etc.), central nervous system acting drugs (e.g., antidepressants such as desipramine, amitriptyline, imipramine, fluoxetine paroxetine, doxepin, carbamazepine etc.), anticonvulsants (e.g., lamotrigine), antiarrhythmics (e.g., mexiletine), acetylcholine receptor ligands (e.g., ABT-594), endothelin receptor-antagonists (e.g., ABT-627), monoamine uptake inhibitors (e.g., tramadol), indoleamine uptake inhibitors (e.g., furoxetine, paroxetine), narcotic analgesics (e.g., morphine), GABA receptor agonists (e.g., gabapentin), GABA uptake inhibitors (e.g., tiagabine), $\alpha_2$ receptor agonists (e.g., clonidine), focal analgesics (e.g., capsaicin), protein kinase C inhibitors (e.g., LY-333531), anxiolytics (e.g., benzodiazepins), phosphodiesterase inhibitors (e.g., sildenafil), dopamine receptor agonists (e.g., apomorphine), anticholinergic agents, $\alpha_1$ receptor blockers (e.g., tamsulosin), muscle relaxants (e.g., baclofen and the like), potassium channel openers (e.g., nicorandil), calcium channel blockers (e.g., nifedipine), prophylactic and/ or therapeutic drug for Alzheimer's disease (e.g., donepezil, rivastigmine, galantamine), therapeutic drug for Parkinsonism (e.g., L-dopa), antithrombotics (e.g., aspirin, cilostazol), NK2 receptor antagonists, therapeutic drug for HIV infection (e.g., saquinavir, zidovudine, lamivudine, nevirapine), therapeutic drug for chronic obstructive pulmonary diseases (e.g., salmeterol, tiotropium bromide, cilomilast) and the like.

For the combined use of the compound of the present invention and the concomitant drug, the timing of the administration of the compound of the present invention and the concomitant drug is not restricted. The compound of the present invention and the concomitant drug can be administered to an administration subject simultaneously, or may be administered at different times. The dose of the concomitant drug may be determined according to the dose clinically used, and can be appropriately selected depending on the administration subject, administration route, disease, combination and the like.

The administration mode of the compound of the present invention and the concomitant drug is not particularly restricted, and it is sufficient if the compound of the present invention and the concomitant drug are combined on administration. Examples of such administration mode include the following:

(1) The compound of the present invention and the concomitant drug are simultaneously produced to give a single preparation which is administered. (2) The compound of the present invention and the concomitant drug are separately produced to give two kinds of preparations which are administered simultaneously by the same administration route. (3) The compound of the present invention and the concomitant drug are separately produced to give two kinds of preparations which are administered by the same administration route only at the different times. (4) The compound of the present invention and the concomitant drug are separately produced to give two kinds of preparations which are administered simultaneously by the different administration routes. (5) The compound of the present invention and the concomitant drug are separately produced to give two kinds of preparations which are administered by the different administration routes only at different times (for example, the compound of the present invention and the concomitant drug are administered in this order, or in the reverse order) and the like. In the following, these administration modes are collectively abbreviated as the concomitant agent of the present invention.

The concomitant agent of the present invention has low toxicity, and for example, the compound of the present invention or (and) the above-mentioned concomitant drug can be mixed, according to a method known per se, with a pharmacologically acceptable carrier to give pharmaceutical compositions, for example, tablets (including a sugar-coated tablet, film-coated tablet), powders, granules, capsules (including a soft capsule), solutions, injections, suppositories, sustained release agents and the like which can be safely administered orally or parenterally (e.g., local, rectum, vein, and the like).

As a pharmacologically acceptable carrier which may be used for preparing the concomitant agent of the present invention, those similar to the ones for the aforementioned pharmaceutical compositions of the present invention can be used.

The compounding ratio of the compound of the present invention to the concomitant drug in the concomitant agent of the present invention can be appropriately selected depending on the administration subject, administration route, diseases and the like.

For example, the content of the compound of the present invention in the concomitant agent of the present invention differs depending on the form of a preparation, and usually in the range from about 0.01 to 100% by weight, preferably from about 0.1 to 50% by weight, further preferably from about 0.5 to 20% by weight, based on the whole preparation.

The content of the concomitant drug in the concomitant agent of the present invention differs depending on the form of the preparation, and is usually in the range from about 0.01 to less than 100% by weight, preferably from about 0.1 to 50% by weight, further preferably from about 0.5 to 20% by weight, based on the whole preparation.

The content of additives such as a carrier and the like in the concomitant agent of the present invention differs depending on the form of a preparation, and usually in the range from about 1 to 99.99% by weight, preferably from about 10 to 90% by weight, based on the whole preparation.

In the case when the compound of the present invention and the concomitant drug are separately prepared respectively, the same contents may be adopted.

The dose of the concomitant agent of the present invention differs depending on the kind of the compound of the present invention, age, body weight, condition, drug form, administration method, administration period and the like, and for example, for one patient suffering from irritable bowel syndrome (adult, body weight: about 60 kg), the combination agent is administered orally, generally at a dose of about 0.01 to about 1000 mg/kg/day, preferably about 0.01 to about 100 mg/kg/day, more preferably about 0.1 to about 100 mg/kg/day, particularly about 0.1 to about 50 mg/kg/day, especially about 1.5 to about 30 mg/kg/day, in terms of the compound of the present invention or the concomitant drug, respectively, once or divided several times in a day. Of course, since the dose as described above varies depending on various conditions, amounts smaller than the above-mentioned dose may sometimes be sufficient, further, amounts over that range sometimes have to be administered.

The amount of the concomitant drug can be set at any value unless its side effects are problematical. The daily dose in terms of the concomitant drug differs depending on the severity, age, sex, body weight, sensitivity difference of the subject, administration period, interval, and nature, pharmacology, kind of the pharmaceutical preparation, kind of effective ingredient, and the like, and not particularly restricted, and the amount of the drug is, in the case of oral administration, for example, usually in the range from about 0.001 to 2000 mg, preferably from about 0.01 to 500 mg, further preferably from about 0.1 to 100 mg, per 1 kg body weight of a mammal and this is usually administered once to 4 portions divided for one day.

For administration of the concomitant agent of the present invention, the compound of the present invention may be administered after administration of the concomitant drug or the concomitant drug may be administered after administration of the compound of the present invention, though they may be administered simultaneously. When administered at a time interval, the interval differs depending on the effective ingredient to be administered, drug form and administration method, and for example, when the concomitant drug is administered first, a method in which the compound of the present invention is administered within time range of from 1 minute to 3 days, preferably from 10 minutes to 1 day, more preferably from 15 minutes to 1 hour after administration of the concomitant drug is exemplified. When the compound of the present invention is administered first, a method in which the concomitant drug is administered within time range of from 1 minute to 1 day, preferably from 10 minutes to 6 hours, more preferably from 15 minutes to 1 hour after administration of the compound of the present invention is exemplified.

EXAMPLES

The present invention is hereinafter described in more detail by means of the following Reference Examples, Examples, Preparation Examples and Experimental Examples, which are not to be construed as limitative.

In the following Reference Examples and Examples, "%" means weight percent, unless otherwise specified.

$^1$H-NMR spectra were measured with tetramethylsilane as an internal standard, using Varian Gemini-200 (200 MHz) spectrometer, Mercury-300 (300 MHz) spectrometer or Bruker AVANCE AV300 (300 MHz) spectrometer. All δ values are shown in ppm.

Other abbreviations used in the specification mean the following.

| | |
|---|---|
| s: | singlet |
| d: | doublet |
| dd: | double doublet |
| t: | triplet |
| q: | quartet |
| m: | multiplet |
| br: | broad |
| J: | coupling constant |
| Hz: | Hertz |
| DMF: | N,N-dimethylformamide |
| CDCl$_3$: | deuterated chloroform |
| DMSO-d$_6$: | dimethyl sulfoxide-d$_6$ |
| Boc: | tert-butoxycarbonyl |
| Cbz: | benzyloxycarbonyl |
| MgSO$_4$: | magnesium sulfate |
| Na$_2$SO$_4$: | sodium sulfate |
| WSC: | 1-ethyl-3-(dimethylaminopropyl)carbodiimide hydrochloride |
| HOBt: | 1-hydroxy-1H-benzotriazole monohydrate |
| DEPC: | diethyl cyanophosphate |
| Dy(OTf)$_3$: | dysprosium triflate |
| TFA: | trifluoroacetic acid |

At room temperature generally means the range of from about 10° C. to 35° C., but it is not particularly limited in a strict sense.

Reference Example 1 tert-Butyl (3aR*,9bR*)-2,3,3a,4,5,5a,9a,9b-octahydro-1H-pyrrolo[3,2-c]quinoline-1-carboxylate

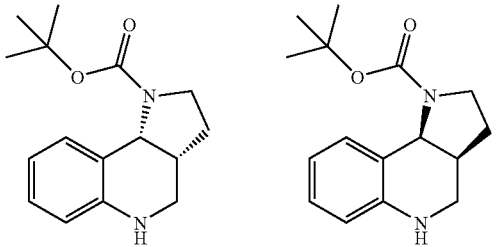

Sodium (1.2 g, 50 mmol) was dissolved in methanol (15 ml), aniline (0.9 g, 10 mmol) was added at room temperature, and the mixture was stirred for 10 min. This mixture was added to a suspension of paraformaldehyde (0.42 g, 14 mmol) in methanol (10 ml), and the mixture was stirred at room temperature for 5 hrs. The reaction mixture was poured into ice water, and the mixture was extracted with diethyl ether. The extract was dried (over anhydrous MgSO$_4$), and the solvent was evaporated under reduced pressure. The residue was dissolved in methanol (20 ml), tert-butyl 2,3-dihydro-1H-pyrrole-1-carboxylate (850 mg, 5 mmol) was added and the mixture was heated under reflux for 18 hrs. The residue was subjected to column chromatography using silica gel (30 g) and eluted with hexane-ethyl acetate (9:1-4:1, v/v) to give the title compound (180 mg, 12%) as an amorphous form.

$^1$H-NMR (CDCl$_3$) δ: 1.48 (9H, d, J=6.1 Hz), 1.76-2.01 (2H, m), 2.23-2.45 (1H, m), 3.13-3.57 (5H, m), 5.09 (1H, dd, J=47.2, 4.0 Hz), 6.54-6.85 (2H, m), 7.10-7.23 (2H, m).

LC/MS (ESI) m/z: 275 (MH$^+$).

Reference Example 2 tert-Butyl (3aR*,4R*,9bR*)-4-phenyl-2,3,3a,4,5,9b-hexahydro-1H-pyrrolo[3,2-c]quinoline-1-carboxylate

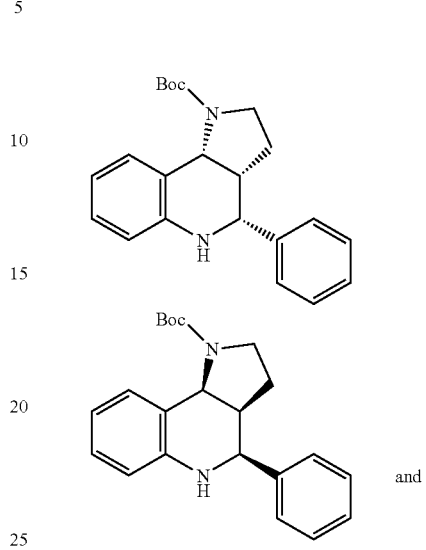

and tert-butyl (3aR*,4S*,9bR*)-4-phenyl-2,3,3a,4,5,9b-hexahydro-1H-pyrrolo[3,2-c]quinoline-1-carboxylate

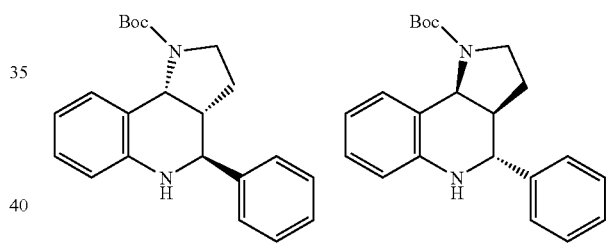

Benzaldehyde (2.92 g, 28 mmol), aniline (2.56 g, 28 mmol), tert-butyl 2,3-dihydro-1H-pyrrole-1-carboxylate (3.4 g, 25 mmol) and Dy(OTf)$_3$ (0.61 g, 1.38 mmol) were stirred in acetonitrile (50 ml) at room temperature for 2 hrs. The reaction mixture was concentrated under reduced pressure, water was added and the mixture was extracted with ethyl acetate. The extract was washed with saturated brine, dried (anhydrous MgSO$_4$), and the solvent was evaporated under reduced pressure. The residue was subjected to column chromatography using silica gel (150 g), and eluted with hexane-ethyl acetate (4:1, v/v). The title compound (3aR*,4R*,9bR*) (2.7 g, 31%) was obtained as an amorphous form from the first eluted fraction.

$^1$H-NMR (CDCl$_3$) δ: 1.42-1.62 (10H, m), 2.08-2.28 (1H, m), 2.52-2.59 (1H, m), 3.32-3.49 (2H, m), 3.92 (1H, m), 4.74 (1H, m), 5.36 (1H, dd, J=42.8, 7.0 Hz), 6.58 (1H, d, J=8.1 Hz), 6.78 (1H, m), 6.98-7.13 (1H, m), 7.23-7.49 (5H, m), 7.55-7.72 (1H, m).

LC/MS (ESI) m/z: 351 (MH$^+$).

The title compound (3aR*,4S*,9bR*) (4.0 g, 46%) was obtained as an amorphous form from the second eluted fraction.

$^1$H-NMR (CDCl$_3$) δ: 1.49 (9H, s), 2.03-2.13 (2H, m), 2.54-2.64 (1H, m), 3.31-3.39 (1H, m), 3.50 (1H, br s), 4.21-

4.24 (1H, m), 4.35-4.38 (1H, m), 4.83 (1H, br s), 6.57 (1H, d, J=7.6 Hz), 6.65-6.79 (1H, m), 7.05-7.34 (6H, m), 7.49 (1H, s).

LC/MS (ESI) m/z: 351 (MH+).

Reference Example 3

1-tert-Butyl 4-ethyl (3aR*,4R*,9bR*)-2,3,3a,4,5,9b-hexahydro-1H-pyrrolo[3,2-c]quinoline-1,4-dicarboxylate

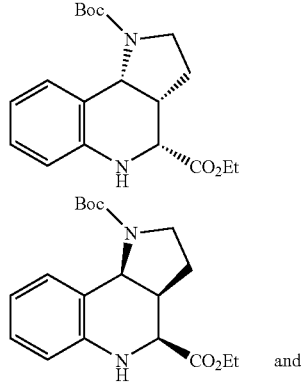

1-tert-butyl 4-ethyl (3aR*,4S*,9bR*)-2,3,3a,4,5,9b-hexahydro-1H-pyrrolo[3,2-c]quinoline-1,4-dicarboxylate

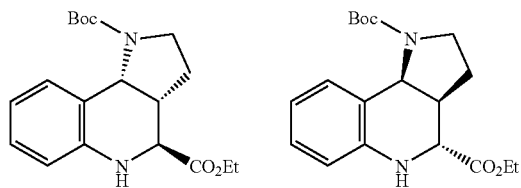

To a solution of ethyl glyoxylate (50% toluene solution, 13.76 g, 67.4 mmol) and aniline (5.6 ml, 61.3 mmol) in toluene (250 ml) was added magnesium sulfate (3.95 g, 32.85 mmol), and the mixture was stirred at 0° C. for 30 min. A solution of tert-butyl 2,3-dihydro-1H-pyrrole-1-carboxylate (10.37 g, 61.3 mmol) in toluene (50 ml) and scandium triflate (1.47 g, 3.0 mmol) were added at 0° C., and the mixture was stirred at room temperature for 16 hrs. Saturated aqueous sodium hydrogen carbonate solution was added, and the mixture was extracted with ethyl acetate. The extract was washed with saturated brine, dried (over anhydrous MgSO4), and the solvent was evaporated under reduced pressure. The residue was subjected to silica gel column chromatography and eluted with hexane-ethyl acetate (4:1-2:1, v/v). The title compound (3aR*,4R*,9bR*) (9.83 g, 46%) was obtained as an oil from the first eluted fraction.

1H-NMR (CDCl3) δ: 1.33 (3H, t, J=7.0 Hz), 1.73-2.10 (2H, m), 2.82-2.99 (1H, m), 3.22-3.64 (2H, m), 4.20-4.38 (4H, m), 5.29 (1H, dd, J=21.2 Hz, 8.0 Hz), 6.57 (1H, d, J=8.0 Hz), 6.72 (1H, t, J=7.8 Hz), 7.04 (1H, t, J=7.8 Hz), 7.55 (1H, dd, J=36.0 Hz, 6.8 Hz).

LC/MS (ESI) m/z: 347 (MH+).

The title compound (3aR*,4S*,9bR*) (6.99 g, 33%) was obtained as an oil from the second eluted fraction.

1H-NMR (CDCl3) δ: 1.23 (3H, t, J=7.4 Hz), 1.52 (9H, s), 2.00-2.17 (2H, m), 2.84-2.99 (1H, m), 3.25-3.63 (2H, m), 3.89 (1H, s), 4.10-4.25 (3H, m), 5.00 (1H, br s), 6.56 (1H, d, J=8.0 Hz), 6.72 (1H, t, J=7.0 Hz), 7.03 (1H, t, J=7.0 Hz), 7.54 (1H, br s).

LC/MS (ESI) m/z: 347 (MH+).

Reference Example 4

Benzyl (3aR*,4R*,9bR*)-4-(4-fluorophenyl)-2,3,3a,4,5,9b-hexahydro-1H-pyrrolo[3,2-c]quinoline-1-carboxylate

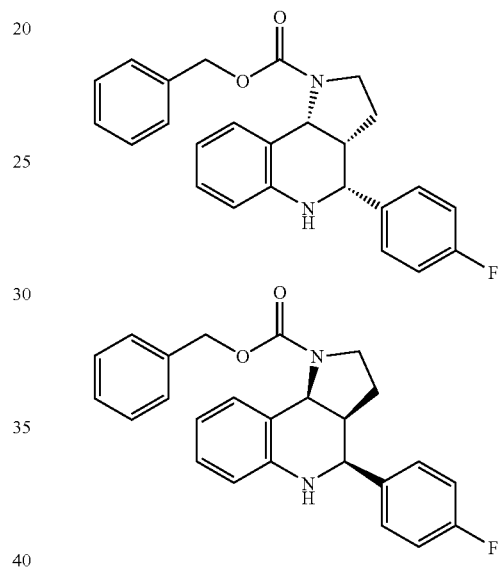

4-Fluorobenzaldehyde (700 mg, 5.6 mmol), aniline (525 mg, 5.6 mmol), N-Cbz-4-aminobutylaldehyde dimethylacetal (1.5 g, 5.6 mmol) and Dy(OTf)3 (170 mg, 0.19 mmol) were stirred at 60° C. for 2 hrs. in acetonitrile (10 ml). The reaction mixture was concentrated under reduced pressure, water was added and the mixture was extracted with ethyl acetate. The extract was washed with saturated brine, dried (over anhydrous MgSO4), and the solvent was evaporated under reduced pressure. The residue was subjected to column chromatography using silica gel (30 g), and eluted with hexane-ethyl acetate (4:1, v/v) to give the title compound (540 mg, 24%) as an amorphous form.

1H-NMR (CDCl3) δ: 1.99-2.34 (1H, m), 2.43-2.61 (1H, m), 3.28-3.54 (2H, m), 3.82-3.94 (1H, m), 4.71 (1H, d, J=2.2 Hz), 5.09-5.54 (3H, m), 6.58 (1H, d, J=7.8 Hz), 6.63-6.82 (1H, m), 7.07 (3H, t, J=8.5 Hz), 7.20-7.76 (9H, m).

LC/MS (ESI) m/z: 403 (MH+).

Using various aldehydes instead of benzaldehyde of Reference Example 2, ethyl glyoxylate of Reference Example 3 and 4-fluorobenzaldehyde of Reference Example 4 as well as various substituted anilines instead of aniline, substituted 2,3,3a,4,5,9b-hexahydro-1H-pyrrolo[3,2-c]quinoline derivatives were synthesized. Synthesized compounds are shown in Table 1

TABLE 1

![structure]

| No. | P | R | X | Y | Z |
|---|---|---|---|---|---|
| 1 | Boc | H | H | H | H |
| 2 | Boc | phenyl | H | H | H |
| 3 | Boc | phenyl | F | H | H |
| 4 | Boc | phenyl | Cl | H | H |
| 5 | Boc | phenyl | Me | H | H |
| 6 | Boc | phenyl | OMe | H | H |
| 7 | Boc | phenyl | CN | H | H |
| 8 | Cbz | phenyl | Bu | H | H |
| 9 | Boc | phenyl | H | F | H |
| 10 | Boc | phenyl | H | Cl | H |
| 11 | Boc | phenyl | H | Me | H |
| 12 | Boc | phenyl | H | OMe | H |
| 13 | Boc | phenyl | H | CN | H |
| 14 | Boc | phenyl | H | H | F |
| 15 | Boc | phenyl | H | H | Cl |
| 16 | Boc | phenyl | H | H | Me |
| 17 | Cbz | 4-fluorophenyl | H | H | H |
| 18 | Boc | 4-fluorophenyl | F | H | H |
| 19 | Cbz | 4-chlorophenyl | H | H | H |
| 20 | Cbz | 4-tolyl | H | H | H |
| 21 | Boc | 4-cyanophenyl | H | H | H |
| 22 | Boc | 4-(methylthio)phenyl | H | H | H |
| 23 | Cbz | 3-chlorophenyl | H | H | H |
| 24 | Cbz | 2-chlorophenyl | H | H | H |
| 25 | Cbz | 1-naphthyl | H | H | H |
| 26 | Boc | 2-furyl | H | H | H |
| 27 | Boc | 3-furyl | H | H | H |
| 28 | Boc | 2-methyl-3-furyl | H | H | H |
| 29 | Boc | 2-thienyl | H | H | H |
| 30 | Boc | 3-thienyl | H | H | H |
| 31 | Cbz | pyridin-2-yl | H | H | H |
| 32 | Cbz | pyridin-3-yl | H | H | H |
| 33 | Cbz | pyridin-4-yl | H | H | H |
| 34 | Boc | 1-Cbz-pyrrol-2-yl | H | H | H |
| 35 | Cbz | 1-Boc-pyrrol-3-yl | H | H | H |
| 36 | Cbz | 1-methylpyrrol-2-yl | H | H | H |
| 37 | Cbz | 1-pivaloyloxymethyl-imidazol-2-yl | H | H | H |
| 38 | Cbz | 1-pivaloyloxymethyl-imidazol-4-yl | H | H | H |
| 39 | Boc | 1,3-thiazol-2-yl | H | H | H |
| 40 | Boc | 1,3-thiazol-5-yl | H | H | H |
| 41 | Boc | 1,3-oxazol-4-yl | H | H | H |
| 42 | Boc | ethyl | H | H | H |
| 43 | Cbz | propyl | H | H | H |
| 44 | Cbz | isopropyl | H | H | H |
| 45 | Boc | cyclopropyl | H | H | H |
| 46 | Cbz | isobutyl | H | H | H |
| 47 | Cbz | tert-butyl | H | H | H |
| 48 | Cbz | butyl | H | H | H |
| 49 | Cbz | hexyl | H | H | H |
| 50 | Boc | benzyloxymethyl | H | H | H |
| 51 | Cbz | (tert-butoxycarbonyl)(methyl)-aminomethyl | H | H | H |
| 52 | Boc | 4-(N-Cbz-piperidinyl) | H | H | H |
| 53 | Cbz | N-Cbz-aminomethyl | H | H | H |
| 54 | Cbz | 2-(N-Cbz-aminoethyl) | H | H | H |
| 55 | Boc | tetrahydro-2H-pyran-4-yl | H | H | H |
| 56 | Cbz | 1-(4-methoxybenzyl)imidazol-2-yl | H | H | H |
| 57 | Cbz | 1-(4-methoxybenzyl)pyrazol-5-yl | H | H | H |
| 58 | Cbz | 1-(trityl)pyrazol-5-yl | H | H | H |
| 59 | Cbz | 1-trityl-1H-1,2,4-triazol-5-yl | H | H | H |
| 60 | Boc | ethoxymethyl | H | H | H |
| 61 | Boc | ethoxycarbonyl | H | H | H |

Reference Example 5 tert-Butyl (3aR*,4R*,9bR*)-4-(hydroxymethyl)-2,3,3a,4,5,9b-hexahydro-1H-pyrrolo[3,2-c]quinoline-1-carboxylate

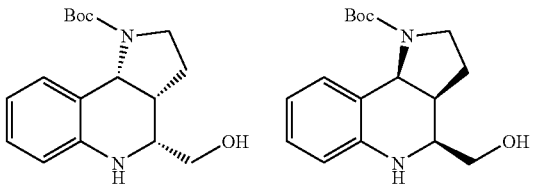

To a solution of calcium chloride (12.5 g, 113.1 mmol) in a mixture of tetrahydrofuran-ethanol (200 ml-200 ml) was added sodium borohydride (8.5 g, 226.2 mmol) at 0° C. and the mixture was stirred for 30 min. A solution of 1-tert-butyl 4-ethyl (3aR*,4R*,9bR*)-2,3,3a,4,5,9b-hexahydro-1H-pyrrolo[3,2-c]quinoline-1,4-dicarboxylate (14.6 g, 46.6 mmol) in tetrahydrofuran (50 ml) was added at 0° C., and the mixture was stirred at room temperature for 16 hrs. Saturated aqueous sodium hydrogen carbonate solution and ethyl acetate were added, and the organic layer was separated, and the aqueous layer was extracted with ethyl acetate. The organic layer was dried (over anhydrous $MgSO_4$) and the solvent was evaporated under reduced pressure. The residue was subjected to silica gel column chromatography and eluted with hexane-ethyl acetate (1:9, v/v) to give the title compound (326 mg, 96%) as an oil.

$^1$H-NMR (CDCl$_3$) δ: 1.53 (9H, d, J=11.8 Hz), 1.67-2.48 (4H, m), 3.22-3.83 (5H, m), 4.17 (1H, br s), 5.21 (1H, dd, J=22.0, 7.8 Hz), 6.53 (1H, d, J=8.2 Hz), 6.71 (1H, t, J=7.2 Hz), 7.03 (1H, t, J=7.2 Hz), 7.55 (1H, dd, J=31.2, 7.0 Hz).

LC/MS (ESI) m/z: 305 (MH$^+$).

Reference Example 6 tert-Butyl (3aR*,4R*,9bR*)-4-(methoxymethyl)-2,3,3a,4,5,9b-hexahydro-1H-pyrrolo[3,2-c]quinoline-1-carboxylate

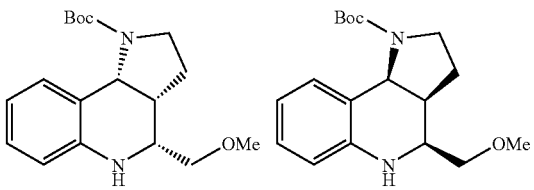

To a solution of the compound (8.34 g, 27.4 mmol) synthesized in Reference Example 5 in tetrahydrofuran (250 ml) was added sodium hydride (60% in oil, 1.21 g, 32.8 mmol) under a nitrogen atmosphere at 0° C., and the mixture was stirred for 30 min. Methyl iodide (2.04 ml, 32.8 mmol) was added, and the mixture was stirred at room temperature for 16 hrs. Water was added and the mixture was extracted with ethyl acetate, dried (over anhydrous $MgSO_4$), and the solvent was evaporated under reduced pressure. The residue was subjected to silica gel column chromatography and eluted with hexane-ethyl acetate (1:2, v/v) to give the title compound (8.11 g, 93%) as a pale-yellow oil.

¹H-NMR (CDCl₃) δ: 1.53 (9H, d, J=11.4 Hz), 1.66-2.09 (2H, m), 2.28-2.47 (1H, m), 3.24-3.55 (4H, m), 3.41 (3H, s), 3.70-3.82 (1H, m), 4.10-4.22 (1H, m), 5.21 (1H, dd, J=22.2, 7.6 Hz), 6.51 (1H, d, J=8.0 Hz), 6.71 (1H, t, J=7.4 Hz), 7.02 (1H, t, J=7.4 Hz), 7.55 (1H, dd, J=34.0 and 7.4 Hz).

LC/MS (ESI) m/z: 319 (MH⁺).

Reference Example 7

(3aR*,9bR*)-2,3,3a,4,5,9b-Hexahydro-1H-pyrrolo[3,2-c]quinoline

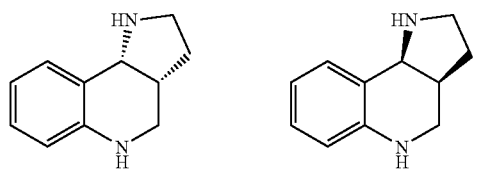

The compound (160 mg, 0.58 mmol) synthesized in Reference Example 1 was dissolved in ethyl acetate (5 ml), a 4N hydrogen chloride in ethyl acetate solution (5 ml) was added and the mixture was stirred for 3 hrs. Insoluble materials were separated by decantation, suspended in ethyl acetate and a saturated aqueous sodium hydrogen carbonate solution was added. This was extracted with ethyl acetate. The extract was dried (over anhydrous MgSO₄), and the solvent was evaporated. The residue was dried under reduced pressure to give the title compound (70 mg, 69%) as an amorphous form.

¹H-NMR (CDCl₃) δ: 1.57-1.72 (1H, m), 2.08-2.24 (1H, m), 2.36-2.59 (1H, m), 2.84 (1H, t, J=11.1 Hz), 2.91-3.01 (1H, m), 3.08-3.20 (2H, m), 3.55-3.77 (1H, m), 3.95-4.09 (2H, m), 6.56-6.80 (2H, m), 7.02-7.42 (2H, m).

LC/MS (ESI) m/z: 175 (MH⁺).

Reference Example 8

(3aS*,4R*,9bR*)-4-Phenyl-2,3,3a,4,5,9b-hexahydro-1H-pyrrolo[3,2-c]quinoline dihydrochloride

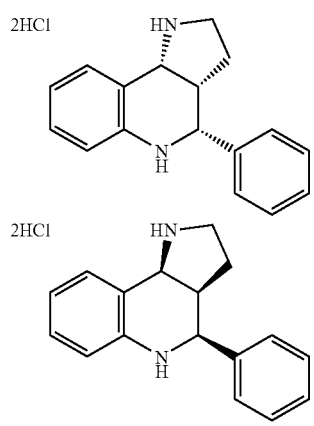

tert-Butyl (3aR*,4R*,9bR)-4-phenyl-2,3,3a,4,5,9b-hexahydro-1H-pyrrolo[3,2-c]quinoline-1-carboxylate (2.65 g, 7.56 mmol) was dissolved in ethyl acetate (10 ml), and a 4N hydrogen chloride in ethyl acetate solution (20 ml) was added, and the mixture was stirred at room temperature for 12 hrs. The precipitated crystals were collected by filtration, washed with ethyl acetate, and dried under reduced pressure to give the title compound (2.60 g, 77%).

¹H-NMR (DMSO-d₆) δ: 1.33-1.45 (1H, m), 1.88-2.04 (1H, m), 2.81-2.92 (1H, m), 2.96-3.11 (2H, m), 4.59 (1H, d, J=2.4 Hz), 4.98-5.46 (3H, m), 6.76 (1H, t, J=7.1 Hz), 6.86 (1H, d, J=8.1 Hz), 7.12 (1H, t, J=7.1 Hz), 7.32 (2H, dd, J=17.9, 7.4 Hz), 7.38-7.49 (4H, m), 8.55 (1H, br s), 10.33 (1H, br s).

LC/MS (ESI) m/z: 251 (MH⁺).

Reference Example 9

(3aS*,4R*,9bR*)-4-(4-Fluorophenyl)-2,3,3a,4,5,9b-hexahydro-1H-pyrrolo[3,2-c]quinoline

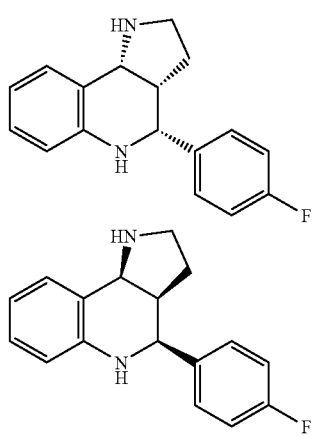

A mixture of benzyl (3aR*,4R*,9bR*)-4-(4-fluorophenyl)-2,3,3a,4,5,9b-hexahydro-1H-pyrrolo[3,2-c]quinoline-1-carboxylate (500 mg, 1.24 mmol) and 10% palladium on carbon (50% aqueous, 0.3 g) in ethanol (20 ml) was stirred at room temperature under hydrogen atmosphere for 2 hrs. The catalyst was filtered off, and the mixture was washed with ethanol. The solvent was evaporated under reduced pressure to give the title compound (350 mg, ca. 100%) as an oil.

¹H-NMR (CDCl₃) δ: 1.34-1.44 (1H, m), 1.84-1.98 (1H, m), 2.51-2.70 (1H, m), 2.72-2.82 (1H, m), 2.86-2.97 (1H, m), 3.76 (1H, s), 4.52 (1H, d, J=8.1 Hz), 4.62 (1H, d, J=3.2 Hz), 6.53-6.70 (1H, m), 6.78-6.84 (1H, m), 6.97-7.12 (3H, m), 7.21-7.30 (2H, m), 7.37-7.46 (2H, m).

LC/MS (ESI) m/z: 269 (MH⁺)

Reference Example 10

(3aS*,4R*,9bR*)-4-(2,3,3a,4,5,9b-Hexahydro-1H-pyrrolo[3,2-c]quinoline-4-yl)benzonitrile ditrifluoroacetate

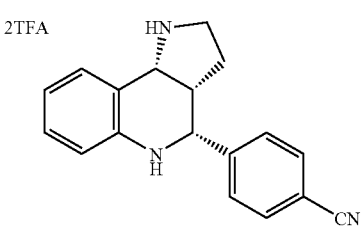

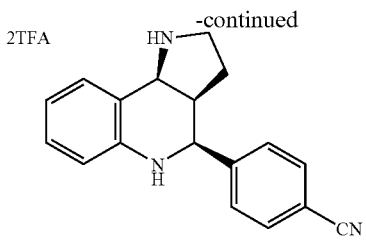

tert-Butyl (3aR*,4R*,9bR*)-4-(2,3,3a,4,5,9b-hexahydro-1H-pyrrolo[3,2-c]quinoline-1-carboxylate (670 mg, 1.78 mmol) was dissolved in chloroform (1 ml), trifluoroacetic acid (1.0 ml) was added and the mixture was stirred at room temperature for 1 hr. The reaction mixture was concentrated under reduced pressure, the residue was suspended in chloroform and the solvent was evaporated again. The residue was washed with ether, and dried under reduced pressure to give the title compound (710 mg, 79%) as colorless crystals.

$^1$H-NMR (DMSO-$d_6$) δ: 1.29-1.45 (1H, m), 1.81-2.02 (1H, m), 2.81-3.20 (3H, m), 4.69 (1H, d, J=3.2 Hz), 4.97-5.13 (1H, m), 6.29 (1H, br s), 6.65 (1H, br s), 6.71-6.94 (2H, m), 7.10-7.33 (1H, m), 7.59-8.10 (5H, m), 8.54 (1H, br s), 9.70 (1H, br s).

LC/MS (ESI) m/z: 276 (MH$^+$).

Reference Example 11

(3aS*,4R*,9bR*)-4-(4-Chlorophenyl)-2,3,3a,4,5,9b-hexahydro-1H-pyrrolo[3,2-c]quinoline dihydrochloride

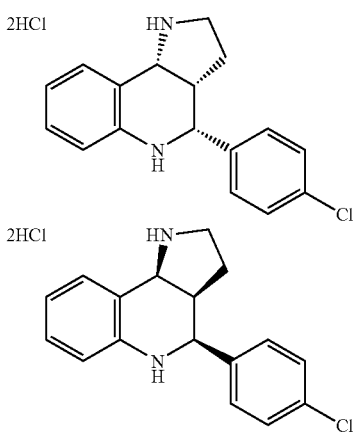

To a mixture of benzyl (3aR*,4R*,9bR*)-4-(4-chlorophenyl)-2,3,3a,4,5,9b-hexahydro-1H-pyrrolo[3,2-c]quinoline-1-carboxylate (730 mg, 1.75 mmol) and 10% palladium on carbon (50% aqueous, 0.3 g) in ethanol (10 ml) was added a hydrogen chloride in methanol solution (1 ml) and the mixture was stirred at room temperature under hydrogen atmosphere for 3 hrs. The reaction mixture was filtered, washed with aqueous methanol, and the filtrate was concentrated. The residue was dried under reduced pressure to give the crude title compound as an oil. (350 mg, ca. 100%)

$^1$H-NMR (CDCl$_3$) δ: 1.28-1.48 (1H, m), 1.86-2.03 (1H, m), 2.79-2.93 (1H, m), 2.95-3.20 (2H, m), 4.18 (1H, br s), 4.61 (1H, s), 5.02 (1H, s), 6.22 (1H, br s), 6.76 (1H, t, J=7.4 Hz), 6.85 (1H, d, J=8.1 Hz), 7.12 (1H, t, J=7.4 Hz), 7.32 (1H, d, J=7.6 Hz), 7.38-7.75 (4H, m), 8.59 (1H, br s), 10.6 (1H, br s).

LC/MS (ESI) m/z: 285 (MH$^+$).

In the same manner as described in Reference Example 7 to Reference Example 11, Cbz group and Boc group were removed from the compounds of Reference Example 6 and Table 1, respectively. The synthesized compounds are shown in Table 2.

TABLE 2

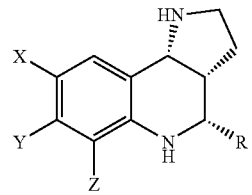

| No. | R | X | Y | Z | salt |
|---|---|---|---|---|---|
| 1 | H | H | H | H | — |
| 2 | phenyl | H | H | H | 2HCl |
| 3 | phenyl | F | H | H | 2HCl |
| 4 | phenyl | Cl | H | H | 2HCl |
| 5 | phenyl | Me | H | H | 2HCl |
| 6 | phenyl | OMe | H | H | 2HCl |
| 7 | phenyl | CN | H | H | 2HCl |
| 8 | phenyl | Bu | H | H | 2HCl |
| 9 | phenyl | H | F | H | 2HCl |
| 10 | phenyl | H | Cl | H | 2HCl |
| 11 | phenyl | H | Me | H | 2HCl |
| 12 | phenyl | H | OMe | H | 2HCl |
| 13 | phenyl | H | CN | H | — |
| 14 | phenyl | H | H | F | 2HCl |
| 15 | phenyl | H | H | Cl | 2HCl |
| 16 | phenyl | H | H | Me | 2HCl |
| 17 | 4-fluorophenyl | H | H | H | — |
| 18 | 4-fluorophenyl | F | H | H | 2HCl |
| 19 | 4-chlorophenyl | H | H | H | 2HCl |
| 20 | 4-tolyl | H | H | H | — |
| 21 | 4-cyanophenyl | H | H | H | 2TFA |
| 22 | 4-(methylthio)phenyl | H | H | H | 2HCl |
| 23 | 3-chlorophenyl | H | H | H | 2HCl |
| 24 | 2-chlorophenyl | H | H | H | 2HCl |
| 25 | 1-naphthyl | H | H | H | — |
| 26 | 2-furyl | H | H | H | 2TFA |
| 27 | 3-furyl | H | H | H | 2TFA |
| 28 | 2-methyl-3-furyl | H | H | H | 2HCl |
| 29 | 2-thienyl | H | H | H | 2TFA |
| 30 | 3-thienyl | H | H | H | 2TFA |
| 31 | pyridin-2-yl | H | H | H | — |
| 32 | pyridin-3-yl | H | H | H | 3TFA |
| 33 | pyridin-4-yl | H | H | H | — |
| 34 | 1-Cbz-pyrrol-2-yl | H | H | H | 2TFA |
| 35 | 1-Boc-pyrrol-3-yl | H | H | H | — |
| 36 | 1-methylpyrrol-2-yl | H | H | H | — |
| 37 | 1-pivaloyloxymethyl-imidazol-2-yl | H | H | H | 2HCl |
| 38 | 1-pivaloyloxymethyl-imidazol-4-yl | H | H | H | — |
| 39 | 1,3-thiazol-2-yl | H | H | H | 2TFA |
| 40 | 1,3-thiazol-5-yl | H | H | H | 2HCl |
| 41 | 1,3-oxazol-4-yl | H | H | H | 2HCl |
| 42 | ethyl | H | H | H | 2HCl |
| 43 | propyl | H | H | H | — |
| 44 | isopropyl | H | H | H | — |
| 45 | cyclopropyl | H | H | H | 2HCl |
| 46 | isobutyl | H | H | H | — |
| 47 | tert-butyl | H | H | H | — |
| 48 | butyl | H | H | H | — |
| 49 | hexyl | H | H | H | — |
| 50 | benzyloxymethyl | H | H | H | 2HCl |
| 51 | (tert-butoxycarbonyl)(methyl)-aminomethyl | H | H | H | — |
| 52 | 4-(N-Cbz-piperidinyl) | H | H | H | 2HCl |
| 53 | N-Cbz-aminomethyl | H | H | H | 2HCl |
| 54 | 2-(N-Cbz-aminoethyl) | H | H | H | 2HCl |

TABLE 2-continued

| No. | R | X | Y | Z | salt |
|---|---|---|---|---|---|
| 55 | tetrahydro-2H-pyran-4-yl | H | H | H | 2HCl |
| 56 | 1-(4-methoxybenzyl)imidazol-2-yl | H | H | H | — |
| 57 | 1-(4-methoxybenzyl)pyrazol-5-yl | H | H | H | — |
| 58 | 1-(trityl)pyrazol-5-yl | H | H | H | — |
| 59 | 1-trityl-1H-1,2,4-triazol-5-yl | H | H | H | — |
| 60 | ethoxymethyl | H | H | H | 2HCl |
| 61 | methoxymethyl | H | H | H | 2HCl |

Reference Example 12 cis-3-(Methoxycarbonyl)bicyclo[2.2.2]oct-5-ene-2-carboxylic acid

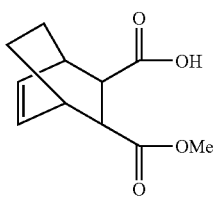

3a,4,7,7a-Tetrahydro-4,7-ethano-2-benzofuran-1,3-dione (10.2 g, 57.2 mmol) was suspended in methanol (70 ml), and the suspension was heated under reflux for 12 hrs. The solvent was evaporated under reduced pressure to give the title compound (11.6 g, 97%) as crystals.

$^1$H-NMR (CDCl$_3$) δ: 1.27-1.38 (2H, m), 1.47-1.64 (2H, m), 2.89-3.27 (4H, m), 3.59 (3H, s), 6.26-6.41 (2H, m).

Reference Example 13

Methyl cis-3-{[(benzyloxy)carbonyl]amino}bicyclo[2.2.2]oct-5-ene-2-carboxylate

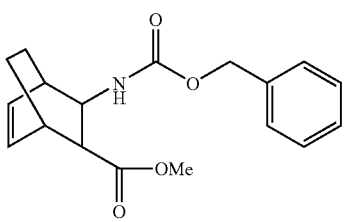

The compound (10.5 g, 50.2 mmol) synthesized in Reference Example 12 was dissolved in dichloromethane (150 ml), triethylamine (5.3 g, 52.7 mmol) and ethyl chlorocarbonate (5.7 g, 52.7 mmol) were added at −10° C. and the mixture was stirred at the same temperature for 20 min. To this mixture was added a mixture of sodium azide (6.5 g, 100 mmol), tetrabutyl ammonium sulfate (3.4 g, 10 mmol) and water (50 ml), and the mixture was stirred at 5° C. for 3 hrs. Water was added to the reaction mixture, and the mixture was extracted with chloroform. The extract was washed with water, dried (over anhydrous Na$_2$SO$_4$) and the solvent was evaporated under reduced pressure to give methyl cis-3-(azidecarbonyl)bicyclo[2.2.2]oct-5-ene-2-carboxylate.

This product (50 mmol) was dissolved in 1,2-dichloroethane (150 ml), p-toluenesulfonic acid hydrate (catalytic amount) was added, and the mixture was heated under reflux for 1.5 hrs. To the reaction mixture were added benzyl alcohol (16.2 g, 150 mmol) and (acetyloxy)(tributyl)stannane (175 mg, 0.5 mmol) and the mixture was heated under reflux for 12 hrs. The solvent was evaporated under reduced pressure. The residue was subjected to column chromatography using silica gel (100 g) and eluted with hexane-ethyl acetate (3:1, v/v) to give the title compound (7.7 g, 46%) as crystals from the first eluted fraction.

$^1$H-NMR (CDCl$_3$) δ: 1.13-1.62 (6H, m), 2.69-2.80 (1H, m), 3.04 (1H, d, J=9.8 Hz), 3.45 (3H, s), 4.29-4.41 (1H, m), 4.96-5.13 (2H, m), 6.16 (1H, t, J=7.2 Hz), 6.54 (1H, t, J=7.2 Hz), 7.29-7.39 (5H, m)

Reference Example 14

Methyl cis-3-aminobicyclo[2.2.2]octane-2-carboxylate

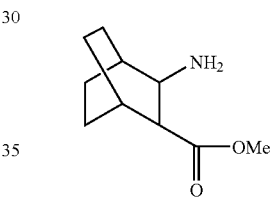

The compound (3.8 g, 11.5 mmol) synthesized in Reference Example 13 was dissolved in methanol (50 ml), and the mixture was stirred in the presence of 10% palladium on carbon (50% aqueous, 1.0 g) at room temperature under hydrogen atmosphere for 12 hrs. The catalyst was filtered off, and the residue was washed with methanol. The filtrate was concentrated under reduced pressure to give the title compound (2.35 g, ca. 100%) as an oil.

$^1$H-NMR (CDCl$_3$) δ: 1.23-2.03 (10H, m), 2.75-2.77 (1H, m), 3.34 (1H, dd, J=9.6, 3.5 Hz), 3.71 (s, 3H).

Reference Example 15

Methyl cis-3-[(tert-butoxycarbonyl)amino]bicyclo[2.2.2]octane-2-carboxylate

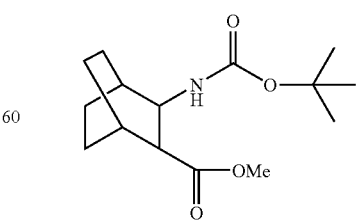

The compound (2.1 g, 11.5 mmol) synthesized in Reference Example 14 was suspended in dichloromethane (400 ml), di-tert-butyl dicarbonate (41.6 g, 19.1 mmol) was added and the mixture was stirred for 2 hrs. Water was added to the reaction mixture, and separated aqueous layer was extracted with chloroform. The organic layers were combined, dried (over anhydrous $Na_2SO_4$), and the solvent was evaporated under reduced pressure. The residue was subjected to column chromatography using silica gel (100 g) and eluted with hexane-ethyl acetate (1:1, v/v) to give the title compound (2.7 g, 83%) as an amorphous form.

$^1$H-NMR (CDCl$_3$) δ: 1.35-1.92 (19H, m), 2.96 (1H, d, J=10.3 Hz), 3.66-3.67 (3H, m), 4.02-4.10 (1H, m), 5.72 (1H, d, J=9.3 Hz).

Reference Example 16 cis 3-[(tert-Butoxycarbonyl)amino]bicyclo[2.2.2]octane-2-carboxylic acid

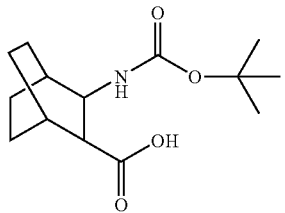

A mixture of the compound (5.7 g, 19.5 mmol) synthesized in Reference Example 15, methanol (5 ml) and 1N aqueous sodium hydroxide solution (5 ml) was stirred at room temperature for 1 hr. 1N Aqueous sodium hydroxide solution (5 ml) was added to the reaction mixture, and the mixture was further stirred for 1 hr, and neutralized with 1N hydrochloric acid. The obtained crystals were collected by filtration, washed with water, and dried under reduced pressure to give the title compound (5.2 g, 94%).

$^1$H-NMR (CDCl$_3$) δ: 1.34-2.33 (18H, m), 2.81-3.08 (1H, m), 4.05-4.17 (1H, m), 5.78-5.85 (1H, m), 7.01-7.10 (1H, m).

Reference Example 17 tert-Butyl {(2R*,3S*)-3-[(3aR*,4R*,9bR*)-(4-phenyl-2,3,3a,4,5,9b-hexahydro-1H-pyrrolo[3,2-c]quinoline-1-yl)carbonyl]bicyclo[2.2.2]oct-2-yl}carbamate

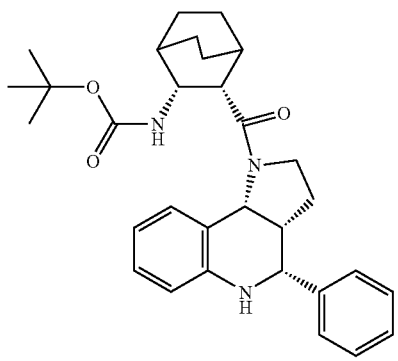

To a mixture of the compound (500 mg, 2.0 mmol) synthesized in Reference Example 8, the compound (566 mg, 2.0 mmol) synthesized in Reference Example 16, triethylamine (0.61 ml, 4.4 mmol), acetonitrile (10 ml) and tetrahydrofuran (10 ml) was added dropwise DEPC (359 mg, 2.2 mmol) under ice-cooling, and the mixture was stirred at the same temperature for 15 min. and at room temperature for 1 hr. To the reaction mixture was added saturated aqueous sodium hydrogen carbonate solution and the mixture was extracted with ethyl acetate. The extract was washed with saturated brine, dried (over anhydrous Na$_2$ SO$_4$), and the solvent was evaporated under reduced pressure. The residue was subjected to column chromatography using silica gel (30 g), and eluted with hexane-ethyl acetate (6:1-2:1, v/v) to give the title compound (750 mg, 75%) as an amorphous form.

LC/MS (ESI) m/z: 502 (MH$^+$).

Reference Example 18

(2R*,3S*)-3-[(3aR*,4R*,9bR*)-(4-Phenyl-2,3,3a,4,5,9b-hexahydro-1H-pyrrolo[3,2-c]quinolin-1-yl)carbonyl]bicyclo[2.2.2]octane-2-amine hydrochloride

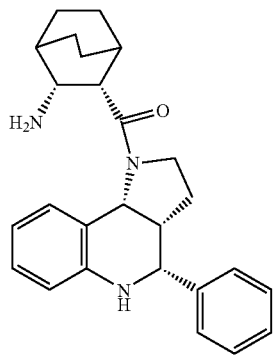

The compound (730 mg, 1.46 mmol) synthesized in Reference Example 17 was dissolved in ethyl acetate (5 ml), a 4N hydrogen chloride in ethyl acetate solution (5 ml) was added and the mixture was stirred for 3 hrs. The obtained crystals were collected by filtration, washed with ethyl acetate, and dried to give the title compound (630 mg, 92%).

LC/MS (ESI) m/z: 402 (MH$^+$).

Reference Example 19 tert-Butyl (1R,2S)-2-{[(3aR,4R,9bR)-4-phenyl-2,3,3a,4,5,9b-hexahydro-1H-pyrrolo[3,2-c]quinolin-1-yl]carbonyl}cyclohexylcarbomate

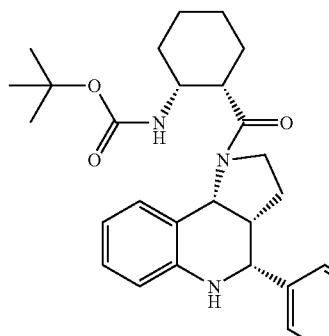

and tert-butyl-(1R,2S)-2-{[(3aS,4S,9bS)-4-phenyl-2,3,3a,
4,5,9b-hexahydro-1H-pyrrolo[3,2-c]quinolin-1-yl]
carbonyl}cyclohexylcarbamate

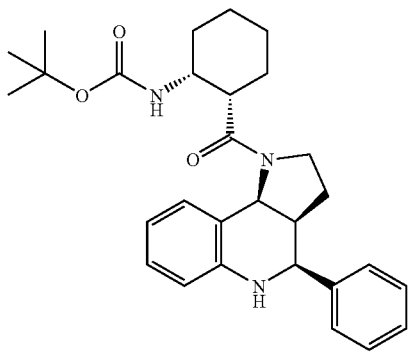

To a solution of the compound (13 g, 40.2 mmol) synthesized in Reference Example 8 and (1S,2R)-2-[(tert-butoxycarbonyl)amino]cyclohexanecarboxylic acid (11.7 g, 48.2 mmol) in DMF (200 ml) were added dropwise triethylamine (16.9 ml, 121 mmol) at 0° C. and subsequently a solution of DEPC (6.74 ml, 40.2 mmol) in DMF (40 ml). The mixture was stirred at the same temperature for 30 min., saturated aqueous sodium hydrogen carbonate solution was added, and the mixture was extracted twice with ethyl acetate. The extract was washed with saturated brine and dried (over anhydrous MgSO4). After concentration under reduced pressure, the obtained residue was subjected to column chromatography using silica gel, and eluted with hexane-ethyl acetate (10:1-1:1, v/v). tert-Butyl (1R,2S)-2-{[(3aR,4R,9bR)-4-phenyl-2,3,3a,4,5,9b-hexahydro-1H-pyrrolo[3,2-c]quinolin-1-yl]carbonyl}cyclohexylcarbamate (9.57 g, 50%) was obtained as a colorless amorphous form from the first object eluted fraction.

LC/MS (ESI) m/z: 476 (MH+).

tert-Butyl (1R,2S)-2-{[(3aS,4S,9bS)-4-phenyl-2,3,3a,4,5,9b-hexahydro-1H-pyrrolo[3,2-c]quinolin-1-yl]carbonyl}cyclohexylcarbamate (9.53 g, 50%) was obtained as a colorless amorphous form from the second object eluted fraction.

LC/MS (ESI) m/z: 476 (MH+).

In the same manner as in Reference Example 19, the compounds in Table 3 were synthesized using the compounds of Table 2.

TABLE 3

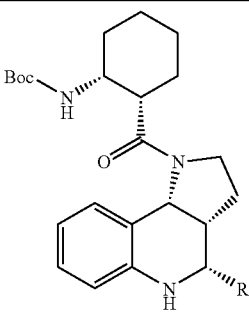

| No. | R |
|---|---|
| 1 | phenyl |
| 2 | 3-thienyl |

TABLE 3-continued

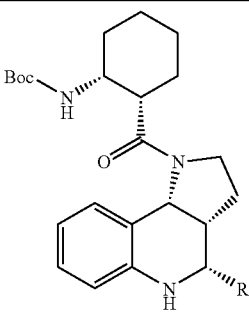

| No. | R |
|---|---|
| 3 | 1-propyl |
| 4 | cyclopropyl |
| 5 | methoxypropyl |
| 6 | 1,3-oxazol-4-yl |
| 7 | 2-methyl-3-furyl |
| 8 | 1,3-thiazol-5-yl |
| 9 | Ethoxymethyl |
| 10 | 1-Cbz-pyrrol-2-yl |
| 11 | tetrahydro-2H-pyran-4-yl |

Reference Example 20

{2-[(3aR*,4R*,9bR*)-1-((1S,2R)-2-[(tert-Butoxycarbonyl)amino]cyclohexyl}carbonyl)-2,3,3a,4,5,9b-hexahydro-1H-pyrrolo[3,2-c]quinolin-4-yl]-1H-imidazol-1-yl}methyl pivalate

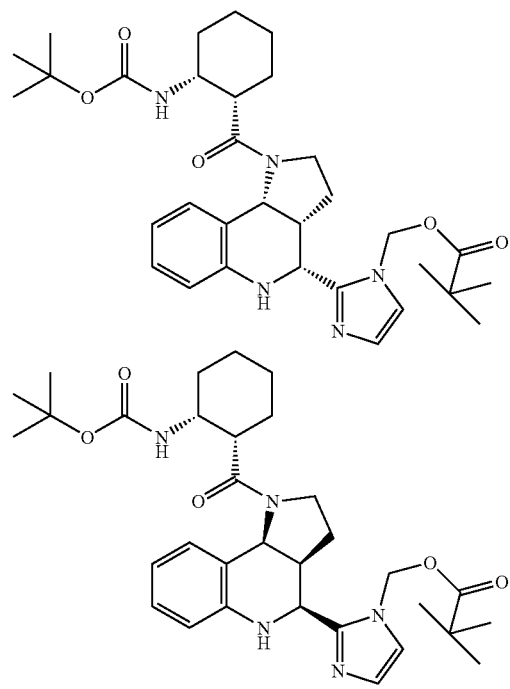

In the same manner as in Reference Example 19 and using {2-[(3aS*,4R*,9bR*)-2,3,3a,4,5,9b-hexahydro-1H-pyrrolo[3,2-c]quinolin-4-yl]-1H-imidazol-1-yl}methyl pivalate dihydrochloride in Table 2, the title compound was obtained.
LC/MS (ESI) m/z: 580 (MH+).

Reference Example 21 tert-Butyl ((1R,2S)-2-{[(3aR,4R,9bR)-4-(1H-imidazol-2-yl)-2,3,3a,4,5,9b-hexahydro-1H-pyrrolo[3,2-c]quinolin-1-yl]carbonyl}cyclohexyl)carbamate

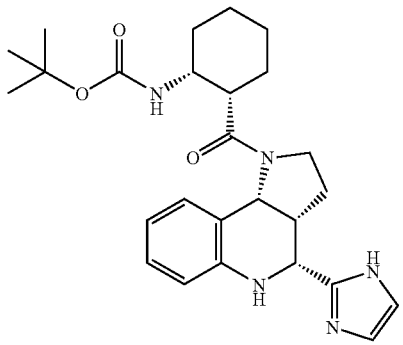

and tert-butyl ((1R,2S)-2-{[(3aS,4S,9bS)-4-(1H-imidazol-2-yl)-2,3,3a,4,5,9b-hexahydro-1H-pyrrolo[3,2-c]quinolin-1-yl]carbonyl}cyclohexyl)carbamate

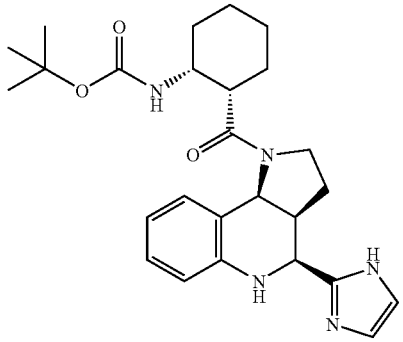

To a solution of the compound (5.81 g, 10 mmol) synthesized in Reference Example 20 in methanol (150 ml) was added 25% aqueous ammonia (120 ml) and the mixture was stirred for 4 hrs. The solvent was evaporated, the obtained residue was subjected to column chromatography using silica gel, and eluted with ethyl acetate-methanol (1:0-9:1, v/v). tert-Butyl ((1R,2S)-2-{[(3aR,4R,9bR)-4-(1H-imidazol-2-yl)-2,3,3a,4,5,9b-hexahydro-1H-pyrrolo[3,2-c]quinolin-1-yl]carbonyl}cyclohexyl)carbamate (2.00 g, 43%) was obtained as a colorless amorphous form from the first fraction.

LC/MS (ESI) m/z: 466 (MH$^+$).

tert-Butyl ((1R,2S)-2-{[(3aS,4S,9bS)-4-(1H-imidazol-2-yl)-2,3,3a,4,5,9b-hexahydro-1H-pyrrolo[3,2-c]quinolin-1-yl]carbonyl}cyclohexyl)carbamate (2.11 g, 45%) was obtained as a colorless amorphous form from the second eluted fraction.

LC/MS (ESI) m/z: 466 (MH$^+$).

Reference Example 22

{2-[(3aR,4R,9bR)-1-({(1S,2R)-2-[(tert-Butoxycarbonyl)amino]cyclohexyl}carbonyl)-2,3,3a,4,5,9b-hexahydro-1H-pyrrolo[3,2-c]quinolin-4-yl]-1H-imidazol-1-yl}methyl pivalate

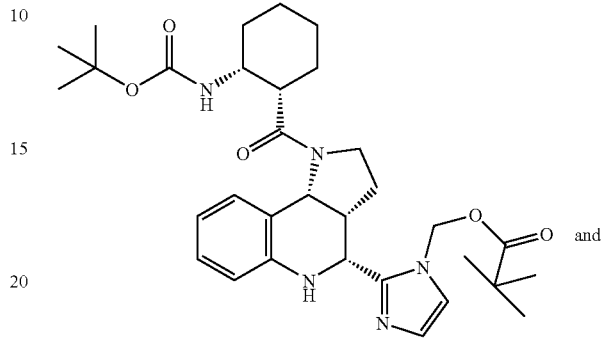

and

{2-[(3aS,4S,9bS)-1-({(1S,2R)-2-[(tert-butoxycarbonyl)amino]cyclohexyl}carbonyl)-2,3,3a,4,5,9b-hexahydro-1H-pyrrolo[3,2-c]quinolin-4-yl]-1H-imidazol-1-yl}methyl pivalate

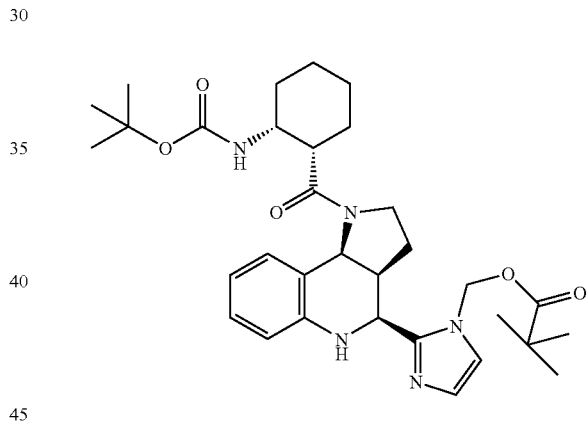

To a solution of the compound (3aR,4R,9bR) (2.42 g, 5.19 mmol) synthesized in Reference Example 21 in DMF (50 ml) was added sodium hydride (60% in oil, 0.27 g, 6.75 mmol) under ice-cooling, and the mixture was stirred at room temperature for 1 hr. Chloromethyl pivalate (0.98 ml, 6.75 mmol) was added dropwise under ice-cooling, and the mixture was stirred at room temperature for 2 hrs. The solvent was evaporated, and the obtained residue was diluted with ethyl acetate, washed with water and saturated brine and dried (over anhydrous MgSO$_4$). After concentration under reduced pressure, the obtained residue was subjected to silica gel column chromatography and eluted with hexane-ethyl acetate (1:1-0:1, v/v). The title compound (2.51 g, 83%) was obtained as a colorless amorphous form from the object fraction.

LC/MS (ESI) m/z: 580 (MH$^+$).

In the same manner and using the compound (3aS,4S,9bS) synthesized in Reference Example 21, {2-[(3aS,4S,9bS)-1-({(1S,2R)-2-[(tert-butoxycarbonyl)amino]cyclohexyl}carbonyl)-2,3,3a,4,5,9b-hexahydro-1H-pyrrolo[3,2-c]quinolin-4-yl]-1H-imidazol-1-yl}methyl pivalate was synthesized.

LC/MS (ESI) m/z: 580 (MH$^+$).

Reference Example 23

(1R,2S)-2-{[(3aR,4R,9bR)-4-Phenyl-2,3,3a,4,5,9b-hexahydro-1H-pyrrolo[3,2-c]quinolin-1-yl]carbonyl}cyclohexylamine dihydrochloride

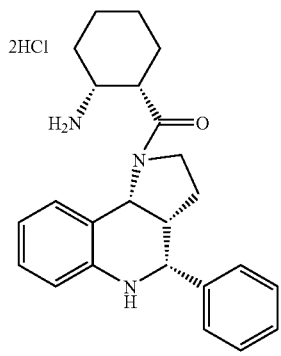

A mixture of tert-butyl (1R,2S)-2-{[(3aR,4R,9bR)-4-phenyl-2,3,3a,4,5,9b-hexahydro-1H-pyrrolo[3,2-c]quinolin-1-yl]carbonyl}cyclohexylcarbamate (2.71 g, 5.7 mmol), a 4N hydrogen chloride in ethyl acetate solution (10 ml) and methanol (30 ml) was stirred overnight at room temperature. The reaction mixture was concentrated under reduced pressure, and the residue was crystallized from ethyl acetate to give the title compound (2.29 g, 90%) as a colorless powder. LC/MS (ESI) m/z: 375 (MH$^+$).

In the same manner as in Reference Example 23 and using the compounds synthesized in Reference Example 22 and compounds on Table 3, the compounds on Table 4 and Table 5 were synthesized.

TABLE 4

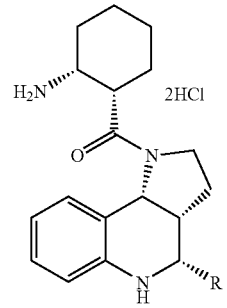

| No. | R |
|-----|---|
| 1 | phenyl |
| 2 | 3-thienyl |
| 3 | 1-pivaloyloxymethyl-imidazol-2-yl |
| 4 | 1-propyl |
| 5 | Cyclopropyl |
| 6 | Methoxymethyl |
| 7 | 1,3-oxazol-4-yl |
| 8 | 2-methyl-3-furyl |
| 9 | 1,3-thiazol-5-yl |
| 10 | ethoxymethyl |
| 11 | 1-Cbz-pyrrol-2-yl |
| 12 | tetrahydro-2H-pyran-4-yl |

TABLE 5

| No. | R |
|-----|---|
| 1 | phenyl |
| 2 | 3-thienyl |
| 3 | 1-pivaloyloxymethyl-imidazol-2-yl |
| 4 | 1-propyl |
| 5 | Cyclopropyl |
| 6 | Methoxymethyl |
| 7 | 1,3-oxazol-4-yl |
| 8 | 2-methyl-3-furyl |
| 9 | 1,3-thiazol-5-yl |
| 10 | Ethoxymethyl |
| 11 | 1-Cbz-pyrrol-2-yl |
| 12 | tetrahydro-2H-pyran-4-yl |

Reference Example 24 tert-Butyl (3aR*,4S*,9bR*)-3a-methyl-4-phenyl-2,3,3a,4,5,9b-hexahydro-1H-pyrrolo[3,2-c]quinoline-1-carboxylate (endo form)

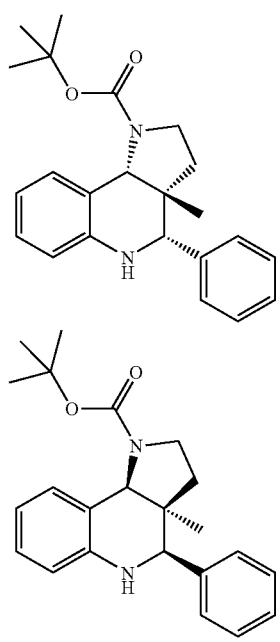

To a mixture of benzaldehyde (425 mg, 4.0 mmol), aniline (372 mg, 4.0 mmol) and acetonitrile (8 ml) were added N-Boc-3-methyldihydropyrrole (732 mg, 4.0 mmol) and Dy(OTf)$_3$ (122 mg, 0.19 mmol) under ice-cooling, and the mixture was stirred at the same temperature for 30 min., and at room temperature for 1 hr. The reaction mixture was concentrated under reduced pressure, water was added and the mixture was extracted with ethyl acetate. The extract was washed with saturated brine, dried (over anhydrous MgSO₄), and concentrated under reduced pressure. The residue was subjected to column chromatography using silica gel (30 g) and eluted with hexane- ethyl acetate (4:1, v/v) to give the title compound (780 mg, 53%) as an amorphous form.

$^1$H-NMR (CDCl₃) δ: 0.88 (3H, s), 1.24-1.36 (1H, m), 1.49-1.59 (9H, m), 2.39-2.56 (1H, m), 3.24-3.58 (2H, m), 3.95-4.02 (1H, m), 4.31-4.35 (1H, m), 4.87 (1H, d, J=54.0 Hz), 6.53 (1H, d, J=8.3 Hz), 6.76 (1H, t, J=7.7 Hz), 7.02-7.11 (1H, m), 7.30-7.40 (4H, m), 7.40-7.48 (1H, m), 7.48-7.79 (1H, m).

LC/MS (ESI) m/z: 365 (MH⁺).

Reference Example 25 tert-Butyl (3aR*,4R*,9bR)-3a-methyl-4-(3-thienyl)-2,3,3a,4,5,9b-hexahydro-1H-pyrrolo[3,2-c]quinoline-1-carboxylate (endo form)

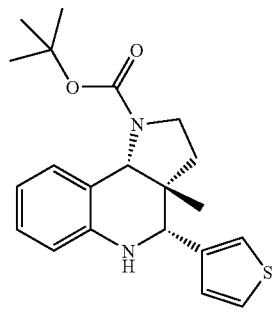

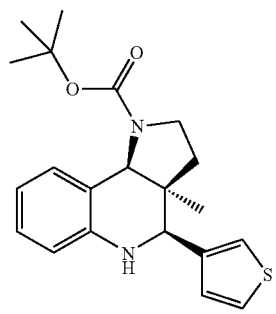

The title compound was synthesized in the same manner as in Reference Example 24 and using 3-thiophenecarbaldehyde.

$^1$H-NMR (CDCl₃) δ: 0.92 (3H, s), 1.23-1.38 (1H, m), 1.53 (9H, d, J=18.3 Hz), 2.36-2.53 (1H, m), 3.23-3.59 (2H, m), 3.94-4.05 (1H, m), 4.47 (1H, d, J=4.4 Hz), 4.76-4.93 (1H, m), 6.52 (1H, d, J=7.8 Hz), 6.76 (1H, t, J=7.6 Hz), 7.02-7.09 (1H, m), 7.11-7.19 (1H, m), 7.21-7.40 (2H, m), 7.60 (1H, dd, J=72.5, 7.3 Hz).

LC/MS (ESI) m/z: 371 (MH⁺).

Reference Example 26

(3aS*,4S*,9bR*)-3a-Methyl-4-phenyl-2,3,3a, 4,5, 9b-hexahydro-1H-pyrrolo[3,2-c]quinoline dihydrochloride

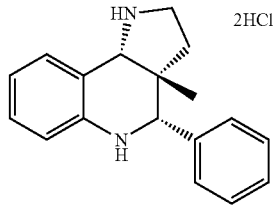

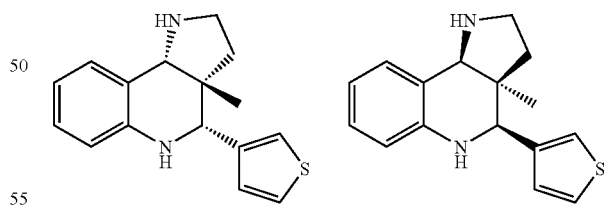

The compound (730 mg, 2.0 mmol) synthesized in Reference Example 24 was dissolved in ethyl acetate (10 ml), a 4N hydrogen chloride in ethyl acetate solution (10 ml) was added and the mixture was stirred for 12 hrs. The obtained crystals were collected by filtration, washed with ethyl acetate, and dried under reduced pressure to give the title compound (685 mg, ca. 100%) as crystals.

LC/MS (ESI) m/z: 265 (MH⁺).

Reference Example 27

(3aS*,4R*,9bR)-3a-Methyl-4-(3-thienyl)-2,3,3a,4,5, 9b-hexahydro-1H-pyrrolo[3,2-c]quinoline

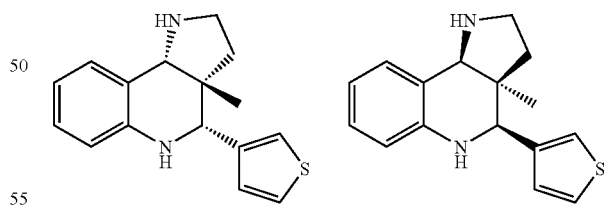

The compound (900 mg, 2.43 mmol) synthesized in Reference Example 25 was suspended in trifluoroacetic acid (5 ml), and the suspension was stirred for 30 min. The reaction mixture was neutralized with saturated aqueous sodium hydrogen carbonate solution, and extracted with chloroform. The extract was dried (over anhydrous MgSO₄) and the solvent was evaporated under reduced pressure to give the title compound (800 mg, ca. 100%) as crystals.

LC/MS (ESI) m/z: 271(M+H⁺)

Reference Example 28

Benzyl (2-oxoethyl)carbamate

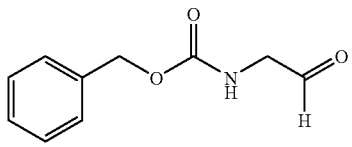

A solution (30 ml) of oxalyl chloride (1.72 ml, 20.0 mmol) in dichloromethane was added dropwise to a solution (10 ml) of dimethyl sulfoxide (2.84 ml, 40.0 mmol) in dichloromethane at −78° C., and the mixture was stirred at the same temperature for 5 min. A solution (45 ml) of benzyl(2-hydroxyethyl)carbamate (1.95 g, 10.0 mmol) in dichloromethane was added to the reaction mixture and the mixture was further stirred for 15 min. Triethylamine (6.93 ml, 50.0 mmol) was added, and the mixture was stirred for 5 min. The temperature was raised to room temperature and the reaction mixture was stirred for 1.5 hrs. The reaction mixture was concentrated under reduced pressure, water was added to the residue, and the mixture was extracted with ethyl acetate. The extract was washed with saturated brine, dried over anhydrous MgSO$_4$, and concentrated under reduced pressure. The obtained residue was subjected to silica gel column chromatography and eluted with hexane-ethyl acetate (7:3-3:2, v/v) to give the title compound (930 mg, 48%) as a colorless oil.

$^1$H-NMR (CDCl$_3$) δ: 4.14 (2H, d, J=5.1 Hz), 5.13 (2H, s), 5.47 (1H, br), 7.31-7.37 (5H, m), 9.64 (1H, s).

Reference Example 29

1,3-Oxazol-4-ylmethanol

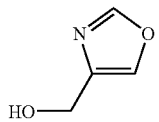

To a suspension of lithium aluminum hydride (2.69 g, 70.9 mmol) in tetrahydrofuran (50 ml) was added dropwise a solution of ethyl 1,3-oxazole-4-carboxylate (5.00 g, 35.4 mmol) in tetrahydrofuran (50 ml) at −78° C. The reaction mixture was stirred at the same temperature for 2 hrs, and the temperature was gradually raised to 0° C. After stirring for 1 hr, water (2.7 ml) was added, then 15% aqueous sodium hydroxide solution (2.7 ml) and then water (8.1 ml) were added and the mixture was stirred. The reaction mixture was dried over anhydrous MgSO$_4$, the precipitate was filtered off through celite, and the filtrate was concentrated. The residue was subjected to silica gel column chromatography and eluted with ethyl acetate to give the title compound (930 mg, 27%) as a colorless oil.

$^1$H-NMR (CDCl$_3$) δ: 3.27 (1H, br s), 4.64 (2H, s), 7.64 (1H, s), 7.90 (1H, s).

Reference Example 30

1,3-Oxazole-4-carbaldehyde

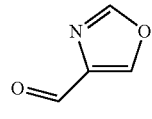

To a solution of 1,3-oxazole-4-ylmethanol (1.88 g, 19 mmol) in chloroform (200 ml) was added manganese dioxide (33.0 g, 379 mmol), and the mixture was stirred overnight at room temperature. Insoluble materials were filtered off and the filtrate was concentrated under reduced pressure to give the title compound (1.00 g, 54%) as a colorless oil.

$^1$H-NMR (CDCl$_3$) δ: 7.99 (1H, s), 8.32 (1H, s), 10.0 (1H, s).

Reference Example 31

(2-Methyl-3-furyl)methanol

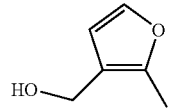

To a suspension of lithium aluminum hydride (5.17 g, 136 mmol) in tetrahydrofuran (300 ml) was added dropwise a solution of ethyl 2-methyl-3-furoate (10.0 g, 64.9 mmol) in tetrahydrofuran (10 ml) at −78° C. The reaction mixture was stirred at the same temperature for 4 hrs, the temperature was gradually raised to 0° C. and the mixture was further stirred for 1 hr. Water and 15% aqueous sodium hydroxide solution were added, and anhydrous MgSO$_4$ was added to the mixture. The mixture was filtered, and the filtrate was concentrated under reduced pressure. The residue was subjected to silica gel column chromatography and eluted with hexane-ethyl acetate (8:2, v/v) to give the title compound (7.98 g, ca. 100%) as a colorless oil.

$^1$H-NMR (CDCl$_3$) δ: 2.29 (3H, s), 4.47 (2H, d, J=5.4 Hz), 6.36 (1H, d, J=1.5 Hz), 7.26 (1H, d, J=1.5 Hz).

Reference Example 32

2-Methyl-3-furaldehyde

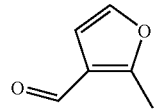

To a solution of (2-methyl-3-furyl)methanol (2.00 g, 17.8 mmol) in chloroform (200 ml) was added manganese dioxide (33.0 g, 379 mmol), and the mixture was stirred at room temperature for 16 hrs and further at 60° C. for 3 hrs. Insoluble materials were filtered off, and the filtrate was concentrated under reduced pressure. The residue was subjected to silica gel column chromatography and eluted with hexane-ethyl acetate (95:5-90:10, v/v) to give the title compound (235 mg, 12%) as a colorless oil.

$^1$H-NMR (CDCl$_3$) δ: 2.59 (3H, s), 6.68 (1H, s), 7.29 (1H, s), 9.93 (1H, s).

Reference Example 33

(4-Formyl-1H-imidazol-1-yl)methyl pivalate

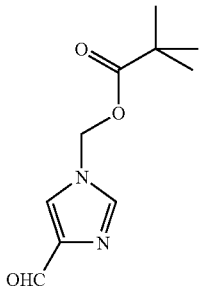

To a suspension of sodium hydride (60% in oil, 1.0 g, 26 mmol) in tetrahydrofuran (10 ml) was added dropwise a solution of 1H-imidazole-4-carbaldehyde (1.92 g, 20 mmol) in DMF (5 ml) at 0° C., and the mixture was stirred at room temperature for 1 hr. Chloromethyl pivalate (3.92 g, 26 mmol) was further added dropwise at 0° C., and the mixture was stirred at room temperature for 1 hr. The reaction mixture was concentrated under reduced pressure, water was added and the mixture was extracted with ethyl acetate. The extract was washed with 6% aqueous sodium hydrogen carbonate solution and saturated brine, dried (over anhydrous $MgSO_4$), and the solvent was evaporated under reduced pressure. The residue was subjected to column chromatography using silica gel (100 g), and eluted with hexane-ethyl acetate (4:1-1:2, v/v) to give the title compound (4.11 g, 98%) as a pale-yellow oil.

$^1$H-NMR ($CDCl_3$) δ: 1.18 (9H, s), 5.90 (2H, s), 7.77-7.79 (2H, m), 9.90 (1H, s).

Reference Example 34

Methyl 4-(aminocarbonyl)-3-methylbenzoate

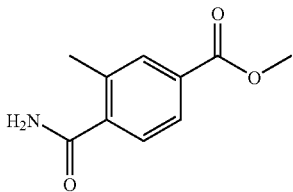

A mixture of 4-bromo-2-methylbenzamide (1.65 g, 7.75 mmol), triethylamine (2.17 ml, 15.5 mmol), palladium acetate (0.0873 g, 0.388 mmol), 1,1'-bis(diphenylphosphino)ferrocene (0.215 g, 0.388 mmol), methanol (5 ml) and DMF (15 ml) was stirred under a carbon monoxide atmosphere at 70° C. for 22 hrs. After cooling to room temperature, the reaction mixture was diluted with ethyl acetate, washed with water and saturated brine, and dried (over anhydrous $MgSO_4$). After concentration under reduced pressure, the obtained crystals were recrystallized from ethyl acetate to give the title compound (1.05 g, 70%) as a pale-brown needle.

$^1$H-NMR ($CDCl_3$) δ: 2.53 (3H, s), 3.39 (3H, s), 5.73-5.96 (2H, m), 7.50 (1H, d, J=7.5 Hz), 7.85-7.94 (2H, m).

Reference Example 35

4-(Aminocarbonyl)-3-methylbenzoic acid

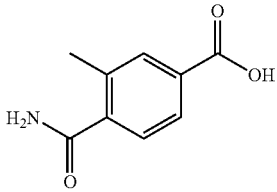

To a solution of the compound (0.759 g, 3.39 mmol) synthesized in Reference Example 34 in methanol (20 ml) was added dropwise 1N aqueous sodium hydroxide solution (7.9 ml, 7.9 mmol), and the mixture was stirred at 60° C. for 2.5 hrs. After cooling to room temperature, and the reaction mixture was concentrated to about half volume under reduced pressure. Water was added and the mixture was washed with diethyl ether. The organic layer was extracted with water, and 6N hydrochloric acid (1.5 ml) was added dropwise to the combined aqueous layers at 0° C. The precipitated colorless powder was collected by filtration, and washed with water to give the title compound (0.643 g, 91%).

$^1$H-NMR (DMSO-$d_6$) δ: 2.40 (3H, s), 7.44 (1H, d, J=7.8 Hz), 7.52 (1H, br s), 7.75-7.89 (3H, m).

Reference Example 36

Ethyl (2E)-3-(1-trityl-1H-imidazol-2-yl)acrylate

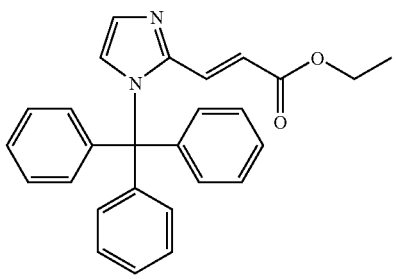

To a suspension of sodium hydride (60% in oil, 0.811 g, 20.3 mmol) in tetrahydrofuran (60 ml) was added dropwise ethyl (diethoxyphosphoryl)acetate (4.33 ml, 21.8 mmol) and the mixture was stirred for 30 min. A solution of 2-formyl-1-tritylimidazole (5.28 g, 15.6 mmol) in tetrahydrofuran (30 ml) was added dropwise and the mixture was stirred for 8 hrs. Water was added to the reaction mixture, and the mixture was extracted with ethyl acetate. The extract was washed with saturated brine and dried (over anhydrous $MgSO_4$). After concentration under reduced pressure, the obtained residue was subjected to silica gel column chromatography and eluted with hexane-ethyl acetate (9:1-1:1, v/v). The title compound (3.28 g, 52%) was obtained as a colorless powder from the object fraction.

$^1$H-NMR ($CDCl_3$) δ: 1.13 (3H, t, J=7.2 Hz), 4.00 (2H, d, J=7.2 Hz), 6.51 (1H, d, J=15.3 Hz), 6.68 (1H, d, J=15.3 Hz), 6.86 (1H, d, J=1.2 Hz), 7.08-7.16 (7H, m), 7.28-7.35 (9H, m).

Reference Example 37

(2E)-3-(1-Trityl-1H-imidazol-2-yl)acrylic acid

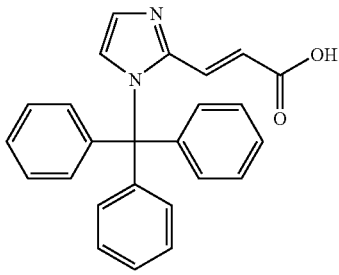

In the same manner as in Reference Example 35 and using the compound obtained in Reference Example 36, the title compound was synthesized.

$^1$H-NMR (DMSO-d$_6$) δ: 6.28 (1H, d, J=15.0 Hz), 6.55 (1H, d, J=15.0 Hz), 6.82 (1H, d, J=1.2 Hz), 7.00-7.08 (6H, m), 7.10 (1H, d, J=1.2 Hz), 7.33-7.45 (9H, m), 12.1 (1H, br s).

Reference Example 38

(2E)-3-(1-Methyl-1H-imidazol-2-yl)acrylic acid

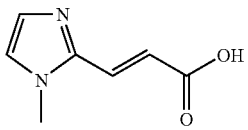

In the same manner as in Reference Example 36 and Reference Example 35 and using 2-formyl-1-methylimidazole instead of 2-formyl-1-tritylimidazole of Reference Example 36, the title compound was synthesized.

$^1$H-NMR (DMSO-d$_6$) δ: 3.76 (3H, s), 6.53 (1H, d, J=15.5 Hz), 7.05 (1H, s), 7.33 (1H, s), 7.46 (1H, d, J=15.3 Hz).

Reference Example 39

Benzyl (3aR*,4R*,9bR*)-5-methyl-4-phenyl-2,3,3a,4,5,9b-hexahydro-1H-pyrrolo[3,2-c]quinoline-1-carboxylate

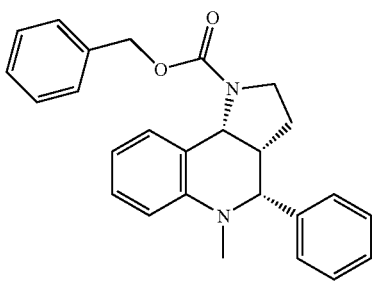

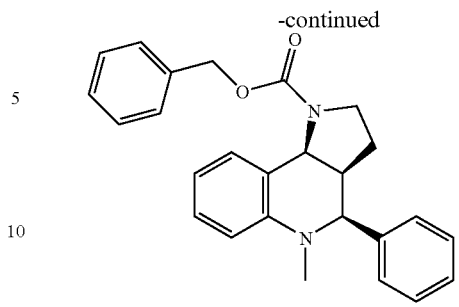

Sodium hydride (60% in oil, 120 mg, 3.0 mmol) was suspended in DMF (12 ml), benzyl (3aR*,4R,9bR)-4-phenyl-2,3,3a,4,5,9b-hexahydro-1H-pyrrolo[3,2-c]quinoline-1-carboxylate (960 mg, 2.5 mmol) was added, and the mixture was stirred at room temperature for 10 min. Thereto was added methyl iodide (426 mg, 3.0 mmol), and the mixture was stirred at room temperature for 3 hrs. Water was added to the reaction mixture, and the mixture was extracted with ethyl acetate. The extract was washed with saturated brine, dried (over anhydrous Na$_2$SO$_4$), and the solvent was evaporated. The residue was subjected to column chromatography using silica gel (30 g) and eluted with hexane-ethyl acetate (5:1, v/v) to give the title compound (330 mg, 33%) as an amorphous form.

$^1$H-NMR (CDCl$_3$) δ: 1.51-1.58 (1H, m), 1.87-2.16 (1H, m), 2.39-2.62 (1H, m), 2.74 (3H, d, J=2.0 Hz), 3.25-3.48 (2H, m), 4.49 (1H, dd, J=6.2, 3.8 Hz), 5.15-5.43 (3H, m), 6.64-6.85 (2H, m), 7.11-7.23 (1H, m), 7.24-7.59 (11H, m).

LC/MS (ESI) m/z: 399 (MH$^+$).

Reference Example 40

(3aR*,4R*,9bR*)-5-Methyl-4-phenyl-2,3,3a,4,5,9b-hexahydro-1H-pyrrolo[3,2-c]quinoline

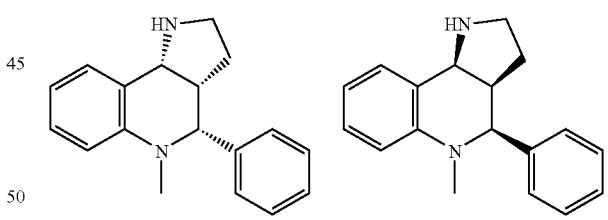

The compound (300 mg, 0.75 mmol) synthesized in Reference Example 39 was dissolved in ethanol (10 ml), and hydrogenation reaction was carried out in the presence of 10% palladium on carbon (50% aqueous, 0.15 g) at room temperature for 2 hrs. The catalyst was filtered off and washed with ethanol. The filtrate and washings were combined and concentrated under reduced pressure to give the title compound as an oil (150 mg, 65%). This product was not purified further and used for the next reaction.

$^1$H-NMR (CDCl$_3$) δ: 1.59-1.73 (2H, m), 1.87-2.02 (1H, m), 2.40-2.56 (1H, m), 2.59-2.69 (1H, m), 2.70-2.86 (4H, m), 4.24-4.32 (1H, m), 4.41 (1H, d, J=4.6 Hz), 6.76-6.83 (2H, m), 7.16-7.39 (7H, m).

LC/MS (ESI) m/z: 265 (MH$^+$).

Reference Example 41

Ethyl 4-[(2-{[tert-butyl(dimethyl)silyl]oxy}ethyl)-amino]benzoate

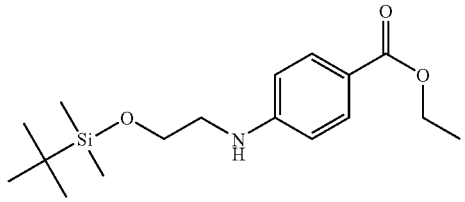

To a solution of {[tert-butyl(dimethyl)silyl]oxy}acetaldehyde (2.00 g, 11.5 mmol) in dichloromethane (50 ml) was added ethyl 4-aminobenzoate (1.90 g, 11.5 mmol), and the mixture was stirred at room temperature for 1 hr. Sodium triacetoxyborohydride (3.41 g, 16.1 mmol) was added, and the mixture was stirred overnight. Saturated aqueous sodium hydrogen carbonate solution was added to the reaction mixture under ice-cooling, and the mixture was extracted with ethyl acetate. The extract was dried over anhydrous $MgSO_4$, and concentrated under reduced pressure. The residue was subjected to silica gel column chromatography and eluted with hexane-ethyl acetate (4:1-1:1, v/v) to give the title compound (3.52 g, 95%) as a colorless oil.

$^1$H-NMR (CDCl$_3$) δ: 0.00 (6H, s), 0.83 (9H, s), 1.29 (3H, t, J=6.9 Hz), 3.21 (2H, t, J=5.1 Hz), 3.75 (2H, t, J=5.1 Hz), 4.24 (2H, q, J=6.9 Hz), 6.50 (2H, d, J=8.1 Hz), 7.80 (2H, d, J=8.1 Hz).

Reference Example 42

Ethyl 4-[(2-{[tert-butyl(dimethyl)silyl]oxy}ethyl)(methyl)amino]benzoate

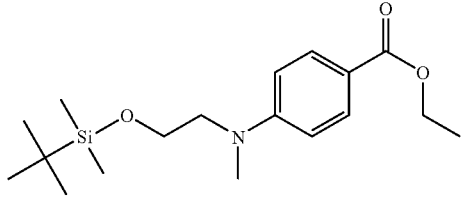

To a solution of ethyl 4-[(2-{[tert-butyl(dimethyl)silyl]oxy}ethyl)amino]benzoate (2.52 g, 7.79 mmol) in dichloromethane (32 ml) were added 37% aqueous formaldehyde solution (2.08 ml, 25.7 mmol) and sodium triacetoxyborohydride (6.93 g, 32.7 mmol) and the mixture was heated under reflux overnight. Aqueous sodium hydrogen carbonate solution was added to the reaction mixture, and the mixture was extracted with ethyl acetate. The organic layer was dried over anhydrous $MgSO_4$, and concentrated under reduced pressure. The residue was subjected to silica gel column chromatography and eluted with hexane-ethyl acetate (1:0-7:3, v/v) to give the title compound (2.33 g, 89%) as a colorless oil.

$^1$H-NMR (CDCl$_3$) δ: 0.00 (6H, s), 0.87 (9H, s), 1.36 (3H, t, J=7.1 Hz), 3.05 (3H, s), 3.53 (2H, t, J=5.9 Hz), 3.78 (2H, t, J=5.9 Hz), 4.31 (2H, q, J=7.1 Hz), 6.64 (2H, d, J=7.2 Hz), 7.88 (2H, d, J=7.2 Hz).

Reference Example 43

Ethyl 4-[(2-hydroxyethyl)(methyl)amino]benzoate

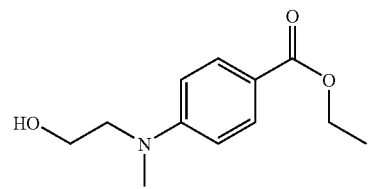

To a solution (30 ml) of ethyl 4-[(2-{[tert-butyl(dimethyl)silyl]oxy}ethyl)(methyl)amino]benzoate (2.33 g, 6.90 mmol) in tetrahydrofuran was added tetrabutyl ammoniumfluoride (1.0 M toluene solution, 10.4 ml, 10.4 mmol) at room temperature and the mixture was stirred overnight. After concentration of the reaction mixture under reduced pressure, the residue was subjected to silica gel column chromatography and eluted with hexane-ethyl acetate (3:2-1:4, v/v) to give the title compound (1.11 g, 72%) as a colorless oil.

$^1$H-NMR (CDCl$_3$) δ: 1.36 (3H, t, J=7.1 Hz), 3.07 (3H, s), 3.57 (2H, t, J=5.4 Hz), 3.84 (2H, t, J=5.4 Hz), 4.31 (2H, q, J=7.1 Hz), 6.70 (2H, d, J=8.0 Hz), 7.89 (2H, d, J=8.0 Hz).

Reference Example 44

4-[(2-Hydroxyethyl)(methyl)amino]benzoic acid

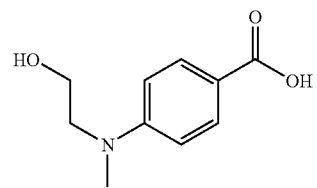

To a solution (10 ml) of ethyl 4-[(2-hydroxyethyl)(methyl)amino]benzoate (500 mg, 2.24 mmol) in methanol was added 1M aqueous sodium hydroxide solution (10 ml), and the mixture was stirred at room temperature for 3 hrs. Water was added to the reaction mixture, and the mixture was washed with diethyl ether. 1M Hydrochloric acid (10 ml) was added, and the mixture was extracted with dichloromethane and concentrated under reduced pressure to give the title compound (119 mg, 27%) as a white solid.

$^1$H-NMR (CDCl$_3$) δ: 3.07 (3H, s), 3.56 (2H, t, J=6.0 Hz), 3.78 (2H, t, J=6.0 Hz), 3.84 (1H, s), 6.70 (2H, d, J=8.9 Hz), 7.90 (2H, d, J=8.9 Hz).

Reference Example 45

Methyl 4-(4-methyl-1H-imidazol-1-yl)benzoate

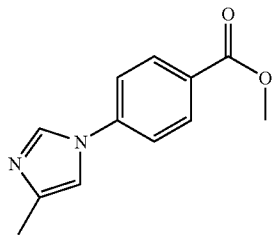

A mixture of methyl 4-fluorobenzoate (1.00 g, 6.49 mmol), 4-methylimidazole (559 mg, 6.81 mmol), potassium carbonate (941 mg, 6.81 mmol) and DMF (30 ml) was stirred at 110° C. for 24 hrs. Water was added to the reaction mixture, and the mixture was extracted with ethyl acetate. The extract was dried over anhydrous $MgSO_4$ and concentrated under reduced pressure. The residue was subjected to column chromatography using basic silica gel and eluted with ethyl acetate-methanol (1:0-1:1, v/v) to give the title compound (137 mg, 10%) as a colorless oil.

$^1$H-NMR (CDCl$_3$) δ: 2.31 (3H, s), 3.95 (3H, s), 7.07 (1H, s), 7.41-7.44 (2H, m), 7.85 (1H, s), 8.11-8.19 (2H, m).

Reference Example 46

4-(4-Methyl-1H-imidazol-1-yl)benzoic acid

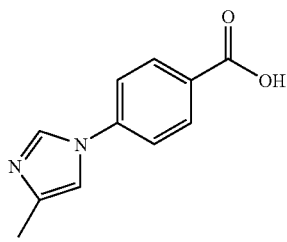

To a solution (5 ml) of methyl 4-(4-methyl-1H-imidazol-1-yl)benzoate (137 mg, 0.635 mmol) in methanol was added 1M sodium hydroxide (5 ml), and the mixture was stirred at room temperature for 3 hrs. 1M Hydrochloric acid (5 ml) was added to the reaction mixture, and the solvent was evaporated under reduced pressure. The residue was used for the next reaction without purification.

$^1$H-NMR (CDCl$_3$) δ: 2.50 (3H, s), 7.68 (1H, s), 7.77 (2H, d, J=8.3 Hz), 8.22 (2H, d, J=8.3 Hz), 9.77 (1H, s).

Reference Example 47

Ethyl 4-[(2-methoxyethyl)(methyl)amino]benzoate

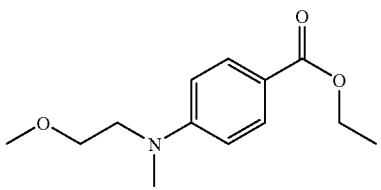

To a solution of ethyl 4-[(2-hydroxyethyl)(methyl)amino]benzoate (611 mg, 2.74 mmol) in DMF (10 ml) were added sodium hydride (60% in oil, 143 mg, 3.56 mmol) and methyl iodide (0.222 ml, 3.56 mmol), and the mixture was stirred overnight at room temperature. Water was added to the reaction mixture, and the mixture was extracted with ethyl acetate. The extract was dried over anhydrous $MgSO_4$, and the solvent was evaporated under reduced pressure. The residue was subjected to silica gel column chromatography and eluted with hexane-ethyl acetate (1:0-7:3, v/v) to give the title compound (467 mg, 72%) as a colorless oil.

$^1$H-NMR (CDCl$_3$) δ: 1.36 (3H, t, J=7.2 Hz), 3.06 (3H, s), 3.35 (3H, s), 3.56-3.58 (4H, m), 4.31 (2H, q, J=7.2 Hz), 6.66 (2H, d, J=7.2 Hz), 7.90 (2H, d, J=7.2 Hz).

Reference Example 48

4-[(2-Methoxyethyl)(methyl)amino]benzoic acid

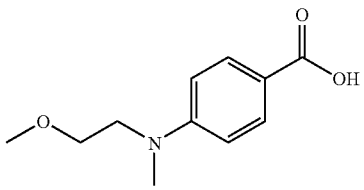

To a solution (10 ml) of ethyl 4-[(2-methoxyethyl)(methyl)amino]benzoate (467 mg, 1.97 mmol) in methanol was added 1M aqueous sodium hydroxide solution (10 ml), and the mixture was stirred at 50° C. for 3 hrs. The reaction mixture was concentrated under reduced pressure, and water and diethyl ether were added to the residue. The organic layer was separated. The aqueous layer was neutralized with 1M hydrochloric acid (10 ml) and extracted with ethyl acetate. The extract was dried over anhydrous $MgSO_4$ and concentrated under reduced pressure to give the title compound (340 mg, 82%) as a white solid.

Reference Example 49

Methyl 4-(bromomethyl)-3-methoxybenzoate

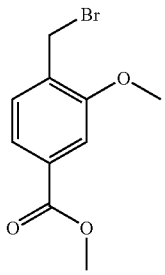

A mixture of methyl 3-methoxy-4-methylbenzoate (10.0 g, 55.5 mmol), N-bromosuccinimide (10.7 g, 60.9 mmol), 2,2'-azobis(isobutyronitrile) (1.6 mg) and ethyl acetate (200 ml) was heated under reflux overnight. The solvent was evaporated under reduced pressure, and hexane was added to the residue. The precipitate was filtered off, and the filtrate was concentrated under reduced pressure. The residue was subjected to silica gel column chromatography and eluted with hexane-ethyl acetate (9:1-7:3, v/v) to give the title compound (12.8 g, 92%) as a colorless oil.

$^1$H-NMR (CDCl$_3$) δ: 3.92 (3H, s), 3.95 (3H, s), 4.55 (2H, s), 7.38 (1H, d, J=8.1 Hz), 7.53 (1H, d, J=1.5 Hz), 7.60 (1H, dd, J=1.5, 8.1 Hz).

Reference Example 50

Methyl 4-formyl-3-methoxybenzoate

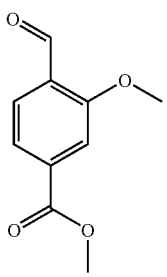

To a solution of methyl 4-(bromomethyl)-3-methoxybenzoate (3.00 g, 11.6 mmol) in dimethyl sulfoxide (16 ml) was added sodium hydrogen carbonate (1.00 g, 13.6 mmol), and the mixture was stirred at 50° C. for 3 hrs. Water was added to the reaction mixture, and the mixture was extracted with ethyl acetate. The extract was dried over anhydrous MgSO$_4$ and the solvent was evaporated under reduced pressure. The residue was subjected to silica gel column chromatography and eluted with hexane-ethyl acetate (1:0-7:3, v/v) to give the title compound (870 mg, 39%) as a colorless oil.

$^1$H-NMR (CDCl$_3$) δ: 3.96 (3H, s), 3.99 (3H, s), 7.67 (1H, s), 7.68 (1H, d, J=8.9 Hz), 7.88 (1H, d, J=8.9 Hz), 10.51 (1H, s).

Reference Example 51

Methyl 4-cyano-3-methoxybenzoate

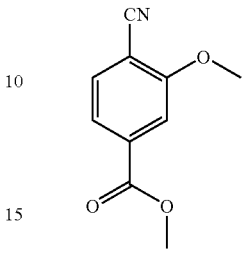

To a solution (20 ml) of methyl 4-formyl-3-methoxybenzoate (870 mg, 4.48 mmol) in formic acid was added hydroxylamine hydrochloride (405 mg, 5.82 mmol), and the mixture was stirred at room temperature for 1 hr. The temperature was raised to 50° C., and the mixture was further stirred for 24 hrs. Water was added to the reaction mixture, the mixture was neutralized with saturated aqueous sodium hydrogen carbonate solution, and extracted with ethyl acetate. The extract was dried over anhydrous MgSO$_4$, and the solvent was evaporated under reduced pressure. The residue was subjected to silica gel column chromatography and eluted with hexane-ethyl acetate (1:0-7:3, v/v) to give the title compound (780 mg, 91%) as a colorless oil.

$^1$H-NMR (CDCl$_3$) δ: 3.96 (3H, s), 3.99 (3H, s), 7.62-7.69 (3H, m).

Reference Example 52

4-Cyano-3-methoxybenzoic acid

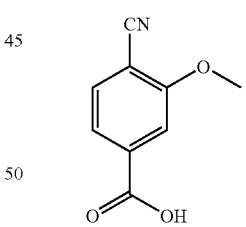

To a solution (37 ml) of methyl 4-cyano-3-methoxybenzoate (700 mg, 3.66 mmol) in methanol was added 1M aqueous sodium hydroxide solution (37 ml), and the mixture was stirred overnight at room temperature. The solvent was evaporated under reduced pressure, the residue was dissolved in water, and the mixture was washed with diethyl ether. The aqueous layer was neutralized with 1M hydrochloric acid and extracted with dichloromethane. The extract was dried over anhydrous MgSO$_4$ and concentrated under reduced pressure to give the title compound (690 mg, ca. 100%) as a white solid.

Reference Example 53

Methyl 6-morpholin-4-ylnicotinate

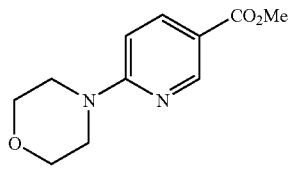

A mixture of methyl 6-chloronicotinate (1.02 g, 5.93 mmol), morpholine (0.57 ml, 6.52 mmol), potassium carbonate (1.06 g, 7.71 mmol) and DMF (20 ml) was stirred at 100° C. for 6 hrs. The reaction mixture was cooled to room temperature, water was added and the mixture was extracted with ethyl acetate. The extract was washed with saturated brine, dried (over anhydrous MgSO$_4$), and concentrated under reduced pressure. The obtained solid was collected by filtration and washed with diisopropy ether to give the title compound (0.93 g, 71%) as a colorless powder.

$^1$H-NMR (CDCl$_3$) δ: 3.64-3.70 (4H, m), 3.78-3.85 (4H, m), 3.88 (3H, s), 6.57 (1H, dd, J=9.0, 0.6 Hz), 8.05 (1H, dd, J=9.0, 2.4 Hz), 8.81 (1H, dd, J=2.4, 0.6 Hz).

Reference Example 54

Methyl 6-(1H-pyrazol-1-yl)nicotinate

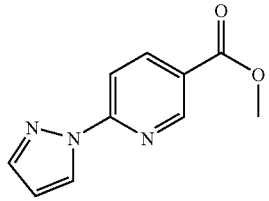

To a suspension of pyrrole (0.356 g, 5.23 mmol) in DMF (20 ml) was added sodium hydride (60% in oil, 0.233 g, 5.81 mmol). After stirring for 5 hrs., methyl 6-chloronicotinate (1.00 g, 5.81 mmol) was added, and the mixture was further stirred for 27 hrs. Water was added to the reaction mixture, and the mixture was extracted with ethyl acetate. The extract was washed with saturated brine and dried (over anhydrous MgSO$_4$). After concentration under reduced pressure, the precipitated solid was collected by filtration and washed with hexane to give the title compound (0.683 g, 64%) as a colorless powder.

$^1$H-NMR (CDCl$_3$) δ: 3.97 (3H, s), 6.51 (1H, dd, J=4.2, 2.4 Hz), 7.75-7.81 (1H, m), 8.05 (1H, dd, J=12.6, 0.9 Hz), 8.40 (1H, dd, J=12.6, 3.3 Hz), 8.62 (1H, dd, J=4.2, 1.2 Hz), 9.03 (1H, dd, J=3.3, 0.9 Hz).

Reference Example 55

Methyl 6-(2-methyl-1H-imidazol-1-yl)nicotinate

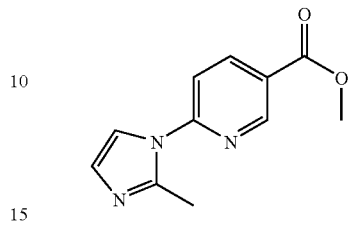

In the same manner as in Reference Example 54 and using 2-methylimidazole, the title compound was synthesized.

$^1$H-NMR (CDCl$_3$) δ: 2.67 (3H, s), 3.99 (3H, s), 7.05 (1H, d, J=1.5 Hz), 7.35-7.43 (2H, m), 8.40-8.47 (1H, m), 9.14-9.17 (1H, m).

The following compounds of Reference Example 56-Reference Example 58 were hydrolyzed at room temperature in the same manner as in Reference Example 35.

Reference Example 56

6-Morpholin-4-ylnicotinic acid

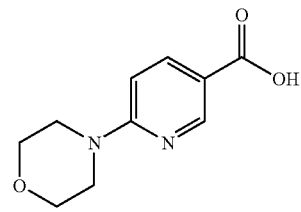

$^1$H-NMR (DMSO-d$_6$) δ: 3.56-3.62 (4H, m), 3.65-3.71 (4H, m), 6.86 (1H, d, J=9.0 Hz), 7.95 (1H, dd, J=9.0, 2.4 Hz), 8.64 (1H, d, J=2.4 Hz).

Reference Example 57

6-(1H-Pyrazol-1-yl)nicotinic acid

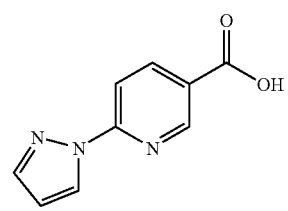

$^1$H-NMR (DMSO-d$_6$) δ-: 6.65 (1H, dd, J=2.7, 1.5 Hz), 7.92 (1H, dd, J=1.5, 0.6 Hz), 8.04 (1H, dd, J=8.7, 0.9 Hz), 8.44 (1H, dd, J=8.7, 2.1 Hz), 8.70 (1H, dd, J=2.7, 0.6 Hz), 8.96 (1H, dd, J=2.1, 0.9 Hz).

Reference Example 58

6-(2-Methyl-1H-imidazol-1-yl)nicotinic acid

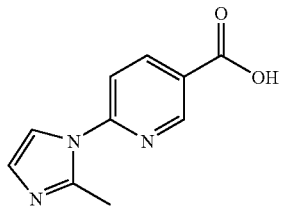

$^1$H-NMR (CD$_3$OD) δ–: 2.05 (3H, s), 6.52 (1H, d, J=2.7 Hz), 7.01-7.05 (2H, m), 7.89 (1H, dd, J=9.6, 3.3 Hz), 8.48 (1H, dd, J=3.3, 1.2 Hz).

Reference Example 59

Ethyl 1-[(benzoylamino)methyl]cyclohexanecarboxylate

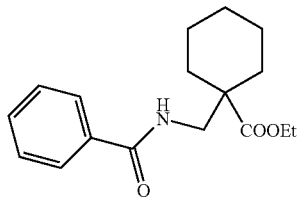

A solution of ethyl 1-cyanocyclohexanecarboxylate (10.0 g, 55.1 mmol) in ethanol (200 ml) was stirred at 40° C. for 12 hrs., in the presence of Raney-nickel (10 g), under a hydrogen atmosphere (4 atm). The catalyst was filtered off, and the filtrate was concentrated under reduced pressure. Ethyl acetate (300 ml) and 10% aqueous sodium carbonate solution (150 ml) were added to the residue, benzoyl chloride (6.34 ml, 55.1 ml) was added dropwise at 0° C., and the mixture was stirred at room temperature for 6 hrs. The organic layer was separated, and the aqueous layer was extracted with ethyl acetate. The organic layers were combined and dried over anhydrous MgSO$_4$. After concentration under reduced pressure, the residue was subjected to silica gel column chromatography and eluted with hexane-ethyl acetate (3:1-1:1, v/v) to give the title compound (10.2 g, 63%) as a colorless oil.

$^1$H-NMR (CDCl$_3$) δ: 1.29 (3H, t, J=7.0 Hz), 1.40-1.70 (8H, m), 2.04 (2H, t, J=8.0 Hz), 3.61 (2H, d, J=6.0 Hz), 4.21 (2H, q, J=7.4 Hz), 6.60 (1H, br s), 7.26-7.53 (3H, m), 7.73-7.78 (2H, m).

Reference Example 60

1-[(Benzoylamino)methyl]cyclohexanecarboxylic acid

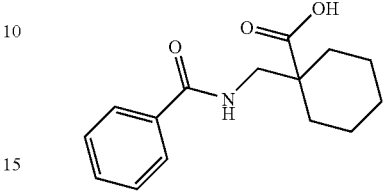

To a solution of ethyl 1-[(benzoylamino)methyl]cyclohexanecarboxylate (10.2 g, 35.1 mmol) in ethanol (50 ml) was added 50% aqueous potassium hydroxide solution (4 ml), and the mixture was heated under reflux for 6 hrs. Water (400 ml) was added and the reaction mixture was washed with diethyl ether. The aqueous layer was acidified (pH 2) with 5N hydrochloric acid, the precipitate was collected by filtration, washed with water and dried at 50° C. under reduced pressure. Recrystallization from ethanol-toluene gave the title compound (6.83 g, 74%) as colorless crystals.

$^1$H-NMR (CDCl$_3$) δ: 1.05-1.63 (8H, m), 1.85-2.03 (2H, br), 3.38 (2H, d, J=6.2 Hz), 7.39-7.58 (3H, m), 7.75-7.88 (2H, m), 8.30 (1H, br s), 12.21 (1H, s).

Reference Example 61

Ethyl (1-hydroxycyclohexyl)acetate

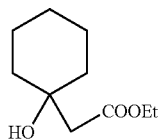

To a solution of cyclohexanone (9.52 g, 97.0 mmol), a zinc powder (7.6 g, 116.4 mmol) and a small amount of iodine in THF (100 ml) was added dropwise ethyl bromoacetate (11.8 ml, 106.7 mmol) under a nitrogen atmosphere, and the mixture was heated under reflux for 5 hrs. 10% Sulfuric acid (100 ml) was carefully added under ice-cooling, and the mixture was extracted with ethyl acetate. The extract was washed with saturated aqueous sodium hydrogen carbonate solution, dried over anhydrous MgSO$_4$, and concentrated under reduced pressure to give the title compound (17.2 g, 94%) as a colorless oil.

$^1$H-NMR (CDCl$_3$) δ: 1.27 (3H, t, J=7.0 Hz), 1.35-1.71 (10H, m), 2.46 (2H, s), 3.43 (1H, s), 4.17 (2H, q, J=7.4 Hz).

Reference Example 62

[1-(Benzoylamino)cyclohexyl]acetic acid

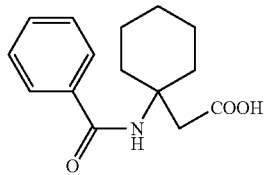

To a mixture of ethyl (1-hydroxycyclohexyl)acetate (17.1 g, 92.1 mmol) and benzonitrile (9.5 ml, 92.1 mmol) was added conc. sulfuric acid (50 ml) at 0° C., and the mixture was stirred at room temperature for 12 hrs. Water (200 ml) was added to the reaction mixture, and the mixture was extracted with ethyl acetate. The extract was washed with saturated aqueous sodium hydrogen carbonate solution, and then with saturated brine and dried over anhydrous $MgSO_4$. After concentration under reduced pressure, ethanol (50 ml) and 50% aqueous potassium hydroxide solution (10 ml) were added to the residue, and the mixture was heated under reflux for 6 hrs. Water (400 ml) was added to the reaction mixture, and the mixture was washed with diethyl ether. The aqueous layer was acidified (pH 2) with 5N hydrochloric acid, and the mixture was extracted with ethyl acetate. The extract was washed with saturated brine, dried over anhydrous $Na_2SO_4$, and concentrated under reduced pressure. The obtained solid was recrystallized from ethanol-toluene to give the title compound (18.1 g, 75%) as colorless crystals.

$^1$H-NMR (CDCl$_3$) δ: 1.14-1.62 (8H, m), 2.25-2.43 (2H, m), 2.74 (2H, s), 3.32 (1H, s), 7.36-7.57 (3H, m), 7.73-7.80 (2H, m), 11.93 (1H, s).

LC/MS (ESI) m/z: 262 (MH$^+$).

Reference Example 63

Ethyl (4-hydroxytetrahydro-2H-pyran-4-yl)acetate

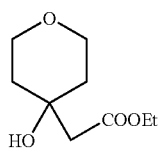

To a solution of tetrahydro-4H-pyran-4-one (5.5 g, 51.6 mmol), a zinc powder (4.05 g, 61.9 mmol) and a small amount of iodine in tetrahydrofuran (60 ml) was added dropwise ethyl bromoacetate (6.28 ml, 56.7 mmol) under a nitrogen atmosphere. After heating under reflux for 6 hrs., 10% sulfuric acid (50 ml) was carefully added under ice-cooling and the mixture was extracted with ethyl acetate. The extract was washed with saturated aqueous sodium hydrogen carbonate solution, dried over anhydrous $MgSO_4$ and concentrated under reduced pressure to give the title compound (6.73 g, 69%) as a colorless oil.

$^1$H-NMR (CDCl$_3$) δ: 1.29 (3H, t, J=7.0 Hz), 1.62-1.68 (4H, m), 2.48 (2H, s), 3.67-4.00 (5H, m), 4.19 (2H, q, J=6.8 Hz).

Reference Example 64

[4-(Benzoylamino)tetrahydro-2H-pyran-4-yl]acetic acid

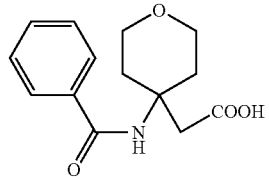

To a mixture of ethyl (4-hydroxytetrahydro-2H-pyran-4-yl)acetate (6.73 g, 35.8 mmol) and benzonitrile (4.05 ml, 39.3 mmol) was added conc. sulfuric acid (25 ml) under ice-cooling. After stirring at room temperature for 16 hrs., the reaction mixture was added to water (100 ml) under ice-cooling, and the mixture was extracted with ethyl acetate. The extract washed with saturated aqueous sodium hydrogen carbonate solution, then with saturated brine and dried over anhydrous $MgSO_4$. After concentration under reduced pressure, ethanol (50 ml) and 50% aqueous potassium hydroxide solution (10 ml) was added to the obtained residue, and the mixture was heated under reflux for 6 hrs. Water (200 ml) was added to the reaction mixture and the mixture was washed with diethyl ether. The aqueous layer was acidified (pH 2) with 5N hydrochloric acid, extracted with ethyl acetate-tetrahydrofuran (2:1, v/v). The extract was washed with saturated brine, dried over anhydrous $Na_2SO_4$, and concentrated under reduced pressure. The obtained solid was collected by filtration and washed with diisopropy ether to give the title compound (1.64 g, 17%) as colorless crystals.

$^1$H-NMR (DMSO-d$_6$) δ: 1.59-1.75 (2H, m), 2.23-2.42 (2H, m), 2.80 (2H, s), 3.50-3.67 (4H, m), 7.38-7.54 (3H, m), 7.76-7.87 (3H, m).

LC/MS (ESI) m/z: 264 (MH$^+$).

Reference Example 65

(1S,2S)-2-(Benzoylamino)cyclohexanecarboxylic acid

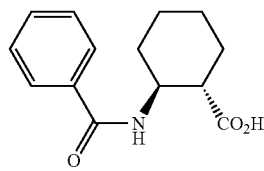

A mixture of (1R,2S)-2-(benzoylamino)cyclohexanecarboxylic acid (2.47 g, 10 mmol), 1-[3-(dimethylamino)propyl]-3-ethylcarbodiimide hydrochloride (2.30 g, 12 mmol), acetonitrile (25 ml) and tetrahydrofuran (25 ml) was stirred at room temperature for 30 min. The reaction mixture was concentrated under reduced pressure, methanol (25 ml) was added, and the mixture was stirred at 60° C. for 3 hrs. The reaction mixture was concentrated under reduced pressure, dil. hydrochloric acid was added, and the mixture was extracted with ethyl acetate. The extract was washed with aqueous sodium hydrogen carbonate solution, then with saturated brine and dried (over anhydrous MgSO₄). The solvent was evaporated under reduced pressure. 28% Sodium methoxide in methanol solution (1.93 g, 10 mmol) and methanol (30 ml) were added to the residue and the mixture was heated under reflux for 5 hrs. 1N Hydrochloric acid (11 ml) was added under ice-cooling, and methanol was evaporated under reduced pressure. Aqueous sodium hydrogen carbonate solution was added to the obtained residue, and the mixture was extracted with ethyl acetate. The extract was washed with saturated brine, dried (over anhydrous MgSO₄), and the solvent was evaporated under reduced pressure. The obtained solid was collected by filtration and washed with diisopropy ether to give methyl (1S,2S)-2-(benzoylamino)cyclohexanecarboxylate (1.33 g, 51%) as a colorless powder.

¹H-NMR (CDCl₃) δ: 1.15-1.85 (6H, m), 1.94-2.05 (1H, m), 2.15-2.27 (1H, m), 2.42 (1H, dt, J=3.4, 11.3 Hz), 3.65 (3H, s), 4.10-4.24 (1H, m), 6.06 (1H, d, J=8.1 Hz), 7.38-7.52 (3H, m), 7.69-7.75 (2H, m).

To the solution of compound (1.23 g, 4.69 mmol) obtained in the above were added methanol (30 ml) and 1N aqueous sodium hydroxide solution (10 ml), and the mixture was stirred at 60° C. for 1 hr. The reaction mixture was concentrated under reduced pressure, and 1N hydrochloric acid (11 ml) was added under ice-cooling. The precipitated solid was collected by filtration and washed with water and dried under reduced pressure to give the title compound (1.14 g, 98%) as a colorless powder.

¹H-NMR (CDCl₃) δ: 1.16-1.90 (6H, m), 1.97-2.08 (1H, m), 2.13-2.24 (1H, m), 2.38 (1H, dt, J=11.3, 3.5 Hz), 4.18 (1H, dt, J=11.0, 4.1 Hz), 7.38-7.52 (3H, m), 7.71-7.77 (2H, m).

Reference Example 66 tert-Butyl (4aR*,5R*,10bR*)-5-phenyl-3,4,4a,5,6,10b-hexahydrobenzo[h]-1,6-naphthyridine-1(2H)-carboxylate

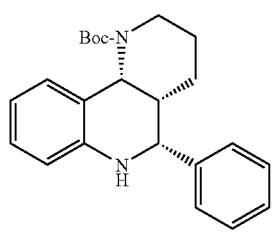

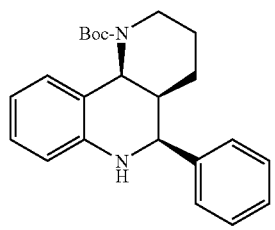

and tert-butyl (4aS*,5R*,10bS*)-5-phenyl-3,4,4a,5,6,10b-hexahydrobenzo[h]-1,6-naphthyridine-1(2H)-carboxylate

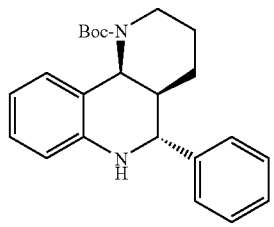

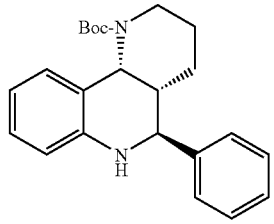

Benzaldehyde (531 mg, 5 mmol) was dissolved in acetonitrile (15 ml), aniline (466 mg, 5 mmol) was added at 0° C., and the mixture was stirred at the same temperature for 1 hr. tert-Butyl 3,4-dihydropyridine-1(2H)-carboxylate (917 mg, 5 mmol) and Dy(OTf)₃ (153 mg, 0.25 mmol) were added at 0° C., and the mixture was further stirred for 1.5 hrs. Water was added to the reaction mixture, and the mixture was extracted with ethyl acetate. The extract was washed with 6% aqueous sodium hydrogen carbonate solution and saturated brine and dried (over anhydrous MgSO₄), and the solvent was evaporated under reduced pressure. The residue was subjected to column chromatography using silica gel (100 g), and eluted with hexane-ethyl acetate (19:1-6:1, v/v). The title compound (4aR*,5R*,10bR*) (109 mg, 6%) was obtained as a colorless amorphous form from the first eluted fraction.

¹H-NMR (CDCl₃) δ: 1.20-1.70 (13H, m), 1.98-2.12 (1H, m), 2.45-2.60 (1H, m), 3.80-4.12 (2H, m), 4.80 (1H, br s), 5.63-5.85 (1H, m), 6.57-6.63 (1H, m), 6.73 (1H, t, J=7.6 Hz), 6.93-7.18 (2H, m), 7.27-7.48 (5H, m).

LC/MS (ESI) m/z: 365 (MH⁺).

The title compound (4aS*,5R*,10bS*) (1.26 g, 69%) was obtained as a colorless amorphous form from the second eluted fraction.

LC/MS (ESI) m/z: 365 (MH⁺).

Reference Example 67 tert-Butyl ((1R,2S)-2-{[(4aR*,5R*,10bR*)-5-phenyl-3,4,4a,5,6,10b-hexahydrobenzo[h]-1,6-naphthyridin-1(2H)-yl]carbonyl}cyclohexyl)carbamate

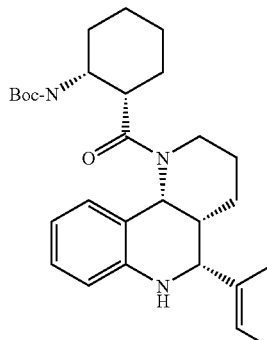

-continued

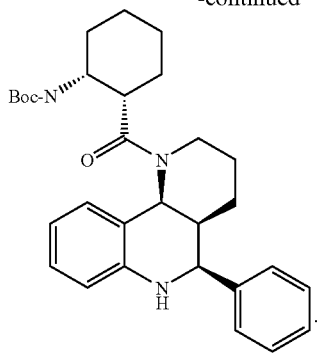

TFA (1 ml) was added to tert-butyl (4aR*,5R*,10bR*)-5-phenyl-3,4,4a,5,6,10b-hexahydrobenzo[h]-1,6-naphthyridine-1(2H)-carboxylate (195 mg, 0.54 mmol), and the mixture was stirred at room temperature for 3 min. Ice water was added to the reaction mixture, basified with 8N aqueous sodium hydroxide solution, and the mixture was extracted with ethyl acetate. The extract was washed with saturated brine, dried (over anhydrous MgSO$_4$), and the solvent was evaporated under reduced pressure. The residue was dissolved in tetrahydrofuran (3 ml), (1S,2R)-2-[(tert-butoxycarbonyl)amino]cyclohexanecarboxylic acid (131 mg, 0.54 mmol) and triethylamine (109 mg, 1.1 mmol) were added, DEPC (88 mg, 0.54 mmol) was added at 0° C., and the mixture was stirred overnight at room temperature. Water was added to the reaction mixture and the mixture was extracted with ethyl acetate. The extract was washed with 6% aqueous sodium hydrogen carbonate solution and saturated brine, dried (over anhydrous MgSO$_4$), and the solvent was evaporated under reduced pressure. The residue was subjected to column chromatography using silica gel (30 g), and eluted with hexane-ethyl acetate (9:1-4:1, v/v) to give the title compound (69 mg, 26%) as a colorless amorphous form.

LC/MS (ESI) m/z: 490 (MH$^+$).

Reference Example 68

{1-[(Anilinocarbonyl)amino]cyclohexyl}acetic acid

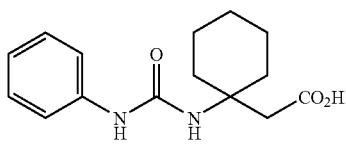

To a solution of (1-aminocyclohexyl)acetic acid (0.232 mg, 1.48 mmol) in a mixture of 1,4-dioxane (9 ml) and water (3 ml) was added 30% aqueous sodium hydroxide solution to pH 9. Phenylisocyanate (0.24 ml, 2.22 mmol) was added dropwise at 35° C. and 30% aqueous sodium hydroxide solution was added to adjust the solution to pH9. The reaction mixture was stirred at 40° C. for 1.5 hrs and concentrated under reduced pressure. 5N Hydrochloric acid was added to acidify the solution (pH3) and the mixture was extracted with ethyl acetate. The extract was washed with saturated brine and dried (over anhydrous MgSO$_4$). After concentration under reduced pressure, the precipitated solid was collected by filtration and washed with diisopropy ether to give the title compound (0.228 g) as a colorless powder with contamination.

$^1$H-NMR (DMSO-d$_6$) δ: 1.12-1.30 (2H, m), 1.35-1.60 (6H, m), 2.04-2.17 (2H, m), 3.32 (2H, s), 6.80-6.90 (1H, m), 7.16-7.24 (2H, m), 7.29-7.40 (2H, m).

Reference Example 69 tert-Butyl (2R)-2-{[(3aR,4R,9bR)-4-phenyl-2,3,3a,4,5,9b-hexahydro-1H-pyrrolo[3,2-c]quinolin-1-yl]carbonyl}piperidine-1-carboxylate (low polarity)

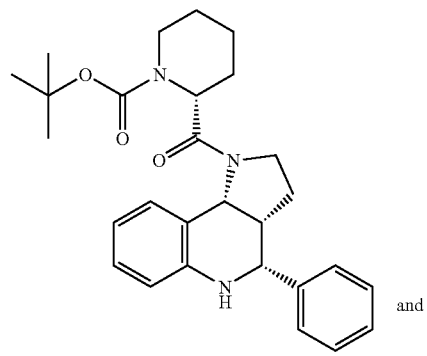

and tert-butyl (2R)-2-{[(3aS,4S,9bS)-4-phenyl-2,3,3a,4,5,9b-hexahydro-1H-pyrrolo[3,2-c]quinolin-1-yl]carbonyl}piperidine-1-carboxylate (high polarity)

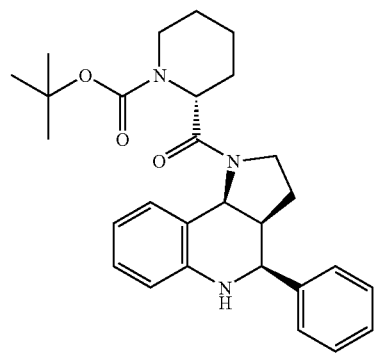

In the same manner as in Reference Example 19 and using N-Boc-D-homoproline instead of (1S,2R)-2-[(tert-butoxycarbonyl)amino]cyclohexanecarboxylic acid, the title compound was synthesized.

(3aR,4R,9bR)-form: $^1$H-NMR (CDCl$_3$) δ: 1.44 (9H, s), 1.54-1.89 (7H, m), 2.25-2.64 (2H, m), 3.44-3.78 (3H, m), 3.84-4.02 (2H, m), 4.66-4.82 (2H, m), 5.76-5.87 (1H, m), 6.58 (1H, d, J=8.1, 1.2 Hz), 6.69-6.77 (1H, m), 7.02-7.10 (1H, m), 7.27-7.53 (6H, m).

(3aS,4S,9bS)-form: $^1$H-NMR (CDCl$_3$) δ: 1.26-1.51 (9H, m), 1.54-2.10 (7H, m), 2.18-2.38 (1H, m), 2.42-2.56 (1H, m), 3.20-3.46 (2H, m), 3.49-3.60 (1H, m), 3.77-4.09 (2H, m), 4.60-4.94 (2H, m), 5.74-5.85 (1H, m), 6.57 (1H, dd, J=8.1, 1.2 Hz), 6.67-6.76 (1H, m), 7.00-7.09 (1H, m), 7.28-7.60 (6H, m).

Reference Example 70

(3aS,4S,9bS)-4-Phenyl-1-[(2R)-piperidin-2-ylcarbonyl]-2,3,3a,4,5,9b-hexahydro-1H-pyrrolo[3,2-c]quinoline dihydrochloride

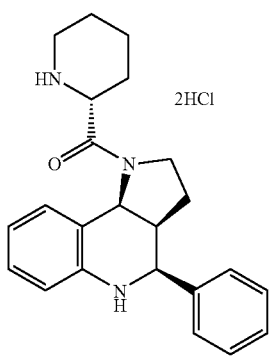

In the same manner as in Reference Example 23 and using tert-butyl (2R)-2-{[(3aS,4S,9bS)-4-phenyl-2,3,3a,4,5,9b-hexahydro-1H-pyrrolo[3,2-c]quinolin-1-yl]carbonyl}piperidine-1-carboxylate (high polarity), the title compound was synthesized.

$^1$H-NMR (CD$_3$OD) δ: 1.60-2.00 (9H, m), 2.18-2.35 (2H, m), 2.67-2.79 (1H, m), 3.02-3.14 (1H, m), 3.34-3.44 (1H, m), 3.47-3.73 (2H, m), 4.03-4.12 (1H, m), 5.69 (1H, d, J=7.2 Hz), 6.82-6.90 (2H, m), 7.10-7.18 (1H, m), 7.31-7.46 (3H, m), 7.50-7.57 (2H, m), 7.60-7.67 (1H, m).

Reference Example 71 tert-Butyl 4-phenyl-2,3-dihydro-1H-pyrrolo[3,2-c]quinoline-1-carboxylate

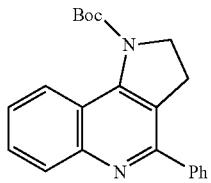

A mixture of tert-butyl (3aR*,4S*,9bR*)-4-phenyl-2,3,3a,4,5,9b-hexahydro-1H-pyrrolo[3,2-c]quinoline-1-carboxylate (20.5 g, 58.6 mmol), manganese dioxide (50.9 g, 586 mmol) and toluene (400 ml) was stirred at 120° C. for 4 hrs. The reaction mixture was cooled to room temperature, insoluble materials were filtered off through celite, and the residue was washed with ethyl acetate. The filtrate and washings were combined and concentrated under reduced pressure. The obtained residue was subjected to column chromatography using basic silica gel, and eluted with hexane-ethyl acetate (10:1-8:1, v/v). The concentrated object fraction was recrystallized from hexane-ethyl acetate to give the title compound (11.7 g, 58%) as colorless needle crystals.

$^1$H-NMR (CDCl$_3$) δ: 1.57 (9H, s), 3.31 (2H, t, J=8.1 Hz), 4.28 (2H, t, J=8.1 Hz), 7.40-7.54 (4H, m), 7.61-7.68 (1H, m), 7.78-7.84 (2H, m), 8.10-8.17 (2H, m).

Reference Example 72

4-Phenyl-2,3-dihydro-1H-pyrrolo[3,2-c]quinoline

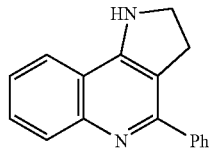

To a solution of the compound (11.7 g, 33.8 mmol) synthesized in Reference Example 71 in methanol (100 ml) was added dropwise 4N hydrogen chloride in ethyl acetate solution (100 ml), and the mixture was stirred at 60° C. for 30 min. The reaction mixture was concentrated under reduced pressure and the obtained powder was collected by filtration and washed with ethyl acetate to give the title compound as hydrochloride (9.14 g, 96%).

Water (2 ml) was added to the above-mentioned hydrochloride (0.206 mg, 0.728 mmol), and the mixture was then basified (pH=11) by adding dropwise 1N aqueous sodium hydroxide solution. The reaction mixture was extracted twice with dichloromethane, and the combined extract was dried (over anhydrous MgSO$_4$) and concentrated under reduced pressure to give the title compound (0.185 g, ca. 100%) as colorless crystals.

$^1$H-NMR (CDCl$_3$) δ: 3.39 (2H, t, J=9.0 Hz), 3.84 (2H, t, J=9.0 Hz), 4.80 (1H, br s), 7.32-7.54 (4H, m), 7.56-7.65 (2H, m), 7.80-7.89 (2H, m), 8.01-8.10 (1H, m).

Reference Example 73

(3aR,4R,9bR)-4-Phenyl-1-[(2R)-piperidin-2-ylcarbonyl]-2,3,3a,4,5,9b-hexahydro-1H-pyrrolo[3,2-c]quinoline dihydrochloride

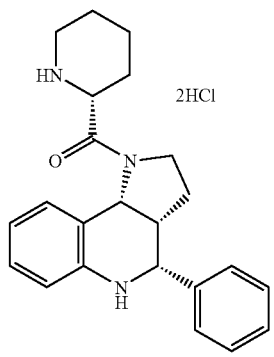

In the same manner as in Reference Example 23 and using tert-butyl (2R)-2-{[(3aR,4R,9bR)-4-phenyl-2,3,3a,4,5,9b-hexahydro-1H-pyrrolo[3,2-c]quinolin-1-yl]carbonyl}piperidine-1-carboxylate (low polarity), the title compound was synthesized.

$^1$H-NMR (CD$_3$OD) δ: 1.61-2.00 (8H, m), 2.10-2.18 (1H, m), 2.20-2.37 (1H, m), 2.58-2.69 (1H, m), 3.02-3.13 (1H, m), 3.21-3.68 (4H, m), 4.08-4.16 (1H, m), 5.79 (1H, d, J=7.5 Hz), 6.71-6.82 (2H, m), 7.05-7.16 (1H, m), 7.30-7.45 (4H, m), 7.49-7.56 (2H, m).

Reference Example 74 tert-Butyl (4-{[((1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexyl)amino]carbonyl}benzyl)carbamate

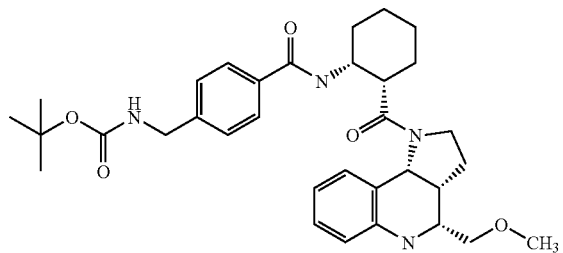

In the same manner as in Reference Example 19 and using 4-{[(tert-butoxycarbonyl)amino]methyl}benzoic acid and (1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexaneamine dihydrochloride, the title compound was synthesized.

LC/MS (ESI) m/z: 577 (MH+).

Example 1

N-((1R,2S)-2-{[(3aR*,4R*,9bR*)-4-Phenyl-2,3,3a,4,5,9b-hexahydro-1H-pyrrolo[3,2-c]quinolin-1-yl]carbonyl}cyclohexyl)benzamide

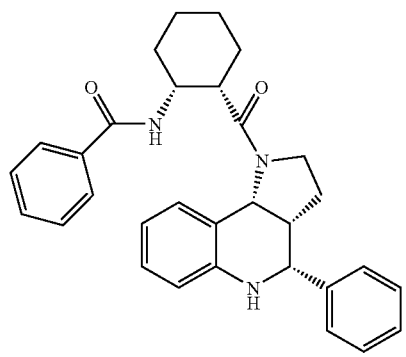

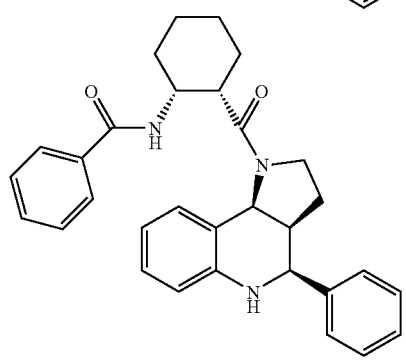

To a mixture of (3aR*,4S*,9bS*)-4-phenyl-2,3,3a,4,5,9b-hexahydro-1H-pyrrolo[3,2-c]quinoline (620 mg, 2.47 mmol), (1S,2R)-2-(benzoylamino)cyclohexanecarboxylic acid (671 mg, 2.7 mmol), triethylamine (0.72 ml, 5.2 mmol), acetonitrile (17 ml) and tetrahydrofuran (17 ml) was added dropwise DEPC (440 mg, 2.7 mmol) under ice-cooling, and the mixture was stirred for 10 min. The mixture was allowed to return to room temperature and the mixture was stirred for 1 hr. Saturated aqueous sodium hydrogen carbonate solution was added to the reaction mixture and the mixture was extracted with ethyl acetate. The extract was dried (over anhydrous Na2 SO4), and the solvent was evaporated. The residue was subjected to column chromatography using silica gel (30 g), and eluted with hexane-ethyl acetate (9:1-7:3, v/v) to give the title compound (735 mg, 62%) as an amorphous form.

LC/MS (ESI) m/z: 480 (MH+).

The following compounds of Example 2-Example 49 were synthesized using the compounds of Reference Example 7—Reference Example 9 and Table 2 in the same manner as in Example 1.

Example 2

N-((1R,2S)-2-{[(3aR*,4R*,9bR*)-8-Fluoro-4-phenyl-2,3,3a,4,5,9b-hexahydro-1H-pyrrolo[3,2-c]quinolin-1-yl]carbonyl}cyclohexyl)benzamide

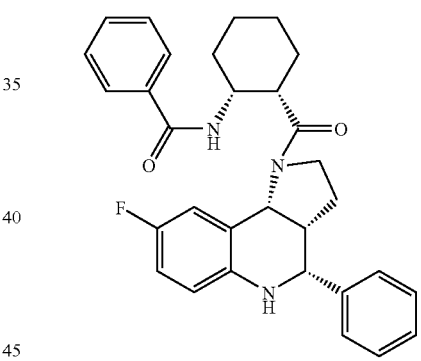

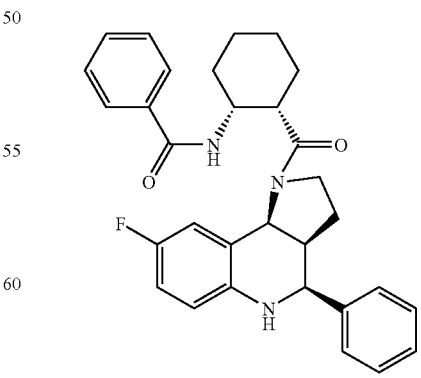

LC/MS (ESI) m/z: 498 (MH+)

Example 3

N-((1R,2S)-2-{[(3aR*,4R*,9bR*)-8-Chloro-4-phenyl-2,3,3a,4,5,9b-hexahydro-1H-pyrrolo[3,2-c]quinolin-1-yl]carbonyl}cyclohexyl)benzamide

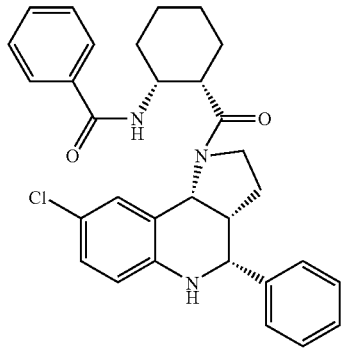

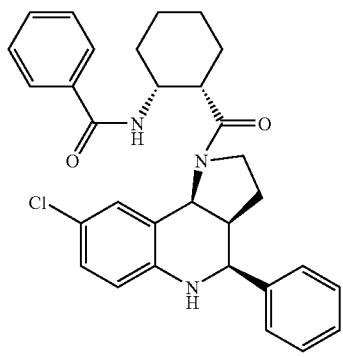

LC/MS (ESI) m/z: 514 (MH$^+$).

Example 4

N-((1R,2S)-2-{[(3aR*,4R*,9bR*)-8-Methyl-4-phenyl-2,3,3a,4,5,9b-hexahydro-1H-pyrrolo[3,2-c]quinolin-1-yl]carbonyl}cyclohexyl)benzamide

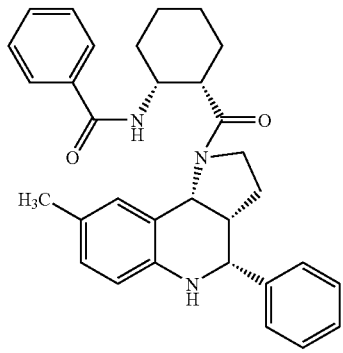

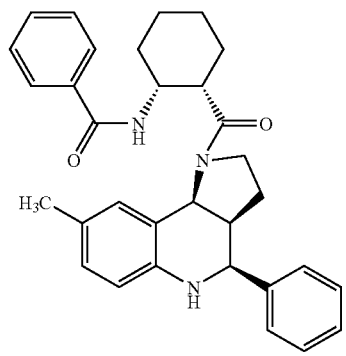

LC/MS (ESI) m/z: 494 (MH$^+$).

Example 5

N-((1R,2S)-2-{[(3aR*,4R*,9bR*)-8-Methoxy-4-phenyl-2,3,3a,4,5,9b-hexahydro-1H-pyrrolo[3,2-c]quinolin-1-yl]carbonyl}cyclohexyl)benzamide

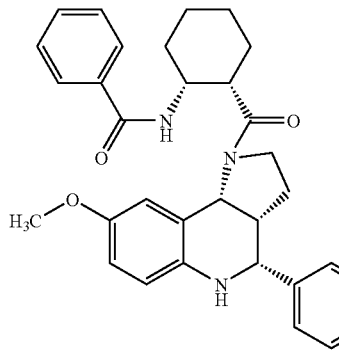

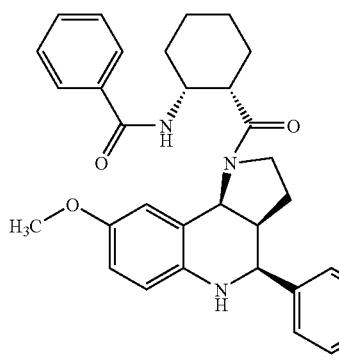

LC/MS (ESI) m/z: 510 (MH$^+$)

Example 6
N-((1R,2S)-2-{[(3aR*,4R*,9bR*)-7-Fluoro-4-phenyl-2,3,3a,4,5,9b-hexahydro-1H-pyrrolo[3,2-c]quinolin-1-yl]carbonyl}cyclohexyl)benzamide
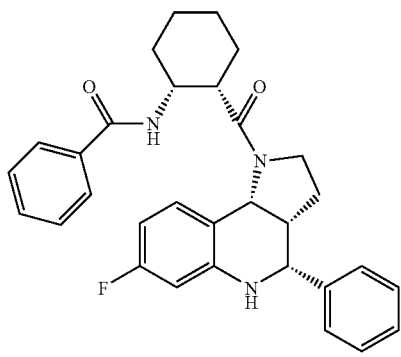
LC/MS (ESI) m/z: 498 (MH+).
Example 7
N-((1R,2S)-2-{[(3aR*,4R*,9bR*)-7-Chloro-4-phenyl-2,3,3a,4,5,9b-hexahydro-1H-pyrrolo[3,2-c]quinolin-1-yl]carbonyl}cyclohexyl)benzamide
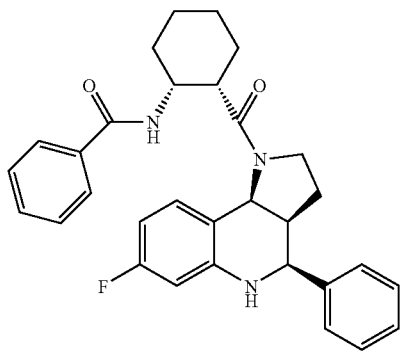
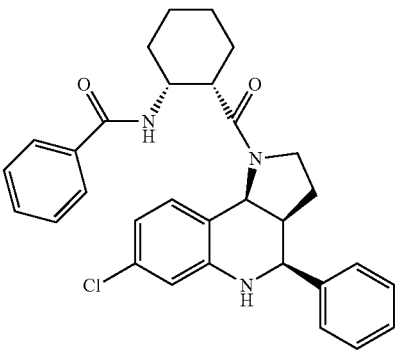
LC/MS (ESI) m/z: 514 (MH+).
Example 8
N-((1R,2S)-2-{[(3aR*,4R*,9bR*)-6-Fluoro-4-phenyl-2,3,3a,4,5,9b-hexahydro-1H-pyrrolo[3,2-c]quinolin-1-yl]carbonyl}cyclohexyl)benzamide
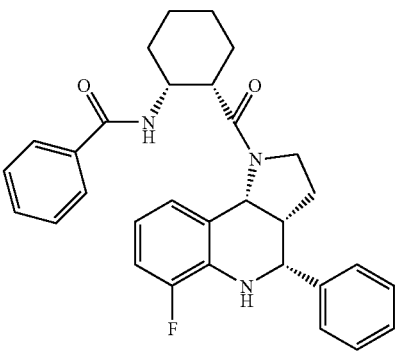
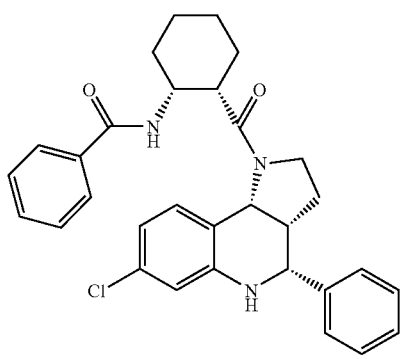
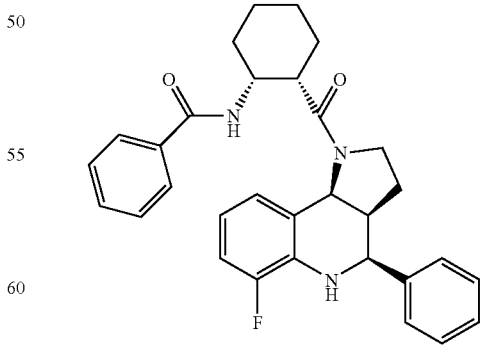
LC/MS (ESI) m/z: 498 (MH+).

Example 9

N-((1R,2S)-2-{[(3aR*,4R*,9bR*)-4-(4-Fluorophenyl)-2,3,3a,4,5,9b-hexahydro-1H-pyrrolo[3,2-c]quinolin-1-yl]carbonyl}cyclohexyl)benzamide

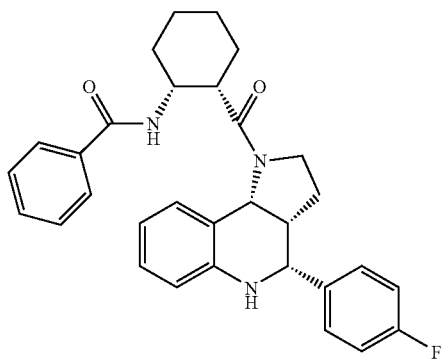

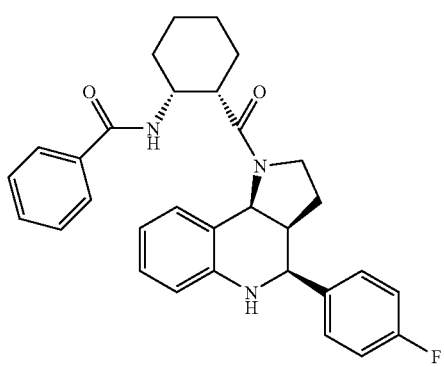

LC/MS (ESI) m/z: 498 (MH+)

Example 10

N-((1R,2S)-2-{[(3aR*,4R*,9bR*)-8-Fluoro-4-(4-fluorophenyl)-2,3,3a,4,5,9b-hexahydro-1H-pyrrolo[3,2-c]quinolin-1-yl]carbonyl}cyclohexyl)benzamide

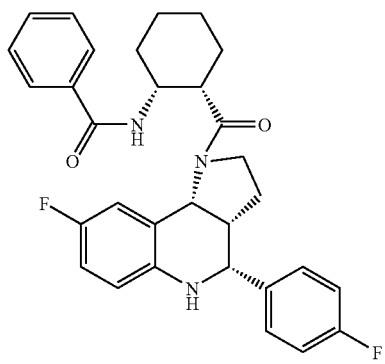

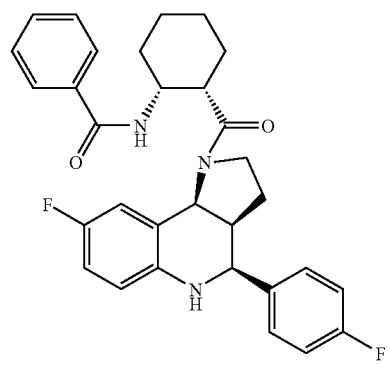

LC/MS (ESI) m/z: 516 (MH+).

Example 11

N-((1R,2S)-2-{[(3aR*,4R*,9bR*)-4-(2-Chlorophenyl)-2,3,3a,4,5,9b-hexahydro-1H-pyrrolo[3,2-c]quinolin-1-yl]carbonyl}cyclohexyl)benzamide

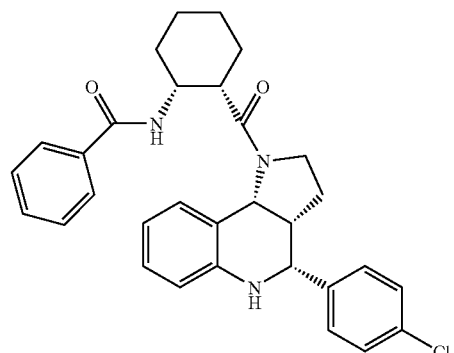

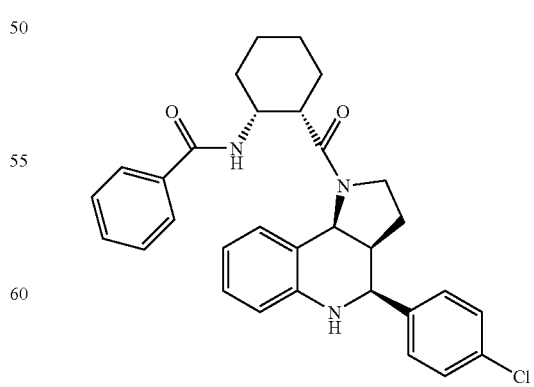

LC/MS (ESI) m/z: 514 (MH+).

Example 12
N-((1R,2S)-2-{[(3aR*,4R*,9bR*)-4-(4-Cyanophenyl)-2,3,3a,4,5,9b-hexahydro-1H-pyrrolo[3,2-c]quinolin-1-yl]carbonyl}cyclohexyl)benzamide
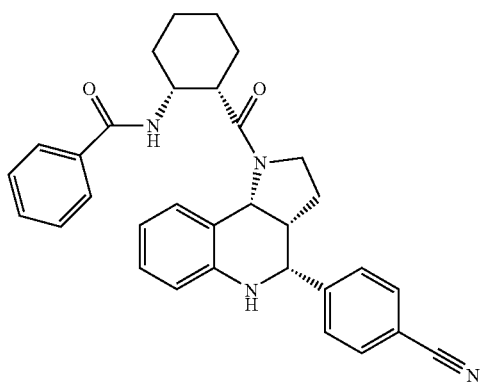
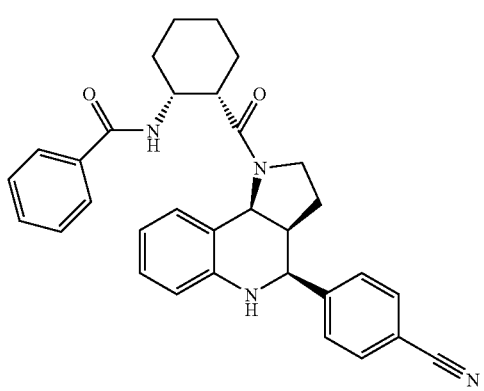
LC/MS (ESI) m/z: 505 (MH+).
Example 13
N-((1R,2S)-2-{[(3aR*,4R*,9bR*)-4-(3-Chlorophenyl)-2,3,3a,4,5,9b-hexahydro-1H-pyrrolo[3,2-c]quinolin-1-yl]carbonyl}cyclohexyl)benzamide
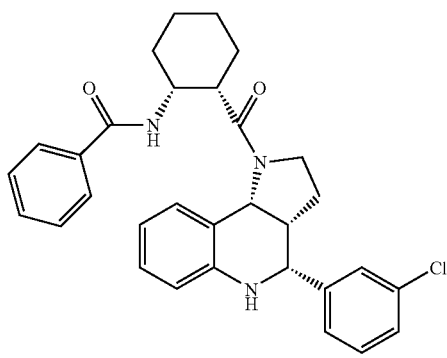
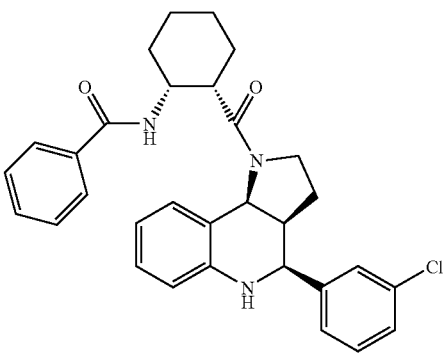
LC/MS (ESI) m/z: 514 (MH+).
Example 14
N-((1R,2S)-2-{[(3aR*,4R*,9bR*)-4-(2-Chlorophenyl)-2,3,3a,4,5,9b-hexahydro-1H-pyrrolo[3,2-c]quinolin-1-yl]carbonyl}cyclohexyl)benzamide
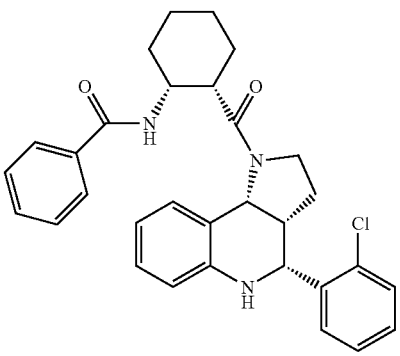
LC/MS (ESI) m/z: 514 (MH+).

Example 15
N-((1R,2S)-2-{[(3aR*,4R*,9bR*)-4-(2-Furyl)-2,3,3a,4,5,9b-hexahydro-1H-pyrrolo[3,2-c]quinolin-1-yl]carbonyl}cyclohexyl)benzamide
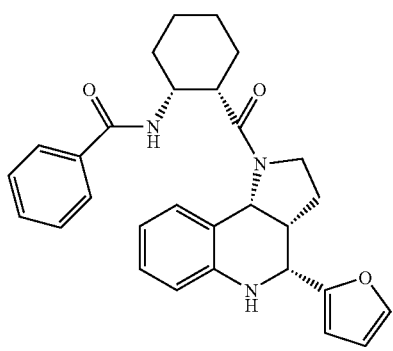
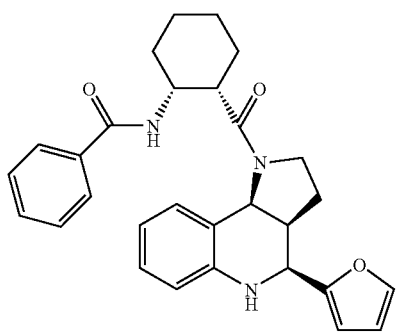
LC/MS (ESI) m/z: 470 (MH⁺).
Example 16
N-((1R,2S)-2-{[(3aR*,4R*,9bR*)-4-(3-Furyl)-2,3,3a,4,59b-hexahydro-1H-pyrrolo[3,2-c]quinolin-1-yl]carbonyl}cyclohexyl)benzamide
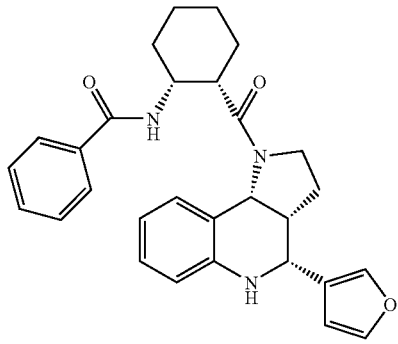
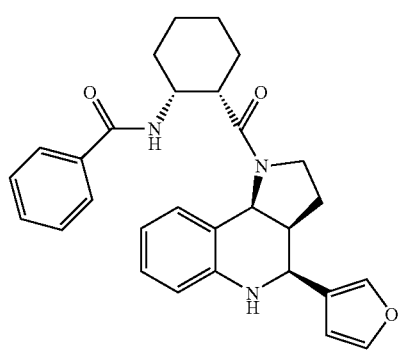
LC/MS (ESI) m/z: 486 (MH⁺).
Example 17
N-((1R,2S)-2-{[(3aR*,4R*,9bR*)-4-(2-Thienyl)-2,3,3a,4,5,9b-hexahydro-1H-pyrrolo[3,2-c]quinolin-1-yl]carbonyl}cyclohexyl)benzamide
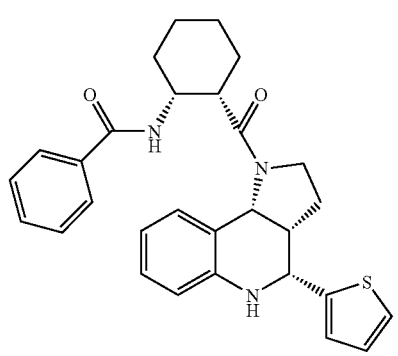
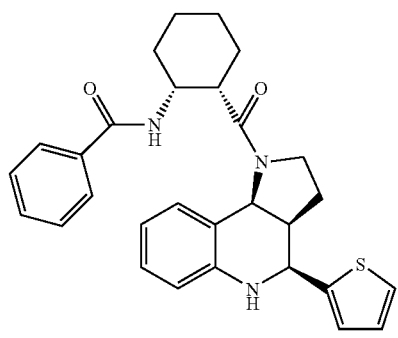
LC/MS (ESI) m/z: 486 (MH⁺).

Example 18
N-((1R,2S)-2-{[(3aS*,4S*,9bS*)-4-(3-Thienyl)-2,3,3a,4,5,9b-hexahydro-1H-pyrrolo[3,2-c]quinolin-1-yl]carbonyl}cyclohexyl)benzamide
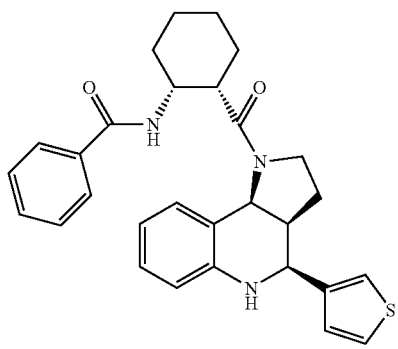
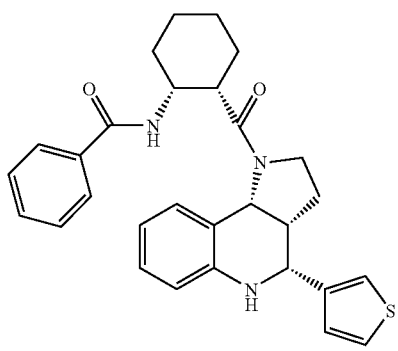
LC/MS (ESI) m/z: 486 (MH+).
Example 19
N-((1R,2S)-2-{[(3aR*,4R*,9bR*)-4-Pyridin-2-yl-2,3,3a,4,5,9b-hexahydro-1H-pyrrolo[3,2-c]quinolin-1-yl]carbonyl}cyclohexyl)benzamide
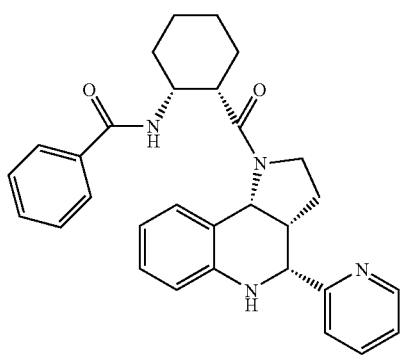
-continued
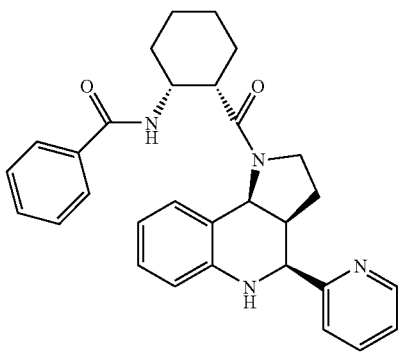
LC/MS (ESI) m/z: 481 (MH+).
Example 20
N-((1R,2S)-2-{[(3aR*,4R*,9bR*)-4-Pyridin-3-yl-2,3,3a,4,5,9b-hexahydro-1H-pyrrolo[3,2-c]quinolin-1-yl]carbonyl}cyclohexyl)benzamide
LC/MS (ESI) m/z: 481 (MH+).

Example 21

Benzyl 2-((3aR*,4R*,9bR*)-1-{[(1S,2R)-2-(benzoylamino)cyclohexyl]carbonyl}-2,3,3a,4,5,9b-hexahydro-1H-pyrrolo[3,2-c]quinolin-4-yl)-1H-pyrrole-1-carboxylate

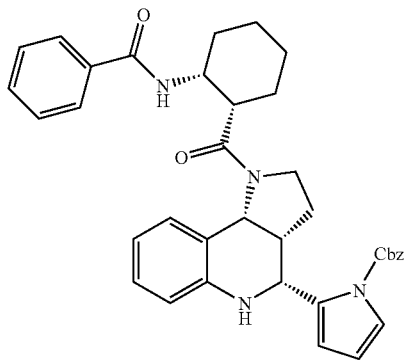

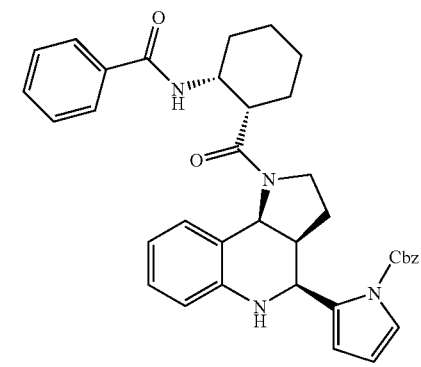

LC/MS (ESI) m/z: 603 (MH+).

Example 22 tert-Butyl 3-((3aR*,4R*,9bR*)-1-{[(1S,2R)-2-(benzoylamino)cyclohexyl]carbonyl}-2,3,3a,4,5,9b-hexahydro-1H-pyrrolo[3,2-c]quinolin-4-yl)-1H-pyrrole-1-carboxylate

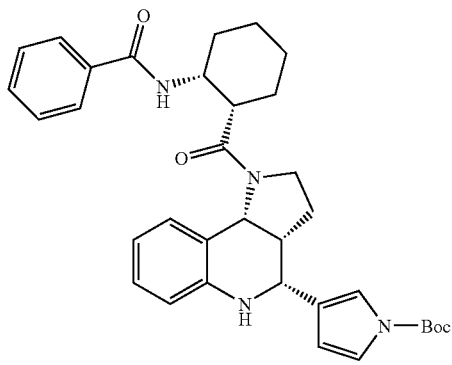

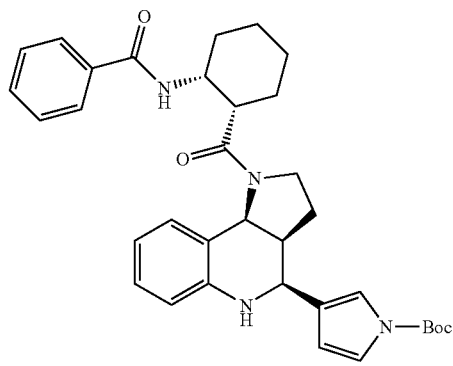

LC/MS (ESI) m/z: 569 (MH+)

Example 23

N-((1R,2S)-2-{[(3aR*,4R*,9bR*)-4-(1-Methyl-1H-pyrrol-2-yl)-2,3,3a,4,5,9b-hexahydro-1H-pyrrolo[3,2-c]quinolin-1-yl]carbonyl}cyclohexyl)benzamide

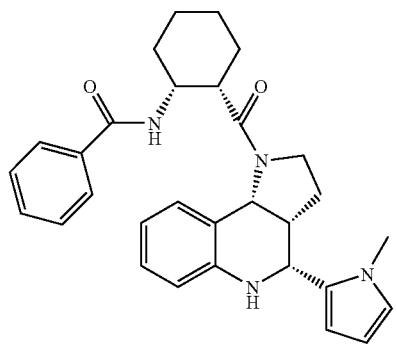

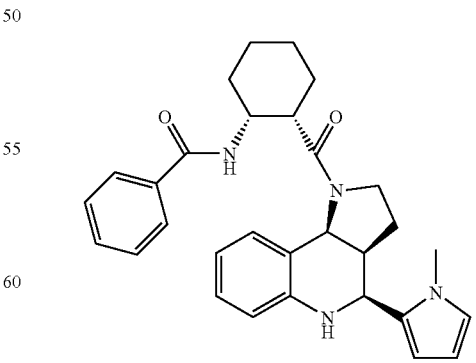

LC/MS (ESI) m/z: 483 (MH+)

Example 24

[2-((3aR*,4R*,9bR*)-1-{[(1S,2R)-2-(Benzoylamino)cyclohexyl]carbonyl}-2,3,3a,4,5,9b-hexahydro-1H-pyrrolo[3,2-c]quinolin-4-yl)-1H-imidazol-1-yl]methyl pivalate

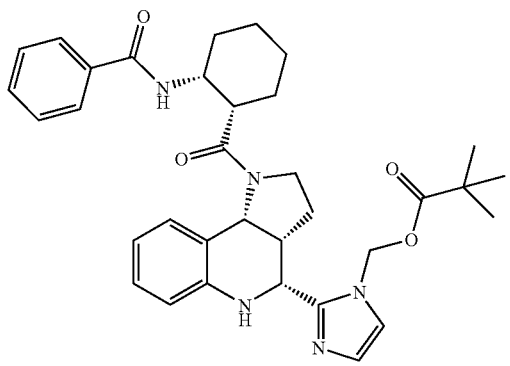

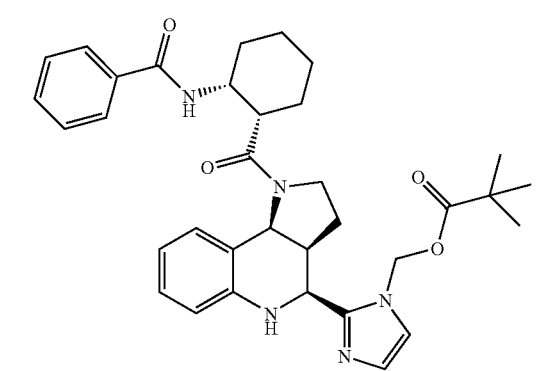

LC/MS (ESI) m/z: δ 84 (MH+).

Example 25

N-((1R,2S)-2-{[(3aR*,4R*,9bR*)-4-(1,3-Thiazol-2-yl)-2,3,3a, 4,5,9b-hexahydro-1H-pyrrolo[3,2-c]quinolin-1-yl]carbonyl}cyclohexyl)benzamide

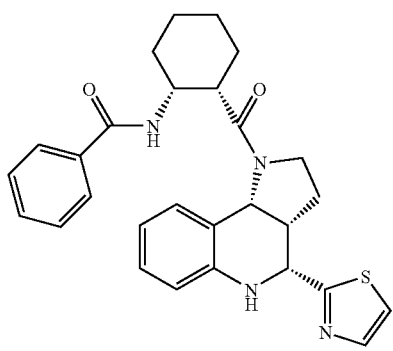

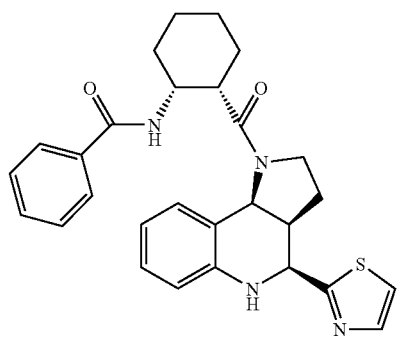

LC/MS (ESI) m/z: 487 (MH+).

Example 26

N-{(1R,2S)-2-[((3aR*,4R*,9bR)-4-Ethyl-2,3,3a,4,5,9b-hexahydro-1H-pyrrolo[3,2-c]quinolin-1-yl)carbonyl]cyclohexyl}benzamide

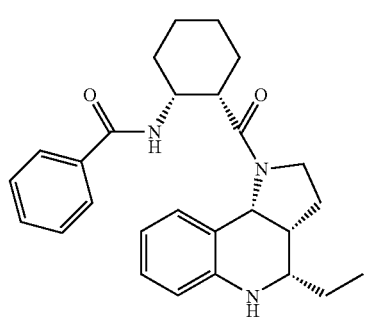

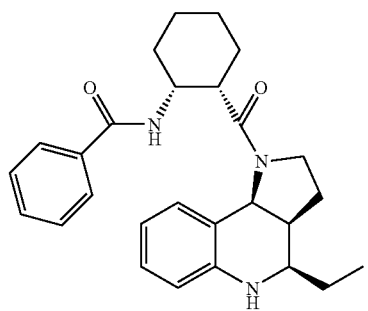

LC/MS (ESI) m/z: 432 (MH+).

Example 27
N-((1R,2S)-2-{[(3aR,4S,9bR*)-4-Propyl-2,3,3a,4,5,9b-hexahydro-1H-pyrrolo[3,2-c]quinolin-1-yl]carbonyl}cyclohexyl)benzamide
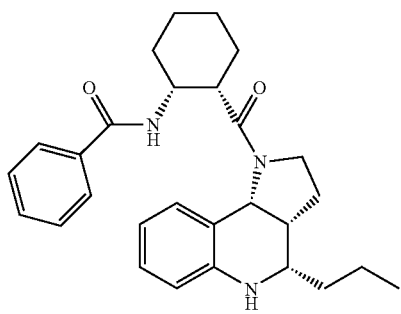
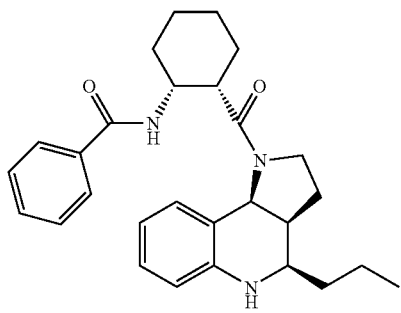
LC/MS (ESI) m/z: 446 (MH+).
Example 28
N-((1R,2S)-2-[(3aR*,4S*,9bR*)-4-Isopropyl-2,3,3a,4,5,9b-hexahydro-1H-pyrrolo[3,2-c]quinolin-1-yl]carbonyl)cyclohexyl)benzamide
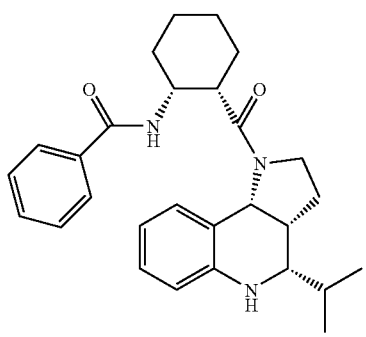
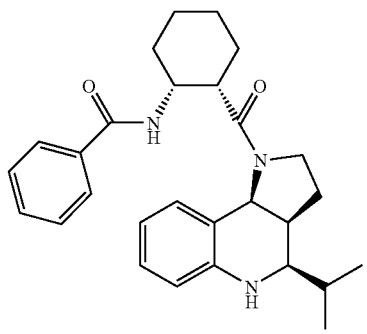
LC/MS (ESI) m/z: 446 (MH+).
Example 29
N-((1R,2S)-2{[(3aR*,4S*,9bR*)-4-Cyclopropyl-2,3,3a,4,5,9b-hexahydro-1H-pyrrolo[3,2-c]quinolin-1-yl]carbonyl}cyclohexyl)benzamide
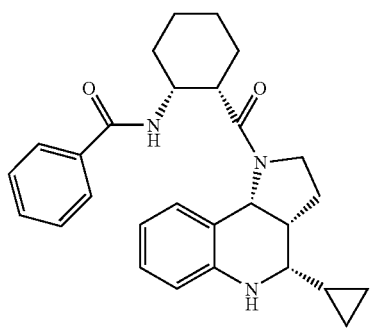
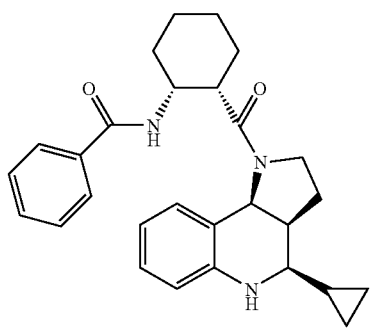
LC/MS (ESI) m/z: 444 (MH+).

Example 30
N-{(1R,2S)-2-[((3aR*,4S*,9bR*)-4-tert-Butyl-2,3,3a,4,5,9b-hexahydro-1H-pyrrolo[3,2-c]quinolin-1-yl)carbonyl]cyclohexyl}benzamide
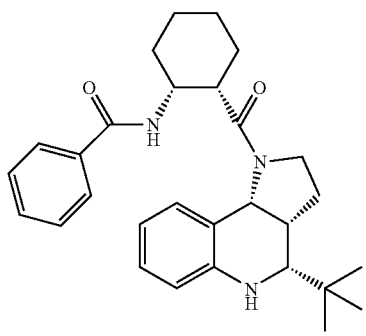
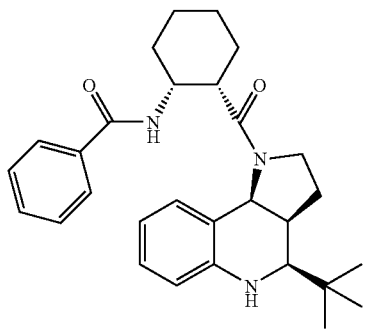
LC/MS (ESI) m/z: 460 (MH+).
Example 31
N-{(1R,2S)-2-[((3aR*,4S*,9bR*)-4-Butyl-2,3,3a,4,5,9b-hexahydro-1H-pyrrolo[3,2-c]quinolin-1-yl)carbonyl]cyclohexyl}benzamide
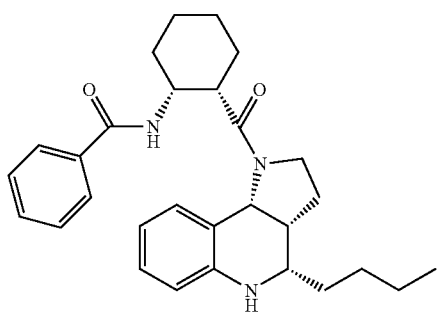
-continued
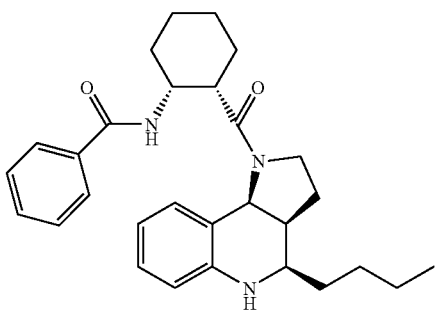
LC/MS (ESI) m/z: 460 (MH+)
Example 32
N-[(1R,2S)-2-({(3aR*,4S*,9bR*)-4-[(Benzyloxy)methyl]-2,3,3a,4,5,9b-hexahydro-1H-pyrrolo[3,2-c]quinolin-1-yl}carbonyl)cyclohexyl]benzamide
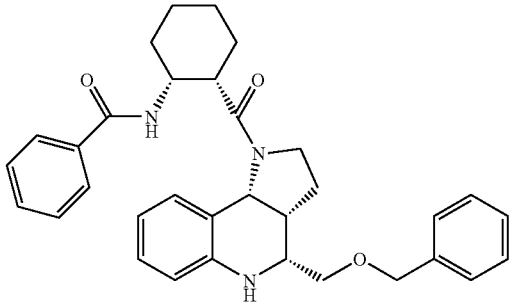
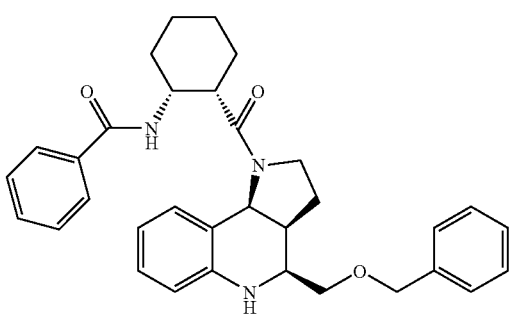
LC/MS (ESI) m/z: 524 (MH+).

Example 33 tert-Butyl [((3aR*,4R*,9bR*)-1-{[(1S,2R)-2-(benzoylamino)cyclohexyl]carbonyl}-2,3,3a,4,5,9b-hexahydro-1H-pyrrolo[3,2-c]quinolin-4-yl)methyl]methylcarbamate

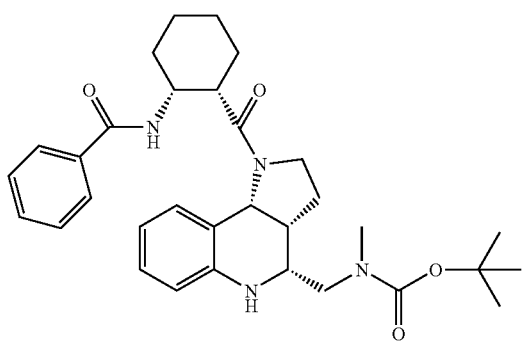

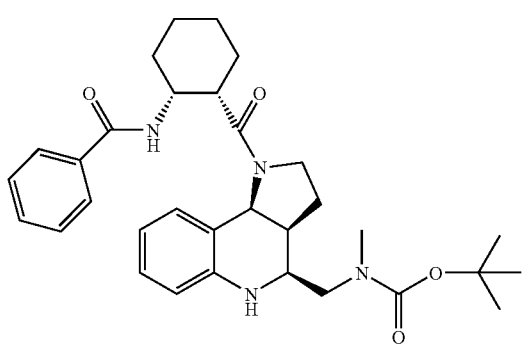

LC/MS (ESI) m/z: 547 (MH+).

Example 34

N-[(1R,2S)-2-({(3aR*,4R*,9bR*)-4-[1-(4-Methoxybenzyl)-1H-imidazol-2-yl]-2,3,3a,4,5,9b-hexahydro-1H-pyrrolo[3,2-c]quinolin-1-yl}carbonyl)cyclohexyl]benzamide

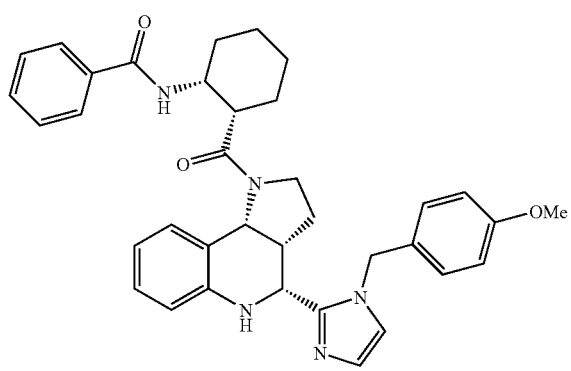

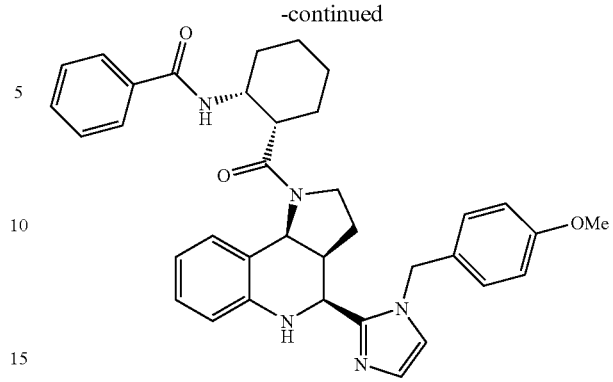

LC/MS (ESI) m/z: 560 (MH+).

Example 35

N-[(1R,2S)-2-({(3aR*,4R*,9bR*)-4-[1-(4-Methoxybenzyl)-1H-pyrazol-5-yl]-2,3,3a,4,5,9b-hexahydro-1H-pyrrolo[3,2-c]quinolin-1-yl}carbonyl)cyclohexyl]benzamide

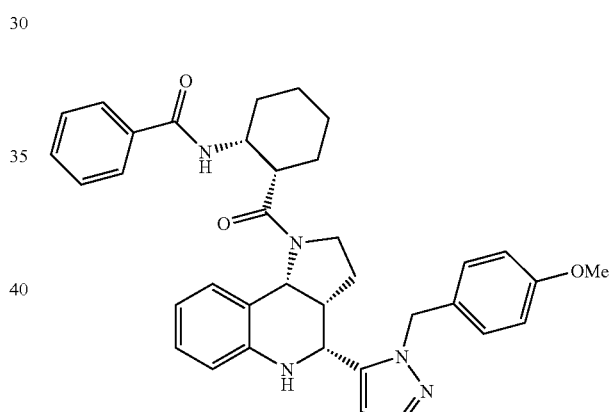

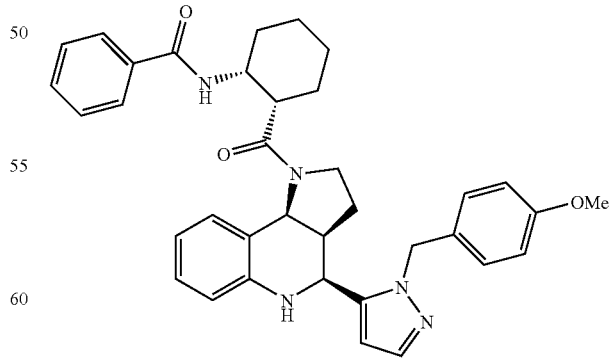

LC/MS (ESI) m/z: 590 (MH+).

Example 36
N-((1R,2S)-2-{[(3aR*,4R*,9bR*)-4-(1-Trityl-1H-pyrazol-5-yl)-2,3,3a,4,5,9b-hexahydro-1H-pyrrolo[3,2-c]quinolin-1-yl]carbonyl}cyclohexyl)benzamide
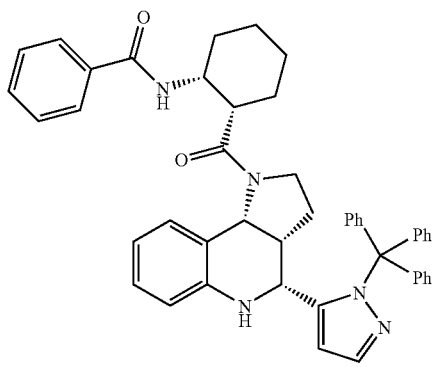
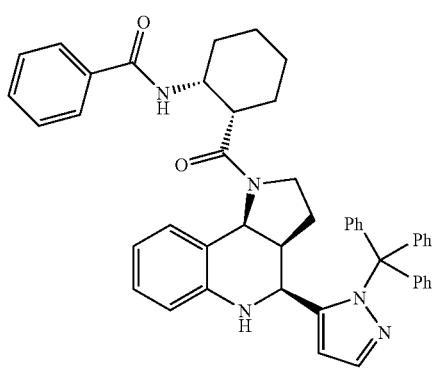
LC/MS (ESI) m/z: 712 (MH+).
Example 37
N-((1R,2S)-2-{[(3aR*,4R*,9bR*)-4-(1-Trityl-1H-1,2,4-triazol-5-yl)-2,3,3a,4,5,9b-hexahydro-1H-pyrrolo[3,2-c]quinolin-1-yl]carbonyl}cyclohexyl)benzamide
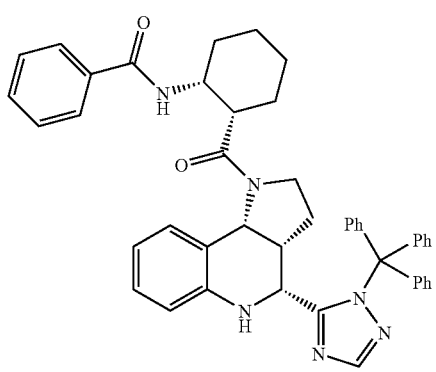
-continued
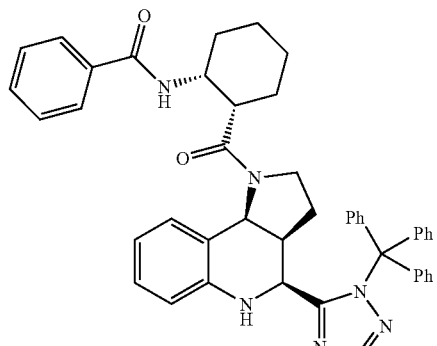
LC/MS (ESI) m/z: 713 (MH+).
Example 38
N-{(1R,2S)-2-[(3aR*,9bR*)-2,3,3a,4,5,9b-Hexahydro-1H-pyrrolo[3,2-c]quinolin-1-ylcarbonyl]cyclohexyl}benzamide
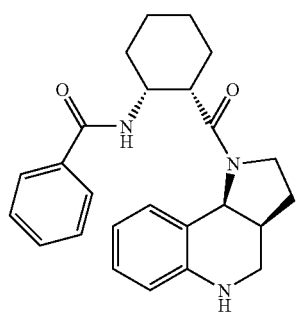
LC/MS (ESI) m/z: 404 (MH+).

Example 39
N-((1R,2S)-2-{[(3aR*,4R*,9bR*)-4-(4-Methylphenyl)-2,3,3a,4,5,9b-hexahydro-1H-pyrrolo[3,2-c]quinolin-1-yl]carbonyl}cyclohexyl)benzamide
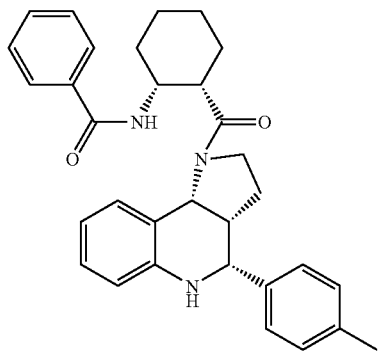
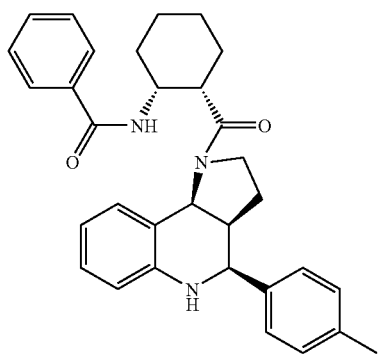
LC/MS (ESI) m/z: 494 (MH+).
Example 40
N-((1R,2S)-2-{[(3aR*,4R*,9bR*)-4-(1-Naphthyl)-2,3,3a,4,5,9b-hexahydro-1H-pyrrolo[3,2-c]quinolin-1-yl]carbonyl}cyclohexyl)benzamide
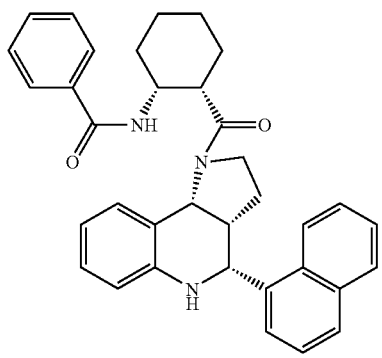
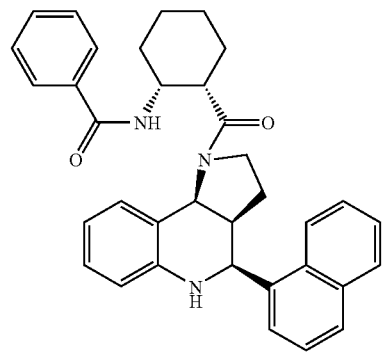
LC/MS (ESI) m/z: 530 (MH+).
Example 41
N-((1R,2S)-2-{[(3aR*,4R*,9bR*)-4-Pyridin-4-yl-2,3,3a,4,5,9b-hexahydro-1H-pyrrolo[3,2-c]quinolin-1-yl]carbonyl}cyclohexyl)benzamide
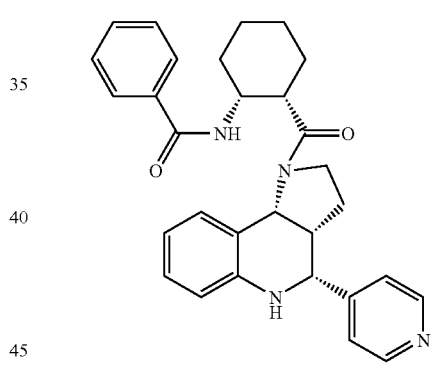
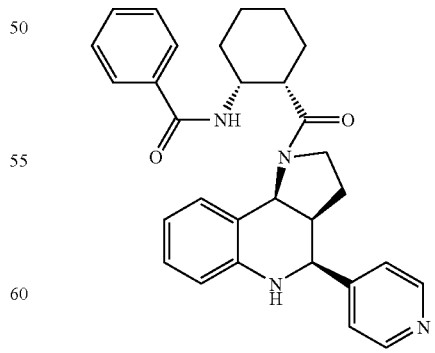
LC/MS (ESI) m/z: 481 (MH+).

Example 42
N-((1R,2S)-2-{[(3aR*,4R*,9bR*)-8-Butyl-4-phenyl-2,3,3a,4,5,9b-hexahydro-1H-pyrrolo[3,2-c]quinolin-1-yl]carbonyl}cyclohexyl)benzamide
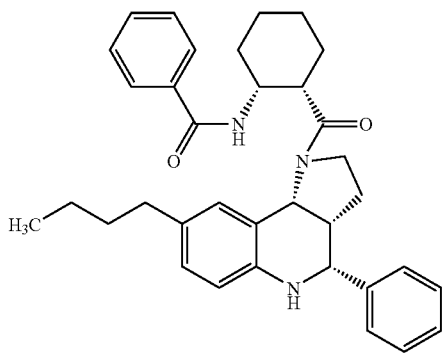
LC/MS (ESI) m/z: 536 (MH+).
Example 43
N-{(1R,2S)-2-[((3aR*,4R*,9bR*)-4-Hexyl-2,3,3a,4,5,9b-hexahydro-1H-pyrrolo[3,2-c]quinolin-1-yl)carbonyl]cyclohexyl}benzamide
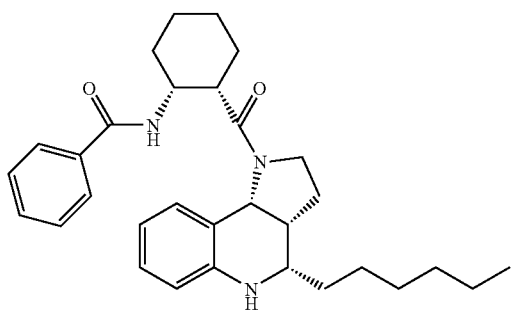
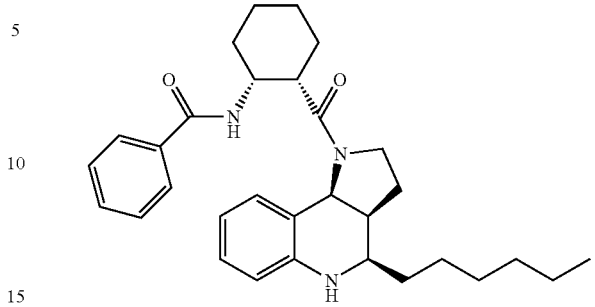
LC/MS (ESI) m/z: 488 (MH+).
Example 44
N-((1R,2S)-2-{[(3aR*,4R*,9bR*)-7-Methyl-4-phenyl-2,3,3a,4,5,9b-hexahydro-1H-pyrrolo[3,2-c]quinolin-1-yl]carbonyl}cyclohexyl)benzamide
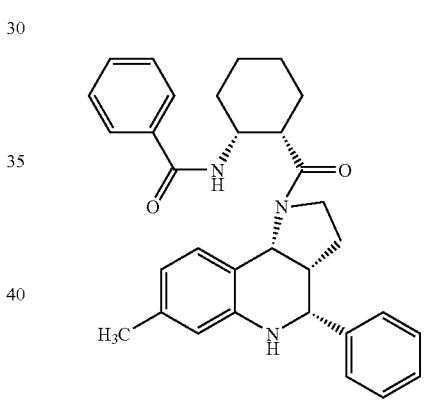
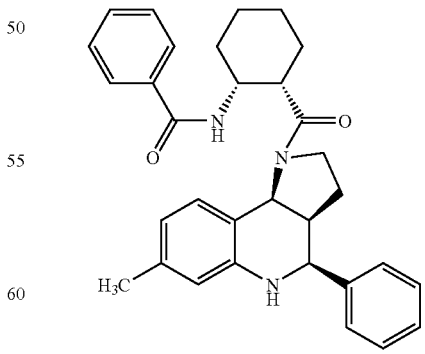
LC/MS (ESI) m/z: 494 (MH+).

Example 45
N-((1R,2S)-2-{[(3aR*,4R*,9bR*)-7-Cyano-4-phenyl-2,3,3a,4,5,9b-hexahydro-1H-pyrrolo[3,2-c]quinolin-1-yl]carbonyl}cyclohexyl)benzamide
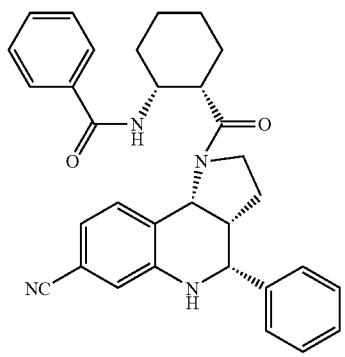
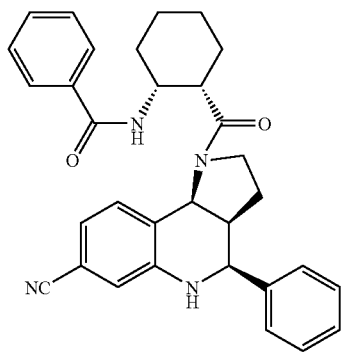
LC/MS (ESI) m/z: 505 (MH+).
Example 46
N-((1R,2S)-2-{[(3aR*,4R*,9bR*)-6-Chloro-4-phenyl-2,3,3a,4,5,9b-hexahydro-1H-pyrrolo[3,2-c]quinolin-1-yl]carbonyl}cyclohexyl)benzamide
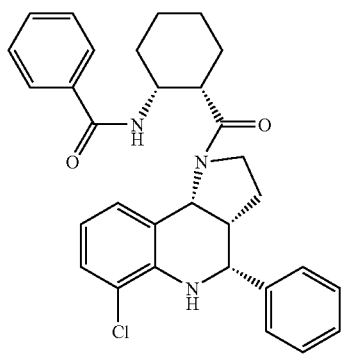
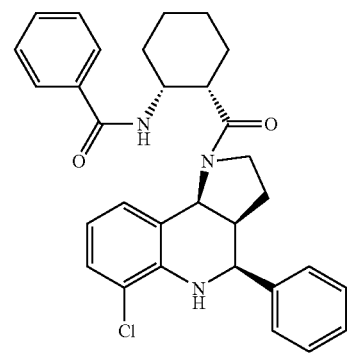
LC/MS (ESI) m/z: 514 (MH+).
Example 47
N-((1R,2S)-2-{[(3aR*,4R*,9bR*)-6-Methyl-4-phenyl-2,3,3a,4,5,9b-hexahydro-1H-pyrrolo[3,2-c]quinolin-1-yl]carbonyl}cyclohexyl)benzamide
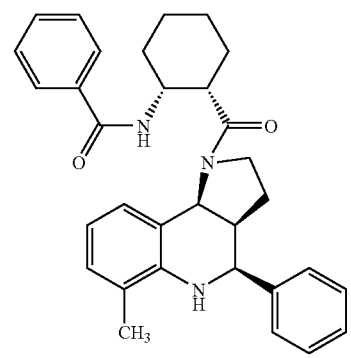
LC/MS (ESI) m/z: 494 (MH+).

Example 48

N-((1R,2S)-2-{[(3aR*,4R*,9bR)-7-Methoxy-4-phenyl-2,3,3a,4,5,9b-hexahydro-1H-pyrrolo[3,2-c]quinolin-1-yl]carbonyl}cyclohexyl)benzamide

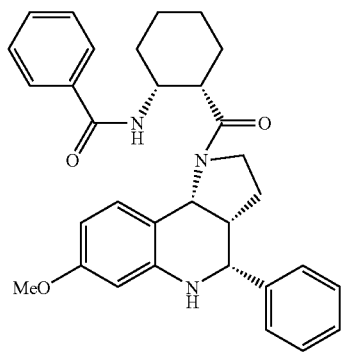

LC/MS (ESI) m/z: 510 (MH+).

Example 49

[4-((3aR*,4R*,9bR*)-1-{[(1S,2R)-2-(Benzoylamino)cyclohexyl]carbonyl}-2,3,3a,4,5,9b-hexahydro-1H-pyrrolo[3,2-c]quinolin-4-yl)-1H-imidazol-1-yl]pivalate

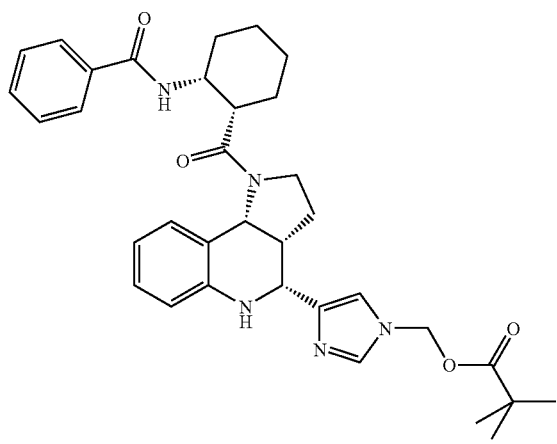

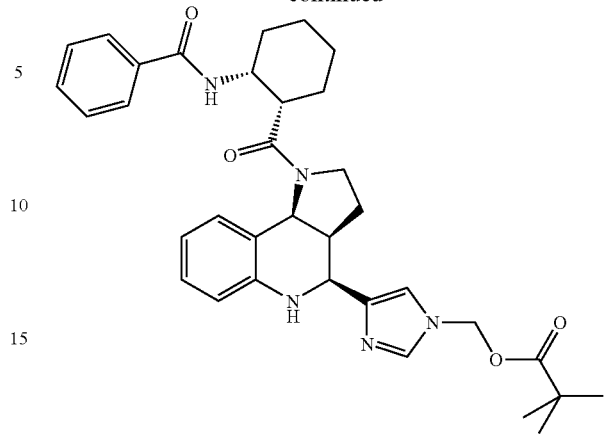

LC/MS (ESI) m/z: 584 (MH+).

Example 50

N-((1R,2S)-2-{[(3aR*,4R*,9bR)-4-(Hydroxymethyl)-2,3,3a,4,5,9b-hexahydro-1H-pyrrolo[3,2-c]quinolin-1-yl]carbonyl}cyclohexyl)benzamide

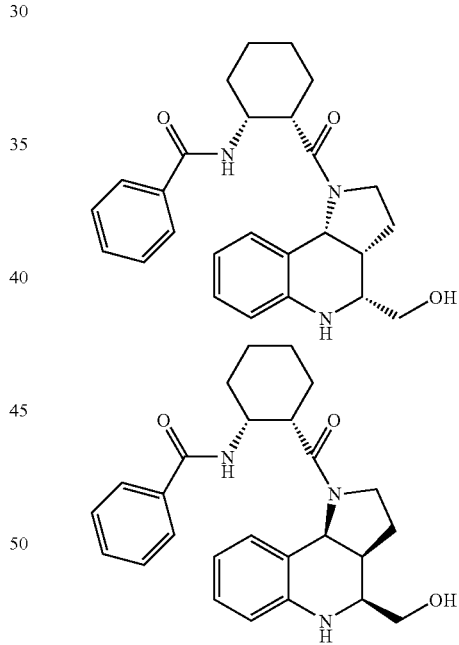

The compound (850 mg, 1.62 mmol) synthesized in Example 32 was dissolved in ethanol (25 ml), and hydrogenation reaction was carried out in the presence of 10% palladium on carbon (50% aqueous, 500 mg) at room temperature for 12 hrs. The reaction mixture was filtered and washed with ethanol. The filtrate and the washings were combined and concentrated under reduced pressure. The residue was subjected to column chromatography using silica gel (10 g), and eluted with hexane-ethyl acetate (4:1-1:1, v/v) to give the title compound (130 mg, 19%) as an amorphous form.

LC/MS (ESI) m/z: 434 (MH+).

Example 51

N-((1R,2S)-2-{[(3aR*,4R*,9bR*)-4-(Methoxymethyl)-2,3,3a,4,5,9b-hexahydro-1H-pyrrolo[3,2-c]quinolin-1-yl]carbonyl}cyclohexyl)benzamide

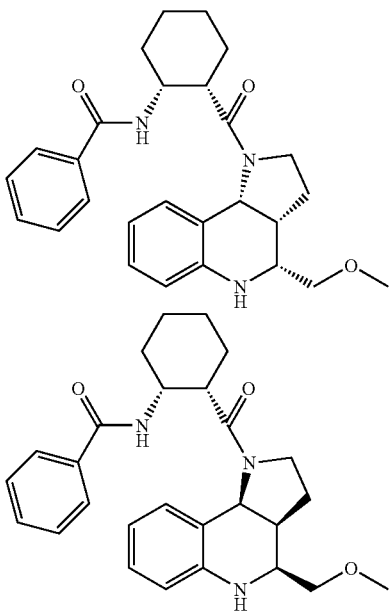

Sodium hydride (60% in oil, 14 mg, 0.1 mmol) was suspended in tetrahydrofuran (1 ml), the compound (35 mg, 0.08 mmol) synthesized in Example 50 was added under ice-cooling, and the suspension was stirred for 1 hr. Methyl iodide (14 mg, 0.1 mmol) was added thereto, and the mixture was stirred under ice-cooling for 30 min., and then at room temperature for 2 hrs. Saturated aqueous sodium hydrogen carbonate solution was added to the reaction mixture, and the mixture was extracted with ethyl acetate. The extract was dried (over anhydrous $Na_2SO_4$), and the solvent was evaporated under reduced pressure. The residue was subjected to column chromatography using silica gel (10 g) and eluted with hexane-ethyl acetate (4:1, v/v) to give the title compound (30 mg, 84%) as an amorphous form.

LC/MS (ESI) m/z: 448 (MH$^+$).

Example 52

N-((1R,2S)-2-{[(3aR*,4R*,9bR*)-4-(1H-Pyrrol-3-yl)-2,3,3a,4,5,9b-hexahydro-1H-pyrrolo[3,2-c]quinolin-1-yl]carbonyl}cyclohexyl)benzamide

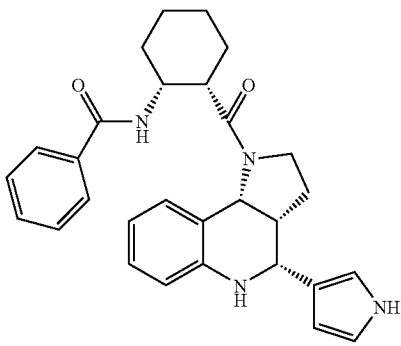

-continued

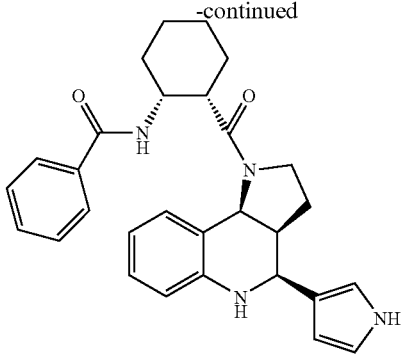

The compound (537 mg, 0.94 mmol) synthesized in Example 22 was dissolved in dichloromethane (3 ml), TFA (1 ml) was added at 0° C., and the mixture was stirred at room temperature for 3 hrs. Ice water was added to the reaction mixture, basified with 8N aqueous sodium hydroxide solution, and the mixture was extracted with ethyl acetate. The extract was washed with saturated brine, dried (over anhydrous $MgSO_4$), and the solvent was evaporated under reduced pressure. The obtained residue was subjected to column chromatography using silica gel (30 g), and eluted with hexane-ethyl acetate (4:1-1:1, v/v) to give the title compound (71 mg, 16%) as a colorless amorphous form.

LC/MS (ESI) m/z: 469 (MH$^+$).

Example 53

N-[(1R,2S)-2-({(3aR*,4R*,9bR*)-4-[(Methylamino)methyl]-2,3,3a,4,5,9b-hexahydro-1H-pyrrolo[3,2-c]quinolin-1-yl}carbonyl)cyclohexyl]benzamide dihydrochloride

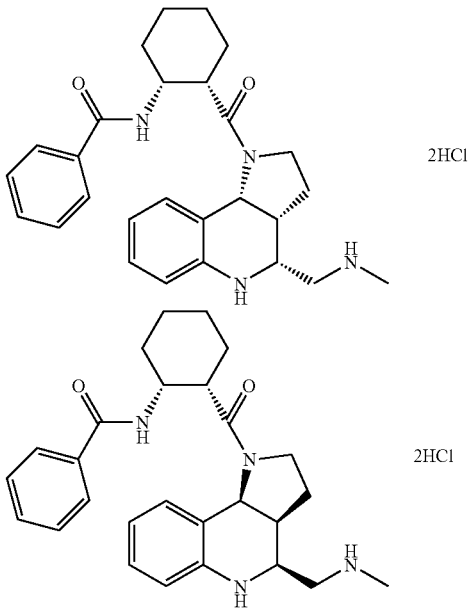

The compound (130 mg, 0.238 mmol) synthesized in Example 33 was dissolved in ethyl acetate (5 ml), a solution of 4N hydrogen chloride in ethyl acetate (5 ml) was added, and the mixture was stirred for 3 hrs. The precipitated crystals were collected by filtration, washed with ethyl acetate, and dried under reduced pressure to give the title compound (110 mg, 89%).

LC/MS (ESI) m/z: 447 (MH$^+$).

Example 54

N-((1R,2S)-2-{[(3aR*,4R*,9bR*)-4-(1H-Imidazol-2-yl)-2,3,3a,4,5,9b-hexahydro-1H-pyrrolo[3,2-c]quinolin-1-yl]carbonyl}cyclohexyl)benzamide

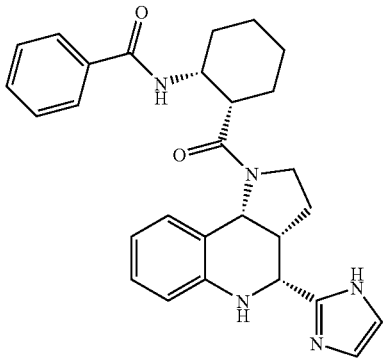

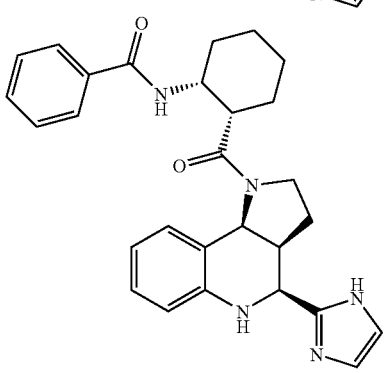

The compound (200 mg, 0.34 mmol) synthesized in Example 24 was dissolved in methanol (4 ml), and 28% aqueous ammonia solution (6 ml) was added at room temperature. The mixture was stirred at room temperature for 4 hrs. The reaction mixture was concentrated under reduced pressure and azeotroped with ethanol. The residue was subjected to column chromatography using basic silica gel (30 g), and eluted with ethyl acetate-methanol (1:0-11:1, v/v) to give the title compound (152 mg, 95%) as a colorless powder.

LC/MS (ESI) m/z: 470 (MH$^+$).

Example 55

N-((1R,2S)-2-{[(3aR*,4R*,9bR*)-4-(1H-Imidazol-4-yl)-2,3,3a,4,5,9b-hexahydro-1H-pyrrolo[3,2-c]quinolin-1-yl]carbonyl}cyclohexyl)benzamide

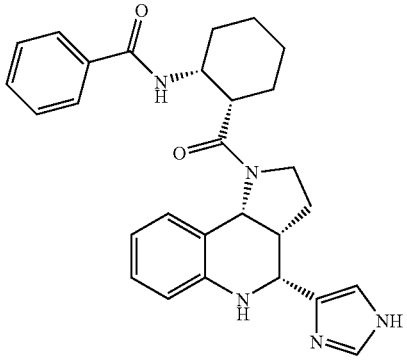

-continued

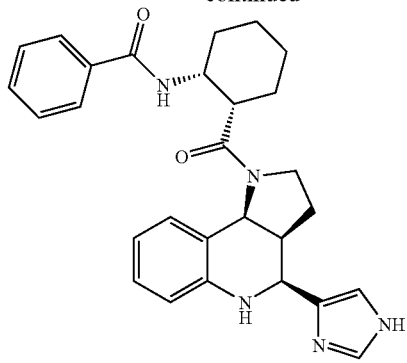

In the same manner as in Example 54 and using the compound synthesized in Example 49, the title compound was synthesized.

LC/MS (ESI) m/z: 470 (MH$^+$).

Example 56

N-((1R,2S)-2-{[(3aR*,4R*,9bR*)-4-(1H-Pyrazol-5-yl)-2,3,3a,4,5,9b-hexahydro-1H-pyrrolo[3,2-c]quinolin-1-yl]carbonyl}cyclohexyl)benzamide

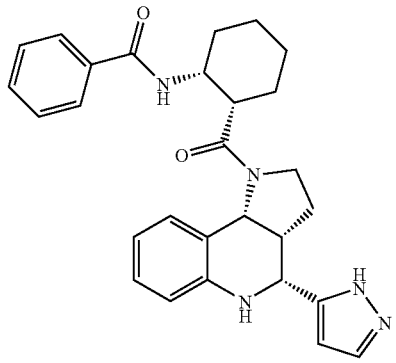

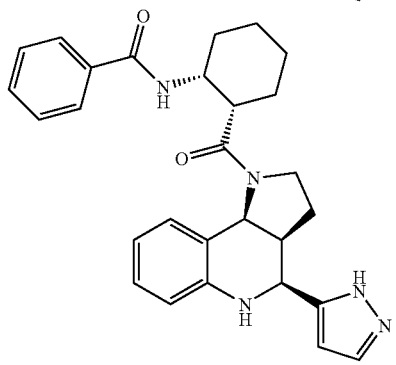

The compound (126 mg, 0.18 mmol) synthesized in Example 36 was dissolved in dichloromethane (3 ml), p-toluenesulfonic acid monohydrate (37 mg, 0.23 mmol) was added at room temperature, and the mixture was stirred for 30 min. Water was added to the reaction mixture, and the mixture was extracted with ethyl acetate. The extract was washed with 6% aqueous sodium hydrogen carbonate solution and saturated brine, dried (over anhydrous MgSO$_4$), and the solvent was 2evaporated under reduced pressure. The residue was subjected to column chromatography using basic silica gel (30 g) and eluted with ethyl acetate-methanol (1:0-19:1, v/v) to give the title compound (65 mg, 79%) as a colorless powder.

LC/MS (ESI) m/z: 470 (MH+).

Example 57

N-((1R,2S)-2-{[(3aR*,4R*,9bR*)-4-(1H-1,2,4-Triazol-5-yl)-2,3,3a,4,5,9b-hexahydro-1H-pyrrolo[3,2-c]quinolin-1-yl]carbonyl}cyclohexyl)benzamide

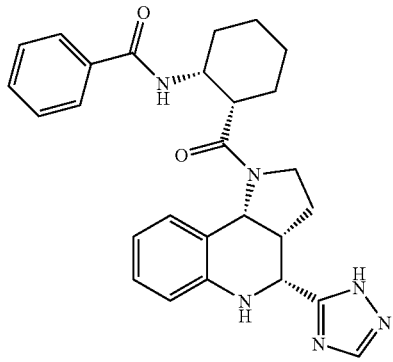

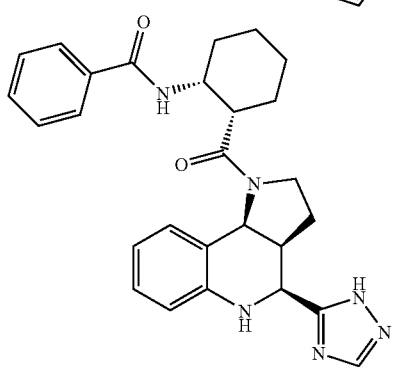

In the same manner as in Example 56 and using the compound of Example 37, the title compound was synthesized.

LC/MS (ESI) m/z: 471 (MH+).

Example 58

N-{(1R,2S)-2-[((3aR,4R,9bR)-4-Phenyl-2,3,3a,4,5,9b-hexahydro-1H-pyrrolo[3,2-c]quinolin-1-yl)carbonyl]cyclohexyl}benzamide

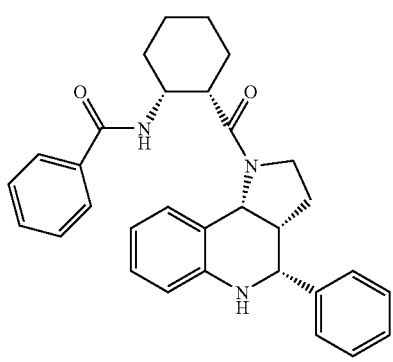

and

N-{(1R,2S)-2-[((3aS,4S,9bS)-4-phenyl-2,3,3a,4,5,9b-hexahydro-1H-pyrrolo[3,2-c]quinolin-1-yl)carbonyl]cyclohexyl}benzamide

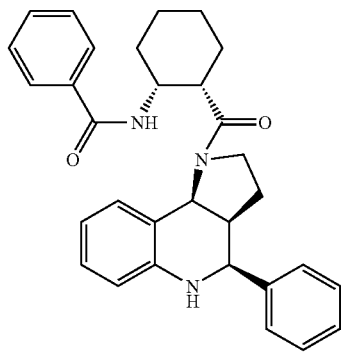

The compound (1.38 g, 2.88 mmol) synthesized in Example 1 was subjected to silica gel column chromatography and eluted with hexane-ethyl acetate (3:1, v/v) to give the title compound (3aR,4R,9bR) (486 mg, 35%) as an amorphous form from the first eluted fraction.

LC/MS (ESI) m/z: 480 (MH+).

The title compound (3aS,4S,9bS) (678 mg, 49%) was obtained as an amorphous form from the second eluted fraction.

LC/MS (ESI) m/z: 480 (MH+).

The following compounds of Example 59-Example 63 were separated by column chromatography in the same manner as in Example 58.

Example 59

N-((1R,2S)-2-[(3aR,4S,9bR)-(4-Cyclopropyl-2,3,3a,4,5,9b-hexahydro-1H-pyrrolo[3,2-c]quinolin-1-yl)carbonyl]cyclohexyl)benzamide

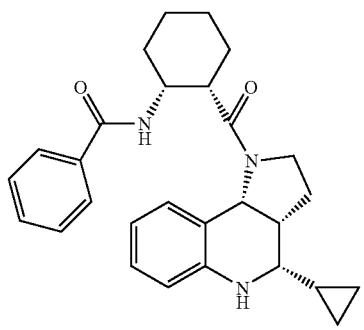

LC/MS (ESI) m/z: 444 (MH+).

Example 60

N-((1R,2S)-2-{[(3aR,4R,9bR)-4-(3-Thienyl)-2,3,3a,4,5,9b-hexahydro-1H-pyrrolo[3,2-c]quinolin-1-yl]carbonyl}cyclohexyl)benzamide

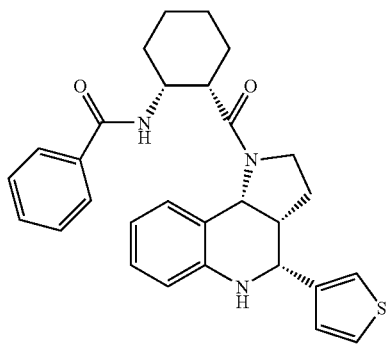

LC/MS (ESI) m/z: 486 (MH+).
and

N-((1R,2S)-2-{[(3aS,4S,9bS)-4-(3-thienyl)-2,3,3a,4,5,9b-hexahydro-1H-pyrrolo[3,2-c]quinolin-1-yl]carbonyl}cyclohexyl)benzamide

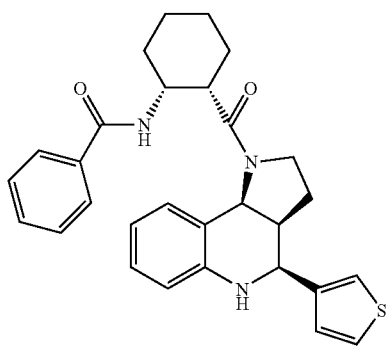

LC/MS (ESI) m/z: 486 (MH+).

Example 61

N-((1R,2S)-2-{[(3aR,4R,9bR)-8-Fluoro-4-phenyl-2,3,3a,4,5,9b-hexahydro-1H-pyrrolo[3,2-c]quinolin-1-yl]carbonyl}cyclohexyl)benzamide

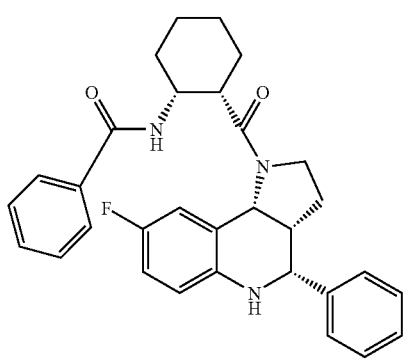

LC/MS (ESI) m/z: 499 (MH+).
and

N-((1R,2S)-2-{[(3aS,4S,9bS)-8-fluoro-4-phenyl-2,3,3a,4,5,9b-hexahydro-1H-pyrrolo[3,2-c]quinolin-1-yl]carbonyl}cyclohexyl)benzamide

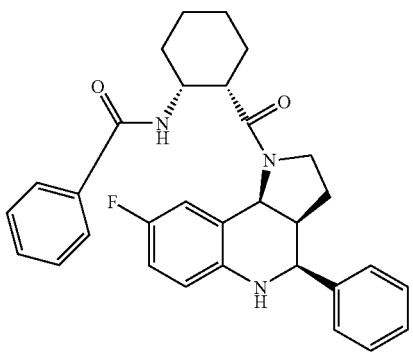

LC/MS (ESI) m/z: 499 (MH+).

Example 62

N-{(1R,2S)-2-[(3aR,4S,9bR)-(4-Propyl-2,3,3a,4,5,9b-hexahydro-1H-pyrrolo[3,2-c]quinolin-1-yl)carbonyl]cyclohexyl}benzamide

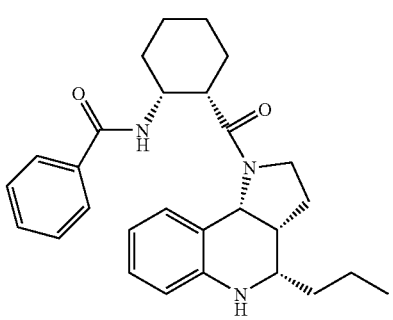

LC/MS (ESI) m/z: 446 (MH+).
and

N-{(1R,2S)-2-[(3aS,4S,9bS)-(4-propyl-2,3,3a,4,5,9b-hexahydro-1H-pyrrolo[3,2-c]quinolin-1-yl)carbonyl]cyclohexyl}benzamide

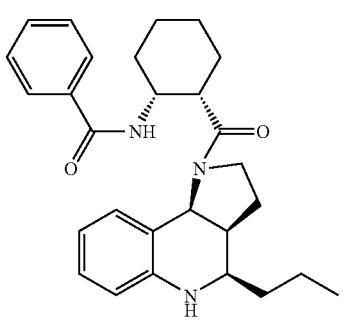

LC/MS (ESI) m/z: 446 (MH+).

Example 63

N-((1R,2S)-2-{[(3aR,4R,9bR)-4-(3-Furyl)-2,3,3a,4,5,9b-hexahydro-1H-pyrrolo[3,2-c]quinolin-1-yl]carbonyl}cyclohexyl)benzamide

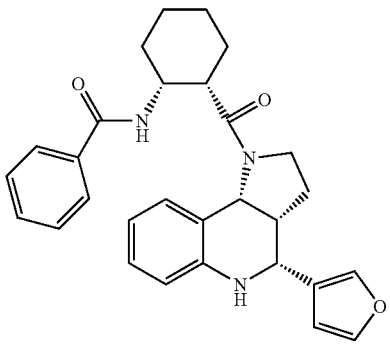

LC/MS (ESI) m/z: 486 (MH⁺).
and

N-((1R,2S)-2-{[(3aS,4S,9bS)-4-(3-furyl)-2,3,3a,4,5,9b-hexahydro-1H-pyrrolo[3,2-c]quinolin-1-yl]carbonyl}cyclohexyl)benzamide

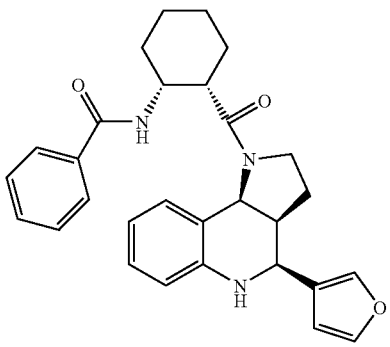

LC/MS (ESI) m/z: 486 (MH⁺).

Example 64

N-((1R,2S)-2-{[(3aR,4R,9bR)-4-(1H-Pyrrol-2-yl)-2,3,3a,4,5,9b-hexahydro-1H-pyrrolo[3,2-c]quinolin-1-yl]carbonyl}cyclohexyl)benzamide

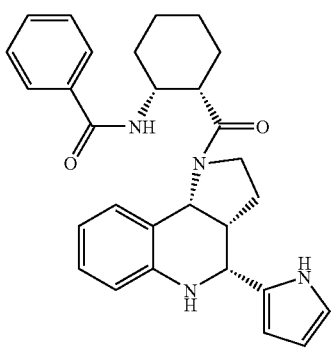

and

N-((1R,2S)-2-{[(3aS,4S,9bS)-4-(1H-pyrrol-2-yl)-2,3,3a,4,5,9b-hexahydro-1H-pyrrolo[3,2-c]quinolin-1-yl]carbonyl}cyclohexyl)benzamide

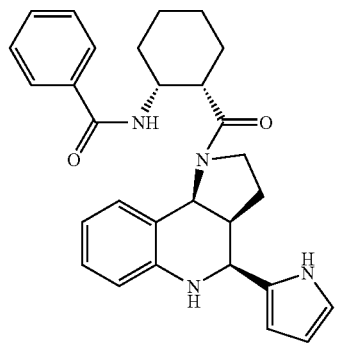

Benzyl 2-((3aR*,4R*,9bR*)-1-{[(1S,2R)-2-(benzoylamino)cyclohexyl]carbonyl}-2,3,3a,4,5,9b-hexahydro-1H-pyrrolo[3,2-c]quinolin-4-yl)-1H-pyrrole-1-carboxylate (407 mg, 0.67 mmol) was dissolved in methanol (3 ml), 10% palladium on carbon (50% aqueous, 240 mg) was added, and the mixture was stirred under hydrogen atmosphere for 2 hrs. The reaction solution was filtered, and the filtrate was concentrated under reduced pressure. The obtained residue was subjected to column chromatography using silica gel (30 g), and eluted with hexane-ethyl acetate (9:1-4:1, v/v). The title compound (3aR,4R,9bR) (64 mg, 20%) was obtained as a colorless amorphous form from the first eluted fraction.

LC/MS (ESI) m/z: 469 (MH⁺).

The title compound (3aS,4S,9bS) (78 mg, 25%) was obtained as a colorless amorphous form from the second eluted fraction.

LC/MS (ESI) m/z: 469 (MH⁺).

Example 65

N-[(1R,2S)-2-({(3aR,4R,9bR)-4-[4-(Methylthio)phenyl]-2,3,3a,4,5,9b-hexahydro-1H-pyrrolo[3,2-c]quinolin-1-yl}carbonyl)cyclohexyl]benzamide,

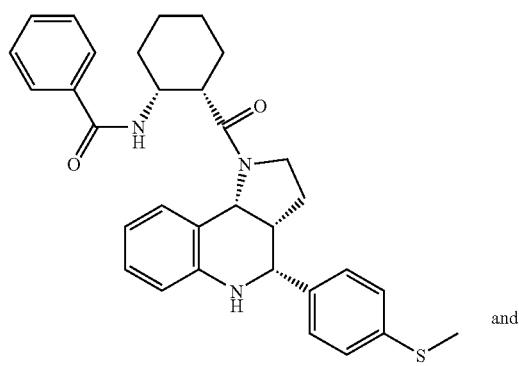

and

N-[(1R,2S)-2-({(3aS,4S,9bS)-4-[4-(methylthio)phenyl]-2,3,3a,4,5,9b-hexahydro-1H-pyrrolo[3,2-c]quinolin-1-yl}carbonyl)cyclohexyl]benzamide

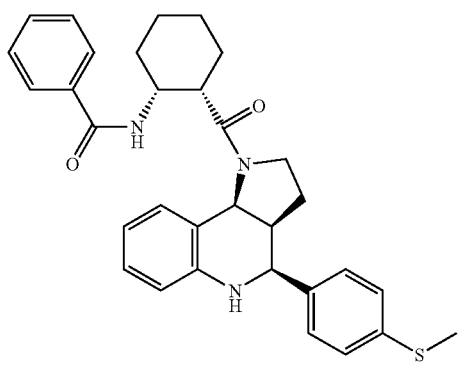

To a suspension of (3aS,4R,9bR)-4-[4-(methylthio)phenyl]-2,3,3a,4,5,9b-hexahydro-1H-pyrrolo[3,2-c]quinoline (1.10 g, 3.0 mmol) and (1S,2R)-2-(benzoylamino)cyclohexanecarboxylic acid (0.74 g, 3.0 mmol) in DMF (20 ml) were added under ice-cooling, triethylamine (0.91 g, 9.0 mmol), and then a solution of DEPC (0.49 g, 3.0 mmol) in DMF (5 ml). The reaction mixture was stirred at room temperature for 16 hrs., the reaction mixture was poured into ice water and the mixture was extracted with diethyl ether. The extract was washed with saturated brine, dried over anhydrous MgSO$_4$, and concentrated under reduced pressure. The residue was subjected to silica gel column chromatography, and eluted with hexane-ethyl acetate (2:1-1:1, v/v) to give N-[(1R,2S)-2-({(3aR,4R,9bR)-4-[4-(methylthio)phenyl]-2,3,3a,4,5,9b-hexahydro-1H-pyrrolo[3,2-c]quinolin-1-yl}carbonyl)cyclohexyl]benzamide (0.45 g, 29%) from the first eluted fraction.

LC/MS (ESI) m/z: 526 (MH$^+$).

N-[(1R,2S)-2-({(3aS,4S,9bS)-4-[4-(methylthio)phenyl]-2,3,3a,4,5,9b-hexahydro-1H-pyrrolo[3,2-c]quinolin-1-yl}carbonyl)cyclohexyl]benzamide (0.42 g, 27%) was obtained from the second eluted fraction.

LC/MS (ESI) m/z: 526 (MH$^+$).

The following compounds of Example 66-Example 68 were synthesized using the compounds of Table 2 in the same manner as in Reference Example 65.

Example 66

N-((1R,2S)-2-{[(3aR,4S,9bR)-4-Isobutyl-2,3,3a,4,5,9b-hexahydro-1H-pyrrolo[3,2-c]quinolin-1-yl]carbonyl}cyclohexyl)benzamide

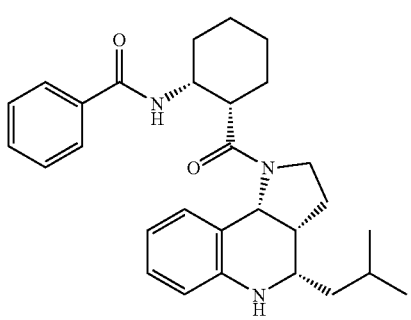

LC/MS (ESI) m/z: 460 (MH$^+$).
and

N-((1R,2S)-2-{[(3aS,4R,9bS)-4-isobutyl-2,3,3a,4,5,9b-hexahydro-1H-pyrrolo[3,2-c]quinolin-1-yl]carbonyl}cyclohexyl)benzamide

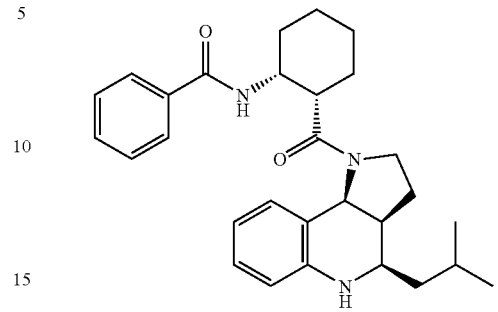

After silica gel column purification, crystallization from ethyl acetate-isopropyl ether gave colorless crystals having a melting point of 173.3-173.4° C.
LC/MS (ESI) m/z: 460 (MH$^+$).

Example 67

Benzyl 4-((3aR,4S,9bR)-1-{[(1S,2R)-2-(benzoylamino)cyclohexyl]carbonyl}-2,3,3a,4,5,9b-hexahydro-1H-pyrrolo[3,2-c]quinolin-4-yl)piperidine-1-carboxylate

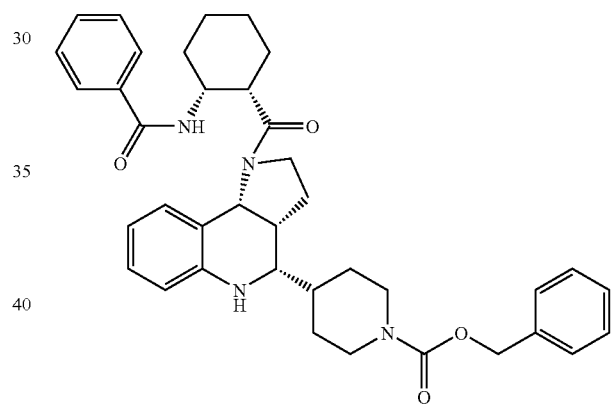

LC/MS (ESI) m/z: 621 (MH$^+$).

Example 68

Benzyl 2-((3aR,4S,9bR)-1-{[(1S,2R)-2-(benzoylamino)cyclohexyl]carbonyl}-2,3,3a,4,5,9b-hexahydro-1H-pyrrolo[3,2-c]quinolin-4-yl)ethylcarbate

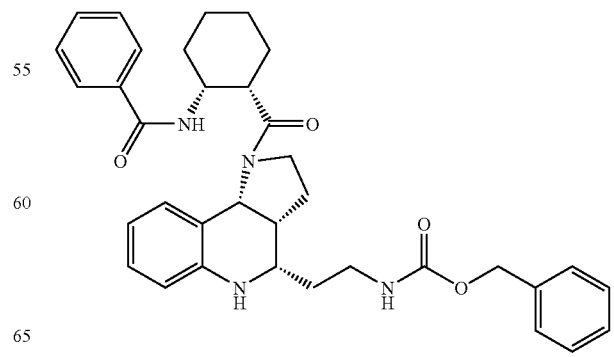

LC/MS (ESI) m/z: 581 (MH$^+$).

Example 69

N-((1R,2S)-2-{[(3aR,4S,9bR)-4-Piperidin-4-yl-2,3,3a,4,5,9b-hexahydro-1H-pyrrolo[3,2-c]quinolin-1-yl]carbonyl}cyclohexyl)benzamide

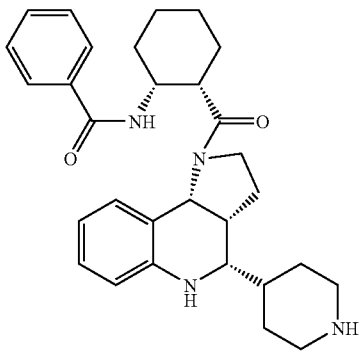

A suspension of the compound (0.41 g, 0.66 mmol) synthesized in Example 67 and 10% palladium on carbon (50% aqueous, 0.04 g) in methanol (50 ml) was stirred at room temperature under hydrogen atmosphere for 48 hrs. The catalyst was filtered off and washed with methanol, and the solvent was evaporated under reduced pressure. The residue was subjected to column chromatography using basic silica gel (30 g), and eluted with ethyl acetate-methanol (3:1, v/v). Recrystallization from methanol-ether gave the title compound (0.16 g, 50%) as white crystals.
LC/MS (ESI) m/z: 487 (MH$^+$).

Example 70

4-((3aR,4S,9bR)-1-{[(1S,2R)-2-(Benzoylamino)cyclohexyl]carbonyl}-2,3,3a,4,5,9b-hexahydro-1H-pyrrolo[3,2-c]quinolin-4-yl)-N-ethylpiperidine-1-carboxamide

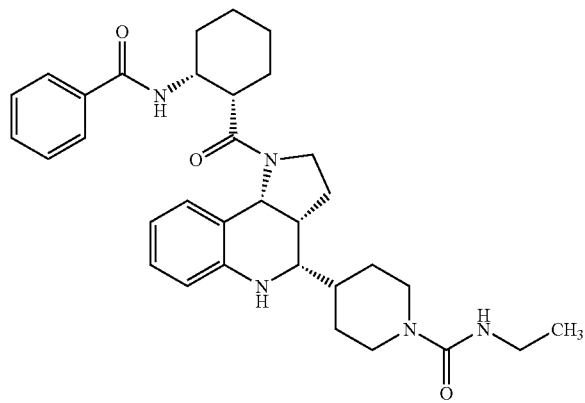

A mixture of the compound (0.20 g, 0.41 mmol) synthesized in Example 69, triethylamine (0.17 g, 1.64 mmol), ethylisocyanate (0.058 g, 0.82 mmol) and tetrahydrofuran (20 ml) was stirred at room temperature for 60 hrs. Water was added to the reaction mixture and the mixture was extracted with ethyl acetate. The extract was washed with saturated brine, dried (over anhydrous Na$_2$SO$_4$, and the solvent was evaporated under reduced pressure. The residue was recrystallized from hexane-ethyl acetate to give the title compound (0.20 g, 81%) as white crystals.
LC/MS (ESI) m/z: 558 (MH$^+$).

Example 71

N-((1R,2S)-2-{[(3aR,4S,9bR)-4-(2-Aminoethyl)-2,3,3a,4,5,9b-hexahydro-1H-pyrrolo[3,2-c]quinolin-1-yl]carbonyl}cyclohexyl)benzamide

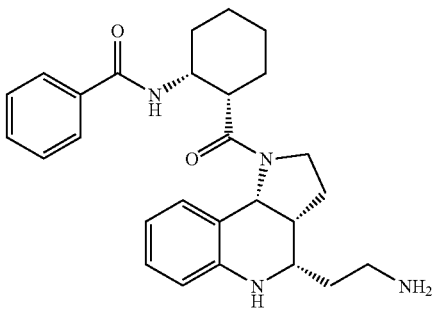

In the same manner as in Example 69 and using the compound synthesized in Example 68, the title compound was synthesized.
LC/MS (ESI) m/z: 447 (MH$^+$).

Example 72

Benzyl ((3aR,4R,9bR)-1-{[1S,2R]-2-(benzoylamino)cyclohexyl}carbonyl)-2,3,3a,4,5,9b-hexahydro-1H-pyrrolo[3,2-c]quinolin-4-yl]methylcarbamate

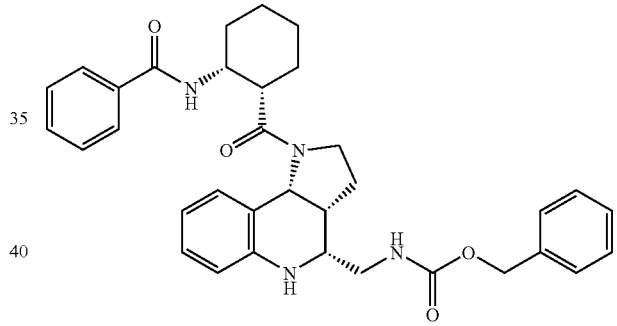

To a solution (14 ml) of tert-butyl (3aR*,4R*,9bR*)-4-({[benzyloxy]carbonyl}amino)methyl)-2,3,3a,4,5,9b-hexahydro-1H-pyrrolo[3,2-c]quinoline-1-carboxylate (1.29 g, 2.93 mmol) in methanol was added dropwise 4N hydrogen chloride in ethyl acetate solution (1.94 ml, 7.77 mmol) under ice-cooling. The reaction mixture was stirred overnight at room temperature, and concentrated under reduced pressure. The residue was dissolved in tetrahydrofuran (15 ml), triethylamine (0.868 ml, 6.21 mmol), (1S,3R)-2-(benzoylamino)cyclohexanecarboxylic acid (563 mg, 2.28 mmol) and DEPC (0.310 ml, 2.07 mmol) were added under ice-cooling, and the mixture was stirred at the same temperature for 2 hrs. Water was added to the reaction mixture, and the mixture was extracted with ethyl acetate. The organic layer was dried over anhydrous MgSO$_4$ and the solvent was concentrated under reduced pressure. The residue was subjected to silica gel column chromatography and eluted with hexane-ethyl acetate (9:1-1:1, v/v) to give the title compound (69.6 mg, 6%) as an amorphous form from the first eluted fraction. Benzyl ((3aR*,4R*,9bR*)-1-{[1S,2R]-2-(benzoylamino)cyclohexyl}carbonyl)-2,3,3a,4,5,9b-hexahydro-1H-pyrrolo[3,2-c]quinolin-4-yl]methylcarbamate (480 mg, 41%) was obtained from the second eluted fraction.
LC/MS (ESI) m/z: 567 (MH$^+$).

Example 73

N-((1R,2S)-2-{[(3aR*,4R*,9bR*)-4-(Aminomethyl)-2,3,3a,4,5,9b-hexahydro-1H-pyrrolo[3,2-c]quinolin-1-yl]carbonyl}cyclohexyl)benzamide

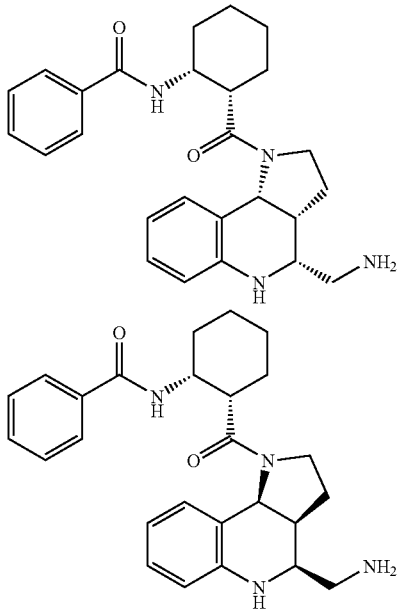

A solution of benzyl ((3aR*,4R*,9bR*)-1-{[1S,2R]-2-(benzoylamino)cyclohexyl}carbonyl)-2,3,3a,4,5,9b-hexahydro-1H-pyrrolo[3,2-c]quinolin-4-yl]methylcarbamate (480 mg, 0.847 mmol) obtained in Example 72 in methanol (8 ml) was stirred in the presence of 10% palladium on carbon (50% aqueous, 100 mg) under a hydrogen atmosphere for 4 days. The catalyst was filtered off, and the filtrate was concentrated under reduced pressure. The residue was subjected to silica gel column chromatography and eluted with hexane-ethyl acetate (1:0-1:1, v/v) to give the title compound (283 mg, 77%) as an amorphous form.

LC/MS (ESI) m/z: 433 (MH$^+$).

Example 74

N-[(1R,2S)-2-({(3aR*,4R*,9bR*)-4-[(Acetylamino)methyl]-2,3,3a,4,5,9b-hexahydro-1H-pyrrolo[3,2-c]quinolin-1-yl}carbonyl)cyclohexyl]benzamide

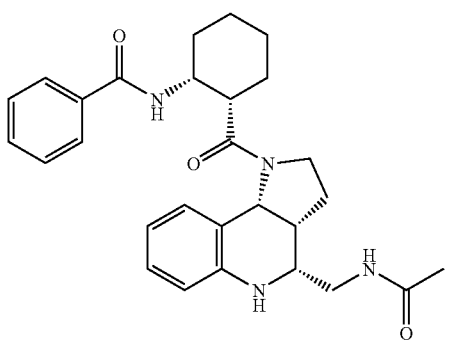

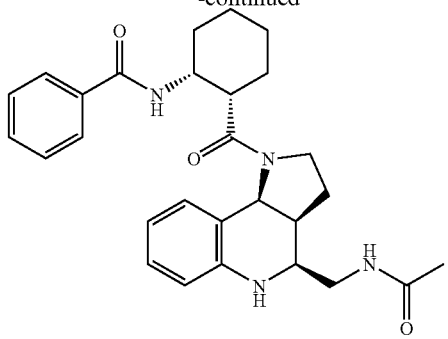

To a solution of the compound (163 mg, 0.377 mmol) synthesized in Example 73 in tetrahydrofuran (3 ml) was added acetic anhydride (0.179 ml, 1.88 mmol) under ice-cooling, and the mixture was stirred at room temperature for 10 min. The reaction mixture was concentrated under reduced pressure, and the residue was subjected to column chromatography using basic silica gel and eluted with hexane-ethyl acetate (8:2-0:1, v/v) to give the title compound (117 mg, 60%) as an amorphous form.

LC/MS (ESI) m/z: 475 (MH$^+$).

Example 75

N-((1R,2S)-2-{[(3aR,4R,9bR)-4-(2-Methyl-3-furyl)-2,3,3a,4,5,9b-hexahydro-1H-pyrrolo[3,2-c]quinolin-1-yl]carbonyl}cyclohexyl)benzamide

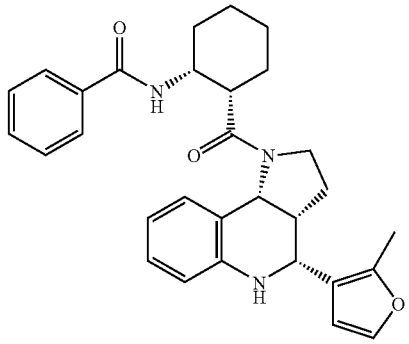

To a suspension of (1R,2S)-2-{[(3aR,4R,9bR)-4-(2-methyl-3-furyl)-2,3,3a,4,5,9b-hexahydro-1H-pyrrolo[3,2-c]quinolin-1-yl]carbonyl}cyclohexaneamine hydrochloride (201 mg, 0.445 mmol) in dichloromethane (5 ml) were added triethylamine (0.203 ml, 1.47 mmol) and benzoylchloride (0.0568 ml, 0.490 mmol) under ice-cooling. The reaction mixture was stirred overnight at room temperature, water was added, and extracted with dichloromethane. The extract was dried over anhydrous MgSO$_4$, and the solvent was evaporated under reduced pressure. The residue was subjected to silica gel column chromatography and eluted with hexane-ethyl acetate (4:1-3:2, v/v) to give the title compound (176 mg, 82%) as an amorphous form.

LC/MS (ESI) m/z: 484 (MH$^+$).

The following compounds of Example 76-Example 80 were synthesized using the compounds shown in Table 3 in the same manner as in Example 75.

Example 76

N-((1R,2S)-2-{[(3aR,4R,9bR)-4-(1,3-Oxazol-4-yl)-2,3,3a,4,5,9b-hexahydro-1H-pyrrolo[3,2-c]quinolin-1-yl]carbonyl}cyclohexyl)benzamide

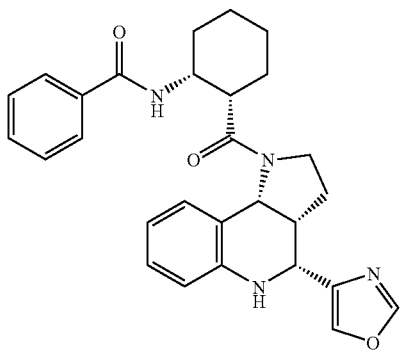

LC/MS (ESI) m/z: 471 (MH$^+$).

Example 77

N-((1R,2S)-2-{[(3aR,4R,9bR)-4-(Ethoxymethyl)-2,3,3a,4,5,9b-hexahydro-1H-pyrrolo[3,2-c]quinolin-1-yl]carbonyl}cyclohexyl)benzamide

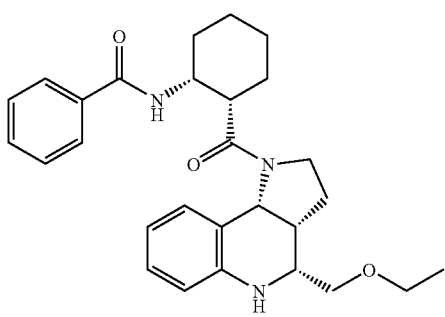

LC/MS (ESI) m/z: 462 (MH$^+$)

Example 78

N-((1R,2S)-2-{[(3aR,4R,9bR)-4-(1,3-Thiazol-5-yl)-2,3,3a,4,5,9b-hexahydro-1H-pyrrolo[3,2-c]quinolin-1-yl]carbonyl}cyclohexyl)benzamide

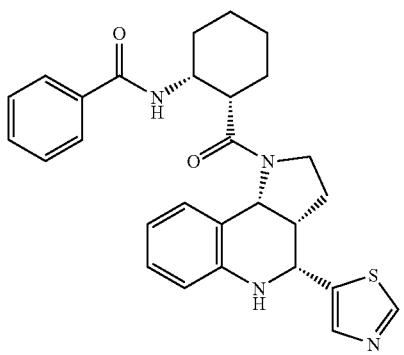

LC/MS (ESI) m/z: 487 (MH$^+$)

Example 79

N-((1R,2S)-2-{[(3aR,4R,9bR)-4-Tetrahydro-2H-pyran-4-yl-2,3,3a,4,5,9b-hexahydro-1H-pyrrolo[3,2-c]quinolin-1-yl]carbonyl}cyclohexyl)benzamide

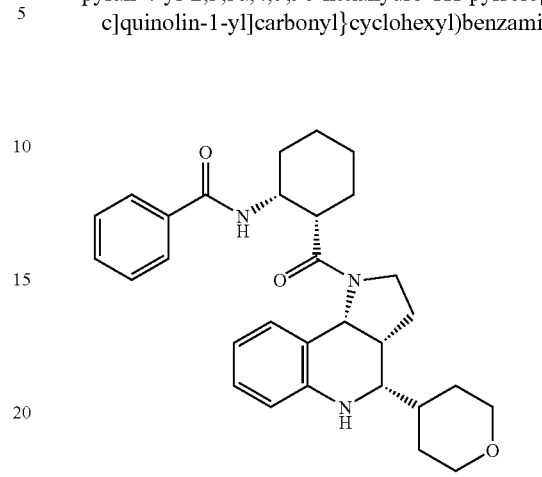

LC/MS (ESI) m/z: 488 (MH$^+$).

Example 80

[2-((3aR,4R,9bR)-1-{[(1S,2R)-2-(Benzoylamino)cyclohexyl]carbonyl}-2,3,3a,4,5,9b-hexahydro-1H-pyrrolo[3,2-c]quinolin-4-)-1H-imidazol-1-yl]methyl pivalate

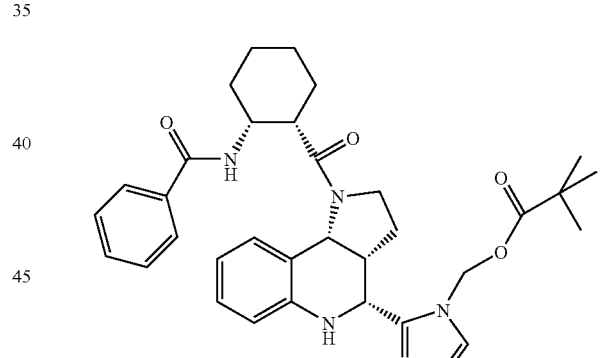

[2-((3aR,4R,9bR)-1-{[(1S,2R)-2-Aminocyclohexyl]carbonyl}-2,3,3a, 4,5,9b-hexahydro-1H-pyrrolo[3,2-c]quinolin-4-yl)-1H-imidazol-1-yl]methyl pivalate dihydrochloride (1.28 g, 2.31 mmol) was dissolved in ethyl acetate (30 ml) and 10% aqueous sodium carbonate solution (15 ml), and benzoylchloride (0.303 ml, 0.260 mmol) was added under ice-cooling. The reaction mixture was stirred at room temperature for 1 hr, and the separated organic layer was washed with saturated brine and dried over anhydrous MgSO$_4$. The solvent was evaporated under reduced pressure. The residue was subjected to silica gel column chromatography and eluted with hexane-ethyl acetate (3:2-1:9, v/v) to give the title compound (1.25 g, 93%) as an amorphous form.

LC/MS (ESI) m/z: 584 (MH$^+$).

Example 81

N-((1R,2S)-2-{[(3aR,4R,9bR)-4-(1H-Imidazol-2-yl)-2,3,3a,4,5,9b-hexahydro-1H-pyrrolo[3,2-c]quinolin-1-yl]carbonyl}cyclohexyl)benzamide

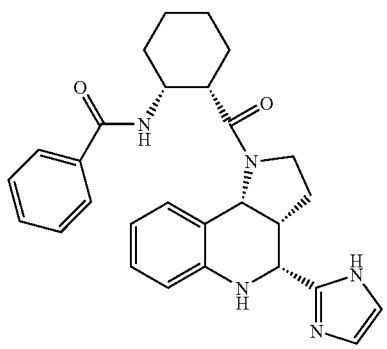

The compound (1.25 g, 2.14 mmol) synthesized in Example 80 was dissolved in methanol (50 ml), 25% aqueous ammonia (25 ml) was added, and the mixture was stirred for 4 hrs. The solvent was evaporated, and the obtained residue was subjected to column chromatography using silica gel and eluted with ethyl acetate-methanol (1:0-9:1, v/v). The title compound (0.929 g, 92%) was obtained as a colorless amorphous form from the object fraction.

$^1$H-NMR (CDCl$_3$) δ: 1.35-2.23 (12H, m), 2.35-2.50 (1H, m), 2.55-2.68 (1H, m), 2.82-2.95 (1H, m), 3.38-3.44 (2H, m), 4.25-4.42 (2H, m), 4.77 (1H, d, J=2.7 Hz), 5.65 (1H, d, J=6.9 Hz), 6.51 (1H, dd, J=8.1, 0.9 Hz), 6.69-6.76 (1H, m), 6.93-7.05 (1H, m), 7.20-7.28 (3H, m), 7.34-7.51 (4H, m), 7.72-7.85 (2H, m).

LC/MS (ESI) m/z: 470 (MH$^+$).

Example 82

N-((1R,2S)-2-{[(3aR,4R,9bR)-4-(1-Methyl-1H-imidazol-2-yl)-2,3,3a,4,5,9b-hexahydro-1H-pyrrolo[3,2-c]quinolin-1-yl]carbonyl}cyclohexyl)benzamide

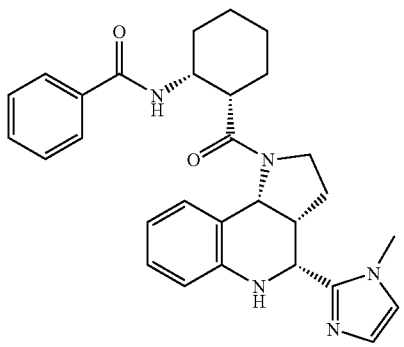

To a solution of the compound (119 mg, 0.252 mmol) synthesized in Example 81 in DMF (1 ml) was added sodium hydride (60% in oil, 12.1 mg, 0.30 mmol) under ice-cooling, and the mixture was stirred for 1 hr. Methyl iodide (0.0187 ml, 0.30 mmol) was added dropwise and the mixture was stirred overnight at room temperature. Water was added to the reaction mixture and the mixture was extracted with ethyl acetate. The extract was dried over anhydrous MgSO$_4$, and the solvent was evaporated under reduced pressure. The residue was subjected to column chromatography using silica gel and eluted with hexane-ethyl acetate (5:95, v/v) to give the title compound (76.5 mg, 63%) as an amorphous form.

LC/MS (ESI) m/z: 484 (MH$^+$).

Example 83

N-((1R,2S)-2-{[(3aR,4S,9bR)-3a-Methyl-4-phenyl-2,3,3a,4,5,9b-hexahydro-1H-pyrrolo[3,2-c]quinolin-1-yl]carbonyl}cyclohexyl)benzamide

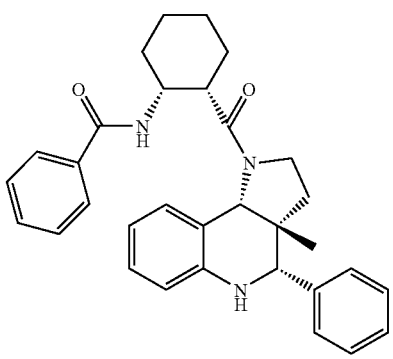

and

N-((1R,2S)-2-{[(3aS,4R,9bS)-3a-methyl-4-phenyl-2,3,3a,4,5,9b-hexahydro-1H-pyrrolo[3,2-c]quinolin-1-yl]carbonyl}cyclohexyl)benzamide

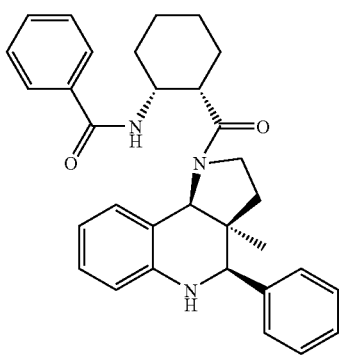

(3aR*,4S*,9bR*)-3a-Methyl-4-phenyl-2,3,3a,4,5,9b-hexahydro-1H-pyrrolo[3,2-c]quinoline hydrochloride (210 mg, 0.62 mmol) was suspended in acetonitrile (3 ml) and tetrahydrofuran (3 ml), triethylamine (263 mg, 2.6 mmol) was added, and the suspension was stirred at room temperature for 15 min. (1S,2R)-2-(benzoylamino)cyclohexanecarboxylic acid (170 mg, 0.68 mmol) was added to this suspension and DEPC (110 mg, 0.68 mmol) was added under ice-cooling, and the mixture was stirred for 10 min. The reaction mixture was allowed to return to room temperature and stirred for 1 hr. Saturated aqueous sodium hydrogen carbonate solution was added, and the mixture was extracted with ethyl acetate. The extract was dried (over anhydrous MgSO$_4$) and the solvent was evaporated under reduced pressure. The residue was subjected to column chromatography using silica gel (10 g), and eluted with hexane-ethyl acetate (9:1-1:1, v/v) to give a diastereomer mixture (170 mg, 56%) as an amorphous form.

The obtained mixture of diastereomers (150 mg) was subjected to column chromatography using silica gel (10 g), and eluted with hexane-ethyl acetate (4:1-1:1, v/v) to give the title compound (3aR,4S,9bR) (40 mg, 27%) as an amorphous form from the first eluted fraction.

LC/MS (ESI) m/z: 494 (MH+).

The title compound (3aS,4R,9bS) (20 mg, 13%) was obtained as an amorphous form from the second eluted fraction LC/MS (ESI) m/z: 494 (MH+).

Example 84

N-((1R,2S)-2-{[(3aR,4R,9bR)-3a-Methyl-4-(3-thienyl)-2,3,3a,4,5,9b-hexahydro-1H-pyrrolo[3,2-c]quinolin-1-yl]carbonyl}cyclohexyl)benzamide

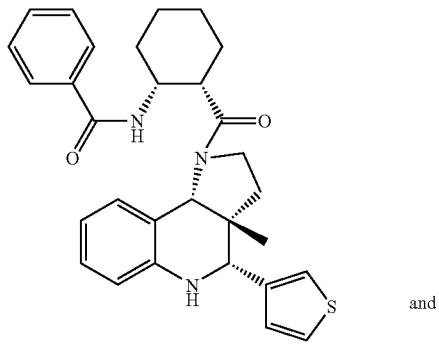

and

N-((1R,2S)-2-{[(3aS,4S,9bS)-3a-methyl-4-(3-thienyl)-2,3,3a,4,5,9b-hexahydro-1H-pyrrolo[3,2-c]quinolin-1-yl]carbonyl}cyclohexyl)benzamide

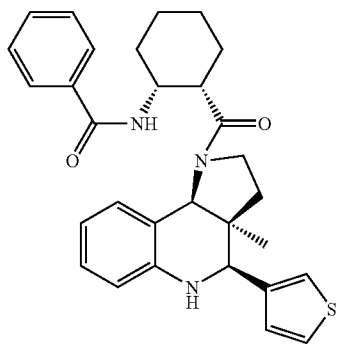

To a mixture of (3aS,4R*,9bR*)-3a-methyl-4-(3-thienyl)-2,3,3a,4,5,9b-hexahydro-1H-pyrrolo[3,2-c]quinoline (750 mg, 2.77 mmol), (1S,2R)-2-(benzoylamino)cyclohexanecarboxylic acid (685 mg, 2.77 mmol), triethylamine (606 mg, 6.10 mmol), acetonitrile (14 ml) and tetrahydrofuran (14 ml) was added DEPC (500 mg, 3.05 mmol) under ice-cooling, and the mixture was stirred for 10 min. The mixture was allowed to return to room temperature and stirred for 12 hrs. Saturated aqueous sodium hydrogen carbonate solution was added to the reaction mixture and the mixture was extracted with ethyl acetate. The extract was dried (over anhydrous Na$_2$SO$_4$), and the solvent was evaporated under reduced pressure. The residue was subjected to column chromatography using silica gel (100 g), and eluted with hexane-ethyl acetate (4:1-1:1, v/v) to give the title compound (3aR,4R,9bR) (110 mg, 8%) as an amorphous form from the first eluted fraction.

LC/MS (ESI) m/z: 500 (MH+).

The title compound (3aS,4S,9bS) (150 mg, 10%) was obtained as an amorphous form from the subsequently eluted fraction.

LC/MS (ESI) m/z: 500 (MH+).

Example 85

N-((1R,2S)-2-{[(3aR,4R,9bR)-4-Phenyl-2,3,3a,4,5,9b-hexahydro-1H-pyrrolo[3,2-c]quinolin-1-yl]carbonyl}cyclohexyl)acetamide

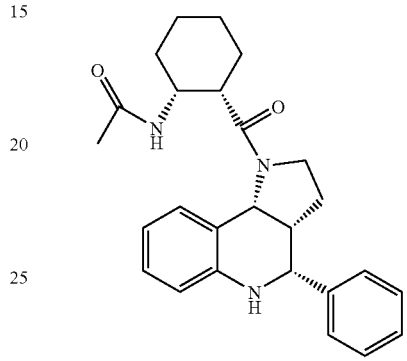

To a mixture of the compound (0.135 g, 0.3 mmol) synthesized in Reference Example 23, 10% aqueous sodium carbonate solution (5 ml) and ethyl acetate (10 ml) was added acetyl chloride (0.032 ml, 0.45 mmol) at room temperature, and the mixture was stirred for 30 min. The reaction mixture was extracted with ethyl acetate. The extract was washed with saturated brine and dried (over anhydrous MgSO$_4$. The solvent was evaporated under reduced pressure, and the obtained residue was subjected to silica gel column chromatography and eluted with hexane-ethyl acetate (3:2-0:1, v/v) to give the title compound (0.124 g, 99%) as an amorphous form the object fraction.

LC/MS (ESI) m/z: 418 (MH+).

The following compounds of Example 86-Example 117 were synthesized using the corresponding acid chlorides in the same manner as in Example 85.

Example 86

N-((1R,2S)-2-{[(3aR,4R,9bR)-4-Phenyl-2,3,3a,4,5,9b-hexahydro-1H-pyrrolo[3,2-c]quinolin-1-yl]carbonyl}cyclohexyl)propanamide

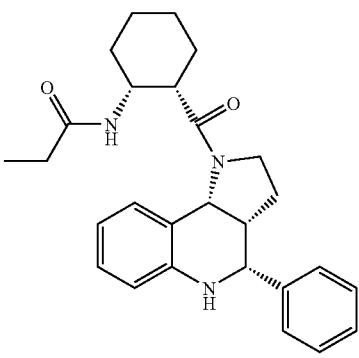

LC/MS (ESI) m/z: 432 (MH+).

Example 87

N-((1R,2S)-2-{[(3aR,4R,9bR)-4-Phenyl-2,3,3a,4,5,9b-hexahydro-1H-pyrrolo[3,2-c]quinolin-1-yl]carbonyl}cyclohexyl)-4-(trifluoromethyl)benzamide

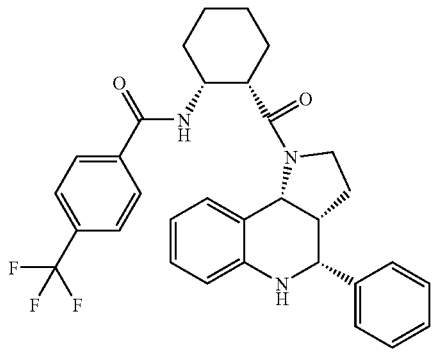

LC/MS (ESI) m/z: 548 (MH+).

Example 88

N-((1R,2S)-2-{[(3aR,4R,9bR)-4-Phenyl-2,3,3a,4,5,9b-hexahydro-1H-pyrrolo[3,2-c]quinolin-1-yl]carbonyl}cyclohexyl)-3,5-bis(trifluoromethyl)benzamide

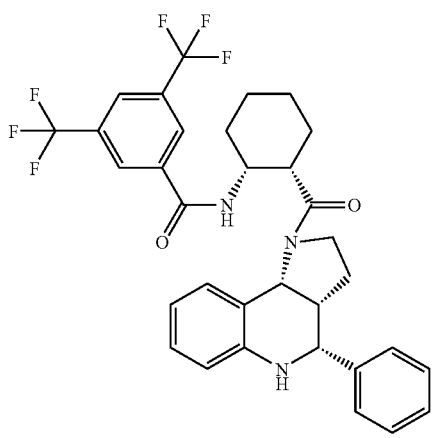

LC/MS (ESI) m/z: 616 (MH+).

Example 89

N-((1R,2S)-2-{[(3aR,4R,9bR)-4-Phenyl-2,3,3a,4,5,9b-hexahydro-1H-pyrrolo[3,2-c]quinolin-1-yl]carbonyl}cyclohexyl)thiophene-2-carboxamide

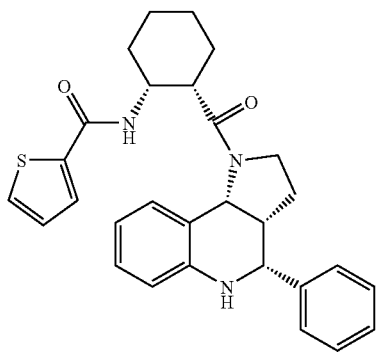

LC/MS (ESI) m/z: 486 (MH+).

Example 90

4-Methoxy-N-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)benzamide

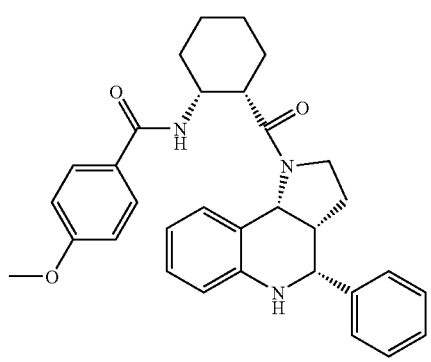

LC/MS (ESI) m/z: 510 (MH+).

Example 91

N-((1R,2S)-2-{[(3aR,4R,9bR)-4-Phenyl-2,3,3a,4,5,9b-hexahydro-1H-pyrrolo[3,2-c]quinolin-1-yl]carbonyl}cyclohexyl)isonicotinamide

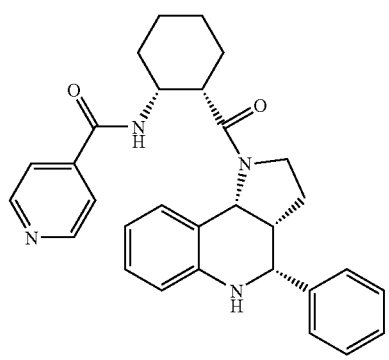

LC/MS (ESI) m/z: 481 (MH+)

Example 92

4-Fluoro-N-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)benzamide

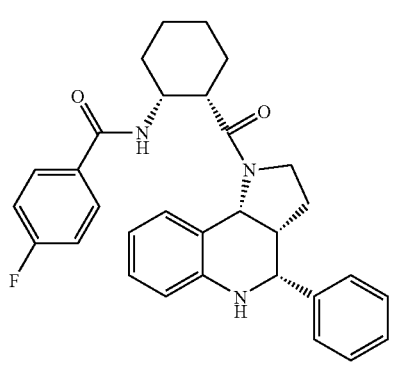

LC/MS (ESI) m/z: 498 (MH+).

Example 93

N-((1R,2S)-2-{[(3aR,4R,9bR)-4-Phenyl-2,3,3a,4,5,9b-hexahydro-1H-pyrrolo[3,2-c]quinolin-1-yl]carbonyl}cyclohexyl)hexanamide

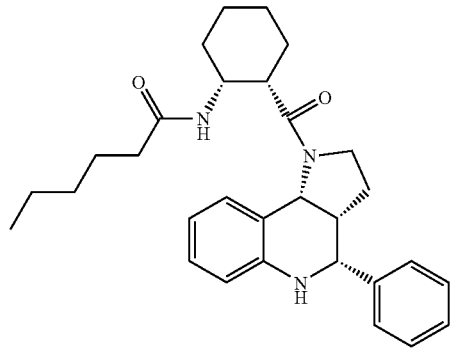

LC/MS (ESI) m/z: 474 (MH+).

Example 94

2-Methoxy-N-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)benzamide

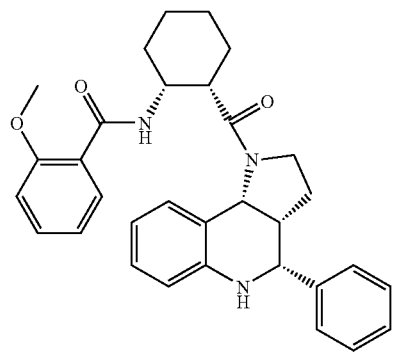

LC/MS (ESI) m/z: 510 (MH+).

Example 95

3-Methoxy-N-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)benzamide

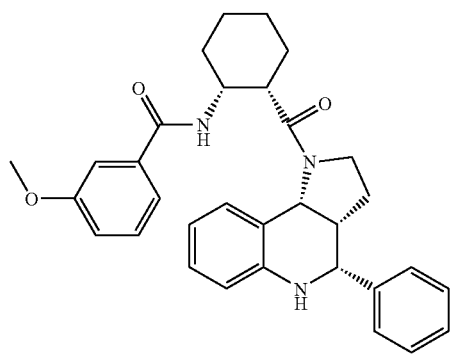

LC/MS (ESI) m/z: 510 (MH+).

Example 96

3-Fluoro-N-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)benzamide

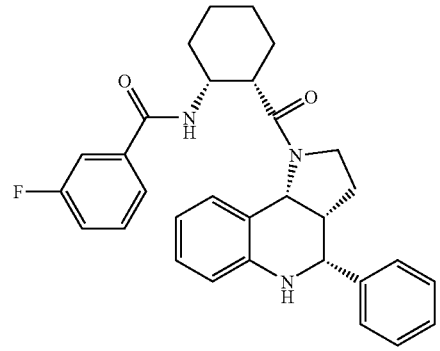

LC/MS (ESI) m/z: 498 (MH+).

Example 97

2-Methyl-N-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)benzamide

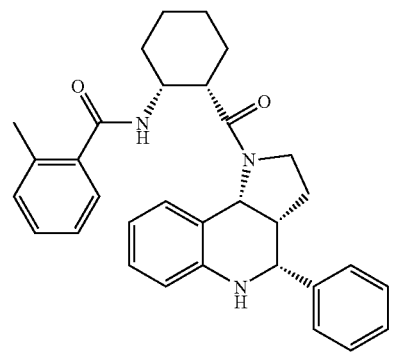

LC/MS (ESI) m/z: 494 (MH+).

Example 98

3-Methyl-N-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)benzamide

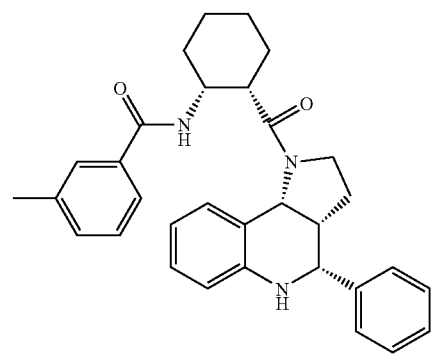

LC/MS (ESI) m/z: 494 (MH+).

Example 99

4-Methyl-N-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)benzamide

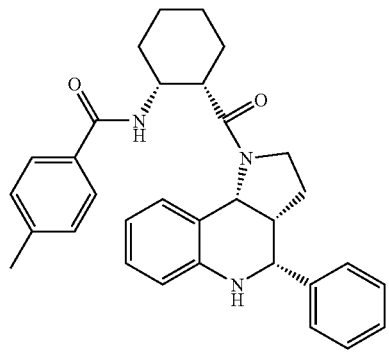

LC/MS (ESI) m/z: 494 (MH+).

Example 100

Methyl 4-{[(((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)amino]carbonyl}benzoate

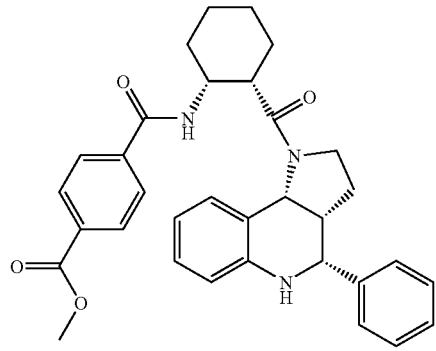

LC/MS (ESI) m/z: 538 (MH+).

Example 101

(2E)-3-Phenyl-N-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)acrylamide

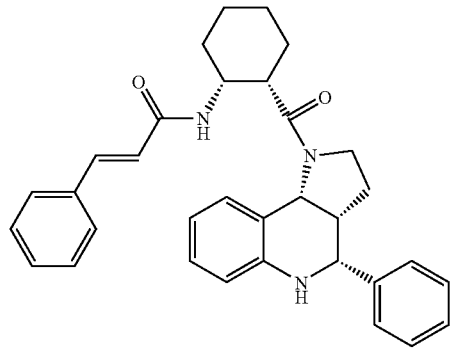

LC/MS (ESI) m/z: 506 (MH+).

Example 102

4-Cyano-N-((1R,2S)-2-([(3aR,4R,9bR)-4-phenyl-2,3,3a,4,5,9b-hexahydro-1H-pyrrolo[3,2-c]quinolin-1-yl]carbonyl)cyclohexyl)benzamide

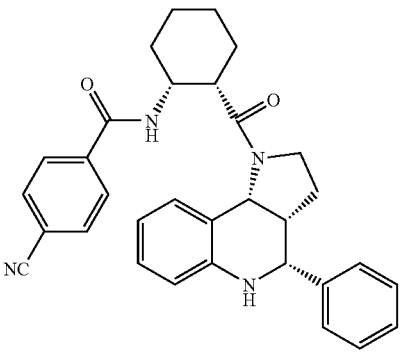

LC/MS (ESI) m/z: 505 (MH+).

Example 103

3-Phenyl-N-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)propanamide

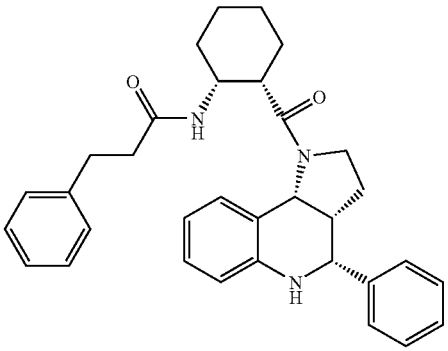

LC/MS (ESI) m/z: 508 (MH+).

Example 104

3,4-Dimethoxy-N-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)benzamide

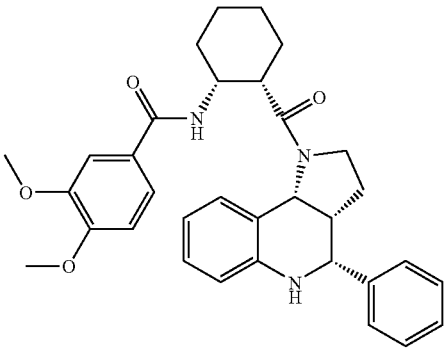

LC/MS (ESI) m/z: 540 (MH+).

Example 105

(2E)-3-(4-Methoxyphenyl)-N-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)acrylamide

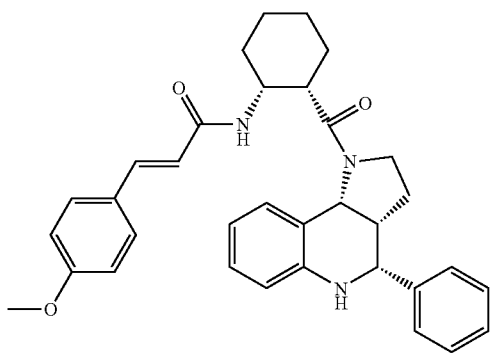

LC/MS (ESI) m/z: 536 (MH+).

Example 106

(2E)-N-((1R,2S)-2-{[(3aR,4R,9bR)-4-Phenyl-2,3,3a,4,5,9b-hexahydro-1H-pyrrolo[3,2-c]quinolin-1-yl]carbonyl}cyclohexyl)-3-[4-(trifluoromethyl)phenyl]acrylamide

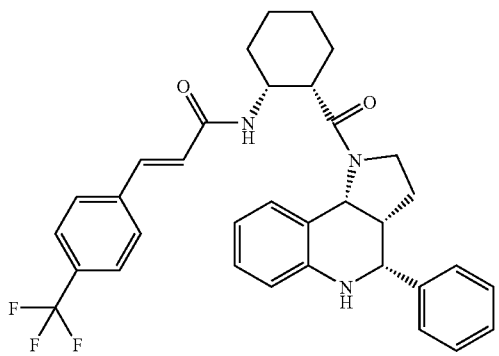

LC/MS (ESI) m/z: 574 (MH+).

Example 107

N-((1R,2S)-2-{[(3aR,4R,9bR)-4-Phenyl-2,3,3a,4,5,9b-hexahydro-1H-pyrrolo[3,2-c]quinolin-1-yl]carbonyl}cyclohexyl)-2-naphthamide

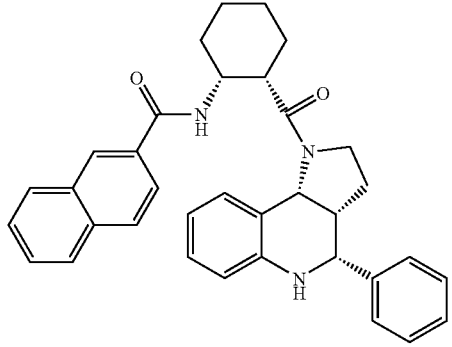

LC/MS (ESI) m/z: 530 (MH+).

Example 108

Ethyl 4-oxo-4-[((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)amino]butanoate

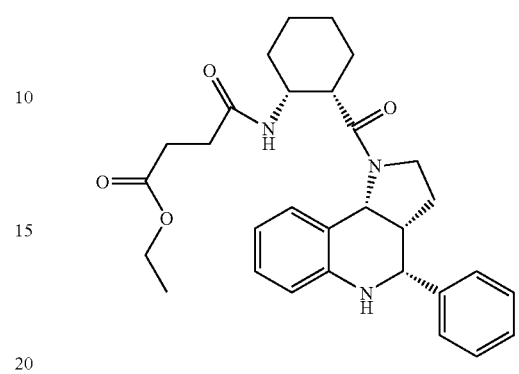

LC/MS (ESI) m/z: 504 (MH+).

Example 109

6-Bromo-N-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)hexanamide

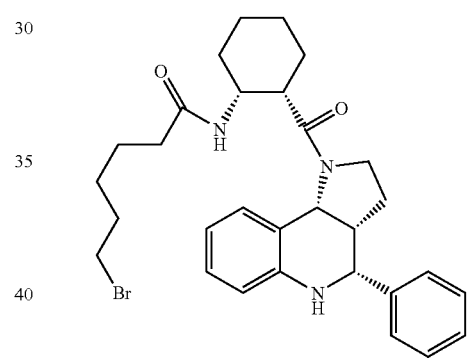

LC/MS (ESI) m/z: 554, 555 (MH+).

Example 110

2-Methyl-N-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)propanamide

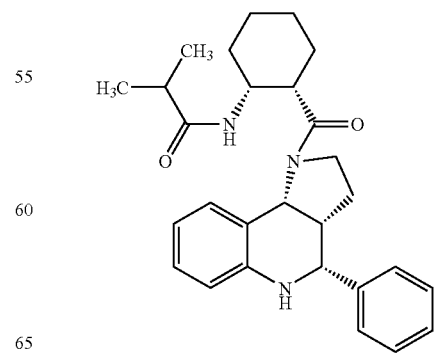

LC/MS (ESI) m/z: 446 (MH+).

Example 111

2,2-Dimethyl-N-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)propanamide

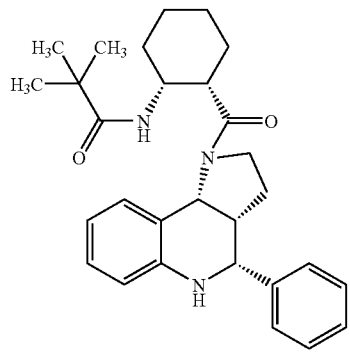

LC/MS (ESI) m/z: 460 (MH+).

Example 112

2-Phenyl-N-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)acetamide

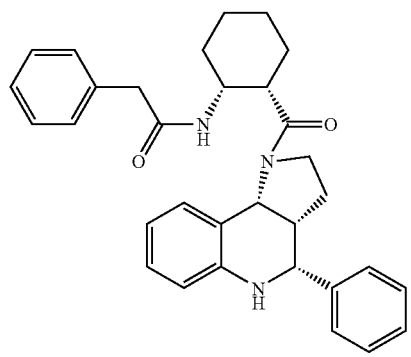

LC/MS (ESI) m/z: 494 (MH+).

Example 113

N-((1R,2S)-2-{[(3aR,4R,9bR)-4-Phenyl-2,3,3a,4,5,9b-hexahydro-1H-pyrrolo[3,2-c]quinolin-1-yl]carbonyl}cyclohexyl)cyclohexanecarboxamide

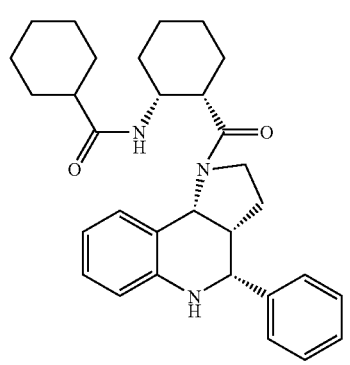

LC/MS (ESI) m/z: 486 (MH+).

Example 114

4-Chloro-N-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)benzamide

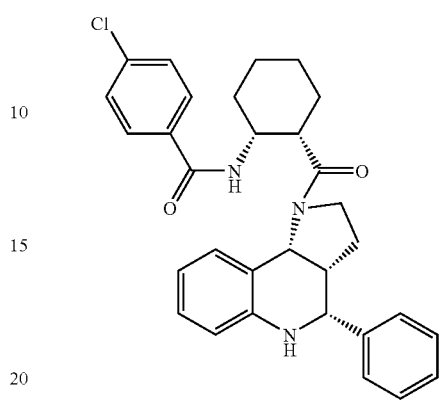

LC/MS (ESI) m/z: 514 (MH+).

Example 115

Ethyl 3-oxo-3-[((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)amino]propanoate

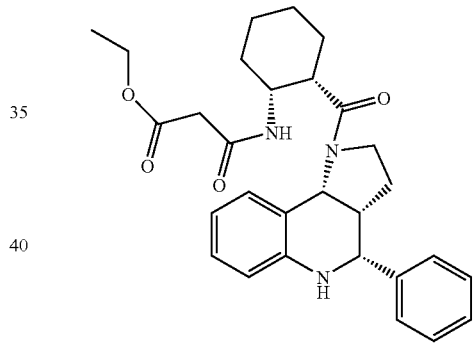

LC/MS (ESI) m/z: 490 (MH+).

Example 116

Methyl 6-oxo-6-[((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)amino]hexanoate

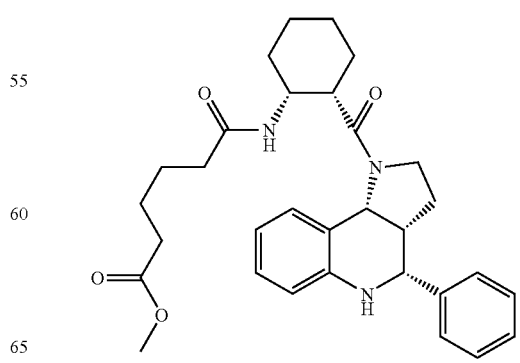

LC/MS (ESI) m/z: 518 (MH+).

Example 117

6-Morpholin-4-yl-N-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)hexanamide

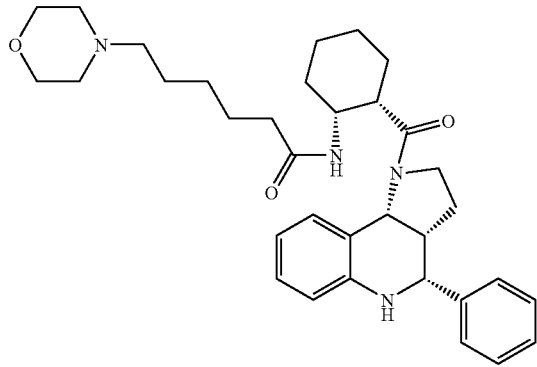

6-Bromo-N-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)hexaneamide (166 mg, 0.30 mmol), morpholine (28 μl, 0.331 mmol) and potassium carbonate (207 mg, 1.5 mmol) were heated under reflux for 6 hrs. in acetonitrile (3 ml). Water was added to the reaction mixture and the mixture was extracted with ethyl acetate. The extract was dried over anhydrous $Na_2SO_4$. The solvent was evaporated under reduced pressure, and the obtained residue was subjected to basic silica gel column chromatography and eluted with ethyl acetate to give the title compound (153 mg, 91%) as a white solid.

LC/MS (ESI) m/z: 559 (MH$^+$).

Example 118

6-[(2-Hydroxyethyl)amino]-N-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)hexanamide

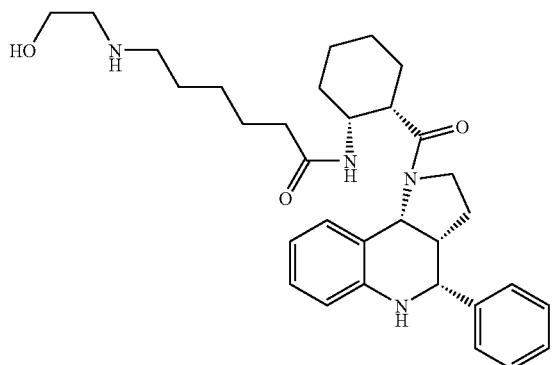

6-Bromo-N-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)hexanamide (150 mg, 0.27 mmol) was stirred in 2-aminoethanol (3 ml) at 60° C. for 6 hrs. Water was added to the reaction mixture and the mixture was extracted with ethyl acetate. The extract was dried over anhydrous $Na_2SO_4$. The solvent was evaporated under reduced pressure, and the obtained residue was subjected to basic silica gel column chromatography and eluted with ethyl acetate-methanol (5:1, v/v) to give the title compound (106 mg, 73%) as a white solid.

LC/MS (ESI) m/z: 533 (MH$^+$).

Example 119

6-Hydroxy-N-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)hexanamide

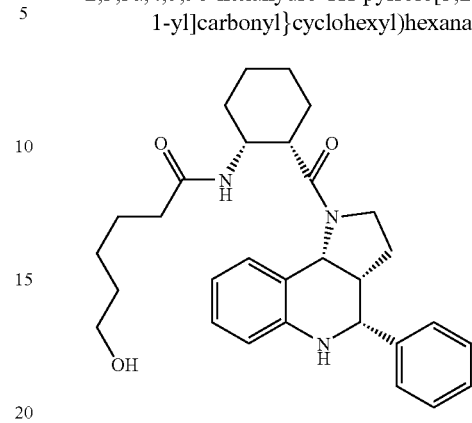

A mixture of calcium chloride (88 mg, 0.8 mmol), sodium borohydride (60 mg, 1.6 mmol), tetrahydrofuran (2.5 ml) and ethanol (2.5 ml) was stirred under a nitrogen atmosphere under ice-cooling for 30 min. To the mixture was added methyl 6-oxo-6-[((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)amino]hexanoate (106 mg, 0.20 mmol) under ice-cooling, and the mixture was stirred at room temperature for 16 hrs. Water was added, and the reaction mixture was extracted with ethyl acetate. The extract was dried over anhydrous $Na_2SO_4$. The solvent was evaporated under reduced pressure, and the obtained residue was subjected to column chromatography using basic silica gel and eluted with ethyl acetate to give the title compound (89 mg, 92%) as a white solid.

LC/MS (ESI) m/z: 490 (MH$^+$).

Example 120

4-(Hydroxymethyl)-N-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)benzamide

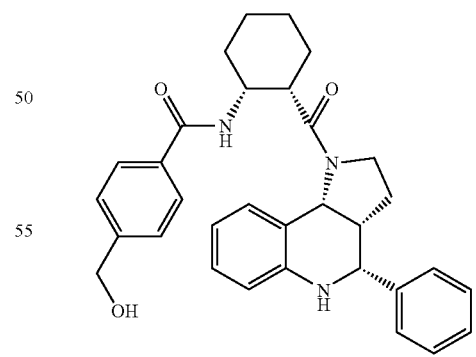

In the same manner as in Example 119 and using methyl 4-{[((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)amino]carbonyl}benzoate, the title compound was synthesized.

LC/MS (ESI) m/z: 510 (MH$^+$).

Example 121

4-Hydroxy-N-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)butanamide

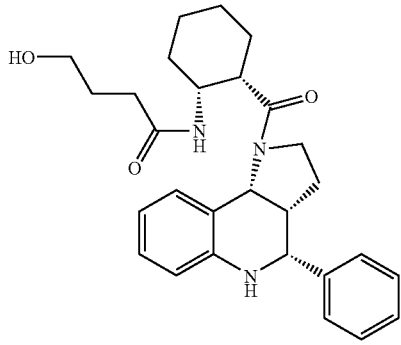

In the same manner as in Example 119 and using ethyl 4-oxo-4-(((1R,2S)-2-(((3aR,4R,9bR)-4-phenyl-2,3,3a, 4,5,9b-hexahydro-1H-pyrrolo[3,2-c]quinolin-1-yl)carbonyl)cyclohexyl)amino)butanoate, the title compound was synthesized.

LC/MS (ESI) m/z: 462 (MH$^+$).

Example 122

4-{[((1R,2S)-2-{[(3aR,4R,9bR)-4-Phenyl-2,3,3a,4,5,9b-hexahydro-1H-pyrrolo[3,2-c]quinolin-1-yl]carbonyl}cyclohexyl)amino]carbonyl}benzoic acid

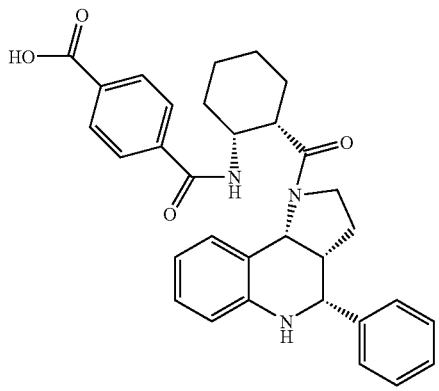

To a solution of methyl 4-{[((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)amino]carbonyl}benzoate (77 mg, 0.14 mmol) in tetrahydrofuran (4 ml) and methanol (1 ml) was added 2N aqueous sodium hydroxide solution (1 ml), and the mixture was stirred at 60° C. for 16 hrs. The reaction mixture was neutralized (pH 7) by adding 3N hydrochloric acid under ice-cooling. The mixture was concentrated under reduced pressure and extracted with a mixed solvent of ethyl acetate-tetrahydrofuran (2:1, v/v). The extract was dried over anhydrous Na$_2$SO$_4$, and the solvent was evaporated under reduced pressure. The obtained solid was washed with isopropyl ether-hexane (1:2, v/v) to give the title compound (51 mg, 68%) as a white solid.

LC/MS (ESI) m/z: 524 (MH$^+$).

Example 123

2-{[((1R,2S)-2-{[(3aR,4R,9bR)-4-Phenyl-2,3,3a,4,5,9b-hexahydro-1H-pyrrolo[3,2-c]quinolin-1-yl]carbonyl}cyclohexyl)amino]carbonyl}benzoic acid

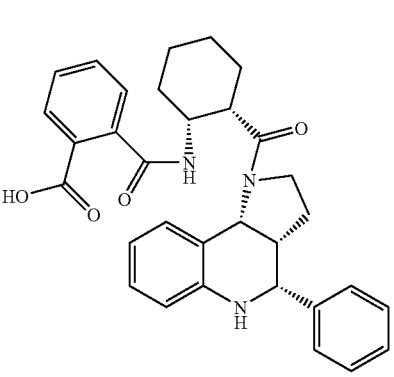

The compound (135 mg, 0.30 mmol) synthesized in Reference Example 23, phthalic anhydride (53 mg, 0.36 mmol) and triethylamine (91.5 μl, 0.66 mmol) were heated under reflux in chloroform (4 ml) for 20 hrs. The solvent was evaporated under reduced pressure, water was added and the mixture was extracted with ethyl acetate. The extract was dried over anhydrous Na$_2$SO$_4$, and the solvent was evaporated under reduced pressure. The obtained residue was recrystallized from ethyl acetate-hexane to give the title compound (136 mg, 87%) as a white solid.

LC/MS (ESI) m/z: 524 (MH$^+$).

Example 124

2-((1R,2S)-2-{[(3aR,4R,9bR)-4-Phenyl-2,3,3a,4,5,9b-hexahydro-1H-pyrrolo[3,2-c]quinolin-1-yl]carbonyl}cyclohexyl)-1H-isoindole-1,3(2H)-dione

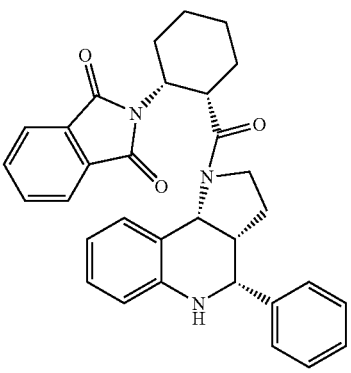

To a solution of the compound (70 mg, 0.13 mmol) of Example 123 and triethylamine (20.9 μl, 0.15 mmol) in DMF (5 ml) was added DEPC (24.5 μl, 0.15 mmol) under ice-cooling, and the mixture was stirred at room temperature for 4 hrs. Water was added to the reaction mixture and the mixture was extracted with ethyl acetate, the extract was washed with saturated brine and dried over anhydrous Na$_2$SO$_4$. The solvent was evaporated under reduced pressure, and the obtained residue was subjected to silica gel column chromatography and eluted with hexane-ethyl acetate (3:1-1:1, v/v) to give the title compound (54 mg, 71%) as a white solid.

LC/MS (ESI) m/z: 506 (MH$^+$).

Example 125

(4-(Dimethylamino)-N-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)butanamide

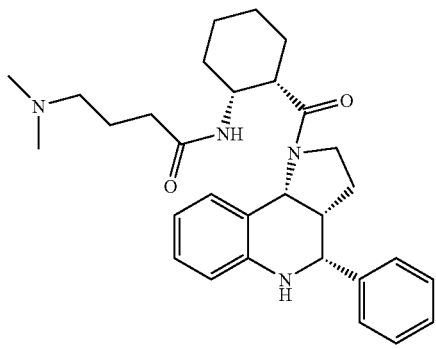

To a mixture of the compound (135 mg, 0.30 mmol) synthesized in Reference Example 23, 4-(dimethylamino)butanoic acid (60 mg, 0.36 mmol) and triethylamine (0.167 ml, 1.2 mmol) in DMF (3 ml) was added DEPC (0.060 ml, 0.36 mmol) under ice-cooling. The reaction mixture was stirred at room temperature for 12 hrs., saturated aqueous sodium hydrogen carbonate solution was added, and the mixture was extracted with ethyl acetate. The extract was washed with saturated brine and dried over anhydrous $Na_2SO_4$. The solvent was evaporated under reduced pressure, and the obtained residue was subjected to basic silica gel column chromatography. The title compound (129 mg, 88%) was obtained as a white solid from a fraction eluted with ethyl acetate-methanol (1:0-9:1, v/v).

LC/MS (ESI) m/z: 489 (MH$^+$).

The following compounds of Example 126-Example 133 were synthesized using the corresponding carboxylic acids in the same manner as in Reference Example 125.

Example 126

4-Morpholin-4-yl-N-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)butanamide

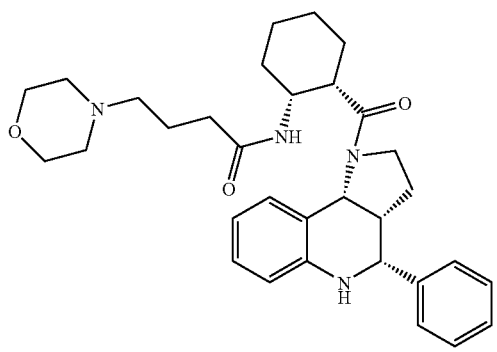

LC/MS (ESI) m/z: 531 (MH$^+$).

Example 127

N-((1R,2S)-2-{[(3aR,4R,9bR)-4-Phenyl-2,3,3a,4,5,9b-hexahydro-1H-pyrrolo[3,2-c]quinolin-1-yl]carbonyl}cyclohexyl)pyrazine-2-carboxamide

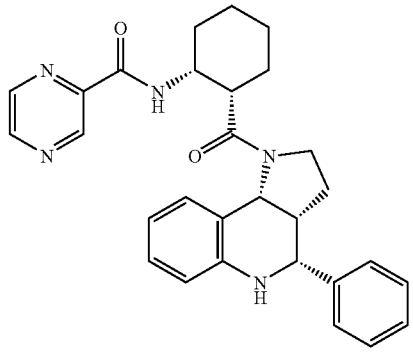

LC/MS (ESI) m/z: 482 (MH$^+$).

Example 128

(2E)-3-(1H-Imidazol-4-yl)-N-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)acrylamide

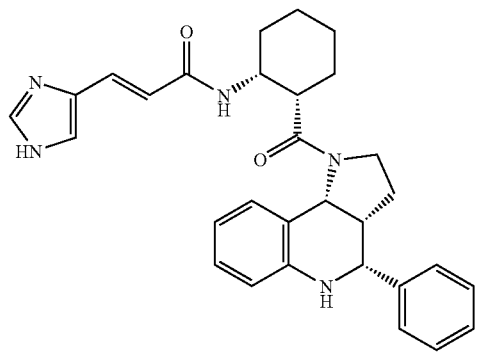

LC/MS (ESI) m/z: 496 (MH$^+$).

Example 129

N-((1R,2S)-2-{[(3aR,4R,9bR)-4-Phenyl-2,3,3a,4,5,9b-hexahydro-1H-pyrrolo[3,2-c]quinolin-1-yl]carbonyl}cyclohexyl)-1H-imidazole-2-carboxamide

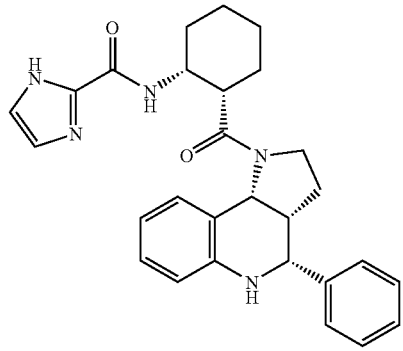

LC/MS (ESI) m/z: 470 (MH$^+$).

Example 130

(2E)-3-(1-Methyl-1H-imidazol-2-yl)-N-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)acrylamide

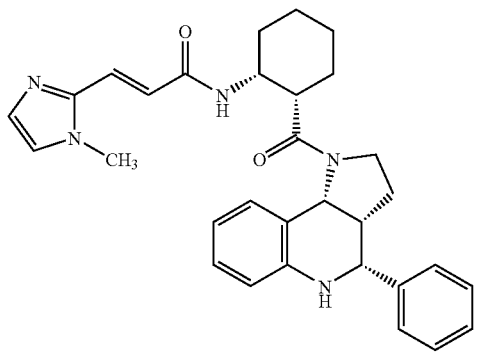

LC/MS (ESI) m/z: 510 (MH⁺).

Example 131

N-((1R,2S)-2-{[(3aR,4R,9bR)-4-Phenyl-2,3,3a,4,5,9b-hexahydro-1H-pyrrolo[3,2-c]quinolin-1-yl]carbonyl}cyclohexyl)-1H-imidazole-5-carboxamide

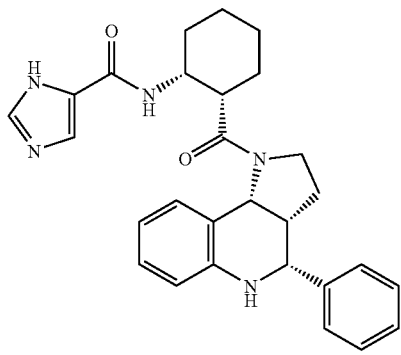

LC/MS (ESI) m/z: 470 (MH⁺).

Example 132

1-Methyl-N-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)-1H-imidazole-2-carboxamide

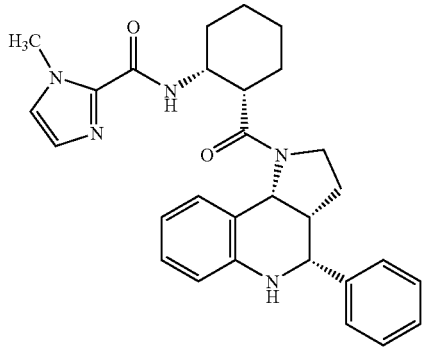

LC/MS (ESI) m/z: 484 (MH⁺).

Example 133

N-((1R,2S)-2-{[(3aR,4R,9bR)-4-Phenyl-2,3,3a,4,5,9b-hexahydro-1H-pyrrolo[3,2-c]quinolin-1-yl]carbonyl}cyclohexyl)-1H-benzimidazole-5-carboxamide

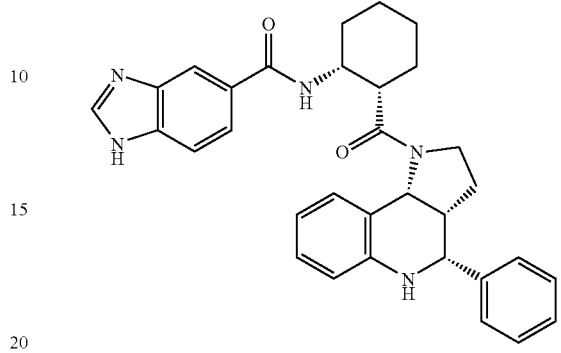

LC/MS (ESI) m/z: 520 (MH⁺).

Example 134

(2E)-3-(1H-Imidazol-2-yl)-N-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)acrylamide

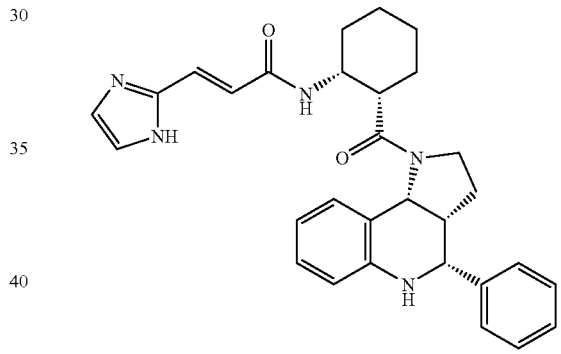

To a mixture of the compound (0.319 g, 0.712 mmol) synthesized in Reference Example 23, (2E)-3-(1-trityl-1H-imidazol-2-yl)acrylic acid (0.298 g, 0.783 mmol) and DMF (10 ml) were added triethylamine (0.3 ml, 2.14 mmol) and then DEPC (0.127 ml, 0.783 mmol) at 0° C. The mixture was stirred at the same temperature for 30 min., water was added, and the mixture was extracted with ethyl acetate. The extract was washed with saturated brine and dried (over anhydrous MgSO₄). After concentration under reduced pressure, the obtained residue was subjected to column chromatography using silica gel, and eluted with hexane-ethyl acetate (4:1-3:7, v/v). (2E)-N-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)-3-(1-trityl-1H-imidazol-2-yl)acrylamide (0.457 g, 87%) was obtained as a colorless amorphous form from the object fraction. The obtained compound was dissolved in tetrahydrofuran (5 ml), 6N hydrochloric acid (0.206 ml, 1.24 mmol) was added dropwise and the mixture was heated under reflux for 30 min. 8N Aqueous sodium hydroxide solution (0.2 ml) was added dropwise at 0° C., and the mixture was extracted with ethyl acetate. The extract was dried (over anhydrous MgSO₄), and after concentration under reduced pressure, the obtained residue was subjected to column chromatography using silica gel, and eluted with ethyl acetate-methanol (1:0-7:3, v/v). The title compound (0.228 g, 74%) was obtained as a colorless amorphous form from the object fraction.

LC/MS (ESI) m/z: 496 (MH⁺).

Example 135

N-Phenyl-N'-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)urea

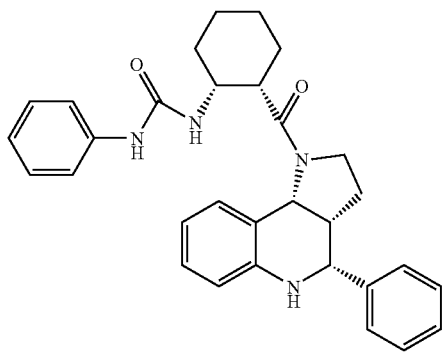

To a mixture of the compound (0.135 g, 0.3 mmol) synthesized in Reference Example 23, ethyl acetate (10 ml) and 10% aqueous sodium carbonate solution (5 ml) was added phenylisocyanate (0.039 ml, 0.36 mmol) at room temperature, and the reaction mixture was stirred for 30 min. The reaction mixture was extracted with ethyl acetate. The extract was washed with saturated brine and dried (over anhydrous MgSO₄). The solvent was evaporated under reduced pressure, and the obtained residue was subjected to column chromatography using silica gel and eluted with hexane-ethyl acetate (9:1-4:6, v/v). The title compound (0.135 g, 91%) was obtained as an amorphous form from the object fraction.

¹H-NMR (CDCl₃) δ: 1.35-2.00 (7H, m), 2.15-2.48 (3H, m), 2.83-2.97 (1H, m), 3.40-3.60 (3H, m), 3.80-4.18 (2H, m), 4.58 (1H, d, J=2.1 Hz), 5.67 (1H, d, J=7.2 Hz), 5.90-6.01 (1H, m), 6.50-6.60 (1H, m), 6.62-6.70 (1H, m), 6.89 (1H, br s), 6.94-7.07 (2H, m), 7.18-7.50 (10H, m).

LC/MS (ESI) m/z: 495 (MH⁺).

Example 136

N-(4-Chlorophenyl)-N'-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)urea

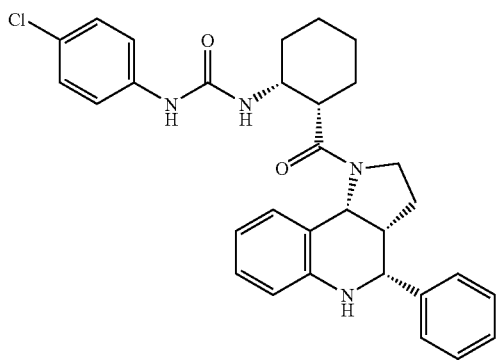

The compound (0.172 g, 0.384 mmol) synthesized in Reference Example 23, triethylamine (0.163 ml, 1.15 mmol) and 4-chlorophenylisocyanate (0.0709 g, 0.461 mmol) were stirred for 4.5 hrs. in tetrahydrofuran (10 ml). Saturated aqueous sodium hydrogen carbonate solution was added to the reaction mixture and the mixture was extracted with ethyl acetate. The extract was washed with saturated brine, dried (over anhydrous MgSO₄), and the solvent was evaporated under reduced pressure. The residue was subjected to column chromatography using silica gel (30 g), and eluted with hexane-ethyl acetate (19:1-1:4, v/v). The title compound (0.210 g, ca. 100%) was obtained as an amorphous form from the object fraction.

LC/MS (ESI) m/z: 529 (MH⁺).

The following compounds of Example 137-Example 155 and Example 159 were synthesized using the corresponding isocyanates in the same manner as in Example 135 or Example 136.

Example 137

N-(4-Methoxyphenyl)-N'-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)urea

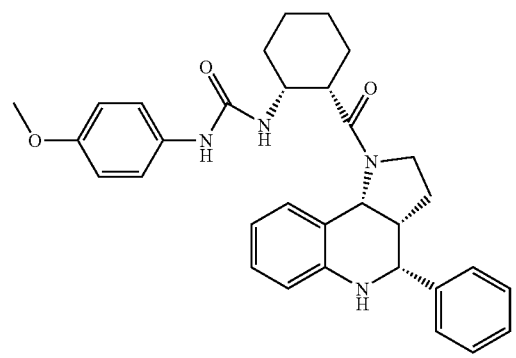

LC/MS (ESI) m/z: 525 (MH⁺).

Example 138

N-(4-Methylphenyl)-N'-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)urea

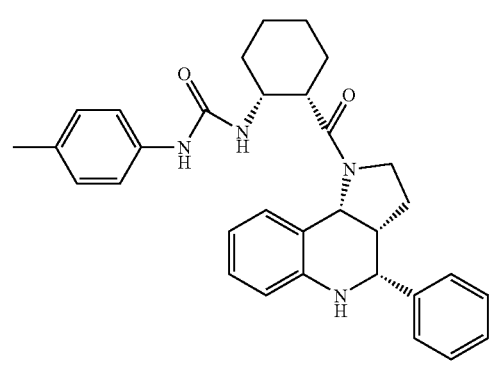

LC/MS (ESI) m/z: 509 (MH⁺).

Example 139

N-(4-Fluorophenyl)-N'-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)urea

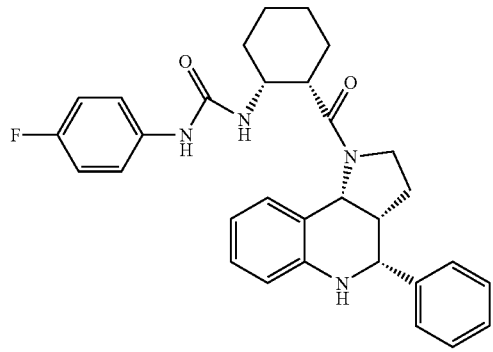

LC/MS (ESI) m/z: 513 (MH$^+$).

Example 140

N-((1R,2S)-2-{[(3aR,4R,9bR)-4-Phenyl-2,3,3a,4,5,9b-hexahydro-1H-pyrrolo[3,2-c]quinolin-1-yl]carbonyl}cyclohexyl)-N'-[4-(trifluoromethyl)phenyl]urea

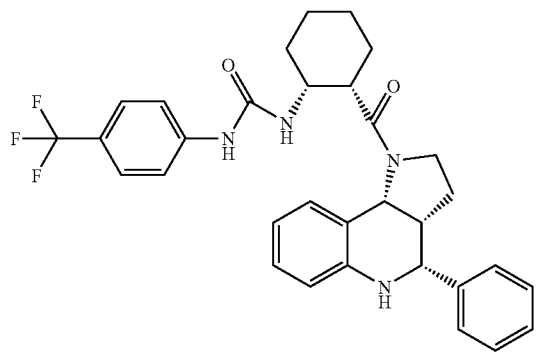

LC/MS (ESI) m/z: 563 (MH$^+$).

Example 141

N-(3-Chlorophenyl)-N'-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)urea

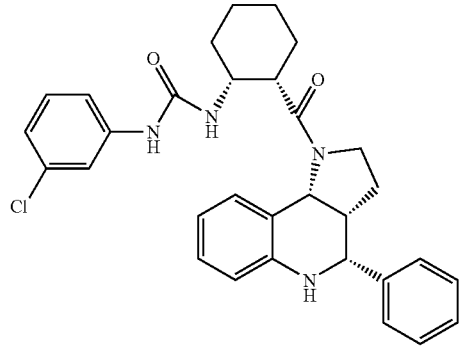

LC/MS (ESI) m/z: 529 (MH$^+$).

Example 142

N-(2-Chlorophenyl)-N'-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)urea

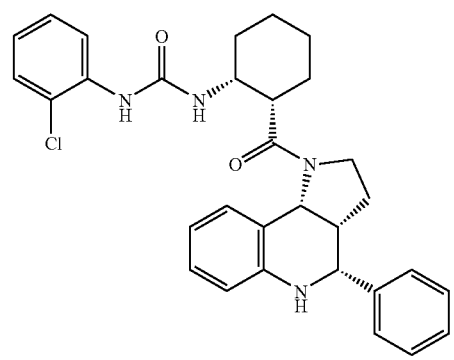

LC/MS (ESI) m/z: 529 (MH$^+$).

Example 143

N-Benzyl-N'-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)urea

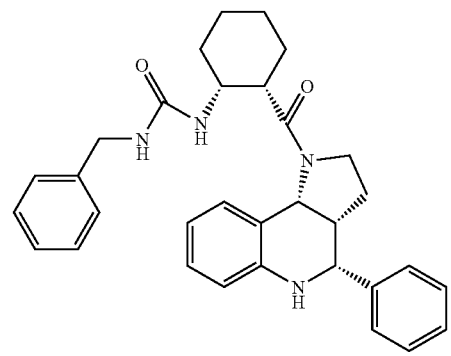

LC/MS (ESI) m/z: 509 (MH$^+$)

Example 144

N-(4-Methoxybenzyl)-N'-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)urea

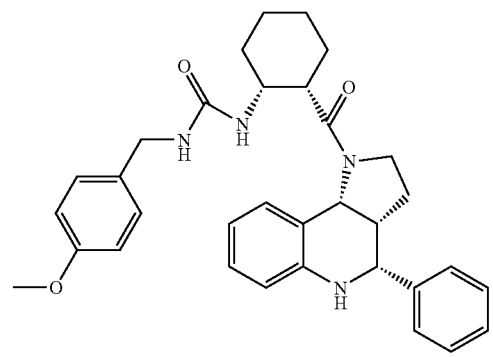

LC/MS (ESI) m/z: 539 (MH$^+$).

Example 145

N-(4-Fluorobenzyl)-N'-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)urea

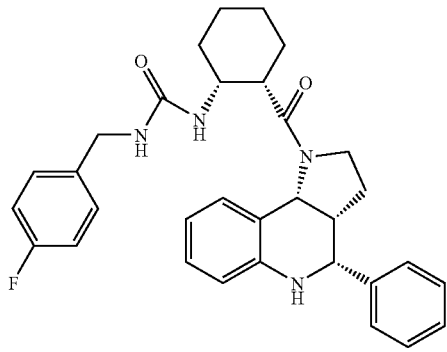

LC/MS (ESI) m/z: 527 (MH+).

Example 146

N-(2-Phenylethyl)-N'-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)urea

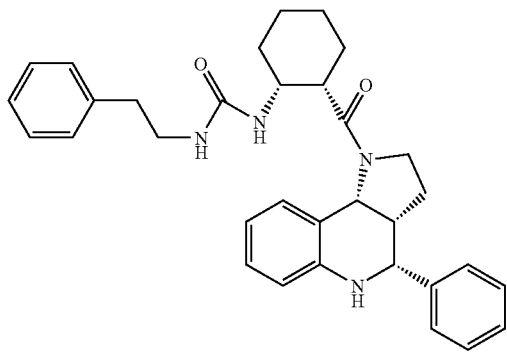

LC/MS (ESI) m/z: 523 (MH+).

Example 147

N-(4-Cyanophenyl)-N'-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)urea

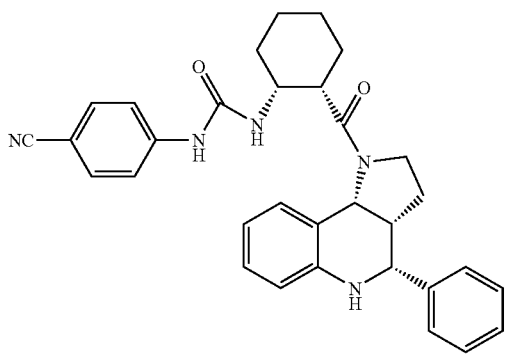

LC/MS (ESI) m/z: 520 (MH+).

Example 148

N-1,3-Benzodioxol-5-yl-N'-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)urea

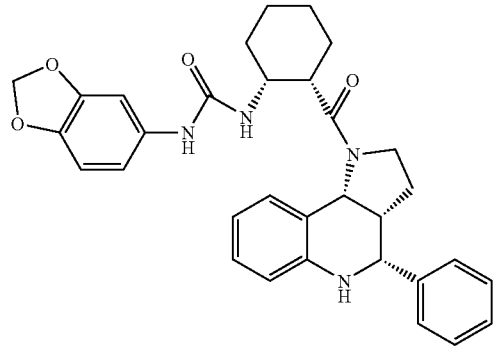

LC/MS (ESI) m/z: 539 (MH+)

Example 149

N-Cyclohexyl-N'-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)urea

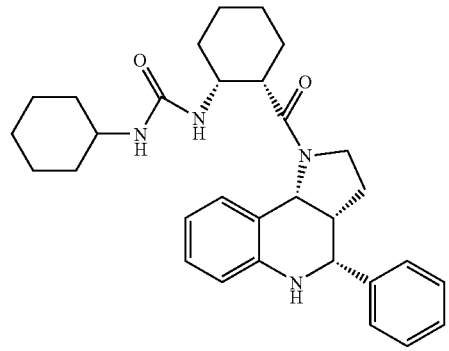

LC/MS (ESI) m/z: 501 (MH+).

Example 150

N-(4-Isopropylphenyl)-N'-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)urea

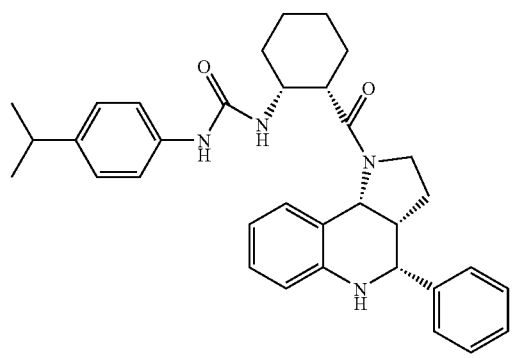

LC/MS (ESI) m/z: 537 (MH+).

Example 151

N-Ethyl-N'-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)urea

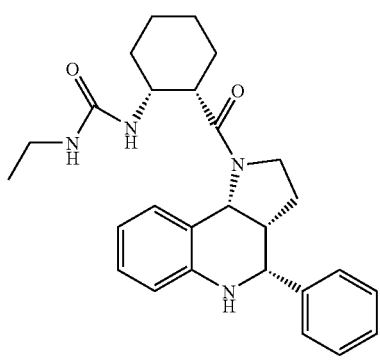

LC/MS (ESI) m/z: 447 (MH+).

Example 152

N-Isopropyl-N'-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)urea

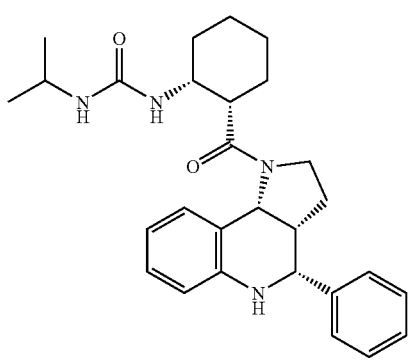

LC/MS (ESI) m/z: 461 (MH+).

Example 153

N-Butyl-N'-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)urea

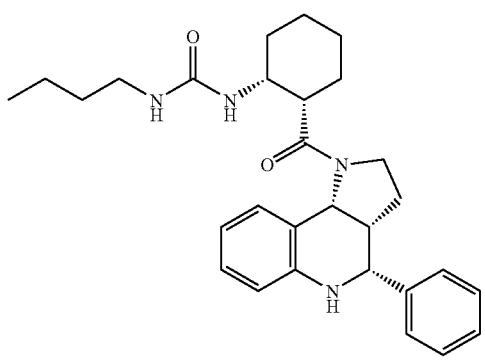

LC/MS (ESI) m/z: 475 (MH+).

Example 154

N-Hexyl-N'-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)urea

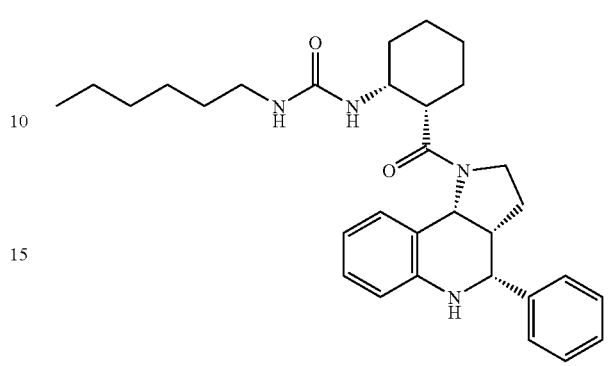

LC/MS (ESI) m/z: 503 (MH+)

Example 155

Ethyl N-{[((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)amino]carbonyl}-beta-alaninate

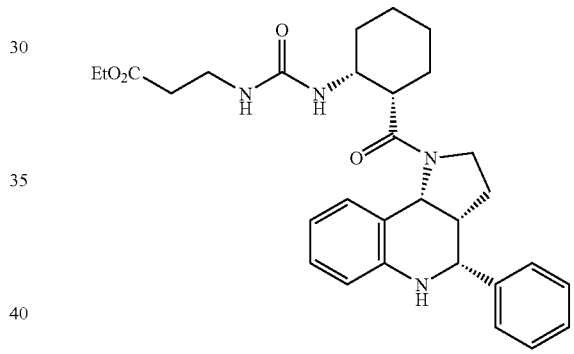

LC/MS (ESI) m/z: 519 (MH+).

Example 156

N-(3-Hydroxypropyl)-N'-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)urea

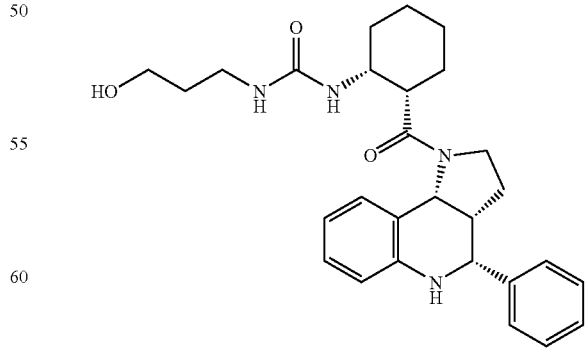

In the same manner as in Example 120 and using the compound synthesized in Example 155, the title compound was synthesized.

LC/MS (ESI) m/z: 477 (MH+).

Example 157

N-{[((1R,2S)-2-{[(3aR,4R,9bR)-4-Phenyl-2,3,3a,4,5,9b-hexahydro-1H-pyrrolo[3,2-c]quinolin-1-yl]carbonyl}cyclohexyl)amino]carbonyl}-beta-alanine

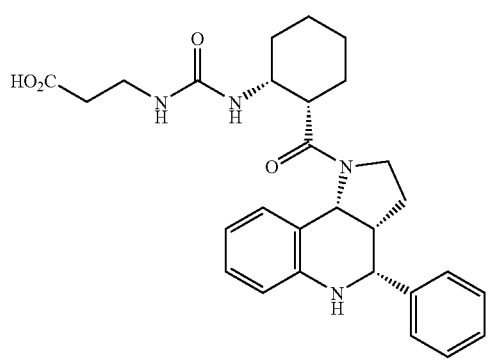

The compound (0.211 g, 0.407 mmol) synthesized in Example 155 and 1N aqueous sodium hydroxide solution (0.814 ml, 0.814 mmol) were stirred in methanol (10 ml) at 60° C. for 2 hrs. After allowing to cool to room temperature, the reaction mixture was diluted with water and 1N hydrochloric acid (0.814 ml) was added. The mixture was extracted twice with dichloromethane and the combined extract was dried (over anhydrous MgSO$_4$), and the solvent was evaporated under reduced pressure. The residue was subjected to column chromatography using silica gel (30 g), and eluted with ethyl acetate-methanol (1:0-4:1, v/v) to give the title compound (0.171 g, 86%) as an amorphous form from the object fraction.

LC/MS (ESI) m/z: 491 (MH$^+$).

Example 158

N$^3$-{[((1R,2S)-2-{[(3aR,4R,9bR)-4-Phenyl-2,3,3a,4,5,9b-hexahydro-1H-pyrrolo[3,2-c]quinolin-1-yl]carbonyl}cyclohexyl)amino]carbonyl}-beta-alaninamide

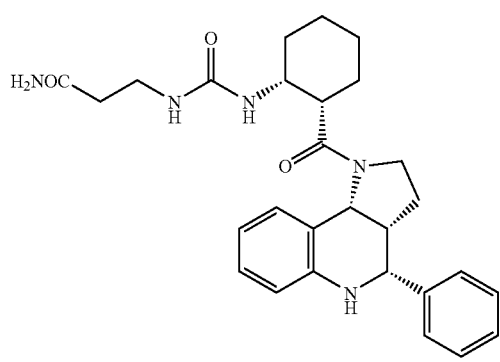

The compound (0.171 g, 0.348 mmol) synthesized in Example 157, ammonium chloride (0.0261 g, 0.488 mmol), triethylamine (0.0685 ml, 0.488 mmol) and diethylcyanophosphonate (0.07 ml, 0.418 mmol) were stirred in DMF (5 ml) under ice-cooling for 1 hr and at room temperature for 1 hr. Saturated aqueous sodium hydrogen carbonate solution and water were added to the reaction mixture and the mixture was extracted with ethyl acetate. The extract was washed with saturated brine, dried (over anhydrous MgSO$_4$), and the solvent was evaporated under reduced pressure. The residue was subjected to column chromatography using basic silica gel (30 g) and eluted with ethyl acetate-methanol (1:0-4:1, v/v) to give the title compound (0.117 g, 69%) as an amorphous form from the object fraction.

LC/MS (ESI) m/z: 490 (MH$^+$).

Example 159

Ethyl 4-({[((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)amino]carbonyl}amino)benzoate

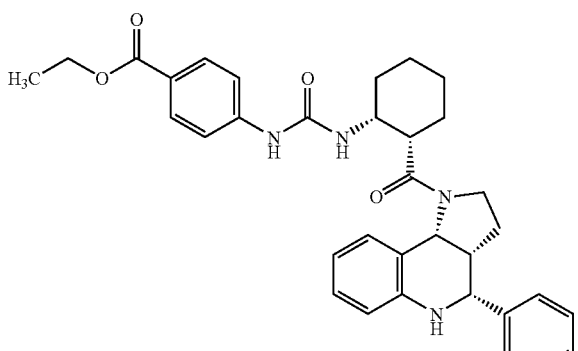

Example 160

4-({[((1R,2S)-2-{[(3aR,4R,9bR)-4-Phenyl-2,3,3a,4,5,9b-hexahydro-1H-pyrrolo[3,2-c]quinolin-1-yl]carbonyl}cyclohexyl)amino]carbonyl}amino)benzamide

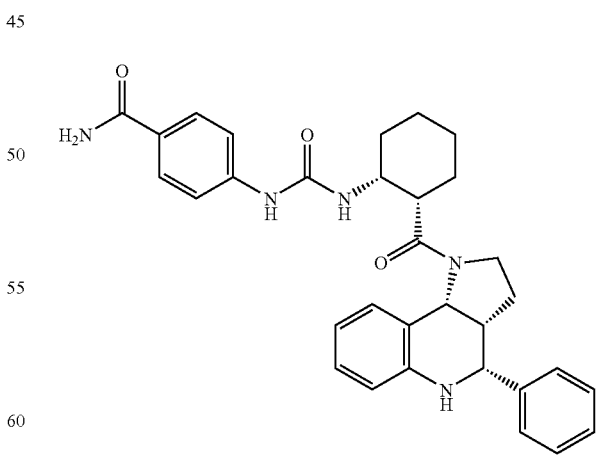

In the same manner as in Example 157 and Example 158 and using the compound synthesized in Example 159, the title compound was synthesized.

LC/MS (ESI) m/z: 538 (MH$^+$).

Example 161

N-(3-Methoxypropyl)-N'-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)urea

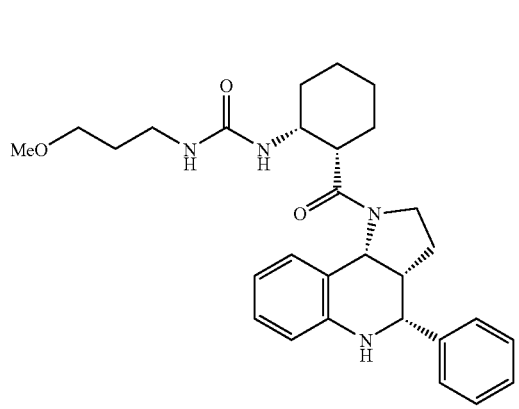

The compound (0.209 g, 0.467 mmol) synthesized in Reference Example 23, 1,1-carbonyldiimidazole (0.151 g, 0.934 mmol) and triethylamine (0.21 ml, 1.49 mmol) were stirred in DMF (5 ml) under ice-cooling for 1 hr. 3-Methoxypropylamine (0.143 ml, 1.4 mmol) and triethylamine (0.196 ml, 1.4 mmol) were added at the same temperature, and the mixture was stirred at room temperature for 14 hrs. Water was added to the reaction mixture and the mixture was extracted with ethyl acetate. The extract was washed with saturated brine, dried (over anhydrous MgSO$_4$), and the solvent was evaporated under reduced pressure. The residue was subjected to column chromatography using silica gel (30 g), and eluted with ethyl acetate-methanol (1:0-4:1, v/v) to give the title compound (0.226 g, 99%) as an amorphous form from the object fraction.

LC/MS (ESI) m/z: 491 (MH$^+$).

The following compounds of Example 162-Example 174 were synthesized using the corresponding amines in the same manner as in Example 161.

Example 162

N-(2-Ethoxyethyl)-N'-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)urea

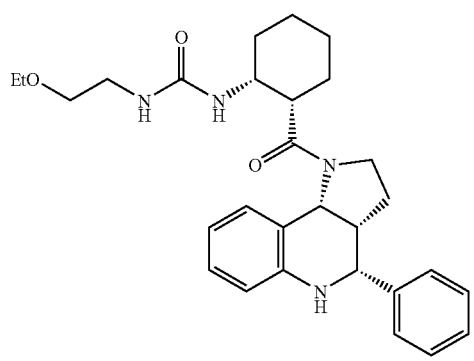

LC/MS (ESI) m/z: 491 (MH$^+$).

Example 163

N-[2-(Methylsulfonyl)ethyl]-N'-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)urea

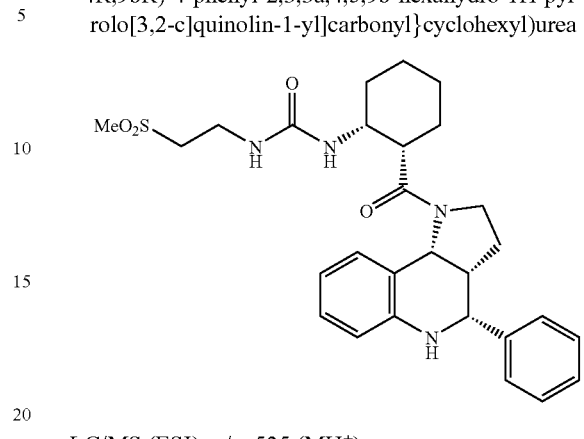

LC/MS (ESI) m/z: 525 (MH$^+$).

Example 164

N-((1R,2S)-2-{[(3aR,4R,9bR)-4-Phenyl-2,3,3a,4,5,9b-hexahydro-1H-pyrrolo[3,2-c]quinolin-1-yl]carbonyl}cyclohexyl)-N'-(2-pyridin-2-ylethyl)urea

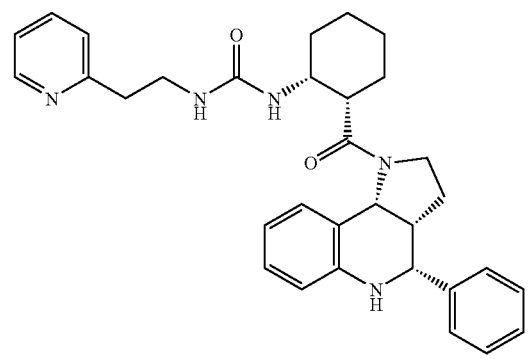

LC/MS (ESI) m/z: 524 (MH$^+$).

Example 165

N-[2-({[((1R,2S)-2-{[(3aR,4R,9bR)-4-Phenyl-2,3,3a,4,5,9b-hexahydro-1H-pyrrolo[3,2-c]quinolin-1-yl]carbonyl}cyclohexyl)amino]carbonyl}amino)ethyl]acetamide

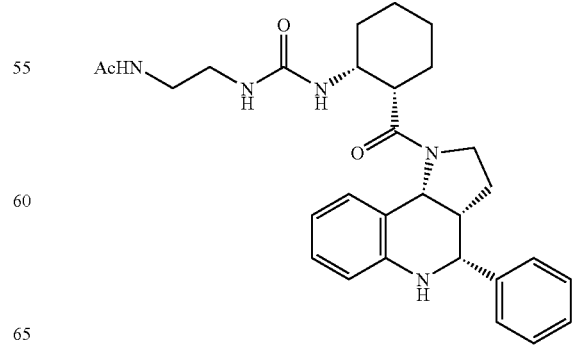

LC/MS (ESI) m/z: 504 (MH$^+$).

Example 166

N-(3-Methylbutyl)-N'-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)urea

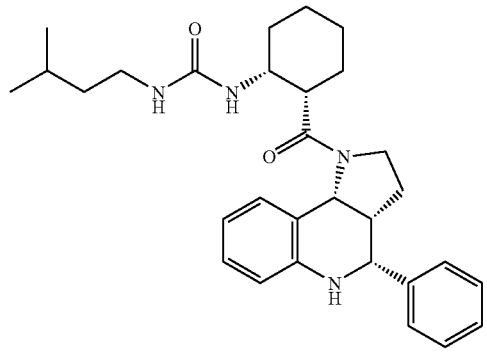

LC/MS (ESI) m/z: 489 (MH$^+$).

Example 167

N-(3-Morpholin-4-ylpropyl)-N'-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)urea

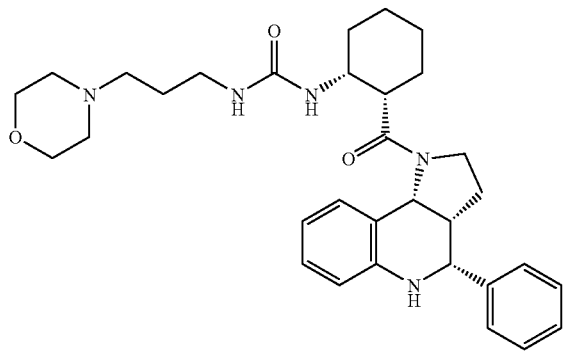

LC/MS (ESI) m/z: 546 (MH$^+$).

Example 168

N-[3-(2-Oxopyrrolidin-1-yl)propyl]-N'-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)urea

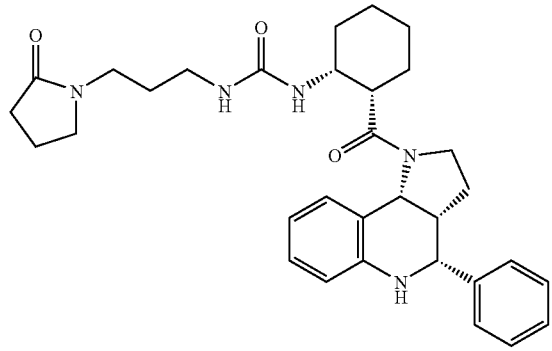

LC/MS (ESI) m/z: 544 (MH$^+$).

Example 169

N-[3-(1H-Imidazol-1-yl)propyl]-N'-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)urea

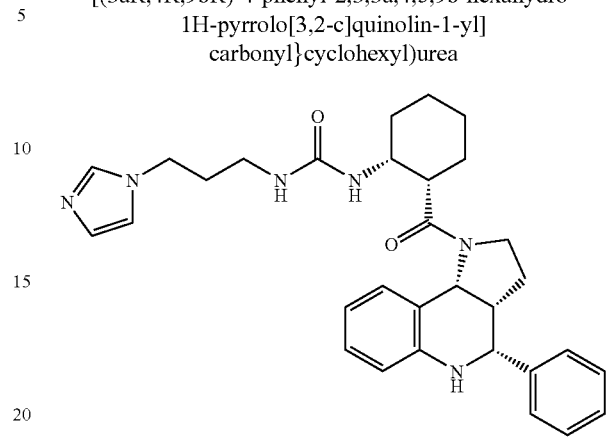

LC/MS (ESI) m/z: 527 (MH$^+$)

Example 170

N-((1R,2S)-2-{[(3aR,4R,9bR)-4-Phenyl-2,3,3a,4,5,9b-hexahydro-1H-pyrrolo[3,2-c]quinolin-1-yl]carbonyl}cyclohexyl)-N'-pyridin-2-ylurea

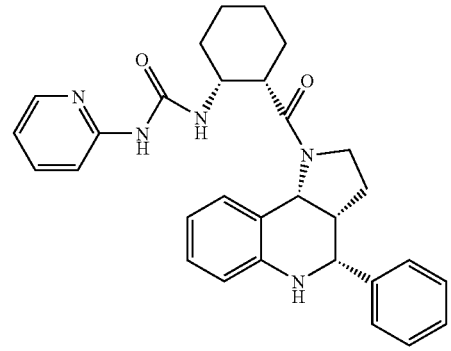

LC/MS (ESI) m/z: 496 (MH$^+$).

Example 171

N-((1R,2S)-2-{[(3aR,4R,9bR)-4-Phenyl-2,3,3a,4,5,9b-hexahydro-1H-pyrrolo[3,2-c]quinolin-1-yl]carbonyl}cyclohexyl)-N'-pyridin-3-ylurea

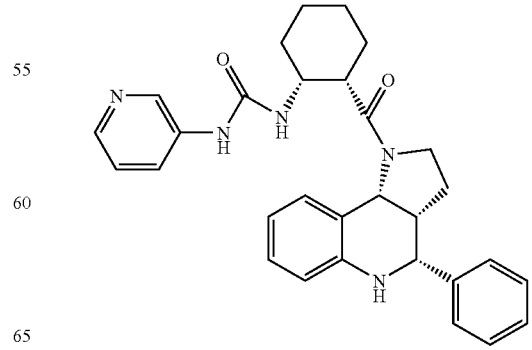

LC/MS (ESI) m/z: 496 (MH$^+$).

Example 172

4-Phenyl-N-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)piperidine-1-carboxamide

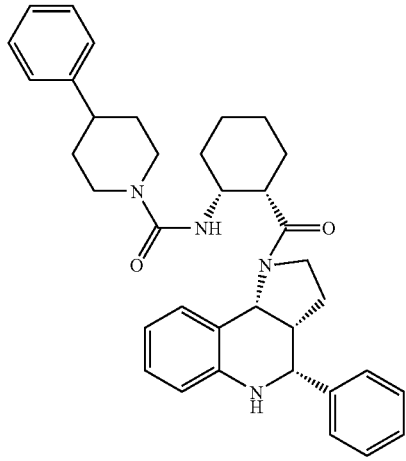

LC/MS (ESI) m/z: 563 (MH$^+$).

Example 173

N-((1R,2S)-2-{[(3aR,4R,9bR)-4-Phenyl-2,3,3a,4,5,9b-hexahydro-1H-pyrrolo[3,2-c]quinolin-1-yl]carbonyl}cyclohexyl)-N'-(2,2,2-trifluoroethyl)urea

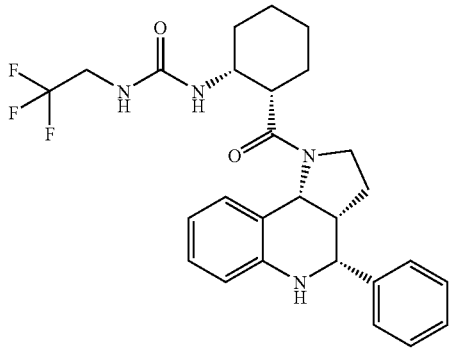

LC/MS (ESI) m/z: 501 (MH$^+$).

Example 174

N-Methoxy-N'-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)urea

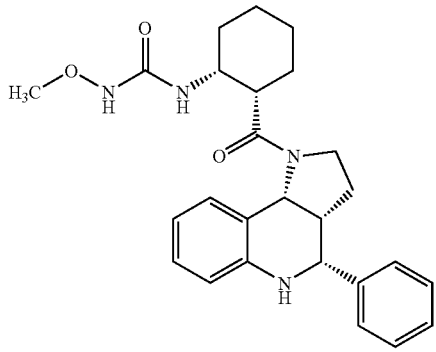

LC/MS (ESI) m/z: 449 (MH$^+$)

Example 175

N-(1-Acetylpiperidin-4-yl)-N'-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)urea

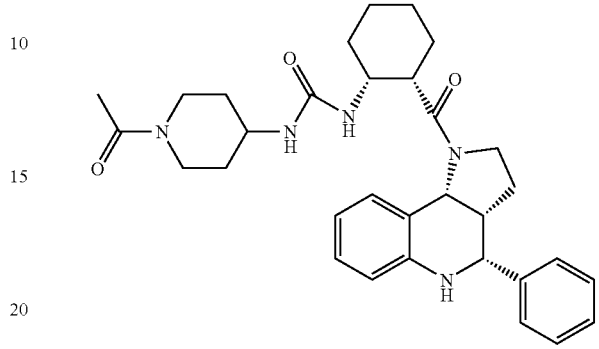

N-Acetylisonipecotinic acid (0.343 g, 2.01 mmol), triethylamine (0.282 ml, 2.01 mmol) and diphenylphosphoryl azide (0.432 ml, 2.01 mmol) were stirred in toluene (10 ml) at 80° C. for 2 hrs. This reaction mixture was allowed to cool to room temperature, added dropwise to a suspension of the compound (0.18 g, 0.402 mmol) synthesized in Reference Example 23 and triethylamine (0.169 ml, 1.21 mmol) in tetrahydrofuran (5 ml), and the mixture was stirred for 21 hrs. Water was added to the reaction mixture and the mixture was extracted with ethyl acetate. The extract was washed with water and saturated brine, dried (over anhydrous MgSO$_4$), and the solvent was evaporated under reduced pressure. The residue was subjected to column chromatography using silica gel (30 g) and eluted with ethyl acetate-methanol (1:0-7:3, v/v) to give the title compound (0.192 g, 88%) as an amorphous form from the object fraction.

LC/MS (ESI) m/z: 544 (MH$^+$).

Example 176

N-Methyl-N-phenyl-N'-((1R,2S)-2-{[(3aR,4R,9bR)-4-phenyl-2,3,3a,4,5,9b-hexahydro-1H-pyrrolo[3,2-c]quinolin-1-yl]carbonyl}cyclohexyl)urea

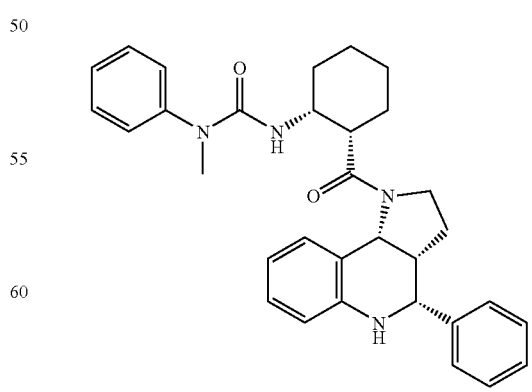

The compound (0.134 g, 0.299 mmol) synthesized in Reference Example 23, triethylamine (0.135 ml, 0.963 mmol)

and N-methyl-N-phenylcarbamoylchloride (0.056 g, 0.33 mmol) were stirred in dichloromethane (5 ml) for 24 hrs. Saturated aqueous sodium hydrogen carbonate solution was added to the reaction mixture and the mixture was extracted with ethyl acetate. The extract was washed with saturated brine, dried (over anhydrous MgSO₄), and the solvent was evaporated under reduced pressure. The residue was subjected to column chromatography using silica gel (30 g) and eluted with hexane-ethyl acetate (7:3-1:4, v/v) to give the title compound (0.139 g, 91%) as an amorphous form from the object fraction.

LC/MS (ESI) m/z: 509 (MH⁺).

Example 177

N-((1R,2S)-2-{[(3aR,4R,9bR)-4-Phenyl-2,3,3a,4,5,9b-hexahydro-1H-pyrrolo[3,2-c]quinolin-1-yl]carbonyl}cyclohexyl)piperidine-1-carboxamide

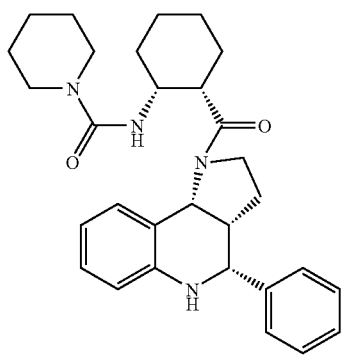

To a mixture of the compound (0.135 g, 0.3 mmol) synthesized in Reference Example 23, ethyl acetate (10 ml) and 10% aqueous sodium carbonate solution (5 ml) was added piperidine-1-carbonyl chloride (0.089 g, 0.6 mmol) at room temperature, and the mixture was stirred for 3 hrs. The reaction mixture was extracted with ethyl acetate, and the extract was washed with saturated brine and dried (over anhydrous MgSO₄). The solvent was evaporated under reduced pressure, and the obtained residue was dissolved in tetrahydrofuran (5 ml). Triethylamine (0.084 ml, 0.6 mmol) and piperidine-1-carbonyl chloride (0.044 g, 0.3 mmol) were added at room temperature, and the mixture was stirred for 3 days. The reaction mixture was concentrated under reduced pressure and 10% aqueous sodium carbonate solution was added. The mixture was extracted with ethyl acetate, and the extract was washed with saturated brine and dried (over anhydrous MgSO₄). The solvent was evaporated under reduced pressure and the residue was subjected to column chromatography using silica gel, and eluted with hexane-ethyl acetate (7:3-0:1, v/v) to give the title compound (0.125 g, 86%) as an amorphous form from the object fraction.

LC/MS (ESI) m/z: 487 (MH⁺).

Example 178

N-((2R,3S)-3-{[(3aR,4R,9bR)-4-Phenyl-2,3,3a,4,5,9b-hexahydro-1H-pyrrolo[3,2-c]quinolin-1-yl]carbonyl}bicyclo[2.2.2]oct-2-yl)benzamide

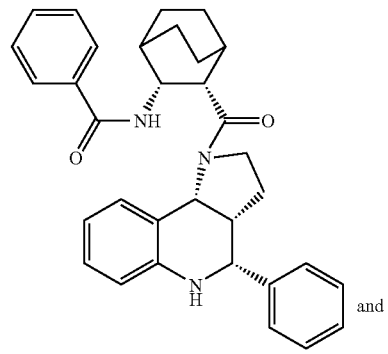

and

N-((2S,3R)-3-{[(3aS,4S,9bS)-4-phenyl-2,3,3a,4,5,9b-hexahydro-1H-pyrrolo[3,2-c]quinolin-1-yl]carbonyl}bicyclo[2.2.2]oct-2-yl)benzamide

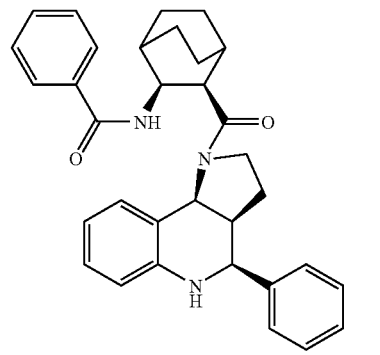

and

N-((2R,3S)-3-{[(3aS,4S,9bS)-4-phenyl-2,3,3a, 4,5,9b-hexahydro-1H-pyrrolo[3,2-c]quinolin-1-yl]carbonyl}bicyclo[2.2.2]oct-2-yl)benzamide

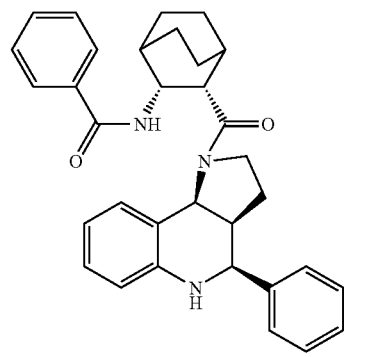

and

183

N-((2S,3R)-3-{[(3aR,4R,9bR)-4-phenyl-2,3,3a,4,5,
9b-hexahydro-1H-pyrrolo[3,2-c]quinolin-1-yl]
carbonyl}bicyclo[2.2.2]oct-2-yl)benzamide

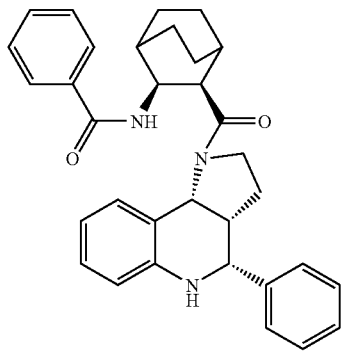

To a solution of the compound (200 mg, 0.42 mmol) synthesized in Reference Example 23 and benzoyl chloride (65 mg, 0.47 mmol) in dichloromethane (4 ml) was added dropwise triethylamine (140 mg, 1.4 mmol), and the mixture was stirred at room temperature for 1 hr. Water was added to the reaction mixture, and the mixture was extracted with chloroform. The extract was dried (over anhydrous Na$_2$SO$_4$), and the solvent was evaporated. The residue was subjected to column chromatography using basic silica gel (5 g), and eluted with hexane-ethyl acetate (6:1-1:1, v/v) to give a mixture of the title compound (170 mg, 80%) as an amorphous form. The mixture was subjected to high performance liquid chromatography using an optically active column and the compound (2R,3S,3aR,4R,9bR) (61 mg) was obtained as an amorphous form from the first eluted fraction, the compound (2S,3R,3aS,4S,9bS) (62 mg) was obtained as an amorphous form from the second eluted fraction, the compound (2R,3S,3aS,4S,9bS) (12 mg) was obtained as an amorphous form from the third eluted fraction, and the compound (2S,3R,3aR,4R,9bR) (10 mg) was obtained as an amorphous form from the fourth eluted fraction.

Example 179

N-{(1R,2S)-2-[(3aR*,4R*,9bR*)-(5-Methyl-4-phenyl-2,3,3a,4,5,9b-hexahydro-1H-pyrrolo[3,2-c]
quinolin-1-yl)carbonyl]cyclohexyl}benzamide

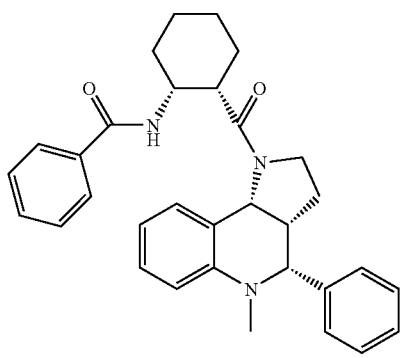

184

-continued

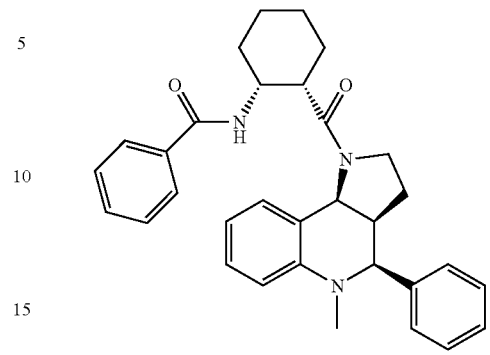

A mixture of 5-methyl-4-phenyl-2,3,3a,4,5,9b-hexahydro-1H-pyrrolo[3,2-c]quinoline (130 mg, 0.48 mmol), (1S,2R)-2-(benzoylamino)cyclohexanecarboxylic acid (131 mg, 0.53 mmol), WSC (116 mg, 0.61 mmol), HOBt (97 mg, 0.63 mmol), acetonitrile (5 ml) and tetrahydrofuran (5 ml) was stirred at room temperature for 12 hrs. Saturated aqueous sodium hydrogen carbonate solution was added to the reaction mixture and the mixture was extracted with ethyl acetate. The extract was washed with saturated brine, dried (over anhydrous Na$_2$SO$_4$), and the solvent was evaporated. The residue was subjected to column chromatography using silica gel (150 g) and eluted with hexane-ethyl acetate (4:1-1:1, v/v) to give the title compound (200 mg, 84%) as an amorphous form.

LC/MS (ESI) m/z: 494 (MH$^+$).

The following compounds were synthesized using the compounds shown in Table 3, carboxylic acids synthesized in Reference Examples and the like in the same manner as in Example 179, unless otherwise specified.

Example 180

N-((1R,2S)-2-{[(3aR,4S,9bR)-4-Cyclopropyl-2,3,3a,
4,5,9b-hexahydro-1H-pyrrolo[3,2-c]quinolin-1-yl]
carbonyl}cyclohexyl)-4-methoxybenzamide

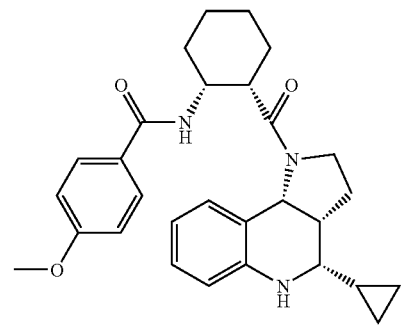

LC/MS (ESI) m/z: 474 (MH$^+$).

Example 181

N-((1R,2S)-2-{[(3aR,4S,9bR)-4-Cyclopropyl-2,3,3a,4,5,9b-hexahydro-1H-pyrrolo[3,2-c]quinolin-1-yl]carbonyl}cyclohexyl)-3-phenylpropanamide

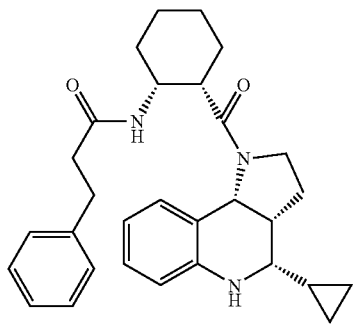

LC/MS (ESI) m/z: 472 (MH$^+$).

Example 182

N-((1R,2S)-2-{[(3aR,4S,9bR)-4-Cyclopropyl-2,3,3a,4,5,9b-hexahydro-1H-pyrrolo[3,2-c]quinolin-1-yl]carbonyl}cyclohexyl)-4-fluorobenzamide

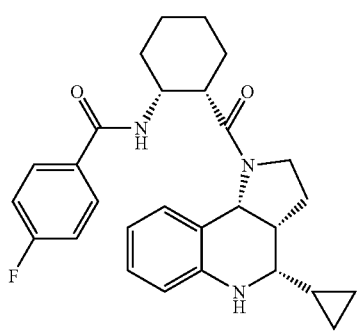

LC/MS (ESI) m/z: 462 (MH$^+$).

Example 183

N-((1R,2S)-2-{[(3aR,4S,9bR)-4-Cyclopropyl-2,3,3a,4,5,9b-hexahydro-1H-pyrrolo[3,2-c]quinolin-1-yl]carbonyl}cyclohexyl)-N'-phenylurea

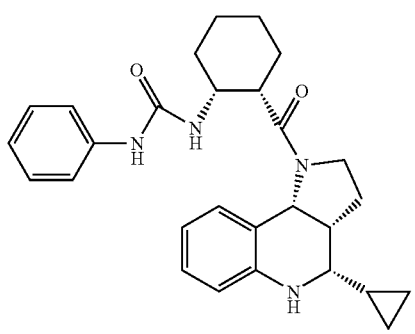

LC/MS (ESI) m/z: 459 (MH$^+$).

Example 184

N-((1R,2S)-2-{[(3aR,4S,9bR)-4-Cyclopropyl-2,3,3a,4,5,9b-hexahydro-1H-pyrrolo[3,2-c]quinolin-1-yl]carbonyl}cyclohexyl)-N'-(4-methoxyphenyl)urea

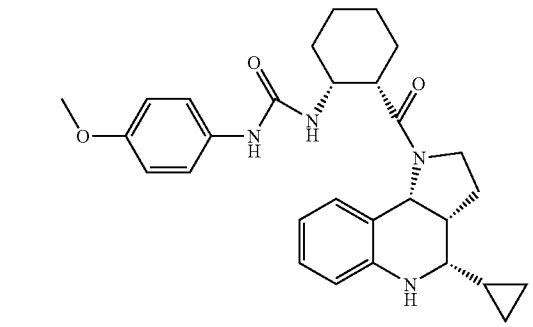

LC/MS (ESI) m/z: 489 (MH$^+$).

Example 185

N-((1R,2S)-2-{[(3aR,4S,9bR)-4-Cyclopropyl-2,3,3a,4,5,9b-hexahydro-1H-pyrrolo[3,2-c]quinolin-1-yl]carbonyl}cyclohexyl)-N'-ethylurea

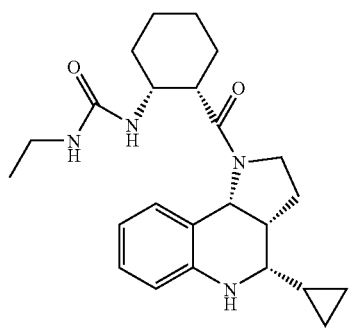

LC/MS (ESI) m/z: 411 (MH$^+$).

Example 186

N-Phenyl-N'-((1R,2S)-2-{[(3aR,4R,9bR)-4-(3-thienyl)-2,3,3a,4,5,9b-hexahydro-1H-pyrrolo[3,2-c]quinolin-1-yl]carbonyl}cyclohexyl)urea

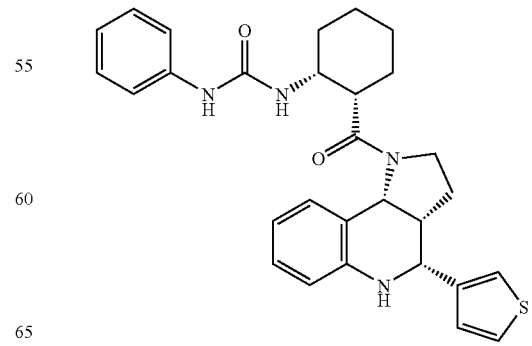

LC/MS (ESI) m/z: 501 (MH$^+$).

Example 187

N-Ethyl-N'-((1R,2S)-2-{[(3aR,4R,9bR)-4-(3-thienyl)-2,3,3a,4,5,9b-hexahydro-1H-pyrrolo[3,2-c]quinolin-1-yl]carbonyl}cyclohexyl)urea

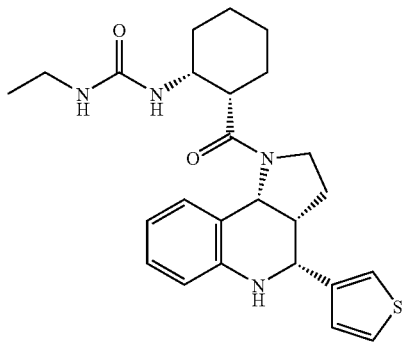

LC/MS (ESI) m/z: 453 (MH$^+$).

Example 188

N-Butyl-N'-((1R,2S)-2-{[(3aR,4R,9bR)-4-(3-thienyl)-2,3,3a,4,5,9b-hexahydro-1H-pyrrolo[3,2-c]quinolin-1-yl]carbonyl}cyclohexyl)urea

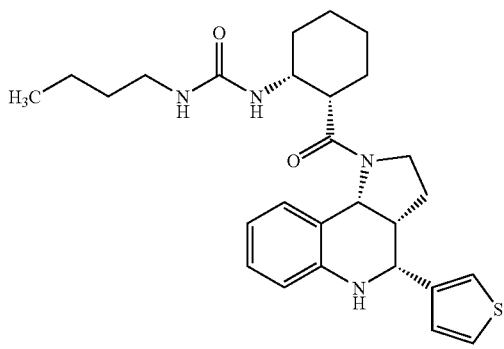

LC/MS (ESI) m/z: 481 (MH$^+$).

Example 189

N-((1R,2S)-2-{[(3aR,4R,9bR)-4-(3-Thienyl)-2,3,3a,4,5,9b-hexahydro-1H-pyrrolo[3,2-c]quinolin-1-yl]carbonyl}cyclohexyl)-1H-1,2,3-benzotriazole-5-carboxamide

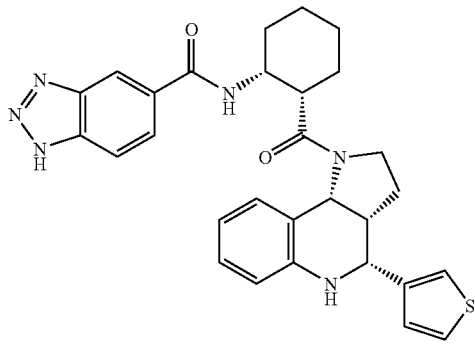

LC/MS (ESI) m/z: 527 (MH$^+$).

Example 190

N-((1R,2S)-2-{[(3aR,4R,9bR)-4-(3-Thienyl)-2,3,3a,4,5,9b-hexahydro-1H-pyrrolo[3,2-c]quinolin-1-yl]carbonyl}cyclohexyl)terephthalamide

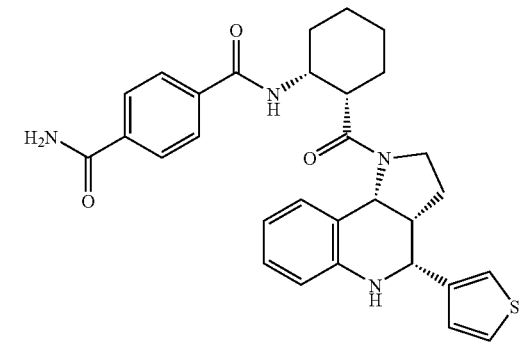

LC/MS (ESI) m/z: 529 (MH$^+$)

Example 191

2-Methyl-N$^4$-((1R,2S)-2-{[(3aR,4R,9bR)-4-(3-thienyl)-2,3,3a,4,5,9b-hexahydro-1H-pyrrolo[3,2-c]quinolin-1-yl]carbonyl}cyclohexyl)terephthalamide

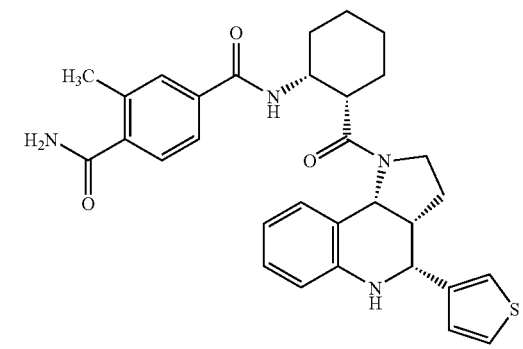

LC/MS (ESI) m/z: 543 (MH$^+$).

Example 192

2-Methyl-N-((1R,2S)-2-{[(3aR,4R,9bR)-4-(3-thienyl)-2,3,3a,4,5,9b-hexahydro-1H-pyrrolo[3,2-c]quinolin-1-yl]carbonyl}cyclohexyl)-1H-benzimidazole-5-carboxamide

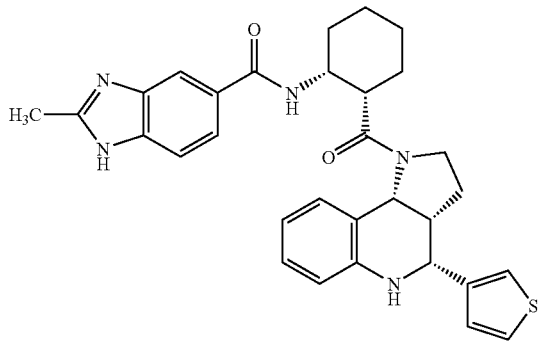

LC/MS (ESI) m/z: 540 (MH$^+$).

Example 193

N-((1R,2S)-2-{[(3aR,4R,9bR)-3a-Methyl-4-(3-thienyl)-2,3,3a,4,5,9b-hexahydro-1H-pyrrolo[3,2-c]quinolin-1-yl]carbonyl}cyclohexyl)benzamide

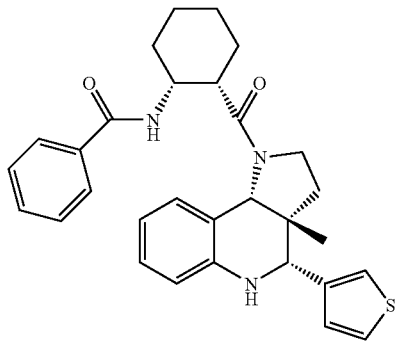

LC/MS (ESI) m/z: 500 (MH⁺).

Example 194

4-Methoxy-N-((1R,2S)-2-{[(3aR,4S,9bR)-4-propyl-2,3,3a,4,5,9b-hexahydro-1H-pyrrolo[3,2-c]quinolin-1-yl]carbonyl}cyclohexyl)benzamide

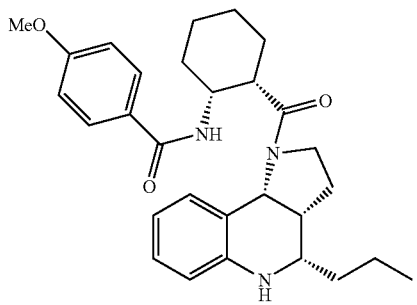

LC/MS (ESI) m/z: 476 (MH⁺).

Example 195

N-Phenyl-N'-((1R,2S)-2-{[(3aR,4S,9bR)-4-propyl-2,3,3a,4,5,9b-hexahydro-1H-pyrrolo[3,2-c]quinolin-1-yl]carbonyl}cyclohexyl)urea

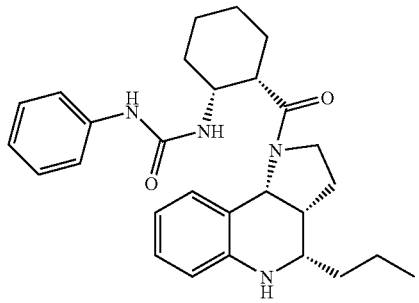

LC/MS (ESI) m/z: 461 (MH⁺).

Example 196

N-(4-Methoxyphenyl)-N'-((1R,2S)-2-{[(3aR,4S,9bR)-4-propyl-2,3,3a,4,5,9b-hexahydro-1H-pyrrolo[3,2-c]quinolin-1-yl]carbonyl}cyclohexyl)urea

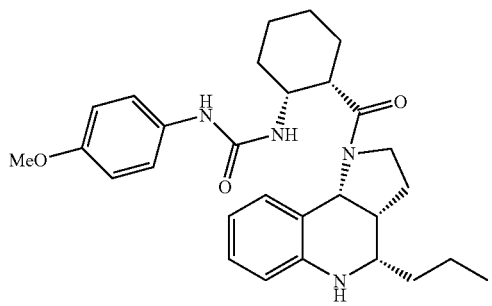

LC/MS (ESI) m/z: 491 (MH⁺).

Example 197

N-(4-Fluorophenyl)-N'-((1R,2S)-2-{[(3aR,4S,9bR)-4-propyl-2,3,3a,4,5,9b-hexahydro-1H-pyrrolo[3,2-c]quinolin-1-yl]carbonyl}cyclohexyl)urea

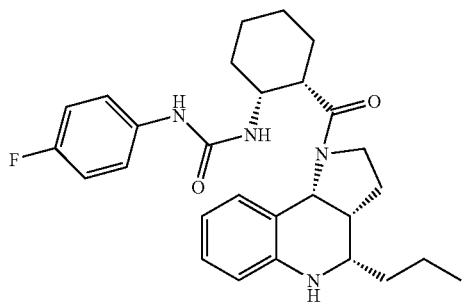

LC/MS (ESI) m/z: 479 (MH⁺).

Example 198

N-Ethyl-N'-((1R,2S)-2-{[(3aR,4S,9bR)-4-propyl-2,3,3a,4,5,9b-hexahydro-1H-pyrrolo[3,2-c]quinolin-1-yl]carbonyl}cyclohexyl)urea

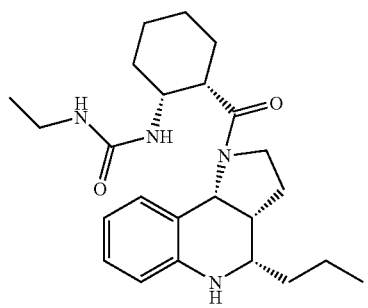

LC/MS (ESI) m/z: 413 (MH⁺)

Example 199

N-Butyl-N'-((1R,2S)-2-{[(3aR,4S,9bR)-4-propyl-2,3,3a,4,5,9b-hexahydro-1H-pyrrolo[3,2-c]quinolin-1-yl]carbonyl}cyclohexyl)urea

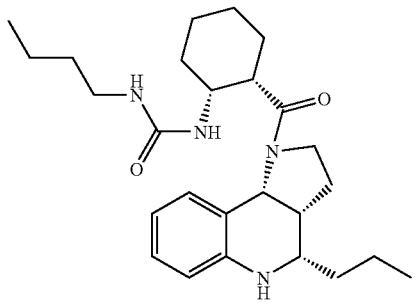

LC/MS (ESI) m/z: 441 (MH+).

Example 200

N-1,3-Benzodioxol-5-yl-N'-((1R,2S)-2-{[(3aR,4S,9bR)-4-propyl-2,3,3a,4,5,9b-hexahydro-1H-pyrrolo[3,2-c]quinolin-1-yl]carbonyl}cyclohexyl)urea

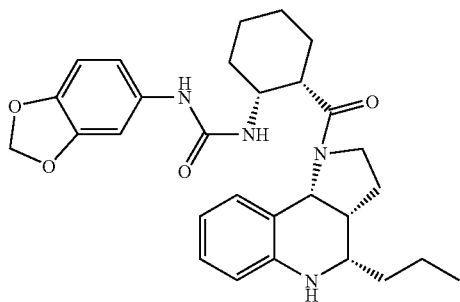

LC/MS (ESI) m/z: 505 (MH+).

Example 201

2-Methyl-N-((1R,2S)-2-{[(3aR,4S,9bR)-4-propyl-2,3,3a,4,5,9b-hexahydro-1H-pyrrolo[3,2-c]quinolin-1-yl]carbonyl}cyclohexyl)-1H-benzimidazole-5-carboxamide

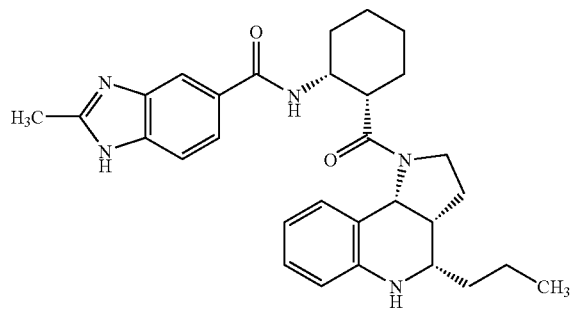

To a suspension of (1R,2S)-2-{[(3aR,4R,9bR)-4-(propyl)-2,3,3a,4,5,9b-hexahydro-1H-pyrrolo[3,2-c]quinolin-1-yl]carbonyl}cyclohexaneamine hydrochloride (203 mg, 0.490 mmol) in DMF (4 ml) were added 2-methyl-1H-benzimidazole-5-carboxylic acid (86.2 mg, 0.490 mmol), triethylamine (0.206 ml, 1.47 mmol) and DEPC (0.0812 ml, 0.490 mmol) under ice-cooling, and the mixture was stirred at room temperature for 15 hrs. Water was added to the reaction solution, and the mixture was extracted with ethyl acetate. The organic layer was washed with saturated brine and dried over anhydrous MgSO$_4$, and concentrated under reduced pressure. The obtained residue was subjected to column chromatography using silica gel and eluted with ethyl acetate-methanol (1:0-9:1) to give the title compound (115 mg, 47%) as an amorphous form.

$^1$H-NMR (CDCl$_3$) δ: 0.94 (3H, t, J=6.6 Hz), 1.20-2.11 (14H, m), 2.25-2.37 (1H, m), 2.47-2.66 (1H, m), 2.62 (3H, s), 2.95-3.04 (1H, m), 3.38-3.67 (3H, m), 4.31-3.42 (1H, m), 5.57 (1H, d, J=6.9 Hz), 6.47 (1H, dd, J=8.1, 0.9 Hz), 6.63-6.70 (1H, m), 6.98-7.04 (1H, m), 7.40-7.72 (3H, m), 8.06 (1H, br s).

LC/MS (ESI) m/z: 500 (MH+).

Example 202

4-Cyano-N-((1R,2S)-2-{[(3aR,4S,9bR)-4-propyl-2,3,3a,4,5,9b-hexahydro-1H-pyrrolo[3,2-c]quinolin-1-yl]carbonyl}cyclohexyl)benzamide

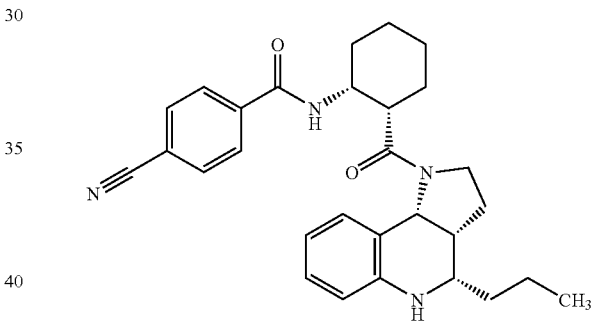

LC/MS (ESI) m/z: 471 (MH+).

Example 203

N-((1R)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)benzamide

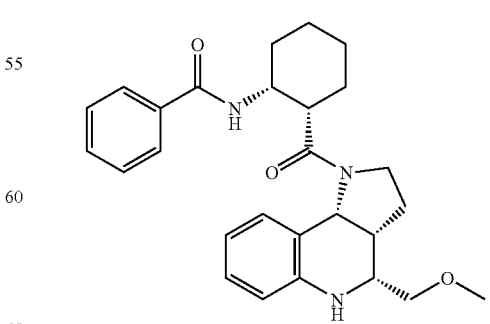

LC/MS (ESI) m/z: 448 (MH+).

Example 204

N-((1R,2S)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)-N'-phenylurea

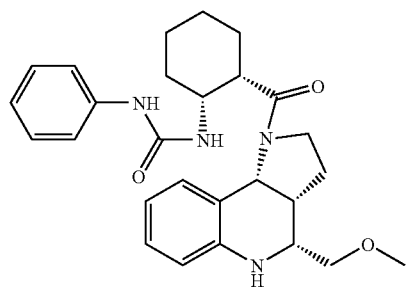

LC/MS (ESI) m/z: 463 (MH+).

Example 205

N-(4-Fluorophenyl)-N'-((1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexyl)urea

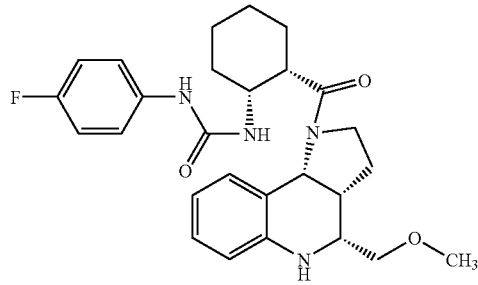

LC/MS (ESI) m/z: 481 (MH+).

Example 206

N-((1R,2S)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)-N'-(4-methoxyphenyl)urea

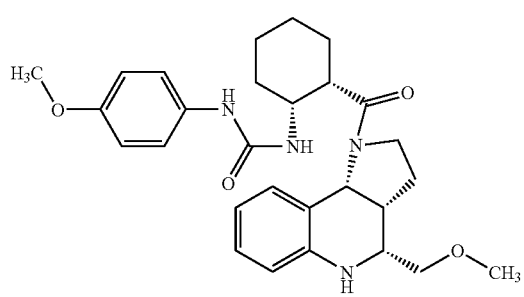

LC/MS (ESI) m/z: 493 (MH+).

Example 207

N-Ethyl-N'-((1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexyl)urea

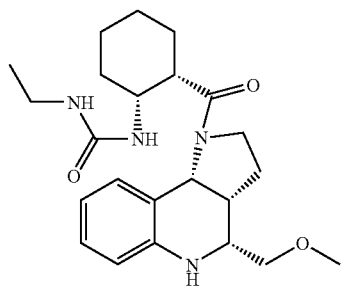

LC/MS (ESI) m/z: 415 (MH+)

Example 208

N-1,3-Benzodioxol-5-yl-N'-((1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexyl)urea

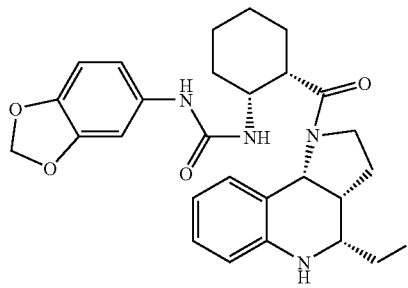

LC/MS (ESI) m/z: 507 (MH+)

Example 209

(2E)-N-((1R,2S)-2-{[(3aR,4R,9bR)-4-(Methoxymethyl)-2,3,3a,4,5,9b-hexahydro-1H-pyrrolo[3,2-c]quinolin-1-yl}carbonyl)cyclohexyl)-3-[4-(trifluoromethyl)phenyl]acrylamide

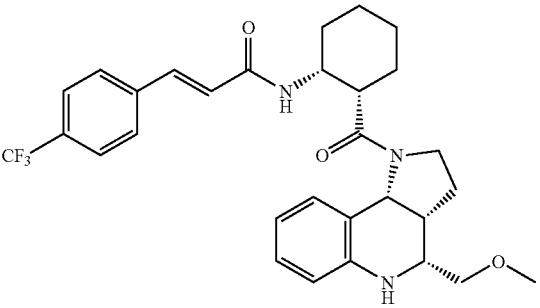

LC/MS (ESI) m/z: 542 (MH+).

Example 210

N-((1R,2S)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)-4-(trifluoromethyl)benzamide

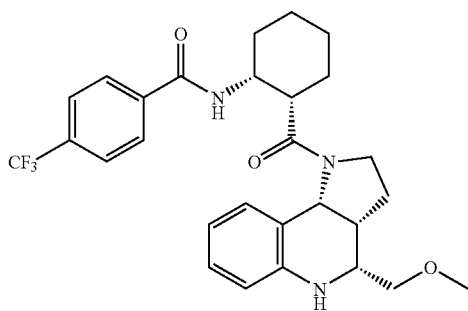

LC/MS (ESI) m/z: 516 (MH$^+$).

Example 211

N-((1R,2S)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)-6-methylnicotinamide

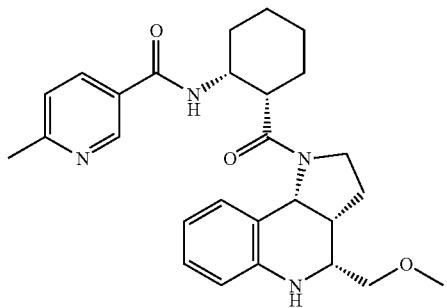

LC/MS (ESI) m/z: 463 (MH$^+$).

Example 212

3,4-Difluoro-N-((1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexyl)benzamide

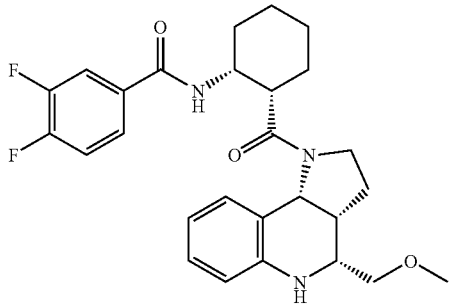

LC/MS (ESI) m/z: 463 (MH$^+$).

Example 213

4-(Dimethylamino)-N-((1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexyl)benzamide

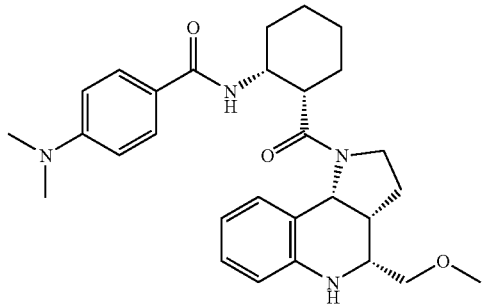

LC/MS (ESI) m/z: 491 (MH$^+$)

Example 214

N-((1R,2S)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)terephthalamide

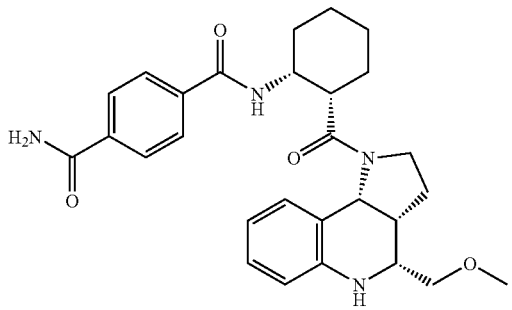

LC/MS (ESI) m/z: 491 (MH$^+$).

Example 215

N-((1R,2S)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)-4-(trifluoromethoxy)benzamide

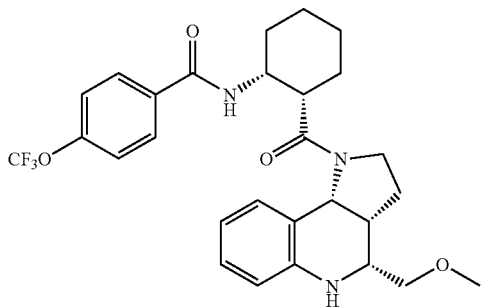

LC/MS (ESI) m/z: 532 (MH$^+$).

Example 216

4-Cyano-N-((1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexyl)benzamide

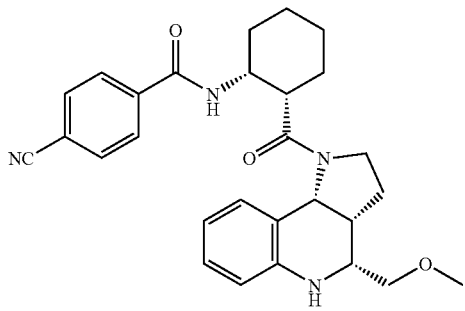

LC/MS (ESI) m/z: 473 (MH⁺).

Example 217

N-(Cyanophenyl)-N'-((1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexyl)urea

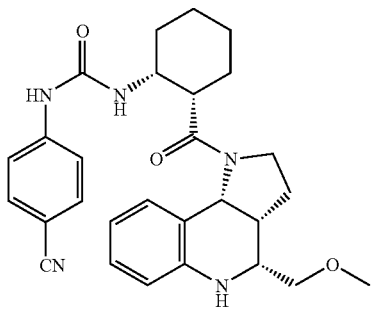

LC/MS (ESI) m/z: 488 (MH⁺).

Example 218

N-((1R,2S)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)-1H-indole-5-carboxamide

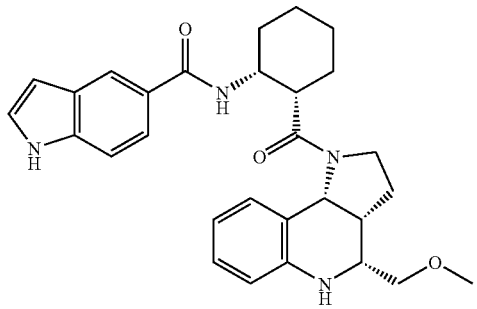

LC/MS (ESI) m/z: 487 (MH⁺).

Example 219

N-((1R,2S)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)-1H-1,2,3-benzotriazole-5-carboxamide

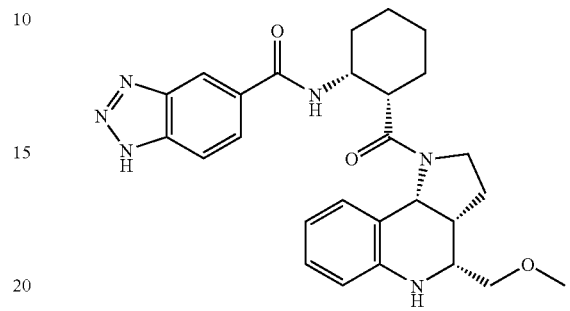

To a solution (5 ml) of (1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexaneamine hydrochloride (200 mg, 0.480 mmol) in THF were added triethylamine (0.199 ml, 1.44 mmol), 1H-1,2,3-benzotriazole-5-carboxylic acid (78.3 mg, 0.480 mmol) and DEPC (0.079 ml, 0.528 mmol) under ice-cooling, and the mixture was stirred at room temperature for 1 hr. Water was added to the reaction solution, and the mixture was extracted with ethyl acetate. The organic layer was dried over anhydrous MgSO₄, and concentrated under reduced pressure. The obtained residue was subjected to column chromatography using silica gel and eluted with hexane:ethyl acetate (1:1-1:9) to give the title compound (187 mg, 80%) as an amorphous form.

¹H-NMR (CDCl₃) δ: 0.86-0.88 (1H, m), 1.26 (1H, m), 1.43-1.96 (10H, m), 2.08-2.21 (2H, m), 2.41 (1H, m), 2.95 (1H, m), 3.37-3.48 (3H, m), 3.58-3.76 (3H, m), 4.57 (1H, m), 5.66 (1H, d, J=6.9 Hz), 6.53 (1H, d, J=7.3 Hz), 6.69 (1H, dd, J=7.6, 7.7 Hz), 7.03 (1H, dd, J=7.3, 7.6 Hz), 7.31-7.34 (1H, m), 7.48 (1H, d, J=7.2 Hz), 7.66 (1H, d, J=7.7 Hz), 8.17 (1H, s).

LC/MS (ESI) m/z: 489 (MH⁺).

Example 220

N-((1R,2S)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)ethanediamide

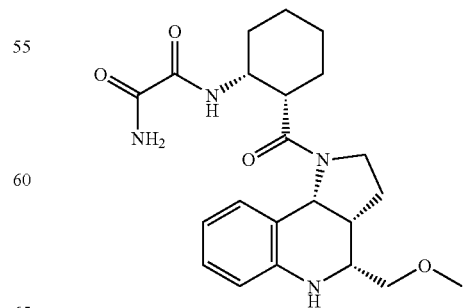

LC/MS (ESI) m/z: 415 (MH⁺).

Example 221

3-Hydroxy-N-((1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexyl)propanamide

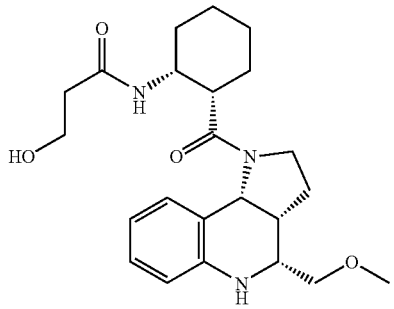

LC/MS (ESI) m/z: 416 (MH+)

Example 222

2-ethoxy-N-((1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexyl)acetamide

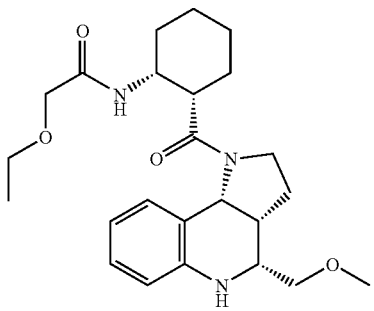

LC/MS (ESI) m/z: 430 (MH+).

Example 223

N²Acetyl-N¹-((1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexyl)glycinamide

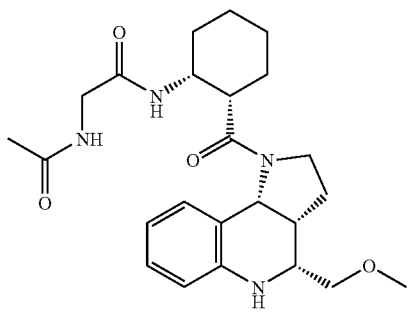

LC/MS (ESI) m/z: 443 (MH+).

Example 224

N²-(Aminocarbonyl)-N¹-((1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexyl)glycinamide

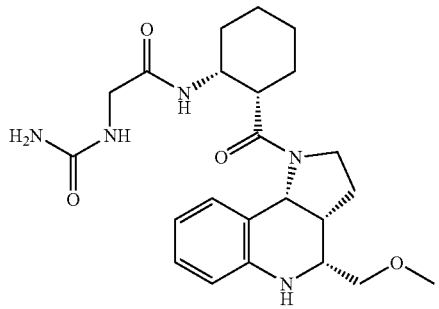

LC/MS (ESI) m/z: 444 (MH+).

Example 225

3-Hydroxy-2,2-dimethyl-N-((1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexyl)propanamide

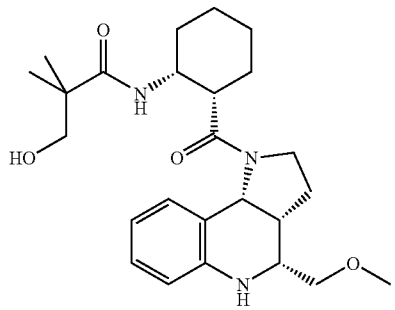

LC/MS (ESI) m/z: 444 (MH+).

Example 226

(2E)-3-(1H-Imidazol-4-yl)-N-((1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexyl)acrylamide

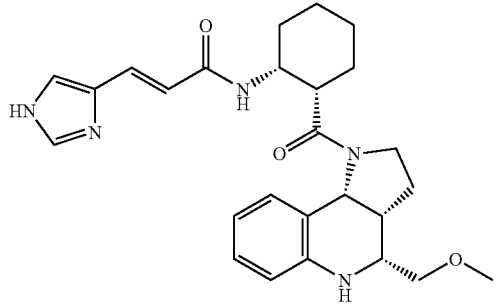

LC/MS (ESI) m/z: 464 (MH+).

Example 227

N-((1R,2S)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)-2-(1H-tetrazol-1-yl)acetamide

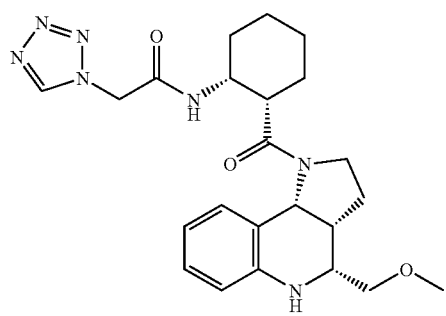

LC/MS (ESI) m/z: 454 (MH+).

Example 228

N-((1R,2S)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)-4-oxo-4H-pyrane-2-carboxamide

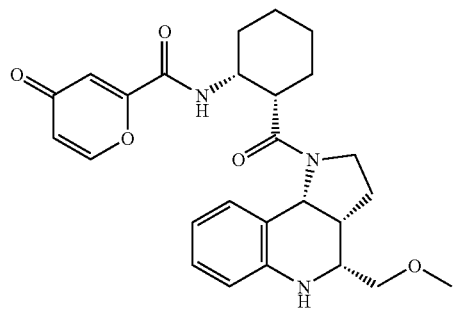

LC/MS (ESI) m/z: 466 (MH+).

Example 229

N-((1R,2S)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)-4H-indole-2-carboxamide

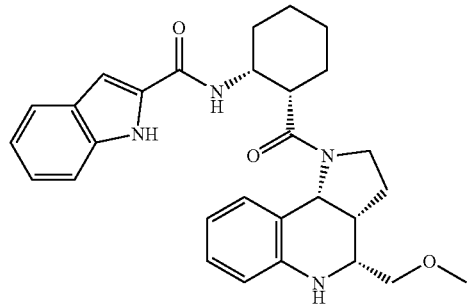

LC/MS (ESI) m/z: 487 (MH+).

Example 230

4-(Acetylamino)-N-((1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexyl)benzamide

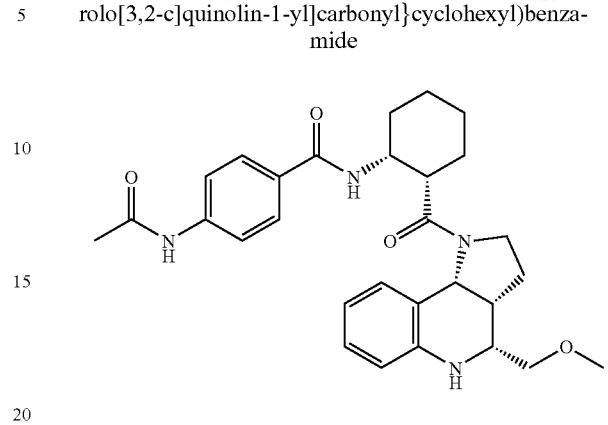

LC/MS (ESI) m/z: 505 (MH+).

Example 231

N-{2-[((1R,2S)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)amino]-2-oxoethyl}-2-furamide

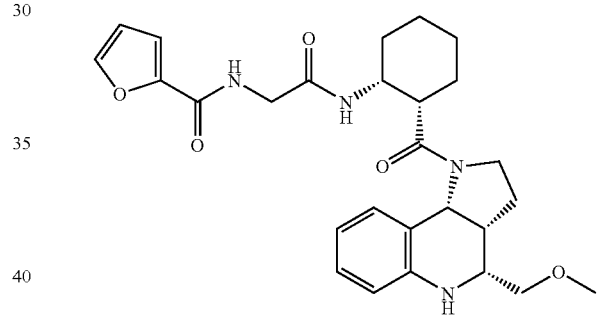

LC/MS (ESI) m/z: 495 (MH+).

Example 232

2-Cyano-N-((1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexyl)benzamide

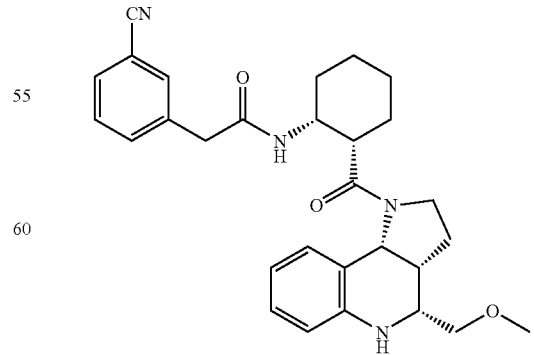

LC/MS (ESI) m/z: 473 (MH+).

Example 233

3-Cyano-N-((1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexyl)benzamide

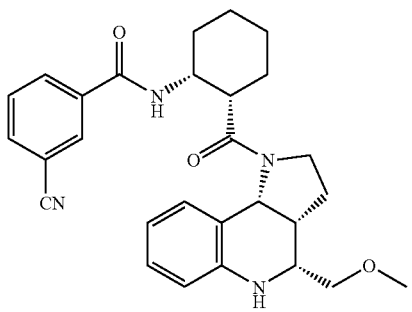

LC/MS (ESI) m/z: 473 (MH⁺).

Example 234

4-(Difluoromethoxy)-N-((1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexyl)benzamide

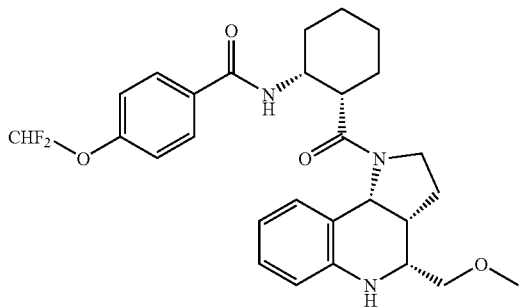

LC/MS (ESI) m/z: 514 (MH⁺).

Example 235

N-((1R,2S)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)-2,6-dioxo-1,2,3,6-tetrahydropyrimidine-4-carboxamide

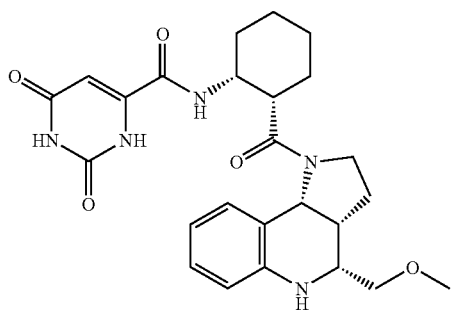

LC/MS (ESI) m/z: 481 (M).

Example 236

3-Amino-N-((1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexyl)-1H-1,2,4-triazole-5-carboxamide

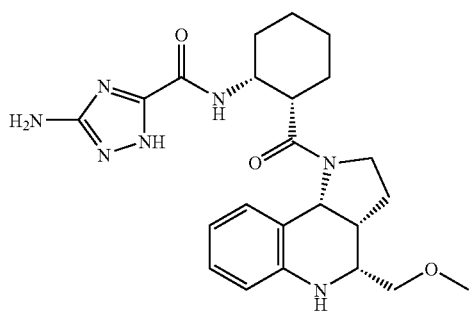

LC/MS (ESI) m/z: 454 (MH⁺).

Example 237

N-((1R,2S)-2-{[(3aR,4R,9bR)-4-(Methoxymethyl)-2,3,3a, 4,5,9b-hexahydro-1H-pyrrolo[3,2-c]quinolin-1-yl]carbonyl}cyclohexyl)-1H-benzimidazole-2-carboxamide

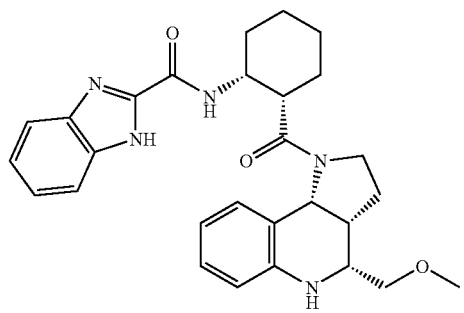

LC/MS (ESI) m/z: 488 (MH⁺).

Example 238

N¹-((1R,2S)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)-N²-phenylglycinamide

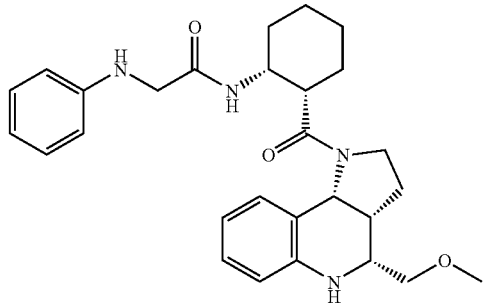

LC/MS (ESI) m/z: 477 (MH⁺).

Example 239

N-((1R,2S)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)-4-(methylamino)benzamide

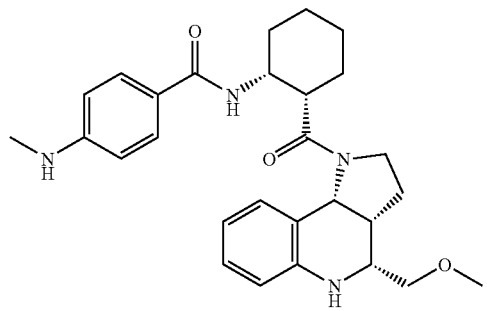

LC/MS (ESI) m/z: 477 (MH$^+$).

Example 240

2-(Dimethylamino)-N-((1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexyl)benzamide

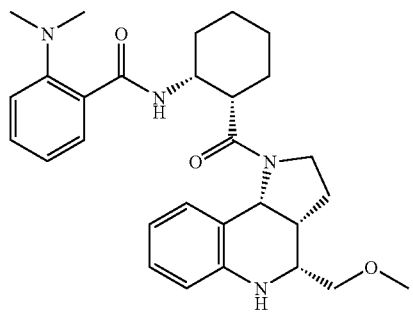

LC/MS (ESI) m/z: 491 (MH$^+$).

Example 241

3-(Dimethylamino)-N-((1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexyl)benzamide

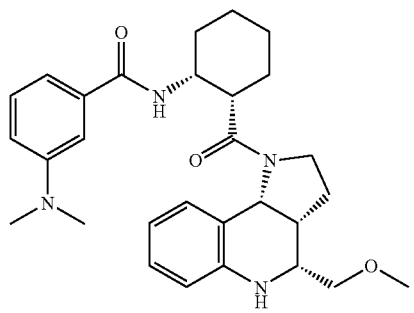

LC/MS (ESI) m/z: 491 (MH$^+$).

Example 242

N-((1R,2S)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)-1H-pyrazole-4-carboxamide

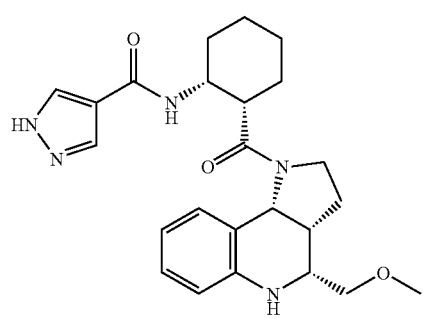

LC/MS (ESI) m/z: 438 (MH$^+$).

Example 243

4-(Acetylamino)-N-((1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexyl)butanamide

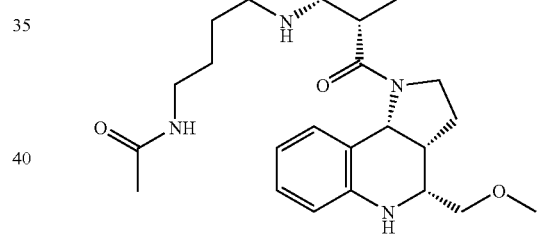

LC/MS (ESI) m/z: 471 (MH$^+$).

Example 244

N-((1R,2S)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)-1H-indole-3-carboxamide

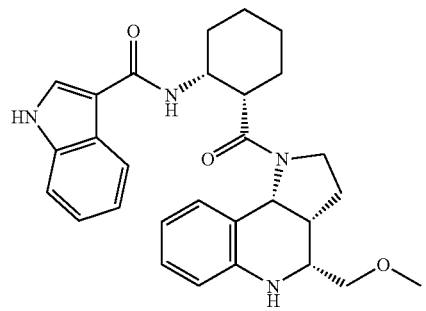

LC/MS (ESI) m/z: 487 (MH$^+$)

Example 245

4-(Aminosulfonyl)-N-((1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexyl)benzamide

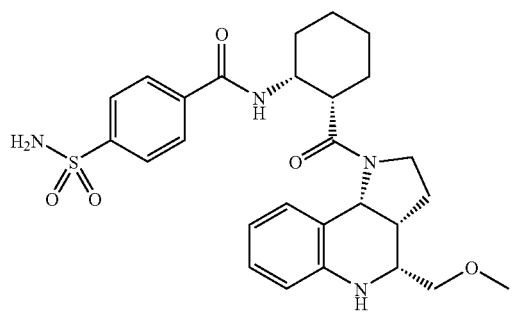

LC/MS (ESI) m/z: 527 (MH$^+$).

Example 246

N-((1R,2S)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)quinoxaline-6-carboxamide

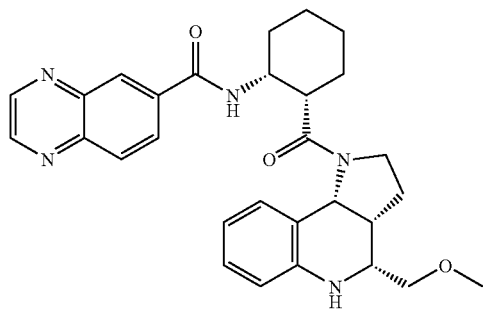

LC/MS (ESI) m/z: 500 (MH$^+$).

Example 247

N-((1R,2S)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)quinoline-2-carboxamide

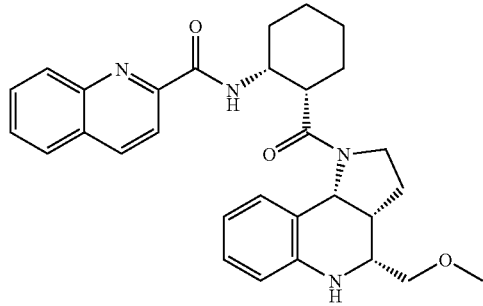

LC/MS (ESI) m/z: 499 (MH$^+$).

Example 248

N-((1R,2S)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)-2,3-dihydro-1-benzofuran-5-carboxamide

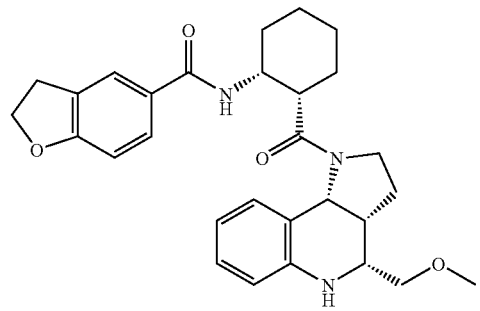

LC/MS (ESI) m/z: 490 (MH$^+$).

Example 249

N-((1R,2S)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)-2,1-benzisoxazole-3-carboxamide

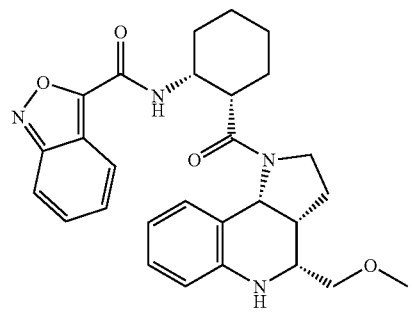

LC/MS (ESI) m/z: 489 (MH$^+$).

Example 250

4-(1H-Imidazol-1-yl)-N-((1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexyl)benzamide

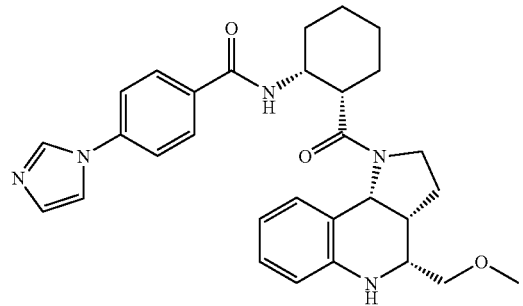

LC/MS (ESI) m/z: 514 (MH$^+$).

Example 251

N-((1R,2S)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)-2-methylimidazo[1,2-a]pyridine-3-carboxamide

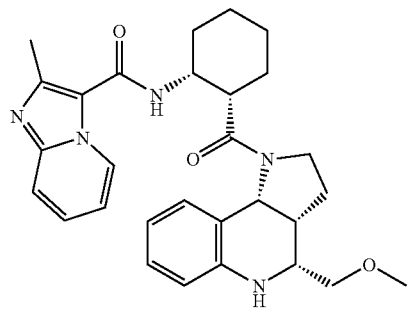

LC/MS (ESI) m/z: 502 (MH$^+$).

Example 252

N-((1R,2S)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)-4-(3-methyl-5-oxo-4,5-dihydro-1H-pyrazol-1-yl)benzamide

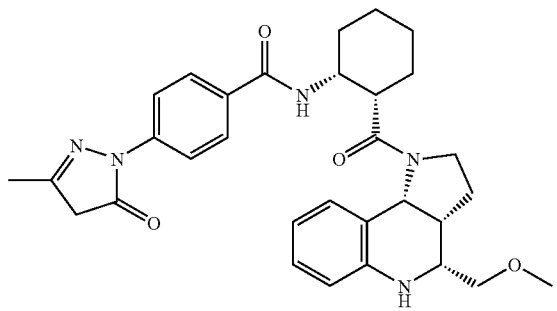

LC/MS (ESI) m/z: 544 (MH$^+$).

Example 253

N-((1R,2S)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)-1,3-benzothiazole-6-carboxamide

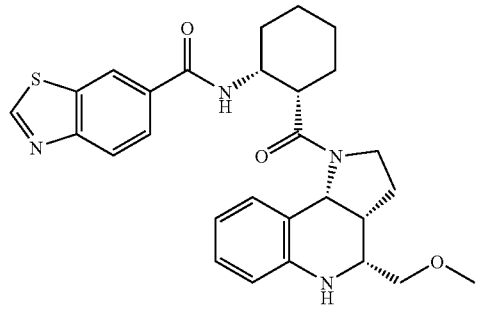

LC/MS (ESI) m/z: 505 (MH$^+$).

Example 254

N-((1R,2S)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)-6-piperidin-1-ylnicotinamide

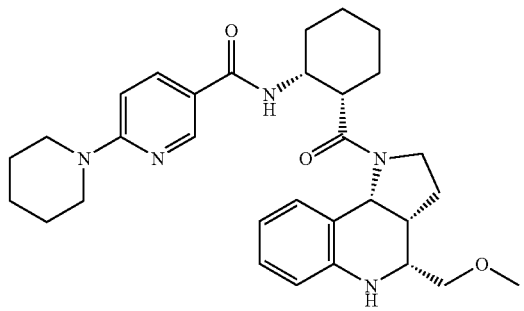

LC/MS (ESI) m/z: 532 (MH$^+$).

Example 255

4-Cyano-2-fluoro-N-((1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexyl)benzamide

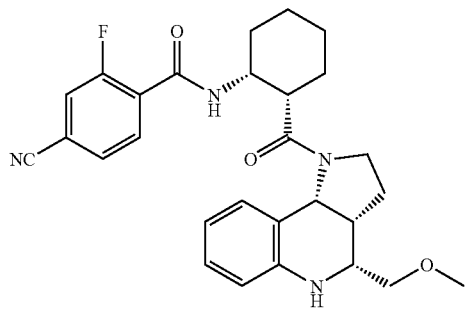

LC/MS (ESI) m/z: 490 (MH$^+$).

Example 256

4-Cyano-N-((1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexyl)-3-methylbenzamide

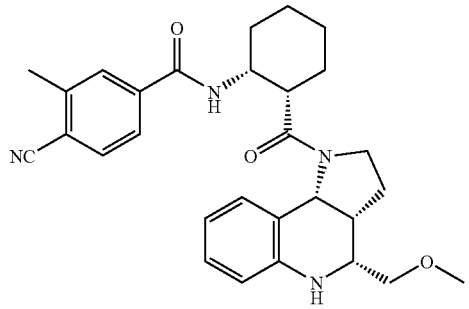

LC/MS (ESI) m/z: 487 (MH$^+$).

Example 257

4-Cyano-3-fluoro-N-((1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexyl)benzamide

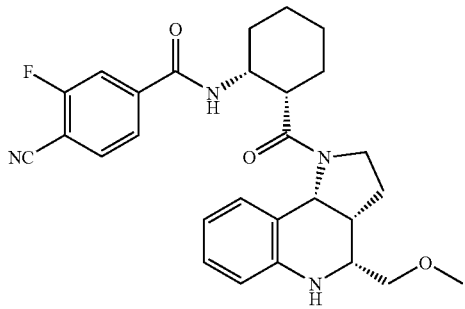

LC/MS (ESI) m/z: 491 (MH+)

Example 258

N-((1R,2S)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)-4-(1H-pyrrol-1-yl)benzamide

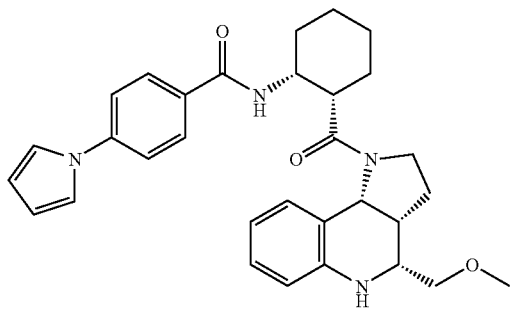

LC/MS (ESI) m/z: 513 (MH+).

Example 259

N-((1R,2S)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)-1H-benzimidazole-5-carboxamide

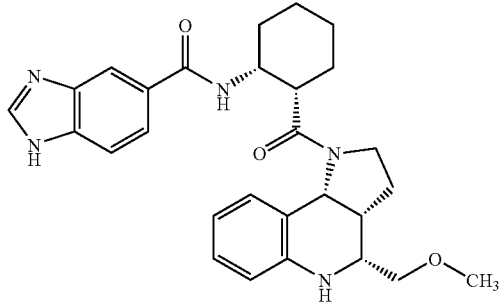

LC/MS (ESI) m/z: 488 (MH+).

Example 260

N-1H-1,2,3-Benzotriazol-6-yl-N'-((1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexyl)urea

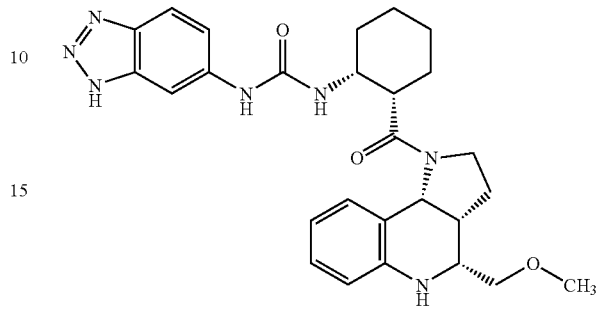

LC/MS (ESI) m/z: 504 (MH+).

Example 261

N-((1R,2S)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)-4-(2-methyl-1,3-thiazol-4-yl)benzamide

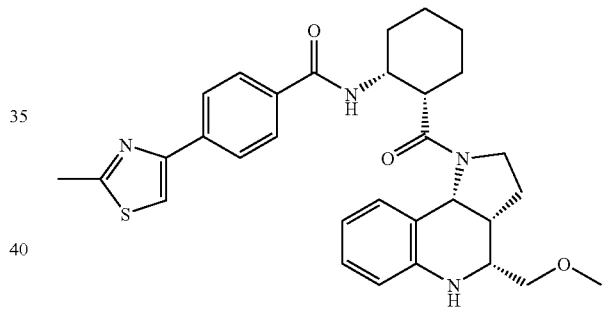

LC/MS (ESI) m/z: 545 (MH+)

Example 262

4-(Aminomethyl)-N-((1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexyl)benzamide dihydrochloride

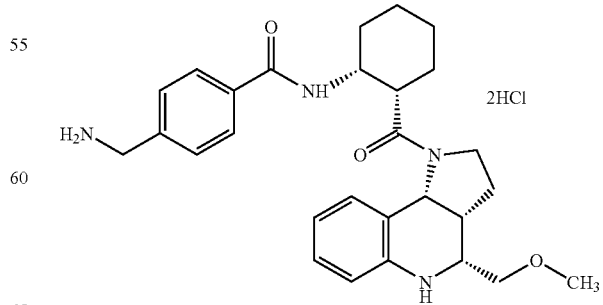

LC/MS (ESI) m/z: 477 (MH+).

Example 263

4-[(Acetylamino)methyl]-N-((1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexyl)benzamide

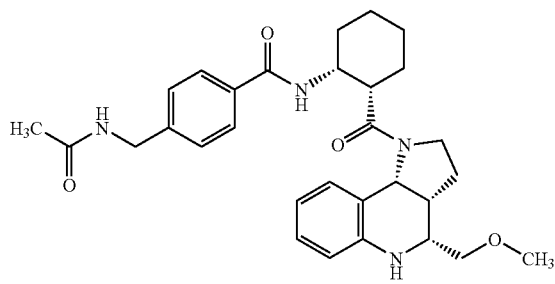

LC/MS (ESI) m/z: 519 (MH+).

Example 264

N-((1R,2S)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)-4-(1H-pyrazol-1-yl)benzamide

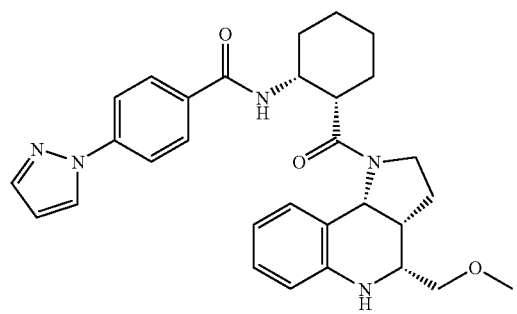

LC/MS (ESI) m/z: 514 (MH+).

Example 265

N-((1R,2S)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)-4-(1H-1,2,4-triazol-1-yl)benzamide

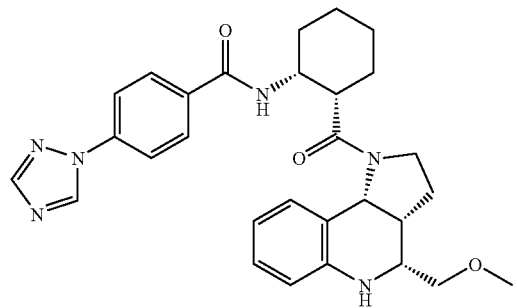

LC/MS (ESI) m/z: 515 (MH+).

Example 266

4-[(2-Hydroxyethyl)amino]-N-((1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexyl)benzamide

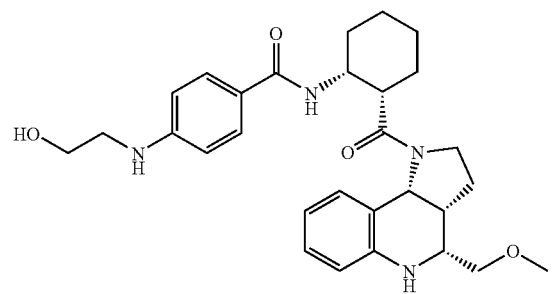

LC/MS (ESI) m/z: 507 (MH+).

Example 267

N-((1R,2S)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)-4-(4-methylpiperazin-1-yl)benzamide

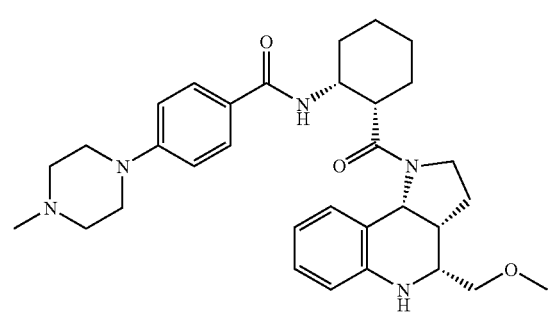

LC/MS (ESI) m/z: 546 (MH+).

Example 268

N-((1R,2S)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)-4-morpholin-4-benzamide

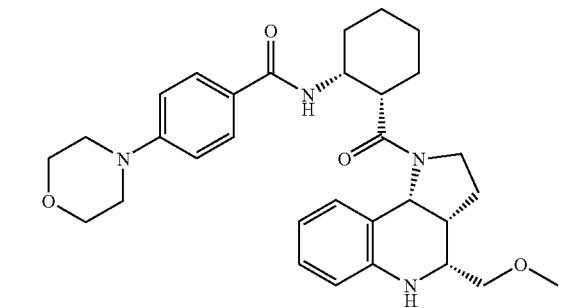

LC/MS (ESI) m/z: 533 (MH+).

Example 269

N-((1R,2S)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)-4-methyl-3,4-dihydro-2H-1,4-benzoxazin-7-carboxamide

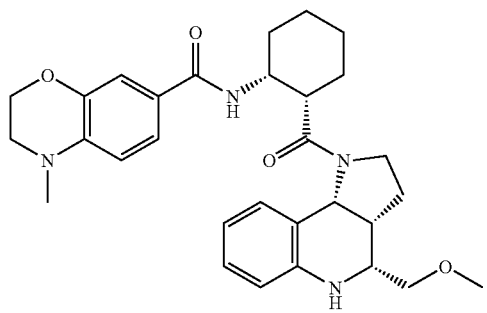

LC/MS (ESI) m/z: 519 (MH+)

Example 270

4-[(2-Hydroxyethyl)(methyl)amino]-N-((1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexyl)benzamide

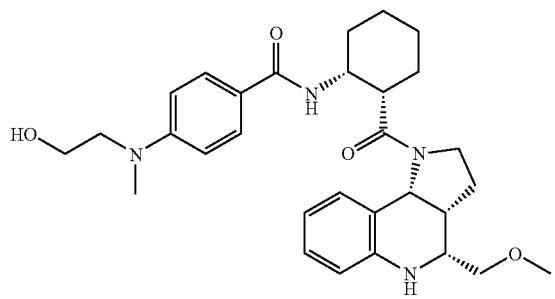

LC/MS (ESI) m/z: 521 (MH+).

Example 271

N-((1R,2S)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)-4-(2-methyl-1H-imidazol-1-yl)benzamide

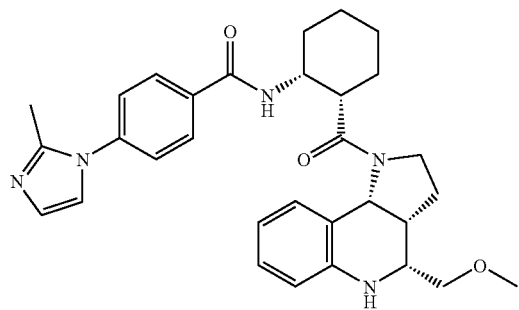

LC/MS (ESI) m/z: 528 (MH+).

Example 272

N-((1R,2S)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)-4-(4-methyl-1H-imidazol-1-yl)benzamide

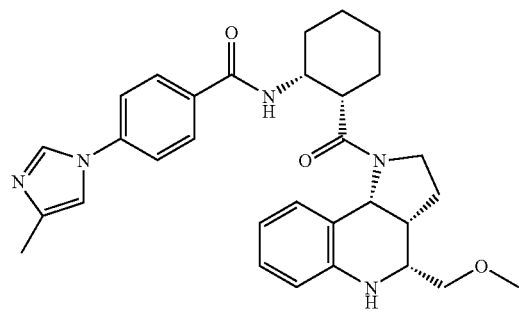

LC/MS (ESI) m/z: 528 (MH+).

Example 273

4-[(2-Methoxyethyl)(methyl)amino]-N-((1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexyl)benzamide

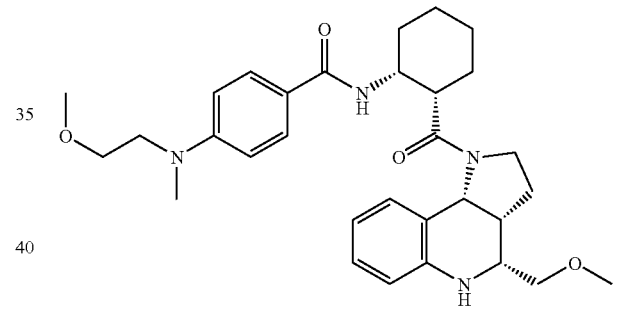

LC/MS (ESI) m/z: 535 (MH+).

Example 274

4-Cyano-3-methoxy-N-((1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexyl)benzamide

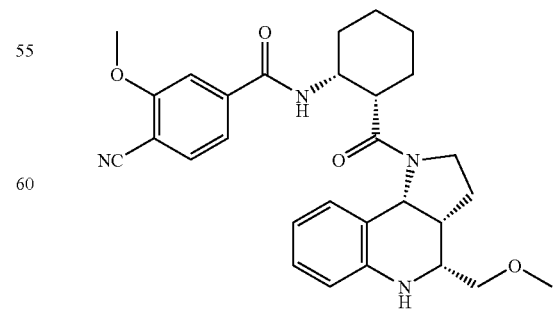

LC/MS (ESI) m/z: 503 (MH+).

Example 275

3-Cyano-4-methoxy-N-((1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexyl)benzamide

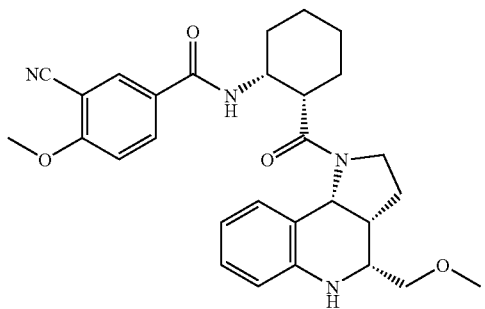

LC/MS (ESI) m/z: 503 (MH+).

Example 276

N-((1R,2S)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)-1,2-dimethyl-1H-benzimidazole-5-carboxamide

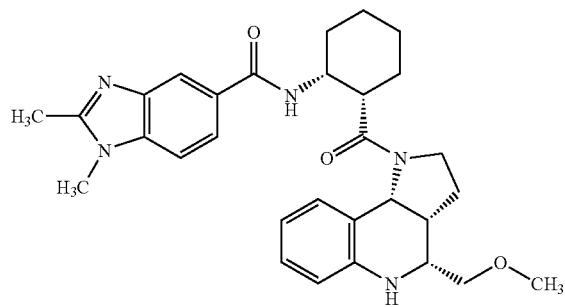

LC/MS (ESI) m/z: 516 (MH+).

Example 277

N-[4-(1H-Imidazol-1-yl)phenyl]-N'-((1R,2S)-2{[(3aR,4R,9bR)-4-(methoxymethyl)-2,3,3a,4,5,9b-hexahydro-1H-pyrrolo[3,2-c]quinolin-1-yl]carbonyl}cyclohexyl)urea

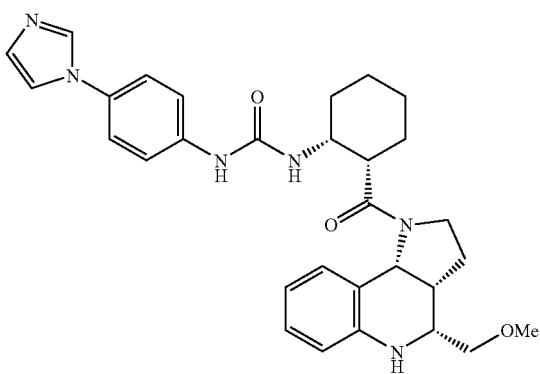

LC/MS (ESI) m/z: 529 (MH+).

Example 278

N-((1R,2S)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)-4-(methylsulfonyl)benzamide

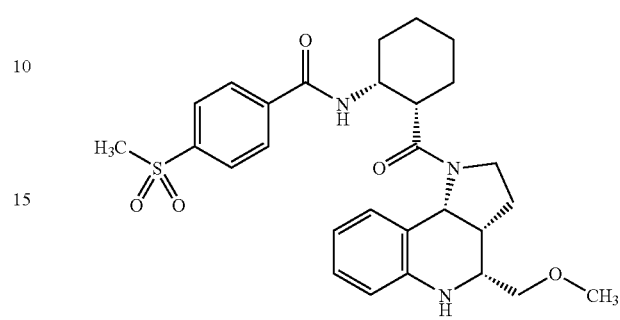

LC/MS (ESI) m/z: 526 (MH+).

Example 279

N-((1R,2S)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)-2-methyl-1H-benzimidazole-5-carboxamide

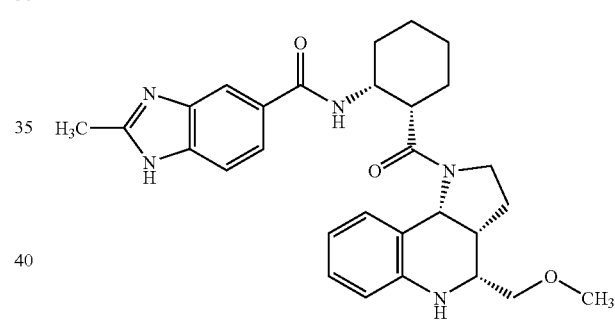

LC/MS (ESI) m/z: 502 (MH+).

Example 280

N-((1R,2S)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)-2-phenyl-1H-imidazole-4-carboxamide

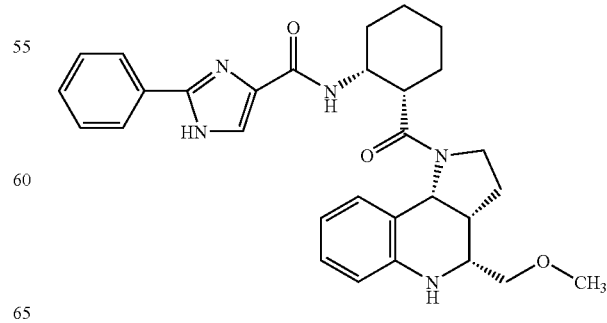

LC/MS (ESI) m/z: 514 (MH+).

Example 281

4-(1H-Imidazol-2-yl)-N-((1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexyl)benzamide

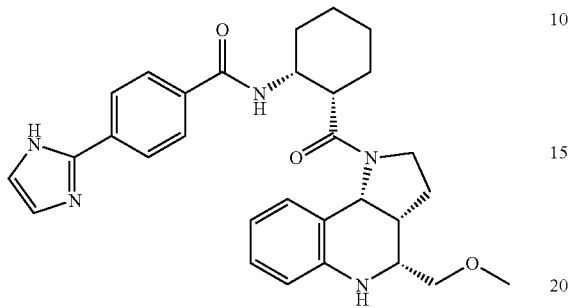

To a solution of (1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexaneamine hydrochloride (200 mg, 0.480 mmol) in tetrahydrofuran (5 ml) were added triethylamine (0.199 ml, 1.44 mmol), 4-(1H-imidazol-2-yl)benzoic acid (99.0 mg, 0.529 mmol) and DEPC (0.079 ml, 0.529 mmol) under ice-cooling, and the mixture was stirred at room temperature for 1 hr. Water was added to the reaction solution, and the mixture was extracted with ethyl acetate. The organic layer was dried over anhydrous MgSO$_4$ and concentrated under reduced pressure. The obtained residue was subjected to column chromatography using silica gel and eluted with ethyl acetate-methanol (1:0-4:1) to give the title compound (150 mg, 61%) as an amorphous form.

$^1$H-NMR (CDCl$_3$) δ: 1.25-2.50 (11H, m), 2.96-2.99 (1H, m), 3.34-3.42 (5H, m), 3.54-3.57 (2H, m), 3.70-3.72 (1H, m), 4.17 (1H, m), 4.30 (1H, m), 5.64 (1H, d, J=6.6 Hz), 6.52 (1H, d, J=7.5 Hz), 6.68 (1H, dd, J=7.5, 7.5 Hz), 7.02 (1H, dd, J=7.5, 7.5 Hz), 7.15-7.20 (2H, m), 7.36 (1H, d, J=7.5 Hz), 7.42 (1H, d, J=7.5 Hz), 7.83-7.93 (4H, m).

LC/MS (ESI) m/z: 514 (MH$^+$).

Example 282

N-((1R,2S)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)-2-(trifluoromethyl)-1H-benzimidazole-5-carboxamide

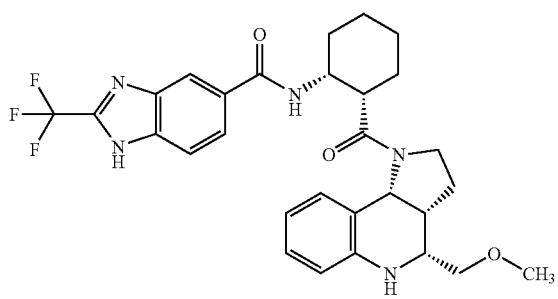

LC/MS (ESI) m/z: 556 (MH$^+$).

Example 283

N-(4-Cyano-3-methylphenyl)-N'-(1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexyl)urea

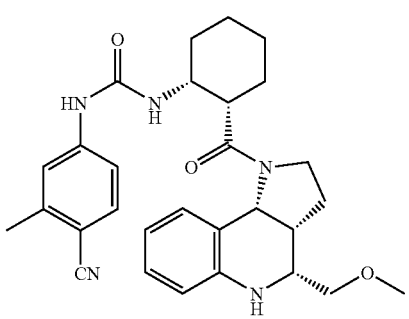

LC/MS (ESI) m/z: 502 (MH$^+$).

Example 284

N-((1R,2S)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)-N'-[4-(1H-pyrazol-1-yl)phenyl]urea

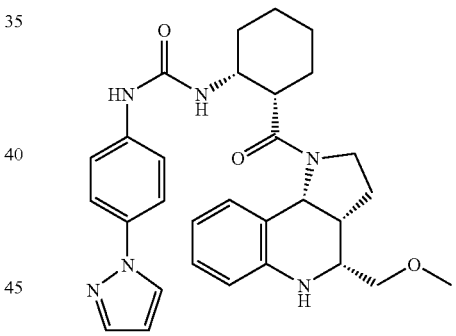

To a suspension of 4-(1H-pyrazol-1-yl)benzoic acid (271 mg, 1.44 mmol) in toluene (5 ml) were added triethylamine (0.200 ml, 1.44 mmol) and diphenylphosphorylazide (0.310 ml, 1.44 mmol) at room temperature, and the mixture was stirred at 80° C. for 2 hrs. This reaction mixture was allowed to cool to room temperature and added dropwise to a solution of (1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexaneamine dihydrochloride (200 mg, 0.480 mmol) and triethylamine (0.200 ml, 1.44 mmol) in tetrahydrofuran (5 ml). The mixture was stirred at room temperature for 3 hrs., water was added, and the mixture was extracted with ethyl acetate. The organic layer was washed with aqueous sodium hydrogen carbonate solution, dried over anhydrous MgSO$_4$, and concentrated under reduced pressure. The obtained residue was subjected to column chromatography using silica gel and eluted with hexane-ethyl acetate (5:5-0:1) to give the title compound (194 mg, 76%) as an amorphous form.

¹H-NMR (CDCl₃) δ: 0.86-2.14 (7H, m), 2.28-2.32 (2H, m), 2.93 (1H, m), 3.32-3.40 (5H, m), 3.52-3.65 (3H, m), 3.81-3.93 (2H, m), 4.11-4.19 (2H, m), 5.57 (1H, d, J=6.9 Hz), 6.07 (1H, d, J=6.0 Hz), 6.41-6.44 (1H, m), 6.50 (1H, d, J=7.8 Hz), 6.64 (1H, dd, J=7.4, 7.4 Hz), 7.01 (1H, dd, J=7.8, 7.8 Hz), 7.15-7.16 (1H, m), 7.39 (2H, d, J=8.9 Hz), 7.51 (2H, d, J=8.9 Hz), 7.70 (1H, s), 7.79 (1H, s).

LC/MS (ESI) m/z: 529 (MH⁺).

Example 285

N-(3-Cyano-4-methoxyphenyl)-N'-((1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexyl)urea

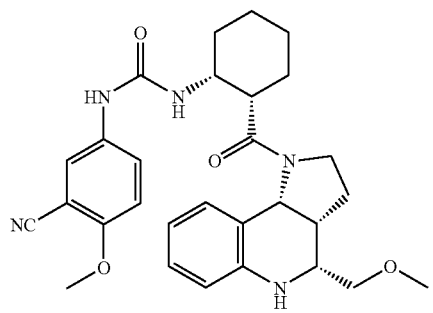

LC/MS (ESI) m/z: 518 (MH⁺).

Example 286

N-((1R,2S)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)-6-morpholin-4-ylnicotinamide

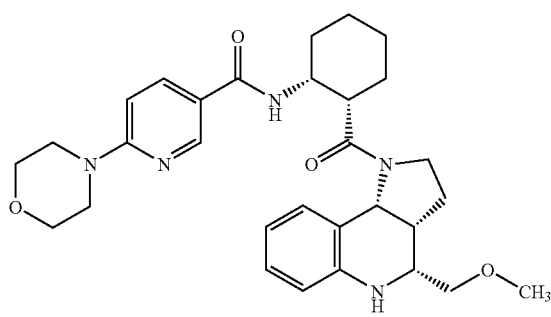

LC/MS (ESI) m/z: 534 (MH⁺).

Example 287

N-((1R,2S)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)-6-(2-methyl-1H-imidazol-1-yl)nicotinamide

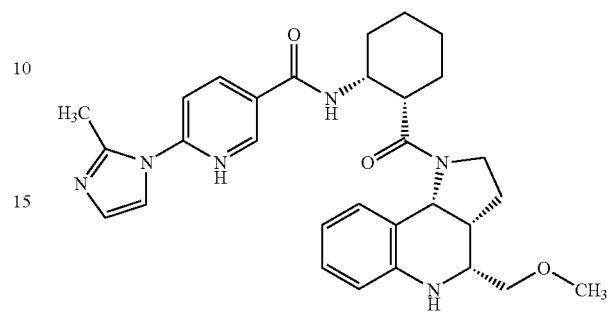

LC/MS (ESI) m/z: 529 (MH⁺).

Example 288

N-((1R,2S)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)-6-(1H-pyrazol-1-yl)nicotinamide

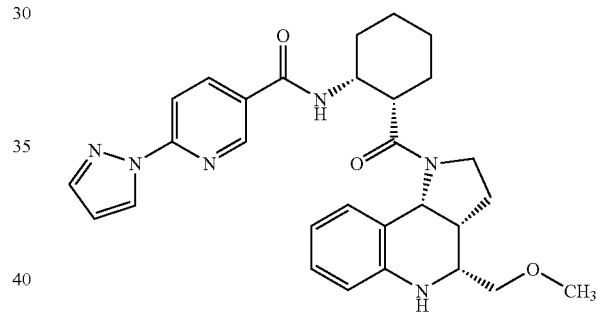

LC/MS (ESI) m/z: 515 (MH⁺).

Example 289

N-((1R,2S)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)-N'-(6-morpholin-4-ylpyridin-3-yl)urea

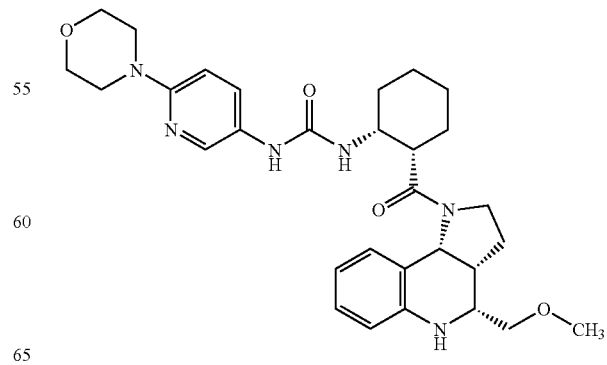

LC/MS (ESI) m/z: 549 (MH⁺).

Example 290

N-((1R,2S)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)-4-(1,3-oxazol-5-yl)benzamide

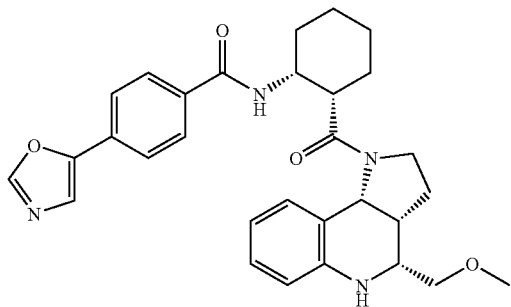

LC/MS (ESI) m/z: 515 (MH$^+$).

Example 291

N-((1R,2S)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)-4-thiomorpholin-4-ylbenzamide

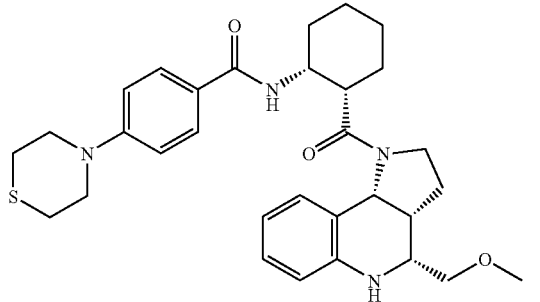

LC/MS (ESI) m/z: 549 (MH$^+$).

Example 292

N-((1R,2S)-2-{[(3aR,4R,9bR)-4-(Methoxymethyl)-2,3,3a,4,5,9b-hexahydro-1H-pyrrolo[3,2-c]quinolin-1-yl]carbonyl}cyclohexyl)-4-(1-oxidothiomorpholin-4-yl)benzamide

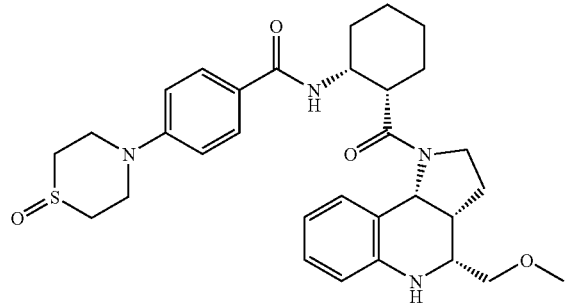

To a solution of the compound (398 mg, 0.725 mmol) of Example 291 in tetrahydrofuran (7 ml) was added an aqueous solution (7 ml) of potassium peroxymonosulfate (267 mg, 0.435 mmol) at 0° C., and the mixture was stirred at the same temperature for 1 hr. Saturated aqueous sodium thiosulfate solution was added, and the mixture was extracted with ethyl acetate. The organic layer was dried over anhydrous magnesium sulfate, and the solvent was evaporated under reduced pressure. The residue was subjected to column chromatography using silica gel and eluted with hexane-ethyl acetate (7:3-0:1) to give the title compound (191 mg, 47%) as a colorless oil.

LC/MS (ESI) m/z: 565 (MH$^+$).

The following compounds of Example 293-Example 310 were synthesized by amidation or ureation using [2-((3aR,4R,9bR)-1-{[(1S,2R)-2-aminocyclohexyl]carbonyl}-2,3,3a,4,5,9b-hexahydro-1H-pyrrolo[3,2-c]quinolin-4-yl)-1H-imidazol-1-yl]methyl pivalate and then removal of pivaloyloxymethyl group in the same manner as in Example 81.

Example 293

N-((1R,2S)-2-{[(3aR,4R,9bR)-4-(1H-Imidazol-2-yl)-2,3,3a,4,5,9b-hexahydro-1H-pyrrolo[3,2-c]quinolin-1-yl]carbonyl}cyclohexyl)-N'-phenylurea

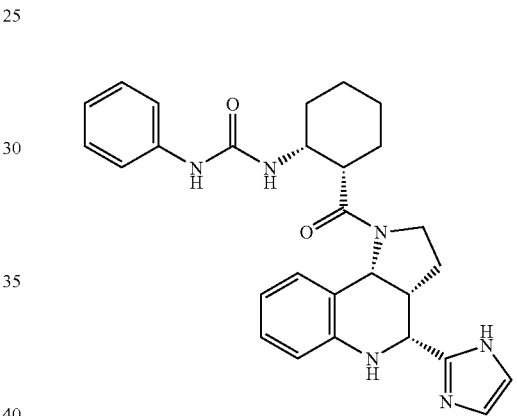

LC/MS (ESI) m/z: 485 (MH$^+$).

Example 294

(2E)-N-((1R,2S)-2-{[(3aR,4R,9bR)-4-(1H-Imidazol-2-yl)-2,3,3a,4,5,9b-hexahydro-1H-pyrrolo[3,2-c]quinolin-1-yl]carbonyl}cyclohexyl)-3-[4-(trifluoromethyl)phenyl]acrylamide

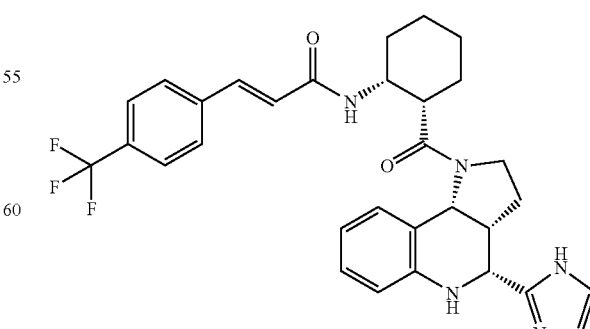

LC/MS (ESI) m/z: 564 (MH$^+$).

Example 295

N-Ethyl-N'-((1R,2S)-2-{[(3aR,4R,9bR)-4-(1H-imidazol-2-yl)-2,3,3a,4,5,9b-hexahydro-1H-pyrrolo[3,2-c]quinolin-1-yl]carbonyl}cyclohexyl)urea

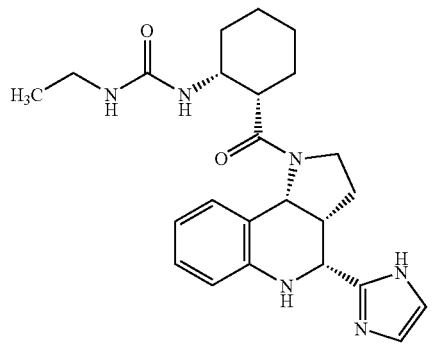

LC/MS (ESI) m/z: 437 (MH⁺).

Example 296

N-((1R,2S)-2-{[(3aR,4R,9bR)-4-(1H-Imidazol-2-yl)-2,3,3a,4,5,9b-hexahydro-1H-pyrrolo[3,2-c]quinolin-1-yl]carbonyl}cyclohexyl)-4-(trifluoromethyl)benzamide

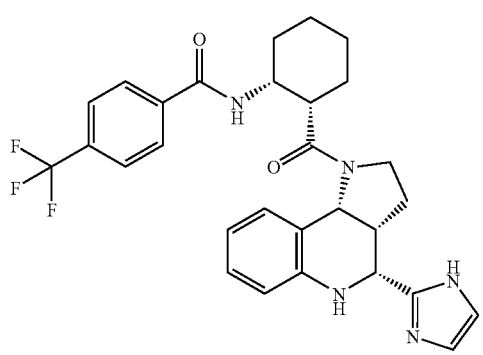

LC/MS (ESI) m/z: 538 (MH⁺)

Example 297

(2E)-3-(4-Fluorophenyl)-N-(1R,2S)-2-{[(3aR,4R,9bR)-4-(1H-imidazol-2-yl)-2,3,3a,4,5,9b-hexahydro-1H-pyrrolo[3,2-c]quinolin-1-yl]carbonyl}cyclohexyl)acrylamide

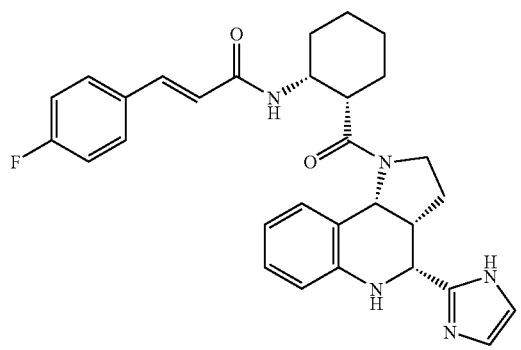

LC/MS (ESI) m/z: 514 (MH⁺).

Example 298

N-(4-Fluorophenyl)-N'-((1R,2S)-2-{[(3aR,4R,9bR)-4-(1H-imidazol-2-yl)-2,3,3a,4,5,9b-hexahydro-1H-pyrrolo[3,2-c]quinolin-1-yl]carbonyl}cyclohexyl)urea

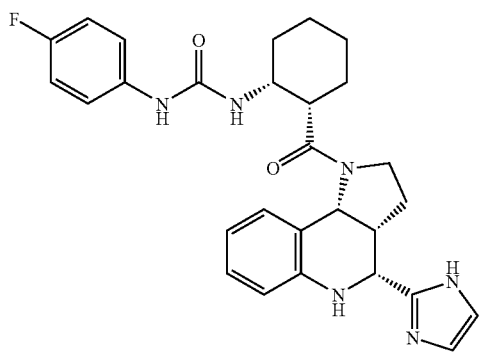

LC/MS (ESI) m/z: 503 (MH⁺).

Example 299

N-Butyl-N'-((1R,2S)-2-{[(3aR,4R,9bR)-4-(1H-imidazol-2-yl)-2,3,3a,4,5,9b-hexahydro-1H-pyrrolo[3,2-c]quinolin-1-yl]carbonyl}cyclohexyl)urea

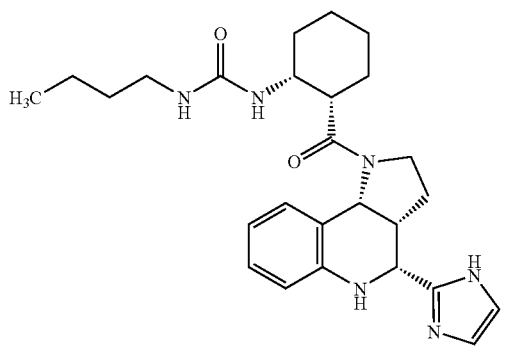

LC/MS (ESI) m/z: 465 (MH⁺).

Example 300

(2E)-N-((1R,2S)-2-{[(3aR,4R,9bR)-4-(1H-Imidazol-2-yl)-2,3,3a,4,5,9b-hexahydro-1H-pyrrolo[3,2-c]quinolin-1-yl]carbonyl}cyclohexyl)-3-thien-2-ylacrylamide

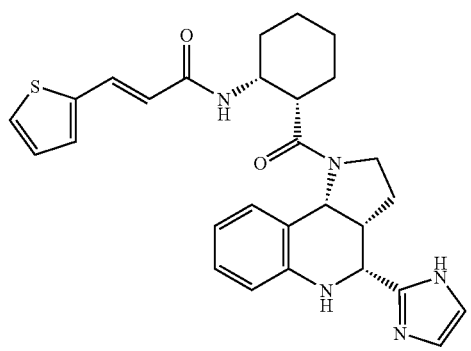

LC/MS (ESI) m/z: 502 (MH⁺).

Example 301

3-Chloro-4-fluoro-N-((1R,2S)-2-{[(3aR,4R,9bR)-4-(1H-imidazol-2-yl)-2,3,3a,4,5,9b-hexahydro-1H-pyrrolo[3,2-c]quinolin-1-yl]carbonyl}cyclohexyl)benzamide

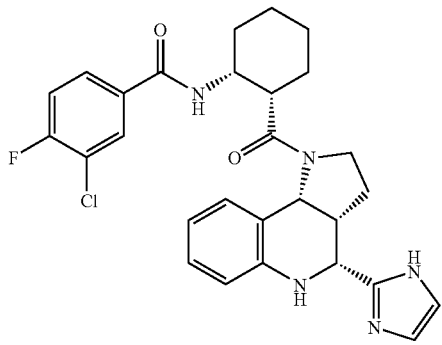

LC/MS (ESI) m/z: 522 (MH+).

Example 302

2-Fluoro-N-((1R,2S)-2-{[(3aR,4R,9bR)-4-(1H-imidazol-2-yl)-2,3,3a,4,5,9b-hexahydro-1H-pyrrolo[3,2-c]quinolin-1-yl]carbonyl}cyclohexyl)benzamide

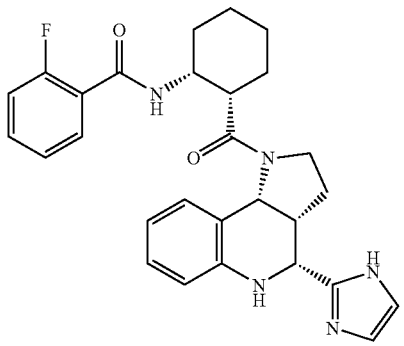

LC/MS (ESI) m/z: 488 (MH+).

Example 303

4-Chloro-N-((1R,2S)-2-{[(3aR,4R,9bR)-4-(1H-imidazol-2-yl)-2,3,3a,4,5,9b-hexahydro-1H-pyrrolo[3,2-c]quinolin-1-yl]carbonyl}cyclohexyl)benzamide

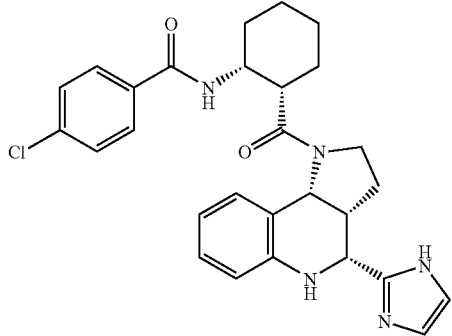

LC/MS (ESI) m/z: 504 (MH+).

Example 304

4-Cyano-N-((1R,2S)-2-{[(3aR,4R,9bR)-4-(1H-imidazol-2-yl)-2,3,3a,4,5,9b-hexahydro-1H-pyrrolo[3,2-c]quinolin-1-yl]carbonyl}cyclohexyl)benzamide

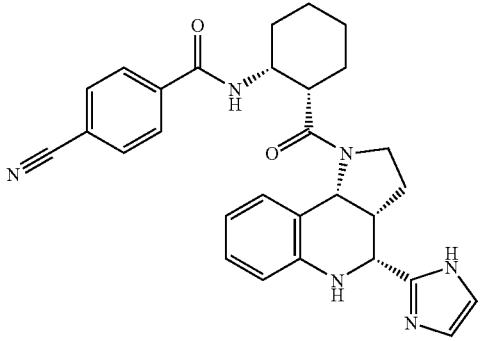

[2-((3aR,4R,9bR)-1-{[(1S,2R)-2-aminocyclohexyl]carbonyl}-2,3,3a,4,5,9b-hexahydro-1H-pyrrolo[3,2-c]quinolin-4-yl)-1H-imidazol-1-yl]methyl pivalate dihydrochloride (7.16 g, 13.0 mmol) was dissolved in ethyl acetate (170 ml) and 10% aqueous sodium carbonate solution (140 ml), and 4-cyanobenzoyl chloride (2.59 g, 15.6 mmol) was added under ice-cooling. The reaction mixture was stirred at room temperature for 2 hrs., and the separated aqueous layer was extracted with ethyl acetate. The combined organic layer was dried over anhydrous magnesium sulfate, and the solvent was evaporated under reduced pressure. The residue was subjected to silica gel column chromatography and eluted with ethyl acetate-methanol (1:0-10:1, v/v) to give an amorphous form. This was dissolved in methanol (200 ml), 28% aqueous ammonia (100 ml) was added dropwise, and the mixture was stirred for 5 hrs. The solvent was evaporated under reduced pressure and the residue was subjected to silica gel column chromatography and eluted with ethyl acetate-methanol (1:0-5:1, v/v) to give the title compound (6.06 g, 94%) as an amorphous form.

$^1$H-NMR (CDCl$_3$) δ: 1.34-2.06 (9H, m), 2.11-2.29 (1H, m), 2.44-2.56 (1H, m), 2.62-2.74 (1H, m), 2.89-2.97 (1H, m), 3.43-3.60 (2H, m), 4.20-4.32 (2H, m), 4.88 (1H, d, J=3.0 Hz), 5.70 (1H, d, J=7.5 Hz), 6.54-6.61 (1H, m), 6.74-6.82 (1H, m), 7.00-7.10 (3H, m), 7.40-7.49 (2H, m), 7.69-7.78 (2H, m), 7.88-7.99 (2H, m), 9.67 (1H, br s).
LC/MS (ESI) m/z: 495 (MH+).

Example 305

N-((1R,2S)-2-{[(3aR,4R,9bR)-4-(1H-Imidazol-2-yl)-2,3,3a,4,5,9b-hexahydro-1H-pyrrolo[3,2-c]quinolin-1-yl]carbonyl}cyclohexyl)-3-(trifluoromethyl)benzamide

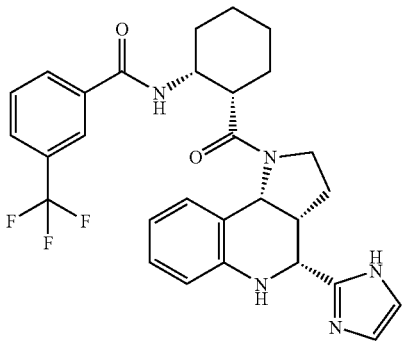

LC/MS (ESI) m/z: 538 (MH+).

Example 306

N-((1R,2S)-2-{[(3aR,4R,9bR)-4-(1H-Imidazol-2-yl)-2,3,3a,4,5,9b-hexahydro-1H-pyrrolo[3,2-c]quinolin-1-yl]carbonyl}cyclohexyl)terephthalamide

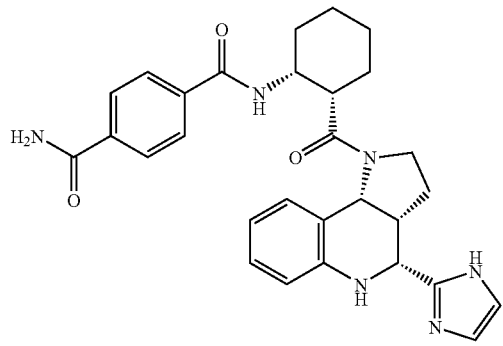

LC/MS (ESI) m/z: 513 (MH+).

Example 307

N-(4-Cyanophenyl)-N'-((1R,2S)-2-{[(3aR,4R,9bR)-4-(1H-imidazol-2-yl)-2,3,3a,4,5,9b-hexahydro-1H-pyrrolo[3,2-c]quinolin-1-yl]carbonyl}cyclohexyl)urea

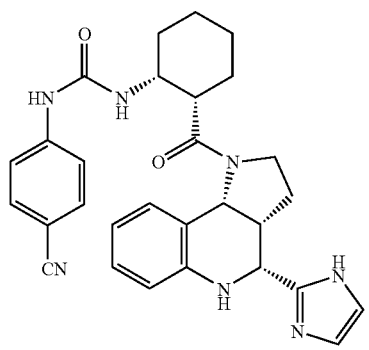

LC/MS (ESI) m/z: 510 (MH+).

Example 308

3-Cyano-N-((1R,2S)-2-{[(3aR,4R,9bR)-4-(1H-imidazol-2-yl)-2,3,3a,4,5,9b-hexahydro-1H-pyrrolo[3,2-c]quinolin-1-yl]carbonyl}cyclohexyl)benzamide

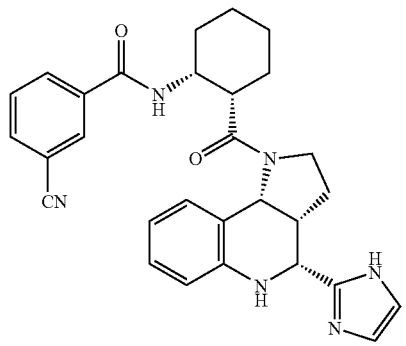

LC/MS (ESI) m/z: 495 (MH+).

Example 309

4-Cyano-N-((1R,2S)-2-{[(3aR,4R,9bR)-4-(1H-imidazol-2-yl)-2,3,3a,4,5,9b-hexahydro-1H-pyrrolo[3,2-c]quinolin-1-yl]carbonyl}cyclohexyl)-3-methylbenzamide

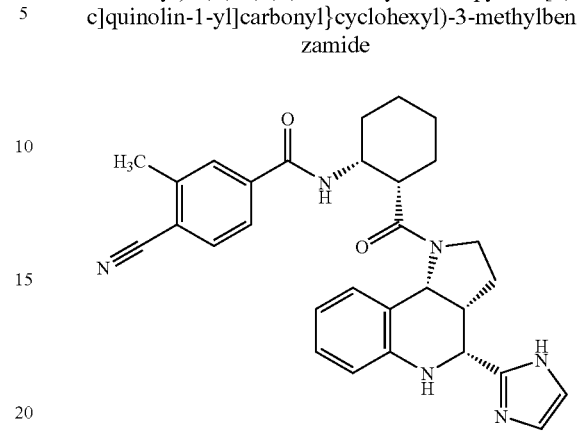

LC/MS (ESI) m/z: 509 (MH+).

Example 310

N-((1R,2S)-2-{[(3aR,4R,9bR)-4-(1H-Imidazol-2-yl)-2,3,3a,4,5,9b-hexahydro-1H-pyrrolo[3,2-c]quinolin-1-yl]carbonyl}cyclohexyl)-1H-1,2,3-benzotriazole-5-carboxamide

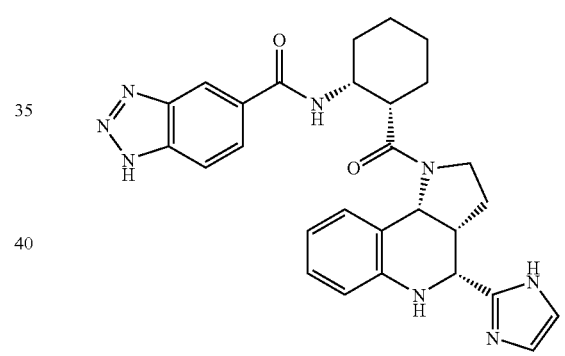

LC/MS (ESI) m/z: 511 (MH+).

Example 311

(1R*,2S*)-N-Phenyl-2-(((3aR*,4R*,9bR*)-4-phenyl-2,3,3a,4,5,9b-hexahydro-1H-pyrrolo[3,2-c]quinolin-1-yl)carbonyl)cyclohexanecarboxamide

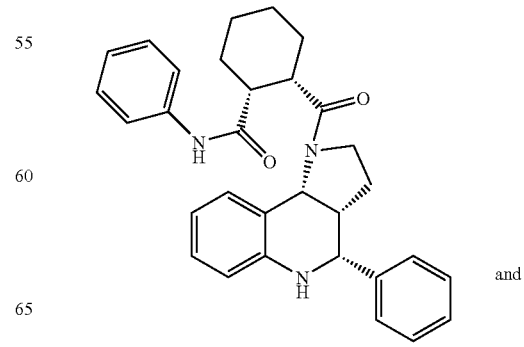

and

231

(1S*,2R*)-N-phenyl-2-{[(3aR*,4R*,9bR*)-4-phenyl-2,3,3a,4,5,9b-hexahydro-1H-pyrrolo[3,2-c]quinolin-1-yl]carbonyl}cyclohexanecarboxamide (racemate)

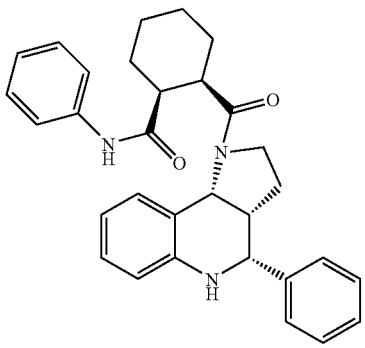

To a mixture of the compound (242 mg, 0.75 mmol) synthesized in Reference Example 8, (1S*,2R*)-2-(anilinocarbonyl)cyclohexanecarboxylic acid (222 mg, 0.90 mmol) and triethylamine (0.313 ml, 2.25 mmol) in DMF (7.5 ml) was added DEPC (0.151 ml, 0.90 mmol) at 0° C., and the mixture was stirred at room temperature for 1 hr. Saturated aqueous sodium hydrogen carbonate solution was added, and the reaction mixture was extracted with ethyl acetate. The extract was washed with saturated brine and dried over anhydrous Na₂SO₄. The solvent was evaporated under reduced pressure, and the obtained residue was subjected to silica gel column chromatography and eluted with hexane-ethyl acetate (2:1, v/v). The title compound (1R*,2S*,3aR*,4R*,9bR*) (163 mg, 45%) was obtained as a white solid from the first eluted fraction LC/MS (ESI) m/z: 480 (MH⁺).

The title compound (1S*,2R*,3aR*,4R*,9bR*) (76 mg, 21%) was obtained as a white solid from the second eluted fraction LC/MS (ESI) m/z: 480 (MH⁺)

Example 312

N-(1-{2-Oxo-2-[(3aR*,4R*,9bR*)-4-phenyl-2,3,3a,4,5,9b-hexahydro-1H-pyrrolo[3,2-c]quinolin-1-yl]ethyl}cyclohexyl)benzamide

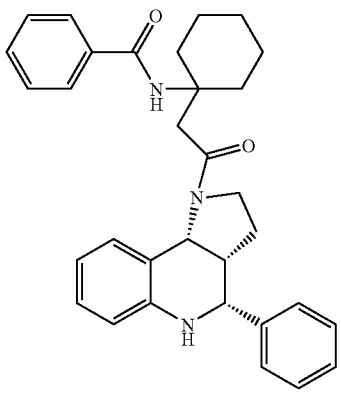

-continued

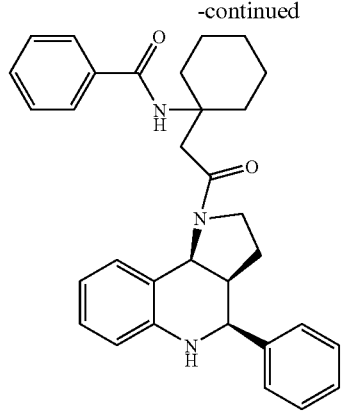

The title compound was synthesized in the same manner as in Example 1 and using [1-(benzoylamino)cyclohexyl]acetic acid.

LC/MS (ESI) m/z: 494 (MH⁺).

Example 313

N-[(1-{[(3aR*,4R*,9bR*)-4-Phenyl-2,3,3a,4,5,9b-hexahydro-1H-pyrrolo[3,2-c]quinolin-1-yl]carbonyl}cyclohexyl)methyl]benzamide

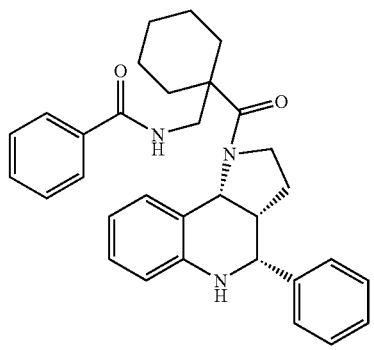

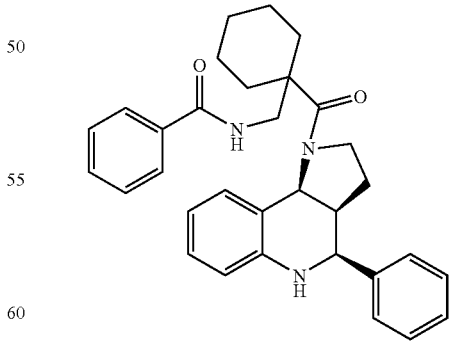

The title compound was synthesized in the same manner as in Example 1 and using 1-[(benzoylamino)methyl]cyclohexanecarboxylic acid.

LC/MS (ESI) m/z: 494 (MH⁺).

Example 314

N-(4-{2-Oxo-2-[(3aR*,4R*,9bR*)-4-phenyl-2,3,3a,4,5,9b-hexahydro-1H-pyrrolo[3,2-c]quinolin-1-yl]ethyl}tetrahydro-2H-pyran-4-yl)benzamide

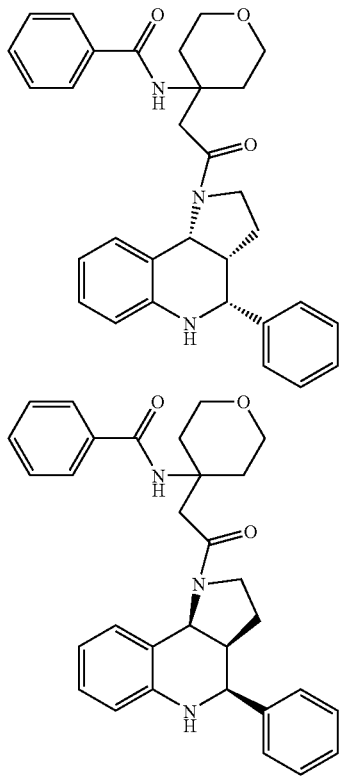

The title compound was synthesized in the same manner as in Example 1 and using [4-(benzoylamino)tetrahydro-2H-pyran-4-yl]acetic acid.

LC/MS (ESI) m/z: 496 (MH⁺).

Example 315

N-((1S,2S)-2-{[(3aR*,4R*,9bR*)-4-Phenyl-2,3,3a,4,5,9b-hexahydro-1H-pyrrolo[3,2-c]quinolin-1-yl]carbonyl}cyclohexyl)benzamide

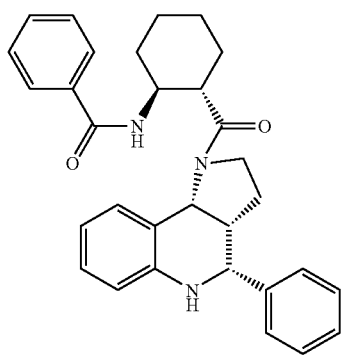

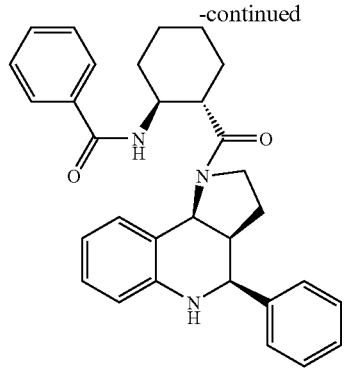

The title compound was synthesized in the same manner as in Example 1 and using (1S,2S)-2-(benzoylamino)cyclohexanecarboxylic acid.

LC/MS (ESI) m/z: 480 (MH⁺).

Example 316

N-{(1R,2S)-2-[(3aR*,4R*,9bR*)-(5-Acetyl-4-phenyl-2,3,3a,4,5,9b-hexahydro-1H-pyrrolo[3,2-c]quinolin-1-yl)carbonyl]cyclohexyl}benzamide

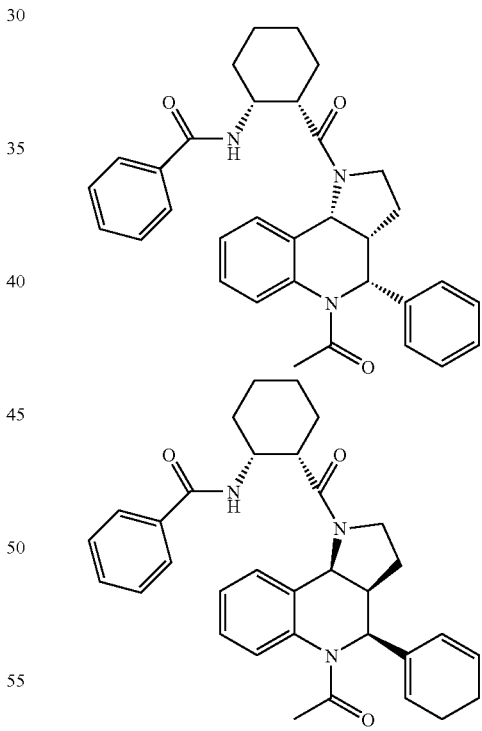

The compound (130 mg, 0.27 mmol) of Example 1 and triethylamine (69 mg, 0.30 mmol) were dissolved in chloroform (2 ml), acetyl chloride (99 mg, 0.33 mmol) was added under ice-cooling, and the mixture was stirred at room temperature for 1 hr. and at 60° C. for 2 hrs. Water was added to the reaction mixture, and the mixture was extracted with ethyl acetate. The extract was washed with saturated brine, dried (over anhydrous MgSO₄), and the solvent was evaporated. The residue was subjected to column chromatography using

Example 317

N-((1R,2S)-2-{[(4aR*,5R*,10bR*)-5-Phenyl-3,4,4a,
5,6,10b-hexahydrobenzo[h]-1,6-naphthyridin-1(2H)-
yl]carbonyl}cyclohexyl)benzamide

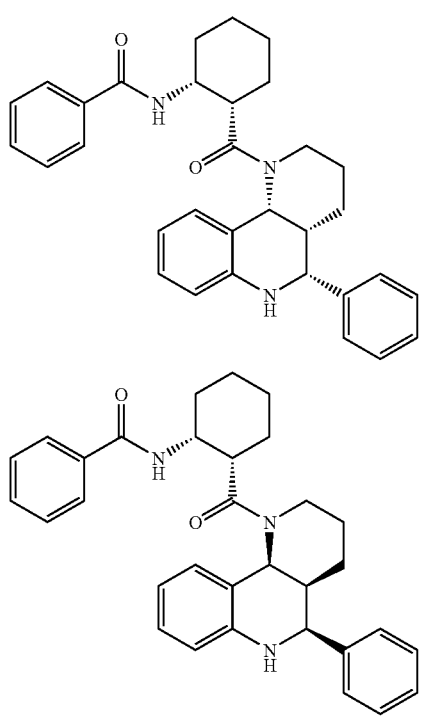

TFA (1 ml) was added to tert-butyl ((1R,2S)-2-{[(4aR*, 5R*,10bR*)-5-phenyl-3,4,4a, 5,6,10b-hexahydrobenzo[h]-1,6-naphthyridin-1(2H)-yl]carbonyl}cyclohexyl)carbamate (69 mg, 0.14 mmol), and the mixture was stirred at room temperature for 3 min. Ice was added to the reaction solution, and the mixture was basified with 8N aqueous sodium hydroxide solution and extracted with ethyl acetate. The extract was washed with saturated brine, dried (over anhydrous $MgSO_4$), and the solvent was evaporated under reduced pressure. The obtained residue was dissolved in dimethylacetamide (2 ml), benzoyl chloride (28 mg, 0.17 mmol) was added at 0° C., and the mixture was stirred at room temperature for 1 hr. Water was added to the reaction mixture and the mixture was extracted with ethyl acetate. The extract was washed with 6% aqueous sodium hydrogen carbonate solution and saturated brine, dried (over anhydrous $MgSO_4$), and the solvent was evaporated under reduced pressure. The residue was subjected to column chromatography using silica gel (10 g), and eluted with hexane-ethyl acetate (7:1-3:1, v/v) to give the title compound (45 mg, 65%) as a colorless amorphous form.

LC/MS (ESI) m/z: 494 ($MH^+$).

Example 318

N-((1R,2S)-2-{[(3aR*,4R*,9bR*)-4-(3-Thienyl)-2,3,
3a,4,5,9b-hexahydro-1H-pyrrolo[3,2-c]quinolin-1-
yl]carbonyl}cyclopentyl)benzamide

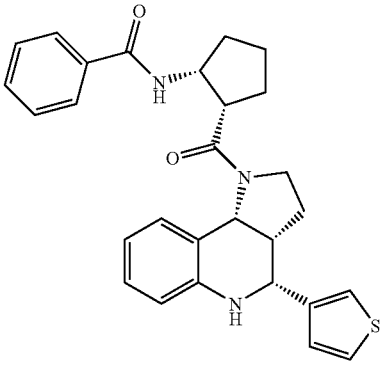

TFA (1 ml) was added to tert-butyl (3aR*,4R*,9bR*)-4-(3-thienyl)-2,3,3a,4,5,9b-hexahydro-1H-pyrrolo[3,2-c]quinoline-1-carboxylate (178 mg, 0.5 mmol), and the mixture was stirred at room temperature for 3 min. Ice was added to the reaction solution, the mixture was basified with 8N aqueous sodium hydroxide solution, and the mixture was extracted with ethyl acetate. The extract was washed with saturated brine, dried (over anhydrous $MgSO_4$), and the solvent was evaporated under reduced pressure. The obtained residue was dissolved in tetrahydrofuran (3 ml), and (1S,2R)-2-(benzoylamino)cyclopentanecarboxylic acid (117 mg, 0.5 mmol) and triethylamine (101 mg, 1.0 mmol) were added. DEPC (82 mg, 0.5 mmol) was added at 0° C. and the mixture was stirred at room temperature for 30 min. Water was added to the reaction mixture and the mixture was extracted with ethyl acetate. The extract was washed with 6% aqueous sodium hydrogen carbonate solution and saturated brine, dried (over anhydrous $MgSO_4$), and the solvent was evaporated under reduced pressure. The residue was subjected to column chromatography using silica gel (30 g), and eluted with hexane-ethyl acetate (5:1-2:1, v/v) to give the title compound (104 mg, 44%) as a colorless powder.

LC/MS (ESI) m/z: 472 ($MH^+$).

Example 319

N-Phenyl-N'-((1R,2S)-2-{[(3aS,4S,9bS)-4-phenyl-2,3,3a,4,5,9b-hexahydro-1H-pyrrolo[3,2-c]quinolin-1-yl]carbonyl}cyclohexyl)urea

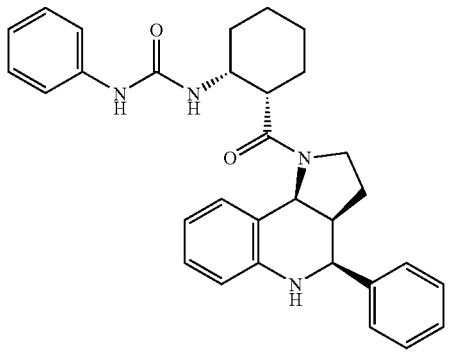

In the same manner as in Example 135 and using (1R,2S)-2-{[(3aS,4S,9bS)-4-phenyl-2,3,3a,4,5,9b-hexahydro-1H-pyrrolo[3,2-c]quinolin-1-yl]carbonyl}cyclohexylamine dihydrochloride, the title compound was synthesized.

LC/MS (ESI) m/z: 495 (MH+).

Example 320

N-(1-{2-Oxo-2-[(3aR*,4R*,9bR*)-4-phenyl-2,3,3a,4,5,9b-hexahydro-1H-pyrrolo[3,2-c]quinolin-1-yl]ethyl}cyclohexyl)-N'-phenylurea

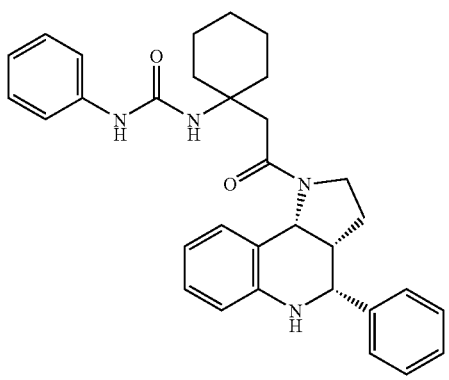

LC/MS (ESI) m/z: 509 (MH+)

Example 321

N-((1R,2S)-2-{[(3aS,4S,9bS)-4-(1H-Imidazol-2-yl)-2,3,3a,4,5,9b-hexahydro-1H-pyrrolo[3,2-c]quinolin-1-yl]carbonyl}cyclohexyl)benzamide

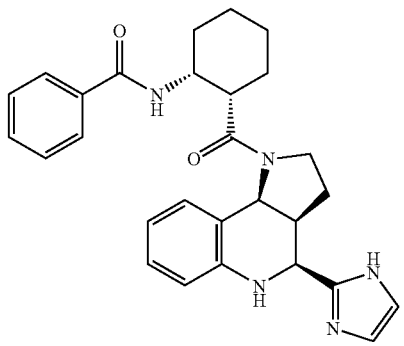

The title compound was synthesized in the same manner as in Examples 80 and 81 and using [2-((3aS,4S,9bS)-1-{[(1S,2R)-2-aminocyclohexyl]carbonyl}-2,3,3a,4,5,9b-hexahydro-1H-pyrrolo[3,2-c]quinolin-4-yl)-1H-imidazol-1-yl]methyl pivalate dihydrochloride.

LC/MS (ESI) m/z: 470 (MH+).

The compounds of Example 322 and Example 323 were synthesized by amidation using benzyl 2-((3aR,4R,9bR)-1-{[(1S,2R)-2-aminocyclohexyl]carbonyl}-2,3,3a,4,5,9b-hexahydro-1H-pyrrolo[3,2-c]quinolin-4-yl)-1H-pyrrole-1-carboxylate and then removal of Cbz group in the same manner as in Example 64.

Example 322

4-Cyano-N-((1R,2S)-2-{[(3aR,4R,9bR)-4-(1H-pyrrol-2-yl)-2,3,3a,4,5,9b-hexahydro-1H-pyrrolo[3,2-c]quinolin-1-yl]carbonyl}cyclohexyl)benzamide

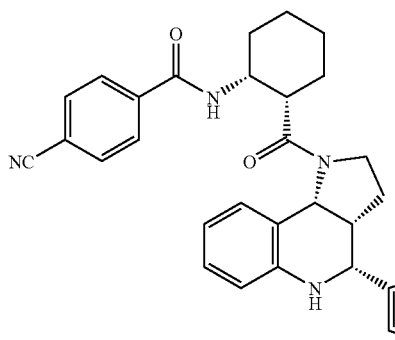

LC/MS (ESI) m/z: 494 (MH+).

Example 323

N-((1R,2S)-2-{[(3aR,4R,9bR)-4-(1H-Pyrrol-2-yl)-2,3,3a,4,5,9b-hexahydro-1H-pyrrolo[3,2-c]quinolin-1-yl]carbonyl}cyclohexyl)terephthalamide

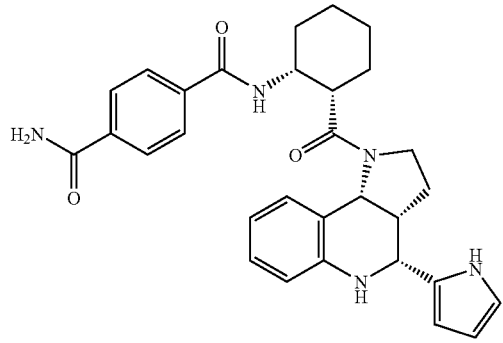

LC/MS (ESI) m/z: 512 (MH+).

Example 324

(3aS,4S,9bS)-1-{[(2R)-1-Benzoylpiperidin-2-yl]carbonyl}-4-phenyl-2,3,3a,4,5,9b-hexahydro-1H-pyrrolo[3,2-c]quinoline

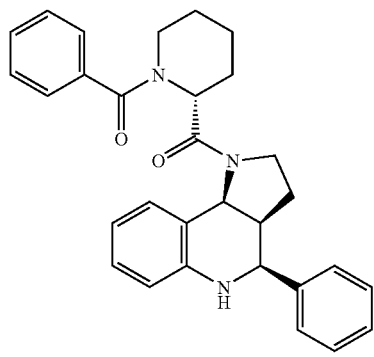

The title compound was synthesized in the same manner as in Example 75 and using (3aS,4S,9bS)-4-phenyl-1-[(2R)-piperidin-2-ylcarbonyl]-2,3,3a,4,5,9b-hexahydro-1H-pyrrolo[3,2-c]quinoline dihydrochloride.

LC/MS (ESI) m/z: 466 (MH+).

Example 325

N-((1R,2S)-2-{[4-(3-Thienyl)-2,3-dihydro-1H-pyrrolo[3,2-c]quinolin-1-yl]carbonyl}cyclohexyl)benzamide

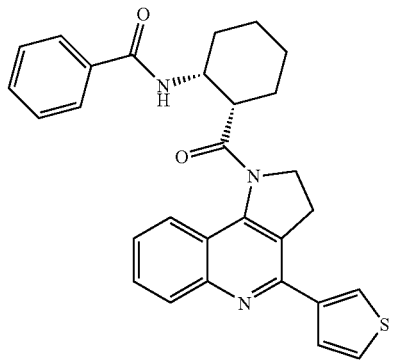

A mixture of N-((1R,2S)-2-{[(3aR*,4R*,9bR*)-4-(3-thienyl)-2,3,3a, 4,5,9b-hexahydro-1H-pyrrolo[3,2-c]quinolin-1-yl]carbonyl}cyclohexyl)benzamide and N-((1R,2S)-2-{[(3aS*,4R*,9bS*)-4-(3-thienyl)-2,3,3a, 4,5,9b-hexahydro-1H-pyrrolo[3,2-c]quinolin-1-yl]carbonyl}cyclohexyl) benzamide (422 mg, 0.87 mmol) was dissolved in toluene (30 ml), manganese dioxide (7.6 g, 87 mmol) was added and the mixture was refluxed overnight. The reaction mixture was filtered through celite and washed with methanol. The filtrate was concentrated under reduced pressure. The residue was subjected to column chromatography using silica gel (30 g), and eluted with hexane-ethyl acetate (9:1-2:1, v/v). Crystallization from diisopropy ether gave the title compound (70 mg, 17%) as pale-brown crystals.

LC/MS (ESI) m/z: 482 (MH+).

Example 326

N-Phenyl-N'-{(1R,2S)-2-[(4-phenyl-2,3-dihydro-1H-pyrrolo[3,2-c]quinolin-1-yl)carbonyl]cyclohexyl}urea

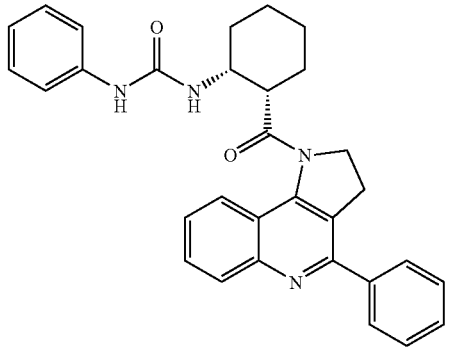

In the same manner as in Example 325 and using N-phenyl-N'-((1R,2S)-2-{[(3aS,4S,9bS)-4-phenyl-2,3,3a,4,5,9b-hexahydro-1H-pyrrolo[3,2-c]quinolin-1-yl]carbonyl}cyclohexyl)urea, the title compound was synthesized.

LC/MS (ESI) m/z: 491 (MH+).

Example 327

Ethyl 1-{[(1S,2R)-2-(benzoylamino)cyclohexyl]carbonyl}-2,3-dihydro-1H-pyrrolo[3,2-c]quinoline-4-carboxylate

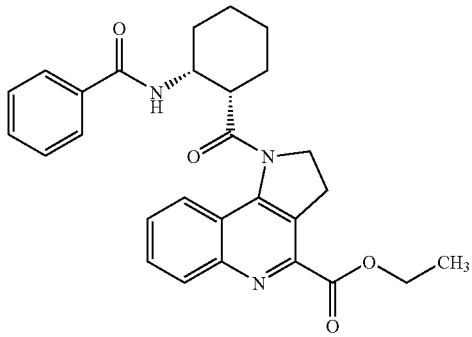

In the same manner as in Example 325 and using ethyl 1-{[(1S,2R)-2-(benzoylamino)cyclohexyl]carbonyl}-2,3,3a,4,5,9b-hexahydro-1H-pyrrolo[3,2-c]quinoline-4-carboxylate, the title compound was synthesized.

LC/MS (ESI) m/z: 472 (MH$^+$).

Example 328

N-((1R,2S)-2-{[4-(1H-Imidazol-2-yl)-2,3-dihydro-1H-pyrrolo[3,2-c]quinolin-1-yl]carbonyl}cyclohexyl)benzamide

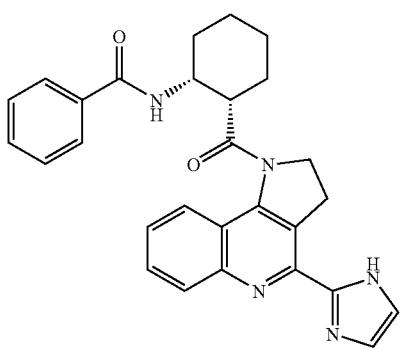

In the same manner as in Example 325, [2-((3aR*,4R*,9bR*)—{[(1S,2R)-2-(benzoylamino)cyclohexyl]carbonyl}-2,3,3a,4,5,9b-hexahydro-1H-pyrrolo[3,2-c]quinolin-4-yl)-1H-imidazol-1-yl]methylpivalate was subjected to the oxidization reaction to synthesize [2-(1-{[(1S,2R)-2-(benzoylamino)cyclohexyl]carbonyl}-2,3-dihydro-1H-pyrrolo[3,2-c]quinolin-4-yl)-1H-imidazol-1-yl]methyl pivalate, and then the title compound was synthesized in the same manner as in Example 81 by removing the pivaloyloxymethyl group.

LC/MS (ESI) m/z: 466 (MH$^+$).

Example 329

N-{1-[2-Oxo-2-(4-phenyl-2,3-dihydro-1H-pyrrolo[3,2-c]quinolin-1-yl)ethyl]cyclohexyl}benzamide

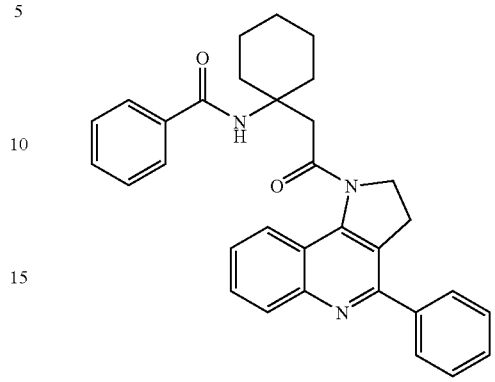

To a mixture of {1-[(anilinocarbonyl)amino]cyclohexyl}acetic acid (0.551 g, 2.11 mmol) and DMF (0.016 ml) in dichloromethane (20 ml) was added dropwise oxalyl chloride (0.275 ml, 3.17 mmol). After stirring for 1 hr, the solvent was evaporated to give the corresponding acid chloride as a powder. To a solution of 4-phenyl-2,3-dihydro-1H-pyrrolo[3,2-c]quinoline (0.346 g, 1.41 mmol) in toluene (10 ml) was added sodium hydride (60% in oil, 0.0676 g, 1.69 mmol), and the mixture was stirred for 30 min. A solution of the above-mentioned acid chloride in dichloromethane (10 ml) was added and the mixture was stirred at room temperature for 1 hr, and at 60° C. for 16 hrs. After cooling to room temperature, water and ethyl acetate were added to the reaction mixture, and separated organic layer was washed with saturated brine and dried (over anhydrous MgSO$_4$). After concentration under reduced pressure, the obtained residue was subjected to column chromatography using silica gel, and eluted with hexane-ethyl acetate (9:1-2:3, v/v) to give the title compound (0.17 g, 25%) as a colorless amorphous form from the object fraction.

LC/MS (ESI) m/z: 490 (MH$^+$).

Example 330

(2R)—N-(2-Phenylethyl)-2-{[(3aR,4R,9bR)-4-phenyl-2,3,3a, 4,5,9b-hexahydro-1H-pyrrolo[3,2-c]quinolin-1-yl]carbonyl}piperidine-1-carboxamide

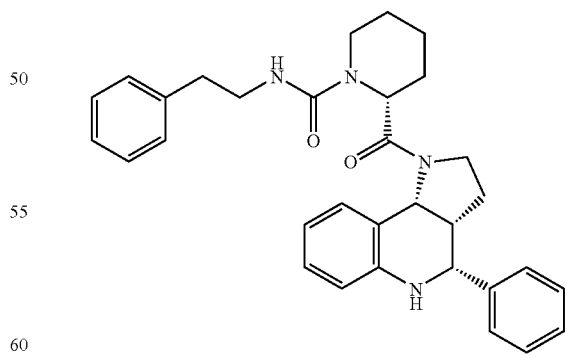

In the same manner as in Example 135 and using (3aS,4S,9bS)-4-phenyl-1-[(2R)-piperidin-2-ylcarbonyl]-2,3,3a,4,5,9b-hexahydro-1H-pyrrolo[3,2-c]quinoline dihydrochloride and phenethylisocyanate, the title compound was synthesized.

LC/MS (ESI) m/z: 509 (MH$^+$)

Example 331

N-(2-{[(3aR*,4R*,9bR*)-4-(3-Thienyl)-2,3,3a, 4,5, 9b-hexahydro-1H-pyrrolo[3,2-c]quinolin-1-yl] carbonyl}phenyl)benzamide

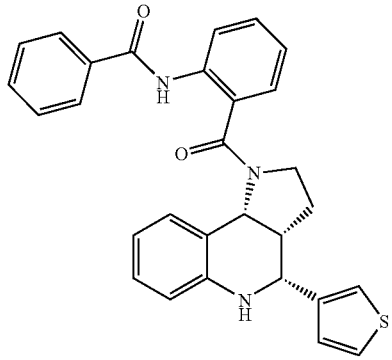

TFA (2 ml) was added to tert-butyl (3aR*,4R*,9bR*)-4-(3-thienyl)-2,3,3a,4,5,9b-hexahydro-1H-pyrrolo[3,2-c]quinoline-1-carboxylate (219 mg, 0.61 mmol), and the mixture was stirred at room temperature for 3 min. Ice was added to the reaction solution, and the mixture was basified with 8N aqueous sodium hydroxide solution and extracted with ethyl acetate. The extract was washed with saturated brine, dried (over anhydrous $MgSO_4$), and the solvent was evaporated under reduced pressure. The obtained residue was dissolved in tetrahydrofuran (3 ml), 2-(benzoylamino)benzoic acid (162 mg, 0.67 mmol) and triethylamine (124 mg, 1.2 mmol) were added. DEPC (99 mg, 0.61 mmol) was added at 0° C. and the mixture was stirred at room temperature for 30 min. Water was added to the reaction mixture and the mixture was extracted with ethyl acetate. The extract was washed with 6% aqueous sodium hydrogen carbonate solution and saturated brine, dried (over anhydrous $MgSO_4$), and the solvent was evaporated under reduced pressure. The residue was subjected to column chromatography using silica gel (30 g), and eluted with hexane-ethyl acetate (9:1-3:1, v/v) to give the title compound (126 mg, 43%) as colorless crystals.

LC/MS (ESI) m/z: 480 (MH$^+$).

Formulation Example 1

| | |
|---|---|
| (1) Compound of Example 1 | 10.0 g |
| (2) Lactose | 70.0 g |
| (3) Cornstarch | 50.0 g |
| (4) Soluble starch | 7.0 g |
| (5) Magnesium stearate | 3.0 g |

The compound of Example 1 (10.0 g) and magnesium stearate (3.0 g) were granulated with an aqueous solution of soluble starch (70 ml, 7.0 g as soluble starch), dried and mixed with lactose (70.0 g) and cornstarch (50.0 g) (lactose, cornstarch, soluble starch and magnesium stearate are all products on the Japanese Pharmacopoeia 14th ed.). The mixture is compressed to give tablets.

Experimental Example 1

Radio-Ligand Receptor Binding Inhibitory Activity Using Membrane Fraction of hNK2 Receptor-Expressing Cho Cell hNK2 receptor-expressing CHO cells (produced by EUROSCREEN) were cultured in HAM-F12 medium containing 400 µg/ml Geneticin, 100 U/mL penicillin, 100 µg/mL streptomycin and 10% inactivated serum. The medium was removed and adhered cells were washed with PBS, and PBS containing 5 mM EDTA was added to detach the cells from the flask. The cells were recovered by centrifugation, suspended in suspending buffer A (15 mM Tris-HCl (pH 7.5), 2 mM $MgCl_2$, 0.3 mM EDTA, 1 mM EGTA), disrupted by POLYTRON homogenizer (manufactured by KINEMATICA) and centrifuged at 800×g for 10 min. The supernatant was recovered and ultracentrifuged at 100000×g for 25 min. The precipitated fraction was suspended in suspending buffer B (7.5 mM Tris-HCl (pH 7.5), 12.5 mM $MgCl_2$, 0.3 mM EDTA, 1 mM, EDTA, 250 mM Sucrose) and cryopreserved (at −80° C.) as a receptor specimen.

An assay buffer (50 µL, 50 mM Tris-HCl (pH 7.4), 0.02% bovine serum albumin, 2 µg/mL chymostatin, 40 µg/mL bacitracin, 40 µg/mL APMSF, 3 mM $MnCl_2$) was added to a 96 well microassay plate. Thereto was added a 20 µg/mL membrane specimen suspended in the assay buffer (50 µL). An assay buffer (50 µL) containing 2% dimethyl sulfoxide was added to examine the total binding, 4 µM unlabeled NKA (produced by Peptide Institute, Inc.) solution (50 µL) diluted with an assay buffer containing 2% dimethyl sulfoxide was added to examine non-specific binding, and a test compound diluted with an assay buffer (50 µL, containing 2% dimethyl sulfoxide) was added to examine the binding inhibitory activity of the test compound. Furthermore, 400 µM [$^{125}$I]-NKA (produced by Amersham Biosciences) solution (50 µL) was added to each well.

After reaction at 25° C. for 30 min., the reaction was stopped by rapid filtration on a unifilter plate (GF/C) (manufactured by PerkinElmer) using a cell harvester (manufactured by PerkinElmer) and the cells were washed 5 times with 50 mM Tris-HCl (pH 7.4) buffer containing 0.02% bovine serum albumin (250 µL). The GF/C filter plate was dried and 20 µL of MicroScinti-O (manufactured by PerkinElmer) was added and the radioactivity was measured in Topcount (manufactured by PerkinElmer). The GF/C filter plate, which had been immersed in 0.3% polyethyleneimine for one day, was used.

Specific binding is shown by the value obtained by subtracting non-specific binding from the total binding. The binding inhibitory activity of the test compound is shown by the ratio of the value obtained by subtracting the measured value associated with the addition of the test compound from the total binding, to the value of the specific binding.

The results are shown in Table 6.

TABLE 6

| Example No. | hNK2 receptor binding inhibitory activity IC$_{50}$ (nM) |
|---|---|
| 1 | <10 |
| 6 | <10 |
| 7 | <10 |
| 8 | <10 |
| 9 | <10 |
| 15 | <10 |
| 16 | <1 |

TABLE 6-continued

| Example No. | hNK2 receptor binding inhibitory activity IC$_{50}$ (nM) |
|---|---|
| 17 | <10 |
| 18 | <1 |
| 19 | <10 |
| 20 | <10 |
| 23 | <10 |
| 25 | <10 |
| 27 | <10 |
| 28 | <10 |
| 29 | <10 |
| 51 | <10 |
| 52 | <10 |
| 53 | <10 |
| 54 | <1 |
| 56 | <10 |
| 58 | <10 |
| 59 | <10 |
| 60 | <1 |
| 61 | <10 |
| 62 | <1 |
| 63 | <1 |
| 64 | <1 |
| 66 | <10 |
| 68 | <10 |
| 75 | <10 |
| 76 | <10 |
| 78 | <10 |
| 79 | <10 |
| 81 | <1 |
| 82 | <10 |
| 83 | <10 |
| 85 | <10 |
| 86 | <10 |
| 87 | <10 |
| 89 | <10 |
| 90 | <1 |
| 91 | <10 |
| 92 | <10 |
| 93 | <10 |
| 94 | <10 |
| 95 | <10 |
| 96 | <10 |
| 97 | <10 |
| 98 | <1 |
| 99 | <10 |
| 100 | <10 |
| 101 | <1 |
| 102 | <10 |
| 103 | <1 |
| 104 | <1 |
| 105 | <1 |
| 106 | <10 |
| 107 | <1 |
| 108 | <10 |
| 109 | <10 |
| 114 | <10 |
| 116 | <10 |
| 117 | <10 |
| 119 | <10 |
| 120 | <10 |
| 127 | <10 |
| 128 | <10 |
| 129 | <10 |
| 132 | <10 |
| 133 | <1 |
| 134 | <1 |
| 135 | <1 |
| 136 | <10 |
| 137 | <1 |
| 138 | <1 |
| 139 | <1 |
| 140 | <10 |
| 141 | <10 |
| 143 | <10 |
| 144 | <10 |
| 145 | <10 |
| 146 | <10 |

TABLE 6-continued

| Example No. | hNK2 receptor binding inhibitory activity IC$_{50}$ (nM) |
|---|---|
| 147 | <10 |
| 148 | <1 |
| 149 | <10 |
| 150 | <10 |
| 151 | <10 |
| 152 | <10 |
| 153 | <1 |
| 154 | <1 |
| 155 | <10 |
| 156 | <10 |
| 159 | <10 |
| 160 | <1 |
| 161 | <10 |
| 162 | <10 |
| 164 | <1 |
| 166 | <1 |
| 168 | <10 |
| 170 | <10 |
| 171 | <10 |
| 172 | <10 |
| 173 | <10 |
| 175 | <10 |
| 178 | <10 |
| 180 | <1 |
| 181 | <1 |
| 182 | <1 |
| 183 | <1 |
| 184 | <1 |
| 185 | <10 |
| 186 | <1 |
| 187 | <1 |
| 188 | <1 |
| 189 | <1 |
| 190 | <1 |
| 191 | <1 |
| 192 | <1 |
| 193 | <1 |
| 194 | <1 |
| 195 | <1 |
| 196 | <1 |
| 197 | <1 |
| 198 | <10 |
| 199 | <10 |
| 200 | <1 |
| 201 | <1 |
| 202 | <1 |
| 204 | <1 |
| 205 | <1 |
| 206 | <1 |
| 208 | <1 |
| 209 | <1 |
| 210 | <1 |
| 211 | <10 |
| 212 | <1 |
| 213 | <1 |
| 215 | <1 |
| 216 | <10 |
| 217 | <1 |
| 218 | <1 |
| 219 | <1 |
| 229 | <1 |
| 232 | <10 |
| 233 | <10 |
| 234 | <1 |
| 237 | <1 |
| 238 | <10 |
| 239 | <1 |
| 241 | <10 |
| 244 | <10 |
| 245 | <10 |
| 246 | <10 |
| 247 | <10 |
| 248 | <1 |
| 249 | <10 |
| 250 | <1 |
| 252 | <1 |

TABLE 6-continued

| Example No. | hNK2 receptor binding inhibitory activity IC$_{50}$ (nM) |
|---|---|
| 253 | <10 |
| 254 | <1 |
| 256 | <1 |
| 258 | <1 |
| 259 | <10 |
| 261 | <1 |
| 263 | <10 |
| 264 | <1 |
| 265 | <1 |
| 266 | <10 |
| 267 | <10 |
| 268 | <10 |
| 269 | <1 |
| 270 | <10 |
| 271 | <10 |
| 272 | <1 |
| 273 | <1 |
| 274 | <10 |
| 275 | <1 |
| 276 | <10 |
| 277 | <1 |
| 278 | <10 |
| 279 | <1 |
| 280 | <1 |
| 281 | <1 |
| 282 | <10 |
| 283 | <1 |
| 284 | <1 |
| 285 | <1 |
| 286 | <10 |
| 287 | <10 |
| 288 | <1 |
| 289 | <10 |
| 290 | <1 |
| 291 | <1 |
| 293 | <1 |
| 294 | <1 |
| 295 | <10 |
| 296 | <1 |
| 297 | <1 |
| 298 | <1 |
| 299 | <1 |
| 300 | <1 |
| 301 | <1 |
| 302 | <1 |
| 303 | <1 |
| 304 | <1 |
| 305 | <1 |
| 306 | <10 |
| 307 | <1 |
| 308 | <1 |
| 309 | <1 |
| 310 | <1 |
| 312 | <10 |
| 321 | <10 |
| 322 | <1 |
| 323 | <1 |
| 326 | <10 |

Experimental Example 2

Evaluation of Antagonistic Activity Determined by Intracellular Calcium Concentration Using Test Compound, Neurokinin A and hNK2 Receptor-Expressing CHO Cell hNK2 receptor-expressing CHO cells were seeded on a 96 well plate at $3\times10^4$ cell/well and cultured for 24 hrs. Then the medium was aspirated and 20 mM HEPES (pH 7.4)-HBSS buffer (50 μL) was added. Thereto was added prepared 1×Reagent buffer (50 μL, FLIPR Calcium Assay Kit: Molecular Devices Corporation, Japan) and the mixture was reacted at 37° C. for 1 hr. A test compound diluted with 20 mM HEPES (pH 7.4)-HBSS buffer (50 μL, containing 0.4% dimethyl sulfoxide) was added to examine antagonistic activity of the test compound. Thereafter, 20 nM Neurokinin A solution (50 μL) was added, and change in the intracellular calcium concentration were measured by FLIPR (Molecular Devices Corporation, Japan). As a result, the test compound inhibited increase in the intracellular calcium concentration due to Neurokinin A. The results are shown in Table 7.

TABLE 7

| Assay of Antagonistic activity | | |
|---|---|---|
| | Inhibitory rate (%) | |
| Test compound | 10 μM | 1 μM |
| Compound of Example 1 | 97 | 45 |

INDUSTRIAL APPLICABILITY

Since compound (I) of the present invention, a salt thereof and a prodrug thereof have a NK2 receptor antagonistic action and has low toxicity, they are particularly useful as agents for the prophylaxis and/or treatment of functional gastrointestinal diseases (e.g., irritable bowel syndrome, non-ulcer dyspepsia and the like.

This application is based on a patent application No. 2004-134705 filed in Japan, the contents of which are all hereby incorporated by reference.

The invention claimed is:

1. 4-(Difluoromethoxy)-N-((1R,2S)-2-{[(3aR,4R,9bR)-4-(methoxymethyl)-2,3,3a,4,5,9b-hexahydro-1H-pyrrolo[3,2-c]quinolin-1-yl]carbonyl}cyclohexyl)benzamide, or a salt thereof.

* * * * *